US012606868B2

(12) United States Patent
Mootha et al.

(10) Patent No.: US 12,606,868 B2
(45) Date of Patent: Apr. 21, 2026

(54) MOLECULAR BIOMARKERS AND TARGETS FOR FUCHS' ENDOTHELIAL CORNEAL DYSTROPHY AND GLAUCOMA

(71) Applicant: THE BOARD OF REGENTS OF THE UNIVERSITY OF TEXAS SYSTEM, Austin, TX (US)

(72) Inventors: Venkateswara Vinod Mootha, Coppell, TX (US); David R. Corey, Dallas, TX (US); Jiaxin Hu, Coppell, TX (US); Yongjun Chu, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 417 days.

(21) Appl. No.: 17/184,360

(22) Filed: Feb. 24, 2021

(65) Prior Publication Data

US 2021/0348234 A1 Nov. 11, 2021

Related U.S. Application Data

(60) Provisional application No. 62/980,690, filed on Feb. 24, 2020.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/156* (2013.01); *C12Q 2600/158* (2013.01)

(58) Field of Classification Search
CPC ............ C12Q 1/6883; C12Q 2600/106; C12Q 2600/118; C12Q 2600/156
See application file for complete search history.

(56) References Cited

U.S. PATENT DOCUMENTS

| | | | |
|---|---|---|---|
| 2008/0305103 A1 | 12/2008 | Saragovi | |
| 2009/0035279 A1 | 2/2009 | Kim et al. | |
| 2010/0184824 A1 | 7/2010 | Mcswiggen et al. | |
| 2014/0018527 A1 | 1/2014 | Jimenez et al. | |
| 2016/0158210 A1 | 6/2016 | Koizumi et al. | |
| 2016/0175380 A1 | 6/2016 | Jurkunas | |
| 2016/0266114 A1 | 9/2016 | Koizumi et al. | |
| 2019/0008985 A1 | 1/2019 | Angel et al. | |
| 2020/0376019 A1* | 12/2020 | Gallant-Behm | ..... A61K 31/713 |
| 2021/0139894 A1 | 5/2021 | Mootha et al. | |
| 2021/0348234 A1* | 11/2021 | Mootha | ................... A61P 27/02 |
| 2023/0310402 A1 | 10/2023 | Koizumi et al. | |
| 2024/0002849 A1 | 1/2024 | Mootha et al. | |

FOREIGN PATENT DOCUMENTS

| | | |
|---|---|---|
| WO | 2015015654 A1 | 2/2015 |
| WO | 2018165541 A1 | 9/2018 |
| WO | 2019109026 A1 | 6/2019 |

OTHER PUBLICATIONS

De Roo, The molecular pathogenesis of late-onset Fuchs' endothelial corneal dystrophy, Doctoral Thesis, Ku Leuven, Publication Date: Sep. 2017 (Year: 2017).*
International Search Report of the International Searching Authority in Application No. PCT/US2021/019467, dated Jun. 22, 2021, 4 pages.
Written Opinion of the International Searching Authority in Application No. PCT/US2021/019467, dated Jun. 22, 2021, 9 pages.
Sarnicola et al, "Fuchs Endothelial Corneal Dystrophy: Update on Pathogenesis and Future Directions", Eye & Contact Lens: Science & Clinical Practice, vol. 45, No. 1, pp. 1-10, Jan. 2019.
Signh et al, "Assembly of Fibroectin Extracellular Matrix", Annual Review of Cell and Development Biology, vol. 26, pp. 397-419, (2010).
Sobczak et al, "RNA Interference Targeting CUG Repeats in a Mouse Model of Myotonic Dystrophy", Molecular Therapy, vol. 21, No. 2, pp. 380-387, Nov. 27, 2012.
Soliman et al, "Correlation of Severity of Fuchs Endothelial Corneal Dystrophy With Triplet Repeat Expansion in TCF4", JAMA Ophthalmol, vol. 133, No. 12, pp. 1386-1391, Sep. 24, 2015.
Stigliani et al, "Deregulation of focal adhesion pathway mediated by mir-659-3p is implicated in bone marrow infiltration of stage M neuroblastoma patients", Oncotarget, vol. 6, No. 15, pp. 13295-13308, Apr. 20, 2015.
Sznajder et al, "Intron retention induced by microsatellite expansion as a disease biomarker", PNAS, vol. 115, No. 6, pp. 4234-4239, Apr. 2, 2018.
Teplova et al, "Structural insights into RNA recognition by the alternative-splicing regulator muscleblind-like MBNL1", Nature Structural & Molecular Biology, vol. 15, No. 12, pp. 1343-1351, Nov. 30, 2008.
Tone et al, "Fuchs endothelial corneal dystrophy: The vicious cycle of Fuchs pathogenesis", Progress in Retinal and Eye Research, vol. 80, 45 pages, May 8, 2021.
Vedana et al, "Fuchs endothelial corneal dystrophy: current perspectives", Clin Ophthalmol, vol. 10, pp. 321-330, (2016).
Wang et al, "Targeting Transforming Growth Factor-β Signaling in Primary Open-Angle Glaucoma", Journal of Glaucoma, vol. 26, No. 4, pp. 390-395, Apr. 2017.
Wang et al, "Transcriptome-wide Regulation of Pre-mRNA Splicing and mRNA Localization by Muscleblind Proteins", Cell, vol. 150, No. 4, pp. 710-724, Aug. 17, 2012.
Weller et al, "Extracellular Matrix Alterations in Late-Onset Fuchs' Corneal Dystrophy", Investigative Ophthalmology & Visual Science, vol. 55, No. 6, pp. 3700-3708, Jun. 2014.

(Continued)

*Primary Examiner* — Peter J Reddig
*Assistant Examiner* — Cheng Lu
(74) *Attorney, Agent, or Firm* — DLA Piper LLP US

(57) ABSTRACT

Molecular biomarkers relating to Fuchs' endothelial corneal dystrophy (FECD), glaucoma, and other degenerative ocular diseases are provided, as well as methods for using such biomarkers methods of treatment. These biomarkers may be used to monitor the progression of FECD, glaucoma, or other degenerative ocular diseases. Furthermore, these biomarkers may be used to monitor the treatment of FECD, glaucoma, or other degenerative ocular diseases.

7 Claims, 53 Drawing Sheets
(31 of 53 Drawing Sheet(s) Filed in Color)

Specification includes a Sequence Listing.

(56) References Cited

OTHER PUBLICATIONS

Wieben et al, "A Common Trinucleotide Repeat Expansion Within the Transcription Factor (TCF4, E2-2) Gene Predicts Fuchs Corneal Dystrophy", PLOS One, vol. 7, No. 11, Nov. 21, 2012.

Wieben et al, "Gene Expression and Missplicing in the Corneal Endothelium of Patients With a TCF4 Trinucleotide Repeat Expansion Without Fuchs Endothelial Corneal Dystrophy", Investigative Ophthalmology & Visual Science, vol. 60, No. 10, pp. 3636-3643, Aug. 2019.

Wieben et al, "Gene expression in the corneal endothelium of Fuchs endothelial corneal dystrophy patients with and without expansion of a trinucleotide repeat in TCF4", PLOS One, pp. 1-15, Jul. 2, 2018.

Wieben et al, "Trinucleotide Repeat Expansion in the Transcription Factor4 (TCF4) Gene Leads to Widespread mRNA Splicing Changes in Fuchs' Endothelial Corneal Dystrophy", Investigative Ophthalmology & Visual Science, vol. 58, No. 1, pp. 343-352, Jan. 2017.

Winkler et al, "Fuchs' Endothelial Corneal Dystrophy in Patients With Myotonic Dystrophy, Type 1", Investigative Ophthalmology & Visual Science, vol. 59, No. 7, pp. 3053-3057, Jun. 2018.

Wojtkowiak-Szlachcic et al, "Short antisense-locked nucleic acids (all-LNAs) correct alternative splicing abnormalities in myotonic dystrophy", Nucleic Acids Research, vol. 43, No. 6, pp. 3318-3331, Mar. 9, 2015.

Xing et al, "Transethnic Replications of Associations of GTC18.1 Repeat Expansion of TCF4 Gene With Fuchs' Corneal Dystrophy in Chinese Implies Common Casual Variant", Investigative Ophthalmology & Visual Science, vol. 55, No. 11, pp. 7073-7078, Nov. 2014.

Zarouchlioti et al, "Antisense Therapy for a Common Dystrophy Ameliorates TCF4 Repeat Expansion-Mediated Toxicity", The American Journal of Human Genetics, vol. 102, No. 4, pp. 528-539, Apr. 5, 2018.

Akhoundzadeh et al, "Effect of stem cell-based therapy on astrogliosis in stroke subjected-mice", Stem Cell Investigation, vol. 7, No. 21, 7 pages, Dec. 15, 2020.

Barrientz et al, "Corneal injury: Clinical and molecular aspects", Experimental Eye Research, vol. 186, 35 pages, Sep. 2019.

Basu et al, "First Report of Bilateral External Auditory Canal Cochlin Aggregates ("Cochlinomas") with Multifocal Amyloid-Like Deposits, Associated with Sensorneural Hearing Loss and a Novel Genetic Variant in COCH Encoding Cochlin", Head and Neck Pathology, vol. 14, pp. 808-816, Sep. 6, 2019.

Bhattacharya et al, "Proteomics Reveal Cochlin Deposits Associated with Glaucomatous Trabecular Meshwork", Journal of Biological Chemistry, vol. 280, No. 7, pp. 6080-6084, Dec. 3, 2004.

Bigar et al, "Specular Microscopy of the Corneal Endothelium", Optical Solutions and Clinical Results, vol. 6, pp. 1-94, (1982).

Borderie et al, "Corneal Endothelial Cell Apoptosis in Patients with Fuchs' Dystrophy", Investigative Ophthalmology & Visual Science, vol. 41, No. 9, pp. 2501-2505, Aug. 2000.

Carreon et al, "Interaction of cochlin and mechanosensitive channel TREK-1 in trabecular meshwork cells influences the regulation of intraocular pressure", Scientific Reports, vol. 7, No. 452, 11 pages, Mar. 28, 2017.

Chi et al, "Histopathology of Primary Endothelial-Epithelial Dystrophy of the Cornea", American Journal of Ophthalmology, vol. 45, No. 4, Pt. 1, pp. 518-535, Apr. 1958.

Cui et al, "Pathological molecular mechanism of symptomatic late-onset Fuchs endothelial corneal dystrophy by bioinformatic analysis", PLOS One, pp. 1-15, May 22, 2018.

Dansithong et al, "MBNL1 Is the Primary Determinant of Focus Formation and Aberrant Insulin Receptor Splicing in DM1", Journal of Biological Chemistry, vol. 280, No. 7, pp. 5773-5780, Nov. 16, 2004.

De Roo et al, "Identification of Circulating Fibrocytes and Dendritic Derivatives in Corneal Endothelium of Patients With Fuchs' Dystrophy", Investigative Ophthalmology & Visual Science, vol. 58, No. 1, pp. 670-681, Jan. 2017.

De Vrieze et al, "Allele-specific antisense oligonucleotide therapy for dominantly inherited hearing impairment DFNA9", bioRxiv, 31 pages, Sep. 30, 2020.

Deng et al, "Descemet Membrane Endothelial Keratoplasty: Safety and Outcomes: A Report by the American Academy of Ophthalmology", Ophthalmology, vol. 125, No. 2, pp. 295-310, Feb. 2018.

Du et al, "RNA Toxicity and Missplicing in the Common Eye Disease Fuchs Endothelial Corneal Dystrophy", Journal of Biological Chemistry, vol. 290, No. 10, pp. 5979-5990, Jan. 15, 2015.

Egharari et al, "Fuchs' corneal dystrophy", Expert Rev Ophtalmol, vol. 5, No. 2, pp. 147-159, Apr. 2010.

Gain et al, "Global Survey of Corneal Transplantation and Eye Banking", JAMA Ophthalmology, vol. 134, No. 2, pp. 167-173, Dec. 3, 2015.

Gattey et al, "Fuchs Endothelial Corneal Dystrophy in Patients with Myotonic Dystrophy: A Case Series", Cornea, vol. 33, No. 1, pp. 96-98, Jan. 2014.

Gudde et al, "A low absolute number of expanded transcripts is involved in myotonic dystrophy type 1 manifestation in muscle", Human Molecular Genetics, vol. 25, No. 8, pp. 1648-1662, Feb. 16, 2016.

Hu et al, "Engineering Duplex RNAs for Challenging Targets: Recognition of GGCCCC/CCCCGG Repeats at the ALS/FTD C9 or f72 Locus", Chemistry & Biology, vol. 22, No. 11, pp. 1505-1511, Nov. 19, 2015.

Hu et al, "Oligonucleotides targeting TCF4 triplet repeat expansion inhibit RNA foci and mis-splicing in Fuchs' dystrophy", Human Molecular Genetics, vol. 27, No. 6, pp. 1015-1026, Jan. 8, 2018.

Jefferson et al, "Amino Acids as Regulators of Gene Expression at the Level of mRNA Translation", The Expression of Nutrition, vol. 133, No. 6, pp. 20465-20515, Jun. 1, 2003.

Jung et al, "Cleaved Cochlin Sequesters Pseudomonas aeruginosa and Activates Innate Immunity in the Inner Ear", Cell Host & Microbe, vol. 25, pp. 513-525, Apr. 10, 2019.

Jurkunas et al, "Evidence of Oxidative Stress in the Pathogenesis of Fuchs Endothelial Corneal Dystrophy", The American Journal of Pathology, vol. 177, No. 5, pp. 2278-2289, Nov. 2010.

Kanadia et al, "Reversal of RNA missplicing and myotonia after muscleblind over expression in a mouse poly(CUG) model for myotonic dystrophy", PNAS, vol. 103, No. 31, pp. 11748-11753, Aug. 1, 2016.

Karin et al, "The characteristics of activated portal fibroblasts/ myofibroblasts in liver fibrosis", Differentiation, vol. 92, No. 3, pp. 84-92, Aug. 31, 2016.

Kino et al, "Muscleblind protein, MBNL1/EXP, binds specifically to CHHG repeats", Human Molecular Genetics, vol. 13, No. 5, pp. 495-507, Jan. 13, 2004.

Klein et al, "Peptide-conjugated oligonucleotides evoke long-lasting myotonic dystrophy correction in patient-derived cells and mice", The Journal of Clinical Investigation, vol. 129, No. 11, pp. 4739-4744, Sep. 30, 2019.

Konieczny et al, "MBNL proteins and their target RNAs, interaction and splicing regulation", Nucleic Acids Research, vol. 42, No. 17, pp. 10873-10887, Sep. 2, 2014.

Krachmer et al, "Corneal Endothelial Dystrophy A Study of 64 Families", Arch Ophthalmol, vol. 96, No. 11, pp. 2036-2039, Nov. 1978.

Kruse et al, "A Stepwise Approach to Donor Preparation and Insertion Increases Safety and Outcome of Descemet Membrane Endothelial Keratoplasty", Cornea, vol. 30, No. 5, pp. 580-587, May 2011.

Laing et al, "Endothelial Mosaic in Fuchs' Dystrophy: A Qualitative Evaluation With the Specular Microscope", Arch Ophthalmology, vol. 99, No. 1, pp. 80-83, Jan. 22, 1981.

Leask et al, "TGF-β signaling and the fibrotic response", The FASEB Journal, vol. 18, No. 7, pp. 816-827, May 2004.

Lee et al, "RNase H-mediated degradation of toxic RNA in myotonic dystrophy type 1", PNAS, vol. 109, No. 111, pp. 4221-4226, Mar. 13, 2012.

Li et al, "The Role of Apoptosis in the Pathogenesis of Fuchs Endothelial Dystrophy of the Cornea", Arch Opthalmol, vol. 119, pp. 1597-1604, Nov. 2001.

(56) References Cited

OTHER PUBLICATIONS

Liu et al, "Cell Therapy of Congenital Corneal Diseases with Umbilical Mesenchymal Stem Cells: Lumican Null Mice", PLOS One, vol. 5, No. 5, 14 pages, May 19, 2010.

Lorenzetti et al, "Central Cornea Guttata: Incidence in the General Population" American Journal of Ophthalmology, vol. 64, No. 6, pp. 1155-1158, Dec. 1967.

LUM | SelfDecode | Genome Analysis, <https://selfdecode.com/gene/lum/#all-ways-to-increase-gene>, Accessed Jun. 7, 2021.

Matthaei et al, "Fuchs Endothelial Corneal Dystrophy: Clinical, Genetic, Pathophysiologic, and Therapeutic Aspects", Annual Review of Vision Science, vol. 5, pp. 151-175, Sep. 2019.

Matthaei et al, "Transcript profile of cellular senescence-related genes in Fuchs endothelial corneal dystrophy", Experimental Eye Research, vol. 129, pp. 13-17, Dec. 2014.

Mootha et al, "Association and Familia Segregation of CTG18.1 Trinucleotide Repeat Expansion of TCF4 Gene in Fuchs' Endothelial Corneal Dystrophy", Investigative Ophthalmology & Visual Science, vol. 55, No. 1, pp. 33-42, Jan. 2014.

Mootha et al, "Fuchs' Endothelial Corneal Dystrophy and RNA Foci in Patients With Myotonic Dystrophy", Investigative Ophthalmology & Visual Science, vol. 58, No. 11, pp. 4579-4585, Sep. 2017.

Mootha et al, "TCF4 Triplet Repeat Expansion and Nuclear RNA Foci in Fuchs' Endothelial Corneal Dystrophy", Investigative Ophthalmology & Visual Science, vol. 56, No. 3, pp. 2003-2011, Mar. 2015.

Murphy-Ullrich, "Thrombospondin-1 regulation of latent TGF-β activation: A therapeutic target for fibrotic disease", Matrix Biology, vol. 68-69, pp. 28-43, Aug. 2018.

Nagarsheth et al, "Relationship Between Fuchs Endothelial Corneal Dystrophy Severity and Glaucoma and/or Ocular Hypertension", Arch Ophthalmol, vol. 130, No. 11, pp. 1384-1388, Jul. 9, 2012.

Picciani et al, "Cochlin in the eye: Functional implications", Progress in Retinal and Eye Research, vol. 26, No. 5, pp. 453-469, Sep. 2007.

Robertson et al, "Cochlin immunostaining of inner ear pathologic deposits and proteomic analysis in DFNA9 deafness and vestibular dysfunction", Human Molecular Genetics, vol. 15, No. 7, pp. 1071-1085, Feb. 15, 2006.

Robertson et al, "Inner ear localization of mRNA and protein products of COCH, mutated in the sensorineural deafness and vestibular disorder, DFNA9", Human Molecular Genetics, vol. 10, No. 22, pp. 2493-2500, Oct. 15, 2001.

Rohilla et al, "RNA biology of disease-associated microsatellite repeat expansions", Acta Neuropathologica Communications, vol. 5, No. 63, pp. 1-22, (2017).

Rong et al, "Quantitative Studies of Muscleblind Proteins and Their Interaction Wit TCF4 RNA Foci Support Involvement in the Mechanism of Fuchs' Dystrophy", IOVS, vol. 60, No. 12, pp. 3980-3991, Sep. 2019.

Samarakoon et al, "TGF-β1-Induced Expression of the Poor Prognosis SERPINE1/PAI-1 Gene Requires EGFR Signaling: A New Target for Anti-EGFR Therapy", Journal of Oncology, vol. 2009, 6 pages, Jan. 30, 2009.

Supplementary European Search Report issued in EP Appl. No. 21761094.8, 19 pages, dated Feb. 19, 2024.

Chu et al, "Analyzing pre-symptomatic tissue to gain insights into the molecular and mechanistic origins of late-onset degenerative trinucleotide repeat disease", Nucleic Acids Research, pp. 1-19, May 6, 2020.

* cited by examiner

FIG. 1
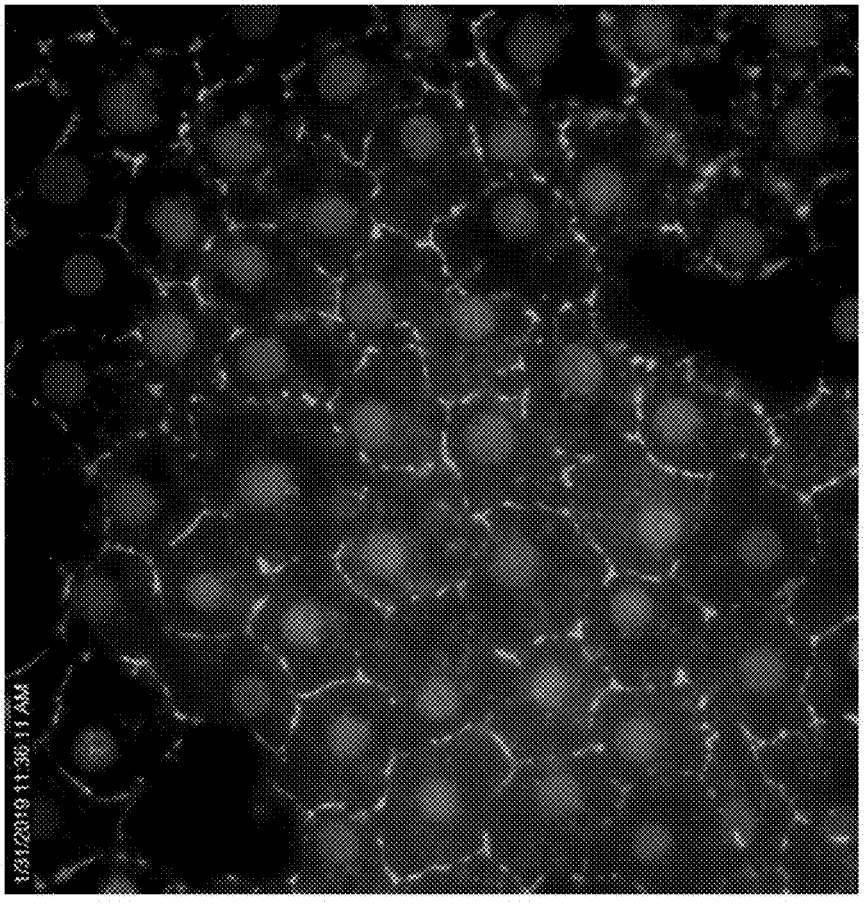
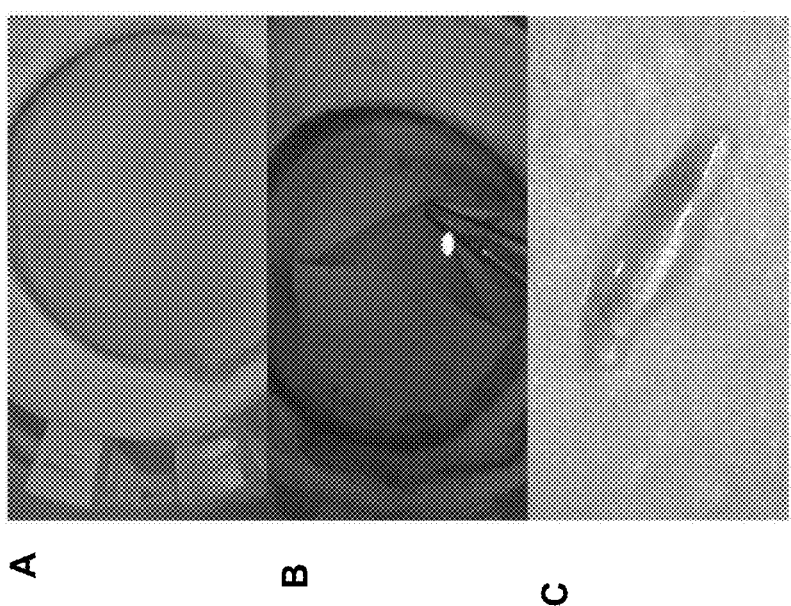

A

B

| Sample_ID | Gender | Age | CTG18.1 | RIN |
|---|---|---|---|---|
| Control_0 | F | 74 | 16, 39 | 7.4 |
| Control_1 | F | 72 | 16, 25 | 7.6 |
| Control_2 | M | 51 | 16, 17 | 8 |
| Control_3 | M | 68 | 18, 25 | 5.2 |
| Control_4 | M | 68 | 18,25 | 7.4 |
| Control_5 | M | 71 | 12, 18 | 5.6 |
| Control_6 | F | 61 | 13,19 | 5.2 |
| Control_7 | M | 74 | 13,18 | 6.4 |
| Control_8 | F | 43 | 12,18 | 6.3 |
| Pre_S_0 | M | 51 | 13, 84 | 7.6 |
| Pre_S_1 | M | 57 | 15, 77 | 5.4 |
| Pre_S_2 | M | 41 | 17, 86 | 6.4 |
| Pre_S_3 | M | 41 | 12, >100 | 6 |
| Pre_S_4 | F | 53 | 12, >100 | 7.8 |
| Pre_S_5 | F | 38 | 12, 66 | 6.9 |
| FECD_REP_0 | F | 67 | 14,87 | 6.3 |
| FECD_REP_1 | M | 66 | 15, 150 | 5.8 |
| FECD_REP_2 | F | 68 | 15, 77 | 8.0 |
| FECD_REP_3 | F | 58 | 16, >100 | 7.3 |
| FECD_REP_4 | F | 69 | 15, >100 | 7 |
| FECD_REP_5 | F | 71 | 19, 130 | 6.4 |
| FECD-NR_0 | F | 71 | 15, 18 | 6.5 |
| FECD-NR_1 | F | 72 | 12, 26 | 5.6 |
| FECD-NR_2 | F | 61 | 12, 38 | 6.2 |
| FECD-NR_3 | F | 71 | 15, 18 | 6.6 |

A

B

| Cell line | Phenotype | TCF4 CUG repeat | CUG RNA foci | RNA half life | | |
|---|---|---|---|---|---|---|
| | | | | mRNA | Intron 2 upstream | Intron 2 downstream |
| F35T | FECD endothelium | 1500 | Yes | > 8 hr | ~ 3hr | 30 min |
| F45SV | FECD endothelium | 1500 | Yes | > 8 hr | ~ 4hr | 30 min |
| W4056 | Control endothelium | <25 | No | > 8 hr | 10 min | 20 min |
| HCNSV | Control endothelium | <25 | No | > 8 hr | 15 min | 20 min |
| WM84 | FECD skin fibroblast | 1000 | No | > 8 hr | 10 min | 10 min |
| C9 | Control skin fibroblast | <25 | No | > 8 hr | 10 min | 15 min |

* Longest repeat number

FIG. 3
C
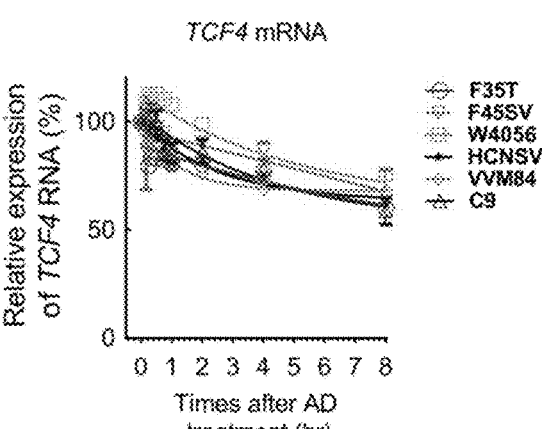
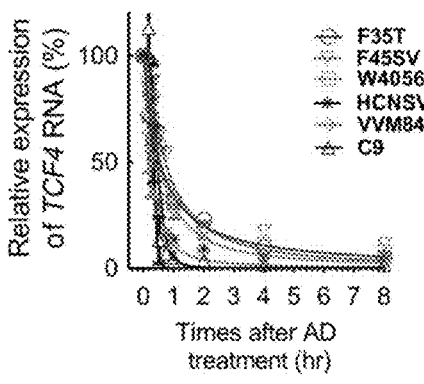
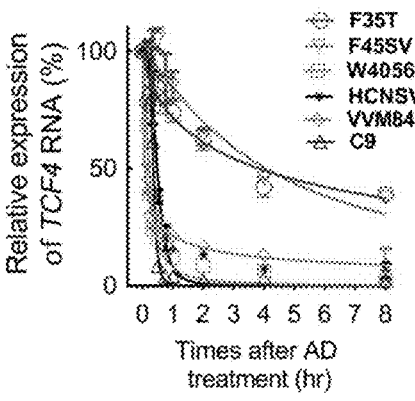

FIG. 4
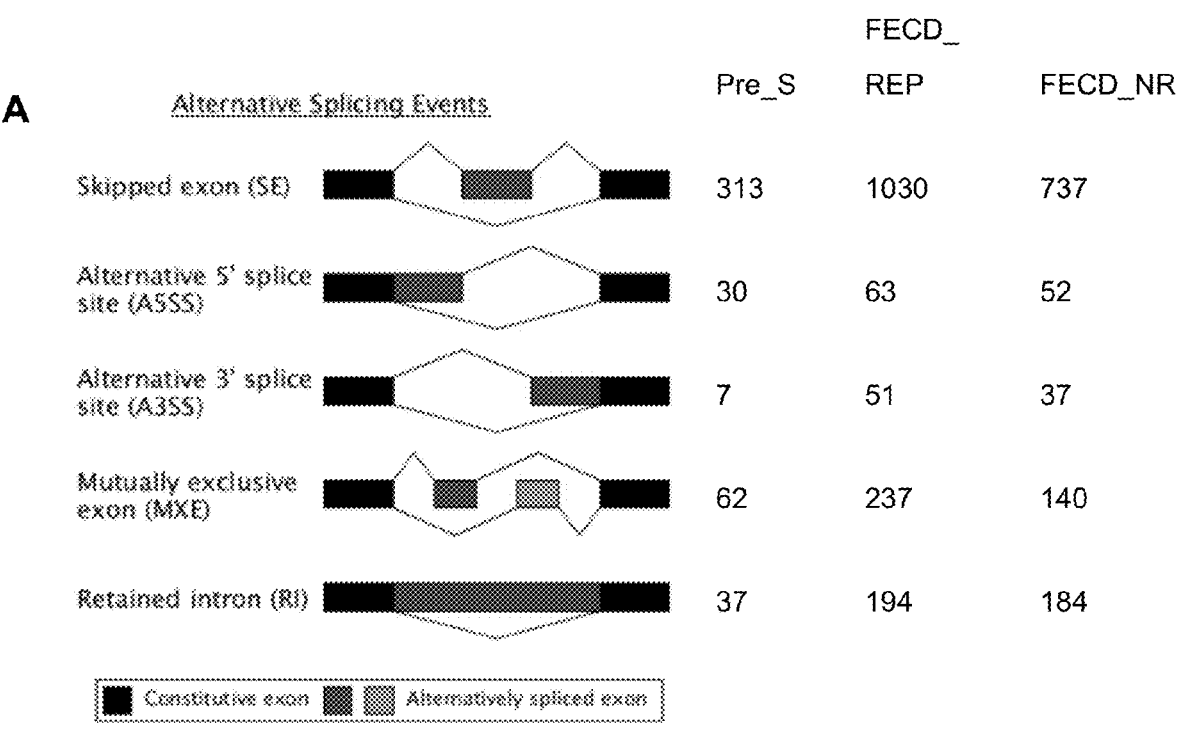
| A | Alternative Splicing Events | Pre_S | FECD_REP | FECD_NR |
|---|---|---|---|---|
| Skipped exon (SE) | | 313 | 1030 | 737 |
| Alternative 5' splice site (A5SS) | | 30 | 63 | 52 |
| Alternative 3' splice site (A3SS) | | 7 | 51 | 37 |
| Mutually exclusive exon (MXE) | | 62 | 237 | 140 |
| Retained intron (RI) | | 37 | 194 | 184 |
Constitutive exon    Alternatively spliced exon
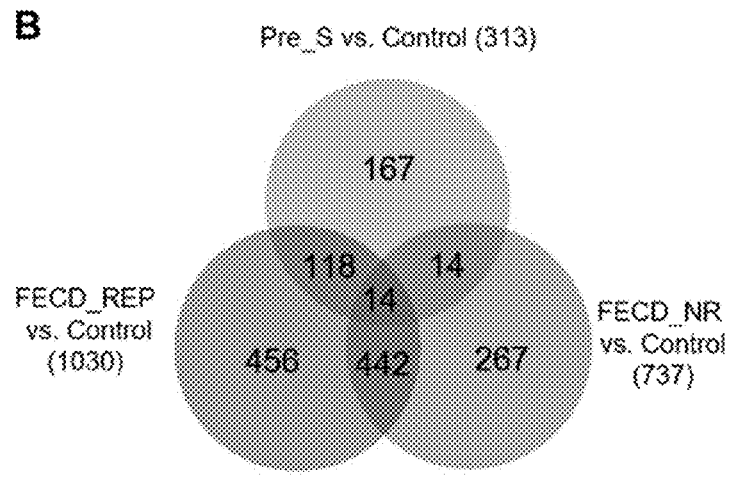
B
Pre_S vs. Control (313)
167
118    14
14
FECD_REP vs. Control (1030)     456    442    267     FECD_NR vs. Control (737)

Top 25 SE events based on Pre_S/FECD_REP only

FIG. 4

| Gene name | Basic function | Gene name | Basic function |
|---|---|---|---|
| EXOC1 | Exocyst complex | SCARB1 | Scavenger receptor |
| CD47 | Cell signalling/adhesion | ARHGEF10L | Nucleotide exchange factor |
| ADD3 | Assembly of the spectrin-actin network | PLD1 | Hydrolysis of phosphatidylcholine |
| COPZ2 | Coatamer protein complex | NUMA1 | Mitototic apparatus |
| MBNL2 | Splicing regulator | PPFIBP1 | Liprin family |
| ZNF248 | Transcription regulator | BICRA | Chromatin remodeling |
| MTA1 | Metastasis associate | VPS39 | Endosome fusion |
| SORBS1 | SH3 domain containing | SYNE1 | Nuclear envelope |
| KIF13A | Kinesin family | PLEKHM2 | Microtubule localization |
| TSPOAP1 | Neurotransmitter Release Cycle | CACNA1D | Calcium channel subunit |
| CLASP1 | Cytoplasmic linker | ITGA6 | Integri subunit |
| INF2 | Actin polymerization | TEAD1 | Transcription factor |

| Canonical Pathways | FECD_MR | FECD_REP | Pre_S |
|---|---|---|---|
| Hepatic Fibrosis | 20.81 | 16.30 | 3.03 |
| Neuroinflammation Signaling | 5.72 | 7.05 | 0.00 |
| GP6 Signaling | 5.71 | 6.78 | 2.27 |
| IL-8 Signaling | 4.39 | 6.62 | 0.98 |
| Th1 and Th2 Activation | 7.83 | 6.33 | 0.00 |
| Osteoblasts/Osteoclasts/Chondrocytes in Rheumatoid Arthritis | 2.94 | 6.23 | 0.88 |
| Axonal Guidance Signaling | 3.62 | 5.80 | 1.24 |
| Macrophages/Fibroblasts/Endothelial Cells in Rheumatoid Arthritis | 3.95 | 5.69 | 0.87 |
| Apelin Liver Signaling | 4.40 | 5.64 | 1.71 |
| Th1 | 5.63 | 5.48 | 0.00 |
| NFAT Regulation/Immune Response | 7.47 | 5.41 | 0.00 |
| Th2 | 6.43 | 5.29 | 0.00 |
| Osteoarthritis | 6.24 | 5.26 | 2.70 |
| CD28 Signaling in T Helper Cells | 5.06 | 5.07 | 0.00 |
| STAT3 Pathway | 3.15 | 5.02 | 0.00 |
| Mitochondrial Dysfunction | 0.00 | 4.96 | 0.38 |
| Dendritic Cell Maturation | 3.79 | 4.93 | 1.09 |
| PTEN Signaling | 1.81 | 4.91 | 1.06 |
| Inhibition of Angiogenesis by TSP1 | 2.79 | 4.56 | 0.61 |
| Inflammasome | 2.83 | 4.53 | 0.00 |
| PKC0 Signaling in T Lymphocytes | 4.49 | 4.51 | 0.00 |
| Molecular Mechanisms of Cancer | 4.80 | 4.39 | 0.37 |
| IGF-1 Signaling | 5.80 | 4.30 | 1.80 |
| Phagosome Formation | 2.00 | 4.26 | 1.53 |
| T Cell Exhaustion Signaling | 2.91 | 4.22 | 0.00 |

B

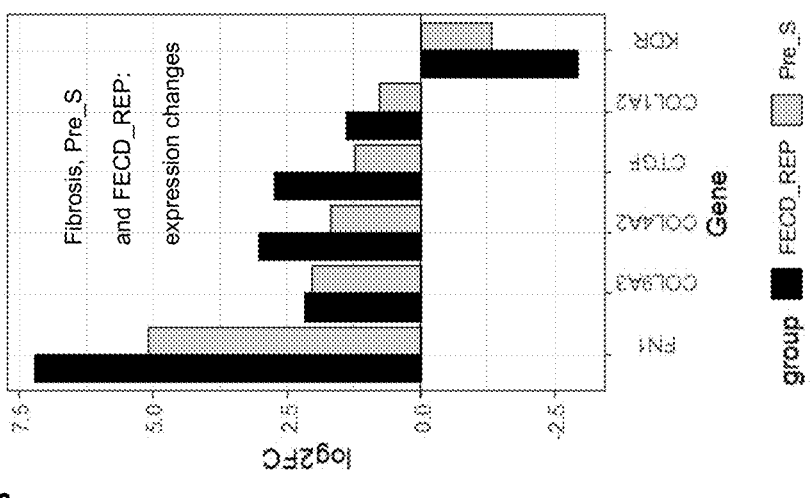

Fibrosis, Pre_S and FECD_REP: expression changes group  ■ FECD_REP  ▨ Pre_S

FIG. 11
A
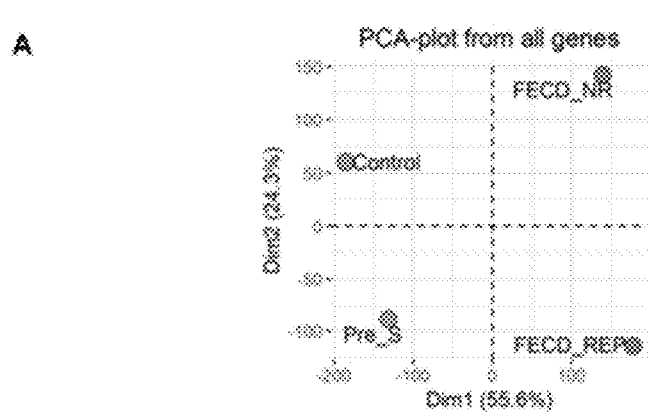
B
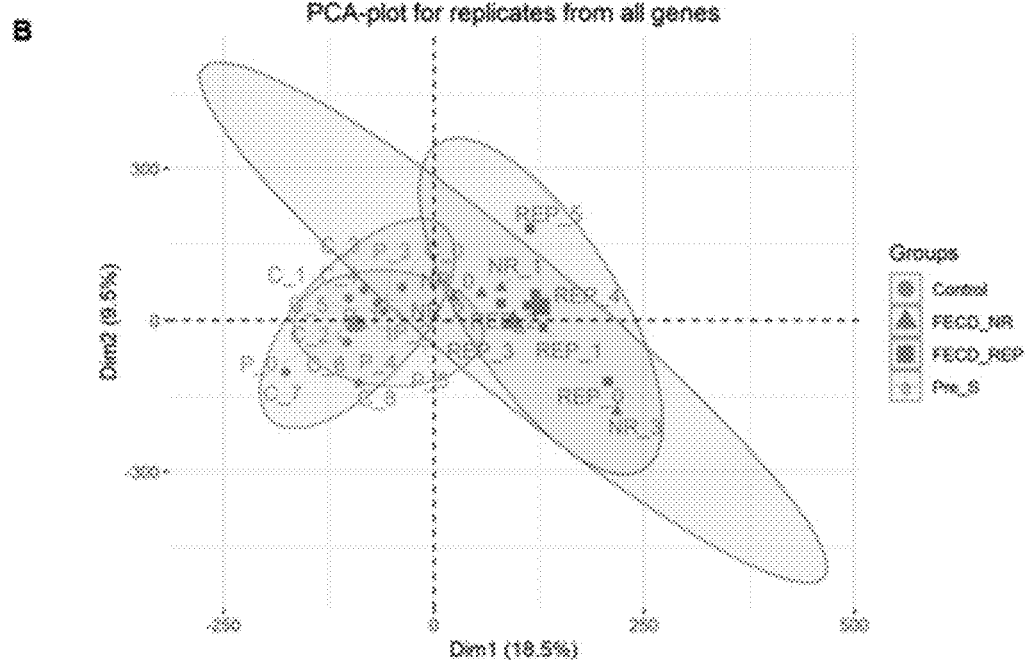

FIG. 12
A
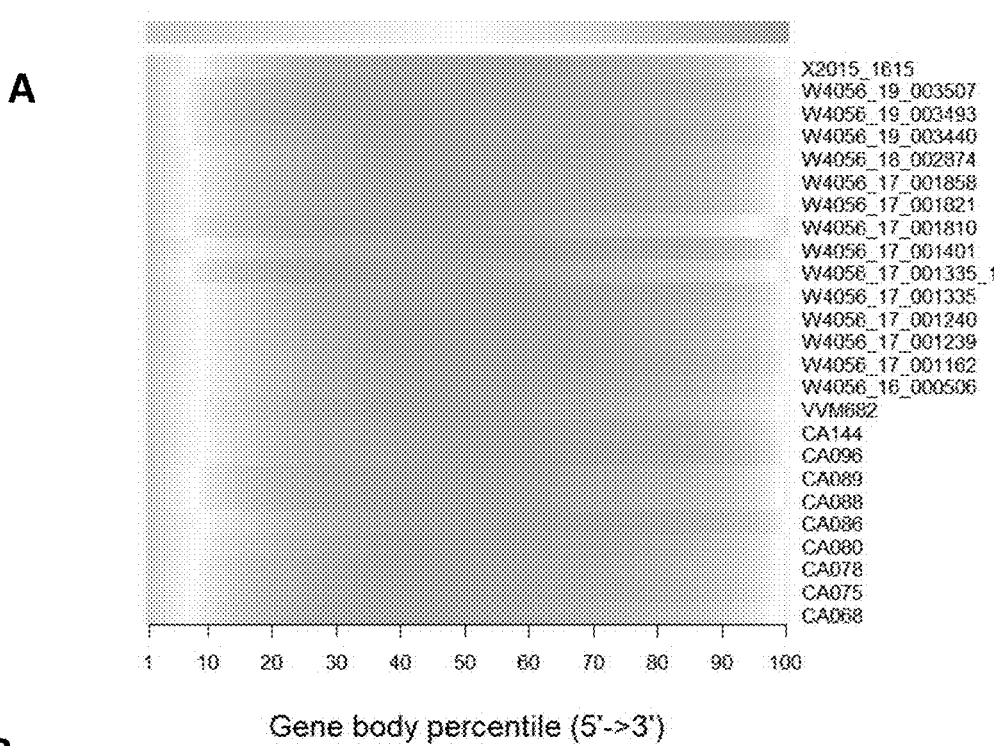
Gene body percentile (5'->3')
B
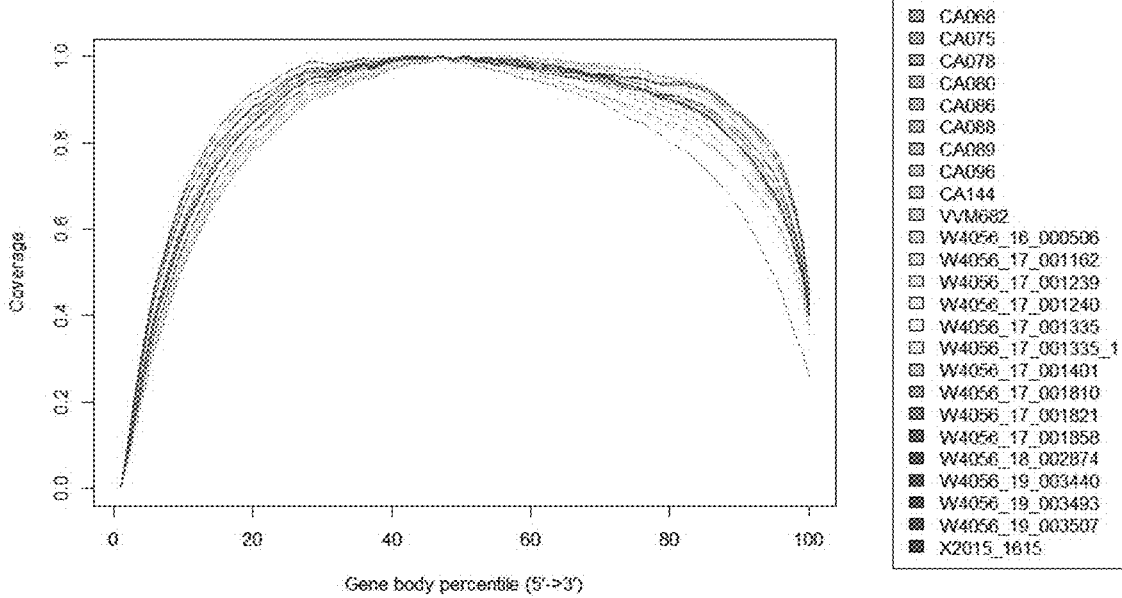

Figure 16:
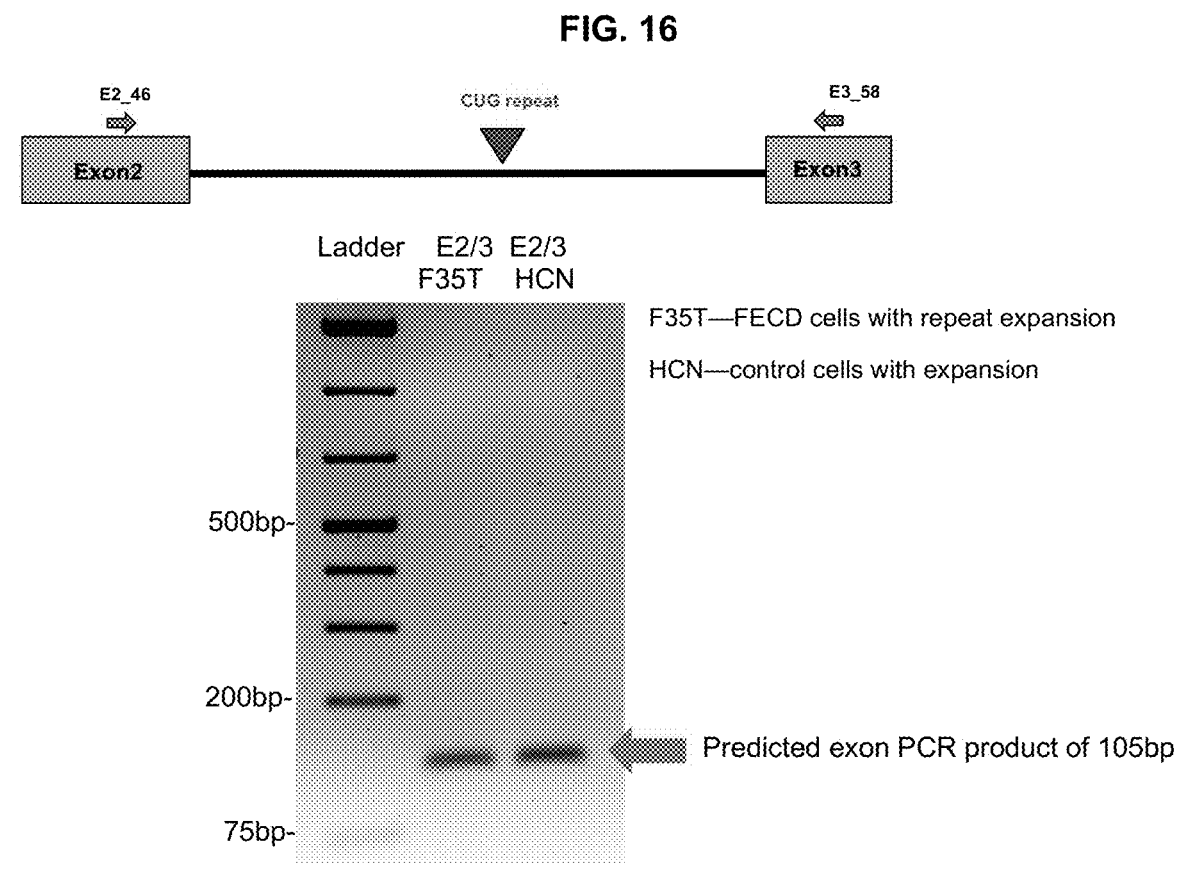

CUG repeat

E3_58

Exon2

Exon3

Ladder    E2/3    E2/3
          F35T    HCN

F35T—FECD cells with repeat expansion

HCN—control cells with expansion

500bp-

200bp-

Predicted exon PCR product of 105bp

75bp-

A

**Alternative 5'
splice site
(A5SS)**

Pre_S vs. Control (30)

FECD_REP
vs. Control
(63)

FECD_NR
vs. Control
(52)

24    5    0    1    29    28    23

B

**Alternative
3'-splice site
(A3SS)**

Pre_S vs. Control (7)

FECD_REP
vs. Control
(51)

FECD_NR
vs. Control
(37)

4    3    0    0    35    13    24

C

**Mutually
exclusive
exon
(MXE)**

Pre_S vs. Control (62)

FECD_REP
vs. Control
(237)

FECD_NR
vs. Control
(140)

44    16    1    1    149    72    66

D

**Retained
intron
(RI)**

Pre_S vs. Control (37)

FECD_REP
vs. Control
(194)

FECD_NR
vs. Control
(184)

26    4    1    6    71    113    64

E

Pre_S vs. Control (313)

DM1_Tibialis_anterior_
muscle vs. Control
muscle (1030)

FECD_REP
vs. Control
(1030)

FIG. 17

| Gene | Location | Control_aver | Pre_S_aver | FECD_REP_aver | Control_muscle_aver | Control_muscle_aver | DM1_muscle_aver |
|------|----------|-------------|-----------|--------------|--------------------|--------------------|-----------------|
| NUMA1 | -:chr11:72010785-72010854:72012400-72012442:72012894-72016260 | 0.62 | 0.12 | 0.23 | 0.94 | | 0.58 |
| COPZ2 | -:chr17:48026166-48026475:48027675-48027789:48028471-48028510 | 0.23 | 0.73 | 0.58 | 0.14 | | 0.51 |
| HOOK3 | +:chr8:42997589-42997637:43000270-43000276:43002106-43002141 | 0.19 | 0.53 | 0.36 | 0.00 | | 0.28 |
| KIF13A | -:chr6:17787775-17787875:17789871-17789910:17794248-17794395 | 0.69 | 0.11 | 0.23 | 0.98 | | 0.83 |
| SOS1 | -:chr2:38987472-38987591:38989269-38989314:38995122-38995387 | 0.94 | 0.57 | 0.50 | 0.91 | | 0.45 |
| MBNL2 | +:chr13:97347040-97347067:97356795-97356849:97357481-97357635 | 0.12 | 0.78 | 0.57 | 0.05 | | 0.25 |
| SORBS1 | -:chr10:95346405-95346452:95351215-95351376:95354881-95354967 | 0.92 | 0.39 | 0.57 | 0.99 | | 0.83 |
| DNM1L | +:chr12:32737104-32737161:32737864-32737942:32740063-32740240 | 0.23 | 0.40 | 0.52 | 0.10 | | 0.37 |
| VPS39 | -:chr15:42191495-42191560:42192065-42192098:42199895-42199961 | 0.78 | 0.20 | 0.21 | 0.82 | | 0.35 |
| TCF4 | -:chr18:55585279-55585352:55586920-55587136:55589296-55589778 | 0.30 | 0.60 | 0.55 | 0.88 | | 0.37 |
| ARHGEF10L | +:chr1:17632320-17632466:17634547-17634562:17634834-17635016 | 0.59 | 0.10 | 0.11 | 0.97 | | 0.64 |
| CLASP1 | -:chr2:121430072-121430177:121445448-121445496:121447336-121447507 | 0.86 | 0.26 | 0.41 | 0.90 | | 0.41 |
| MYH10 | -:chr17:8569719-8569812:8576642-8576672:8577235-8577338 | 0.46 | 0.31 | 0.26 | 0.04 | | 0.67 |

NUMA1: Nuclear matrix component
COPZ2: Adaptor protein/intracellular transport
HOOK3: Microtubule tethering
KIF13A: Kinesin family member.
SOS1: Rac guanine nucleotide exchange factor
MBNL2: Alternative splicing
SORBS1: Sortilin related VPS10 domain containing receptor
DNM1L: Mitochondrial and peroxisomal division
VPS39: Promote clustering and fusion of late endosomes and lysosomes
TCF4: Transcription factor
ARHGEF10L: Rho guanine nucleotide exchange factor
CLASP1: microtubule-associated protein
MYH10: Regulation of cytokinesis, cell motility, and cell polarity

A

B

C

A

DE genes in pathway: Hepatic Fibrosis / Hepatic Stellate Cell Activation

FIG. 21 (Cont.)

DE genes in pathway: Hepatic Fibrosis / Hepatic Stellate Cell Activation

DE genes in pathway: Th1 and Th2 Activation Pathway

DE genes in pathway: Role of NFAT in Regulation of the Immune Response

DE genes in pathway: Neuroinflammation Signaling Psthway

FIG. 21 (Cont.)

Condition
Control
Pre_S
FECD_REP
FECD_NR

Expression level (FPKM)

| Gene | Log2FC | Gene | Log2FC | Gene | Log2FC | Gene | Log2FC |
|---|---|---|---|---|---|---|---|
| AC079598.2,LINC02258 | >11 | CLEC5A | 10.5263 | PSPHP1 | <-11 | CXCL3 | -5.39144 |
| CD86 | >11 | MARCH1 | 9.64843 | CDH12 | -10.1984 | RNU2-63P | -5.30508 |
| DLK1 | >11 | GPC3 | 9.27756 | IL17REL | -7.36808 | CXCL2 | -5.24128 |
| FOXF2 | >11 | HLA-DQA1 | 9.18926 | SAA2,SAA2-SAA4,SAA4 | -6.40902 | HMGN2P17 | -5.23317 |
| GMNC | >11 | HLA-DRA | 9.0188 | CSF3 | -6.13122 | RASD1 | -5.22904 |
| GPR34 | >11 | CYBB | 8.64696 | ARC | -6.12911 | AC005820.2 | -5.19689 |
| IGKV3-20 | >11 | AC105383.1,AC110751.1 | 8.5003 | UBE2W | -5.79138 | AL049839.2,SERPINA3,SERPINA4,SERPINA5 | -5.18164 |
| IGKV6D-21 | >11 | GRM5,NOX4 | 8.43459 | RNU5E-1 | -5.7127 | AC083899.2 | -5.15117 |
| TMEM255A | >11 | IGKC,IGKJ1,IGKJ2 | 8.42556 | CXCL8 | -5.68791 | AC011511.2 | -5.12989 |
| CDKN2A | 10.6305 | C3AR1 | 8.42367 | LINC00881,LINC02029 | -5.63529 | RNU6-1208P | -5.11613 |

B

| Gene | Log2FC | Gene | Log2FC | Gene | Log2FC | Gene | Log2FC |
|---|---|---|---|---|---|---|---|
| CD86 | >12 | FAM198B | 9.0256 | UTY | -13.4226 | RNU5E-1 | -5.4933 |
| GPR34 | >12 | FCGR1B | 8.9323 | CD24P4,RNU6-255P,TTTY14 | -11.1463 | STK40 | -5.44692 |
| DCX | >12 | HLA-DRA | 8.83383 | KDM5DP1,TTTY10 | -9.66082 | AC105129.2,RNU5B-1 | -5.39899 |
| AC007336.2,MMP2-AS1 | 11.9088 | HLA-DQA1 | 8.78128 | NLGN4Y | -9.51863 | LINC01783,RNU1-6P | -5.26868 |
| CDKN2A | 11.1268 | FOLR2 | 8.77685 | SAA2,SAA2-SAA4,SAA4 | -7.91287 | AC005820.2 | -5.20258 |
| CLEC5A | 10.8412 | FCGR3A | 8.67225 | IL17REL | -7.61487 | LINC00881,LINC02029 | -5.15433 |
| CYBB | 9.39057 | TNFRSF11B | 8.58545 | CSF3 | -6.43948 | BX284668.2,RNU1-5P | -5.14755 |
| MARCH1 | 9.38126 | PSG4 | 8.52816 | AC015813.4 | -5.81436 | CXCL2 | -5.05523 |
| ADGRG7 | 9.366 | AC105383.1,AC110751.1 | 8.44715 | RNU1-59P | -5.74863 | EPS8L1 | -5.02175 |
| LYVE1 | 9.29724 | KRT7 | 8.43267 | ZFY | -5.54493 | AL096677.1,AL390037.1 | -4.97445 |

FIG. 23

| Symbol | log2FC_RECD_REP_vs_C | q_value_FECD_REP | log2FC_Pre_S_vs_C | q_value_Pre_S |
|---|---|---|---|---|
| COL1A2 | 1.378 | 0.00226 | 0.773381 | 0.00738683 |
| COL3A1 | 1.63 | 0.00226 | -1.71016 | 0.00414755 |
| COL4A2 | 3.045 | 0.00226 | 1.68119 | 0.00226223 |
| COL9A3 | 2.182 | 0.00226 | 2.04259 | 0.00226223 |
| CTGF | 2.723 | 0.00226 | 1.22263 | 0.00226223 |
| FN1 | 7.225 | 0.00226 | 5.08031 | 0.00226223 |
| KDR | -2.927 | 0.00226 | -1.30521 | 0.00226223 |
| BAMBI | 3.936 | 0.00226 | 0.880549 | 0.703482 |
| COL11A2 | -1.337 | 0.0363 | -0.534815 | 0.824853 |
| COL1A1 | 4.067 | 0.00226 | 0.17908 | 0.999784 |
| COL27A1 | -1.302 | 0.00226 | -0.406276 | 0.549341 |
| COL4A1 | 3.112 | 0.00226 | 1.70879 | 0.149814 |
| COL5A2 | 0.829 | 0.00226 | 0.294152 | 0.70792 |
| COL6A1 | 1.075 | 0.00891 | -0.215987 | 0.999784 |
| COL6A2 | 4.794 | 0.00226 | 0.90987 | 0.750228 |
| CSF1 | -1.53 | 0.00226 | -0.496574 | 0.51737 |
| CXCL3 | -5.391 | 0.00226 | -0.288417 | 0.999784 |
| CXCL8 | -5.688 | 0.00226 | -1.30287 | 0.156507 |
| FGFR2 | 0.681 | 0.0457 | 0.369273 | 0.658643 |
| IFNGR1 | 1.289 | 0.00226 | 0.355356 | 0.868174 |
| IGFBP4 | 2.646 | 0.00226 | -1.01873 | 0.542776 |
| IGFBP5 | 1.89 | 0.00226 | 0.336963 | 0.756909 |
| IL1RAP | 2.861 | 0.00226 | 0.716579 | 0.486386 |
| MET | 1.009 | 0.00226 | 0.0417758 | 0.999784 |
| MYH14 | -2.326 | 0.00226 | -0.504027 | 0.802993 |
| NFKB1 | -0.957 | 0.0457 | 0.0288995 | 0.999784 |
| SMAD7 | -1.079 | 0.0169 | -0.048409 | 0.999784 |
| TGFB2 | 1.616 | 0.00226 | 0.418369 | 0.659669 |
| TGFBR1 | 1.235 | 0.00415 | -0.249032 | 0.999784 |
| TGFBR2 | 1.378 | 0.00226 | 0.50825 | 0.396355 |
| VEGFA | -2.232 | 0.00226 | -0.326395 | 0.74898 |
| BCL2 | 3.004 | 0.00226 | NA | NA |
| COL16A1 | 2.454 | 0.00226 | NA | NA |
| COL18A1 | 4.992 | 0.00226 | NA | NA |
| COL5A1 | 4.67 | 0.00226 | NA | NA |
| COL9A2 | 2.557 | 0.00226 | NA | NA |
| EDN1 | 4.109 | 0.00226 | NA | NA |
| FLT1 | 2.443 | 0.00415 | NA | NA |
| IGF1 | 6.021 | 0.00226 | NA | NA |
| IL10RA | 7.616 | 0.00226 | NA | NA |
| TLR4 | 4.397 | 0.00226 | NA | NA |
| TNFRSF11B | 7.586 | 0.00226 | NA | NA |

A

COCH expression by RNA_Seq

| Gene | Pre-S/Con | FECD-REP/Con | FECD-NR/Con |
|------|-----------|--------------|-------------|
| | | Fold change | |
| COCH | 18.9 | 22.4 | 15.3 |

B

C

FIG. 25
A
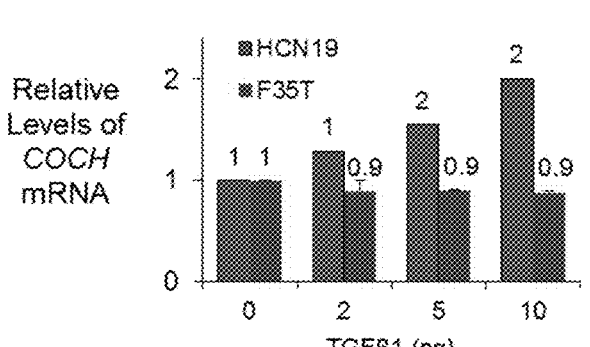
B
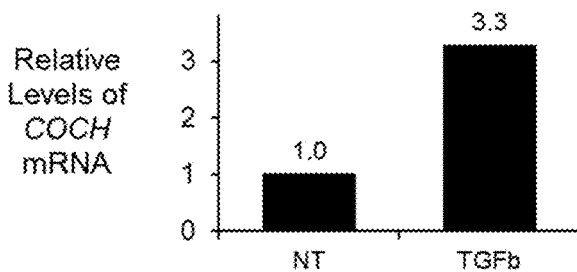

FIG. 26
A
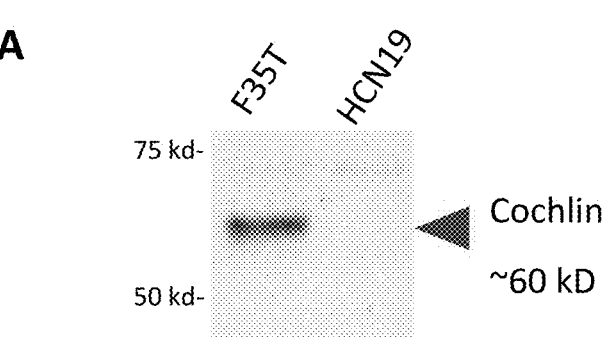
B
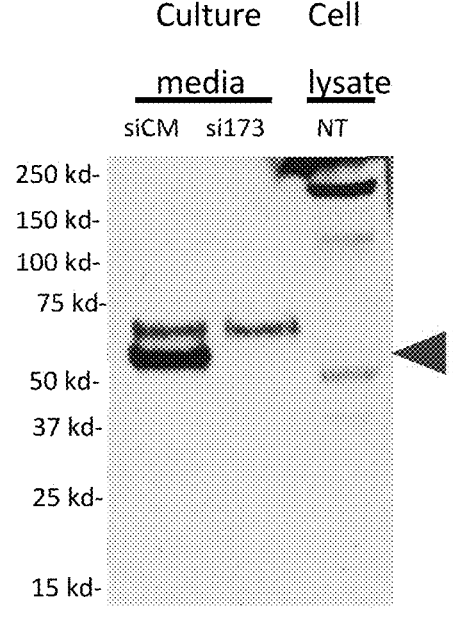

FIG. 28
A
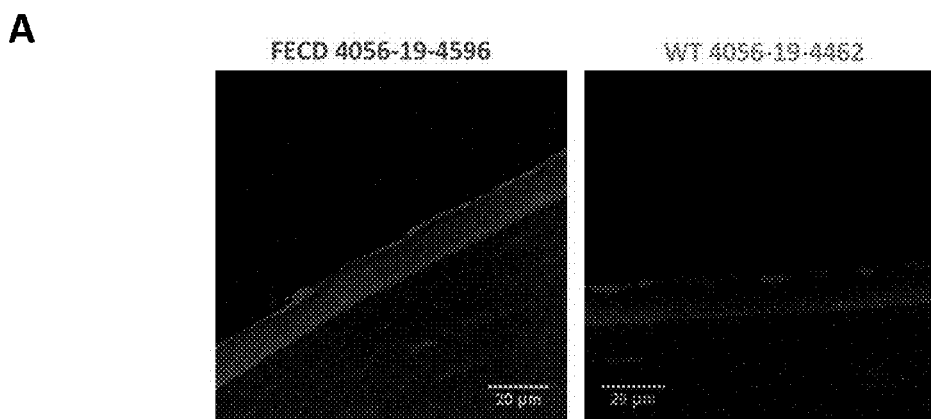
B
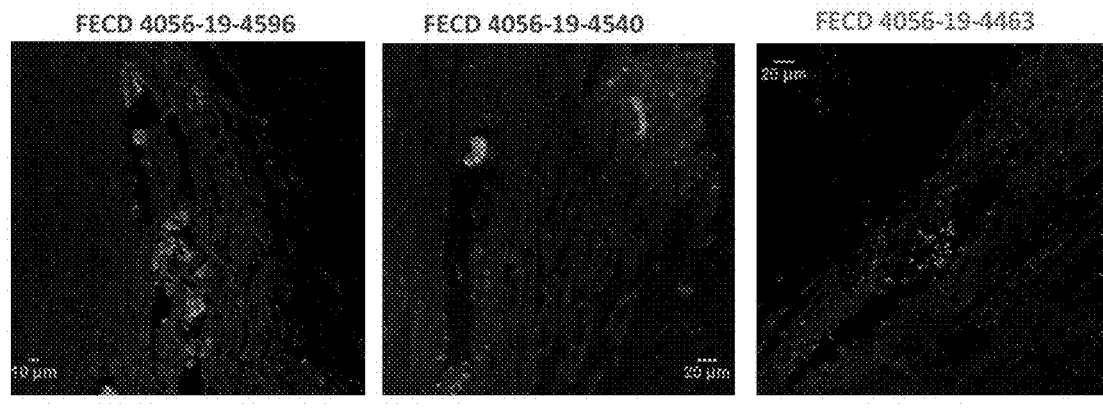

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Primer for STR analysis and TR-PCR assay of CTG18.1 locus

<400> SEQUENCE: 1
aatccaaacc gccttccaag t                                                21

<210> SEQ ID NO 2
<211> LENGTH: 23
<212> TYPE: DNA
<213> ORGANISM: Artificial Sequence
<220> FEATURE:
<223> OTHER INFORMATION: Primer for STR analysis and TR-PCR assay of CTG18.1 locus

<400> SEQUENCE: 2
caaaacttcc gaaagccatt tct                                              23

<210> SEQ ID NO 3
<211> LENGTH: 21
<212> TYPE: DNA
<213> ORGANISM: Artificial Sequence
<220> FEATURE:
<223> OTHER INFORMATION: Primer for STR analysis and TR-PCR assay of CTG18.1 locus

<400> SEQUENCE: 3
tacgcatccc agtttgagac g                                                21

<210> SEQ ID NO 4
<211> LENGTH: 36
<212> TYPE: DNA
<213> ORGANISM: Artificial Sequence
<220> FEATURE:
<223> OTHER INFORMATION: Primer for STR analysis and TR-PCR assay of CTG18.1 locus

<400> SEQUENCE: 4
tacgcatccc agtttgagac gcagcagcag cagcag                                36

```
<210> SEQ ID NO 5
<211> LENGTH: 20
<212> TYPE: DNA
<213> ORGANISM: Artificial Sequence
<220> FEATURE:
<223> OTHER INFORMATION: Forward TCF4 mRNA primer (5'-3')

<400> SEQUENCE: 5
tgacgatgag gacctgacac                                             20

<210> SEQ ID NO 6
<211> LENGTH: 20
<212> TYPE: DNA
<213> ORGANISM: Artificial Sequence
<220> FEATURE:
<223> OTHER INFORMATION: Reverse TCF4 mRNA primer (5'-3')

<400> SEQUENCE: 6
gtctggggct tgtcactctt                                             20

<210> SEQ ID NO 7
<211> LENGTH: 23
<212> TYPE: DNA
<213> ORGANISM: Artificial Sequence
<220> FEATURE:
<223> OTHER INFORMATION: Forward TCF4 intron-upstream primer (5'-3')

<400> SEQUENCE: 7
gtagtcgtag gatcagcaca aag                                         23

<210> SEQ ID NO 8
<211> LENGTH: 20
<212> TYPE: DNA
<213> ORGANISM: Artificial Sequence
<220> FEATURE:
<223> OTHER INFORMATION: Reverse TCF4 intron-upstream primer (5'-3')

<400> SEQUENCE: 8
ggaagcaaag ggatggagaa                                             20

<210> SEQ ID NO 9
<211> LENGTH: 22
<212> TYPE: DNA
<213> ORGANISM: Artificial Sequence
<220> FEATURE:
<223> OTHER INFORMATION: Forward TCF4 intron-downstream primer (5'-3')

<400> SEQUENCE: 9
gagagaggga gtgaaagaga ga                                          22

<210> SEQ ID NO 10
<211> LENGTH: 20
<212> TYPE: DNA
<213> ORGANISM: Artificial Sequence
<220> FEATURE:
<223> OTHER INFORMATION: Reverse TCF4 intron-downstream primer (5'-3')

<400> SEQUENCE: 10
ggcaatgtcc atttccatct                                             20

<210> SEQ ID NO 11
<211> LENGTH: 22
<212> TYPE: DNA
<213> ORGANISM: Artificial Sequence
<220> FEATURE:
```

-continued

```
<223> OTHER INFORMATION: Forward CTGF primer (5'-3')

<400> SEQUENCE: 11
gctgacctgg aagagaacat ta                                             22

<210> SEQ ID NO 12
<211> LENGTH: 22
<212> TYPE: DNA
<213> ORGANISM: Artificial Sequence
<220> FEATURE:
<223> OTHER INFORMATION: Reverse CTGF primer (5'-3')

<400> SEQUENCE: 12
gtcggtacat actccacaga at                                             22

<210> SEQ ID NO 13
<211> LENGTH: 22
<212> TYPE: DNA
<213> ORGANISM: Artificial Sequence
<220> FEATURE:
<223> OTHER INFORMATION: Forward COCH primer (5'-3')

<400> SEQUENCE: 13
gatgggcagt cctatgatga tg                                             22

<210> SEQ ID NO 14
<211> LENGTH: 22
<212> TYPE: DNA
<213> ORGANISM: Artificial Sequence
<220> FEATURE:
<223> OTHER INFORMATION: Reverse COCH primer (5'-3')

<400> SEQUENCE: 14
gcatgagact ccttcggttt ag                                             22

<210> SEQ ID NO 15
<211> LENGTH: 20
<212> TYPE: DNA
<213> ORGANISM: Artificial Sequence
<220> FEATURE:
<223> OTHER INFORMATION: Forward MSI1 primer (5'-3')

<400> SEQUENCE: 15
gtttcggctt cgtcactttc                                                20

<210> SEQ ID NO 16
<211> LENGTH: 21
<212> TYPE: DNA
<213> ORGANISM: Artificial Sequence
<220> FEATURE:
<223> OTHER INFORMATION: Reverse MSI1 primer (5'-3')

<400> SEQUENCE: 16
cttcgttcga gtcaccatct t                                              21

<210> SEQ ID NO 17
<211> LENGTH: 22
<212> TYPE: DNA
<213> ORGANISM: Artificial Sequence
<220> FEATURE:
<223> OTHER INFORMATION: Forward LUM primer (5'-3')

<400> SEQUENCE: 17
ggtctccctg tctctcttct aa                                             22
```

-continued

```
<210> SEQ ID NO 18
<211> LENGTH: 22
<212> TYPE: DNA
<213> ORGANISM: Artificial Sequence
<220> FEATURE:
<223> OTHER INFORMATION: Reverse LUM primer (5'-3')

<400> SEQUENCE: 18
agccagttcg ttgtgagata aa                                            22

<210> SEQ ID NO 19
<211> LENGTH: 20
<212> TYPE: DNA
<213> ORGANISM: Artificial Sequence
<220> FEATURE:
<223> OTHER INFORMATION: Forward KDR primer (5'-3')

<400> SEQUENCE: 19
agcaggatgg caaagactac                                              20

<210> SEQ ID NO 20
<211> LENGTH: 22
<212> TYPE: DNA
<213> ORGANISM: Artificial Sequence
<220> FEATURE:
<223> OTHER INFORMATION: Reverse KDR primer (5'-3')

<400> SEQUENCE: 20
tacttcctcc tcctccatac ag                                            22

<210> SEQ ID NO 21
<211> LENGTH: 21
<212> TYPE: DNA
<213> ORGANISM: Artificial Sequence
<220> FEATURE:
<223> OTHER INFORMATION: Forward MBNL2 (RT-PCR) primer (5'-3')

<400> SEQUENCE: 21
acaccgtaac cgtttgtatg g                                            21

<210> SEQ ID NO 22
<211> LENGTH: 23
<212> TYPE: DNA
<213> ORGANISM: Artificial Sequence
<220> FEATURE:
<223> OTHER INFORMATION: Reverse MBNL2 (RT-PCR) primer (5'-3')

<400> SEQUENCE: 22
gcatcatggg tactgttgga atg                                          23

<210> SEQ ID NO 23
<211> LENGTH: 20
<212> TYPE: DNA
<213> ORGANISM: Artificial Sequence
<220> FEATURE:
<223> OTHER INFORMATION: COCH CRISPR Guide RNA or crRNA 1

<400> SEQUENCE: 23
gcttctgtat cgagcatatg                                              20

<210> SEQ ID NO 24
<211> LENGTH: 20
<212> TYPE: DNA
<213> ORGANISM: Artificial Sequence
<220> FEATURE:
<223> OTHER INFORMATION: COCH CRISPR Guide RNA or crRNA 2
```

```
<400> SEQUENCE: 24
accggctccc tcgctgcccg                                                          20

<210> SEQ ID NO 25
<211> LENGTH: 20
<212> TYPE: DNA
<213> ORGANISM: Artificial Sequence
<220> FEATURE:
<223> OTHER INFORMATION: COCH CRISPR Guide RNA or crRNA 3

<400> SEQUENCE: 25
cacccaccga ggccgagagc                                                          20

<210> SEQ ID NO 26
<211> LENGTH: 20
<212> TYPE: DNA
<213> ORGANISM: Artificial Sequence
<220> FEATURE:
<223> OTHER INFORMATION: COCH CRISPR Guide RNA or crRNA 4

<400> SEQUENCE: 26
tacacagaga attcctcaag                                                          20

<210> SEQ ID NO 27
<211> LENGTH: 20
<212> TYPE: DNA
<213> ORGANISM: Artificial Sequence
<220> FEATURE:
<223> OTHER INFORMATION: COCH CRISPR Guide RNA or crRNA 5

<400> SEQUENCE: 27
cagtcaccat gtccgcagcc                                                          20

<210> SEQ ID NO 28
<211> LENGTH: 20
<212> TYPE: DNA
<213> ORGANISM: Artificial Sequence
<220> FEATURE:
<223> OTHER INFORMATION: COCH CRISPR Guide RNA or crRNA 6

<400> SEQUENCE: 28
cccgcgggca gcgagggagc                                                          20

<210> SEQ ID NO 29
<211> LENGTH: 20
<212> TYPE: DNA
<213> ORGANISM: Artificial Sequence
<220> FEATURE:
<223> OTHER INFORMATION: FN1 CRISPR Guide RNA or crRNA 1

<400> SEQUENCE: 29
gacctaccta ggcaatgcgt                                                          20

<210> SEQ ID NO 30
<211> LENGTH: 20
<212> TYPE: DNA
<213> ORGANISM: Artificial Sequence
<220> FEATURE:
<223> OTHER INFORMATION: FN1 CRISPR Guide RNA or crRNA 2

<400> SEQUENCE: 30
tacaaaccaa cgcattgcct                                                          20

<210> SEQ ID NO 31
<211> LENGTH: 20
```

```
<212> TYPE: DNA
<213> ORGANISM: Artificial Sequence
<220> FEATURE:
<223> OTHER INFORMATION: FN1 CRISPR Guide RNA or crRNA 3

<400> SEQUENCE: 31
gctcataagt gtcacccact                                                    20

<210> SEQ ID NO 32
<211> LENGTH: 20
<212> TYPE: DNA
<213> ORGANISM: Artificial Sequence
<220> FEATURE:
<223> OTHER INFORMATION: FN1 CRISPR Guide RNA or crRNA 4

<400> SEQUENCE: 32
gaatggacct gcaagcccat                                                    20

<210> SEQ ID NO 33
<211> LENGTH: 20
<212> TYPE: DNA
<213> ORGANISM: Artificial Sequence
<220> FEATURE:
<223> OTHER INFORMATION: FN1 CRISPR Guide RNA or crRNA 5

<400> SEQUENCE: 33
tcacacacct atgggcttgc                                                    20

<210> SEQ ID NO 34
<211> LENGTH: 20
<212> TYPE: DNA
<213> ORGANISM: Artificial Sequence
<220> FEATURE:
<223> OTHER INFORMATION: FN1 CRISPR Guide RNA or crRNA 6

<400> SEQUENCE: 34
gactgtacct gcatcggggc                                                    20

<210> SEQ ID NO 35
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 1

<400> SEQUENCE: 35
cctcaccttg caggtacacg                                                    20

<210> SEQ ID NO 36
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 2

<400> SEQUENCE: 36
ctgcgccagt ccatcctttg                                                    20

<210> SEQ ID NO 37
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 3

<400> SEQUENCE: 37
```

-continued

```
gcagcattcg ccttccacaa                                    20

<210> SEQ ID NO 38
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 4

<400> SEQUENCE: 38
cgaatgataa ccagtttctc                                    20

<210> SEQ ID NO 39
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 5

<400> SEQUENCE: 39
agcaagaagg gttgccagca                                    20

<210> SEQ ID NO 40
<211> LENGTH: 20
<212> TYPE: DNA
<213> ORGANISM: Artificial Sequence
<220> FEATURE:
<223> OTHER INFORMATION: THBS2 CRISPR Guide RNA or crRNA 6

<400> SEQUENCE: 40
cctagtgttt gaaaactctg                                    20
```

MOLECULAR BIOMARKERS AND TARGETS FOR FUCHS' ENDOTHELIAL CORNEAL DYSTROPHY AND GLAUCOMA

PRIORITY

This application claims the benefit of U.S. Ser. No. 62/980,690, filed Feb. 24, 2020, which is incorporated by reference herein in its entirety.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Aug. 3, 2021 is named "426871-000179_seq_listing_1_ST25.txt" and is about 8.4 KB in size.

STATEMENT REGARDING FEDERALLY SPONSORED RESEARCH OR DEVELOPMENT

This invention was made with government support under R01EY022161 awarded by the National Eye Institute of the National Institute for Health (NIH). The government has certain rights in the invention.

BACKGROUND

Corneal diseases represent one of the leading causes of vision loss and blindness globally. Inherited corneal dystrophies can compromise the structure and transparency of the cornea. Late-onset Fuchs' endothelial corneal dystrophy (FECD) is one of the most common genetic disorders, affecting four percent of the population in the United States over the age of forty.

Fuchs' endothelial corneal dystrophy (FECD; phenotype MIM 136800) is a late-onset degenerative disease involving the endothelial layer of the cornea. The corneal endothelium is the inner hexagonal monolayer responsible for maintenance of stromal dehydration and corneal clarity. In FECD, the post-mitotic endothelium undergoes premature senescence and apoptosis. Descemet's membrane, the basement membrane of the endothelium, becomes diffusely thickened and develops focal excrescences called guttae. Guttae are clinically diagnostic of FECD by slit-lamp biomicroscopy. Confluence of central guttae and concomitant loss of endothelial cell density results in corneal edema, scarring, and loss of vision, making FECD the leading indication for corneal transplantation in the United States and developed world.

Two thirds of FECD cases are caused by an expansion of the trinucleotide CUG within the TCF4 gene making the corneal dystrophy the most common human disorder mediated by simple DNA repeats. FECD can also be caused by a CUG expansion within the 3'-untranslated region (3'-UTR) of the DMPK gene, implicating mutant expanded CUG RNA as the root cause for repeat-associated FECD (FECD_REP). The remaining one third of FECD patients lack the expanded repeat (FECD_NR), but the two types of FECD are indistinguishable during normal clinical observation.

Early stage FECD is characterized by loss of endothelial cell and presence of guttae, as visible on slit lamp exam. As the disease progresses, fluid from the anterior chamber collects in the corneal stroma increasing the thickness of the corneal stroma and reducing vision. With more advanced FECD, the swelling, or edema, collects in the epithelial layer of the cornea causing small blisters called bullae. In late-stage FECD with chronic edema, fibrotic tissue will form in the subepithelial space and invade the cornea leading to further corneal opacification. Permanent scar tissue eventually will develop in the cornea that will require surgery to remove.

The severity of FECD is currently assessed based on the distribution of guttae and the presence of edema using the Krachmer grading scale. The Krachmer grading scale is used to subjectively evaluate disease progression as follows: grade 0 (G0) negative; 0-12 central guttae (G1); greater than 12 central nonconfluent guttae (G2); 1-2 mm of confluent central guttae (G3); 2-5 mm of confluent central guttae (G4); greater than 5 mm of confluent central guttae or G4 with stromal or epithelial edema (G5). Despite being used since 1978, this method has some limitations concerning its reproducibility, variance between observers, and grading mild corneal edema.

Cochlin is a secreted extracellular matrix protein originally identified in the cochlear cells of the inner ear. The cochlin protein has two van Willebrand factor A (vWFA) domains on the C-terminal end, which enables its multimerization and adhesion with other ECM components, especially those containing vWFA domains such as collagen proteins. Importantly, the LCCL domain on the N-terminal end can be cleaved off to recruit innate immune cells in the inner ear in response to infection. Mutations in COCH result in deafness, resulting from distinct aggregative extracellular histopathology in the inner ear similar to protein aggregates seen in neurodegenerative disorders such as Huntington's disease.

Therefore, methods are needed in the art for detecting early stage or late stage Fuchs' endothelial corneal dystrophy, for monitoring treatment of early stage or late stage FECD, for monitoring progression of early stage or late stage FECD, for detecting glaucoma, for monitoring treatment of glaucoma, and for monitoring progression of glaucoma.

BRIEF SUMMARY

An embodiment provides a method of detecting Fuchs' endothelial corneal dystrophy (FECD) in a subject comprising: (a) detecting an increase of expression of one or more of ADGRG7, FN1, KCNA1, VSIG2, CNN1, ABCB1, ABCB4, COCH, MAGED4, IGSF5, PCP4, MARVELD3, MIR5188, FRZB, ELMOD1, MSI1, HPGD, TPBG, F5, THBS2, ECEL1P1/2, CPVL, LINC02258, CD86, DLK1, FOXF2, GMNC, GPR34, IGKV3-20, IGKV6D-21, TMEM255A, CDKN2A, CLEC5A, MARCH1, GPC3, HLA-DQA1, HLA-DRA, CYBB, GRM5, NOX4, IGKC, IGKJ1, IGKJ2, C3AR1, DCX, MMP2-AS1, LYVE1, FAM198B, FCGR1B, FOLR2, FCGR3A, TNFRSF11B, PSG4, KRT7, COL4A2, CTGF, COL9A3, COL1A2, FGFR2, NOTCH2, TGFBR1, IFNGR1, TGFBR2, NOTCH1, HLA-DPB1, IL18, JAG1, CD4, SPI1, PIK3R5, ITGB2, NFATC2, HLA-DPA1, HLA-DOA, IKZF1, IL10RA, MAPK10, BCL2, COL5A2, ROR2, ACKR1, CADM3, VIPR2, ADAM33, CADM3-AS1, TSHR, DPP10, CLIC6, TMEM30B, LGR6, CST4, ICA1, ALPK2, RARRES2, MMP19, DCDC2C, CST1, ITPRIPL1, WNT3, SLC5A1, ARSJ, GREB1L, SLC16A9, EPHB6, MROH9, ENOX1, PLAC9, KIF21B, ADAMTS12, ITIH5, ANXA3, PROS1, PTPN3, or DCLK1; (b) detecting a decrease of expression of one or more of SAA2/4, NPBWR1, GFAP, DNER, INPP5D, SYNDIG1, CSF3, SPATA18, CLEC4GP1, OVCH1, LINC01811, CLIC5, FAM107A, PNMT, CYTL1, SERPINA3/4/5, TMOD1, HMGN2P17, GPRC5B, DRD2, PSPHP1, CDH12, IL17REL, ARC, UBE2W, RNU5E-1, CXCL8, LINC00881, LINC02029, CXCL3, RNU2-63P, CXCL2, RASD1, RNU6-1208P, UTY, CD24P4, RNU6-255P, TTTY14, KDM5DP1, TTTY10, NLGN4Y, RNU1-59P, ZFY, STK40, RNU5B-1, LINC01783, RNU1-6P, RNU1-5P, EPS8L1, LUM, KDR, SOD3, IRF1, JUN, SOCS3, NFIL3, FGFR4, NFKB1, SOD2, MAOA, CYCS, SNCA, PDHA1, UQCRH, COX7B, COX5B, NDUFV1, UQCRC2, NDUFA1, CYC1, UQCRB, VDAC2, COX4I1, SDHB, COX6B1, or MAOB; or (c) detecting one or more skipped exon events as shown in Table 8 in a sample obtained from the subject.

The sample can be corneal tissue, aqueous humor, plasma, serum, blood, tear film, trabecular meshwork, or a combination thereof. The method can further comprise treating the subject with steroidal eye drops, sodium chloride eye drops, keratoprosthesis implantation, therapeutic contacts, corneal transplant, endothelial keratoplasty, penetrating kerato-plasty, prostaglandins, beta blockers, alpha-adrenergic ago-nists, carbonic anhydrase inhibitors, rho kinase inhibitors, miotic or cholinergic agents, or combinations thereof. The method can further comprise treating the subject with one or more therapeutic agents that decrease the amount of expres-sion of one or more of ADGRG7, FN1, KCNA1, VSIG2, CNN1, ABCB1, ABCB4, COCH, MAGED4, IGSF5, PCP4, MARVELD3, MIR5188, FRZB, ELMOD1, MSI1, HPGD, TPBG, F5, THBS2, ECEL1P1/2, CPVL, LINC02258, CD86, DLK1, FOXF2, GMNC, GPR34, IGKV3-20, IGKV6D-21, TMEM255A, CDKN2A, CLEC5A, MARCH1, GPC3, HLA-DQA1, HLA-DRA, CYBB, GRM5, NOX4, IGKC, IGKJ1, IGKJ2, C3AR1, DCX, MMP2-AS1, LYVE1, FAM198B, FCGR1B, FOLR2, FCGR3A, TNFRSF11B, PSG4, KRT7, COL4A2, CTGF, COL9A3, COL1A2, FGFR2, NOTCH2, TGFBR1, IFNGR1, TGFBR2, NOTCH1, HLA-DPB1, IL18, JAG1, CD4, SPI1, PIK3R5, ITGB2, NFATC2, HLA-DPA1, HLA-DOA, IKZF1, IL10RA, MAPK10, BCL2, COL5A2, ROR2, ACKR1, CADM3, VIPR2, ADAM33, CADM3-AS1, TSHR, DPP10, CLIC6, TMEM30B, LGR6, CST4, ICA1, ALPK2, RARRES2, MMP19, DCDC2C, CST1, ITPRIPL1, WNT3, SLC5A1, ARSJ, GREB1L, SLC16A9, EPHB6, MROH9, ENOX1, PLAC9, KIF21B, ADAMTS12, ITIH5, ANXA3, PROS1, PTPN3, or DCLK1. The therapeutic agents can be small molecule inhibitors, oligonucleotides, siRNAs, antibodies, RNAi, shRNA, miRNA, viral vectors, non-viral delivery, and CRISPR-Cas system, zinc finger nucleases, and TALENs. The method can further comprise treating the subject with one or more therapeutic agents that increase the amount of expression of one or more of SAA2/4, NPBWR1, GFAP, DNER, INPP5D, SYNDIG1, CSF3, SPATA18, CLEC4GP1, OVCH1, LINC01811, CLIC5, FAM107A, PNMT, CYTL1, SERPINA3/4/5, TMOD1, HMGN2P17, GPRC5B, DRD2, PSPHP1, CDH12, IL17REL, ARC, UBE2W, RNU5E-1, CXCL8, LINC00881, LINC02029, CXCL3, RNU2-63P, CXCL2, RASD1, RNU6-1208P, UTY, CD24P4, RNU6-255P, TTTY14, KDM5DP1, TTTY10, NLGN4Y, RNU1-59P, ZFY, STK40, RNU5B-1, LINC01783, RNU1-6P, RNU1-5P, EPS8L1, LUM, KDR, SOD3, IRF1, JUN, SOCS3, NFIL3, FGFR4, NFKB1, SOD2, MAOA, CYCS, SNCA, PDHA1, UQCRH, COX7B, COX5B, NDUFV1, UQCRC2, NDUFA1, CYC1, UQCRB, VDAC2, COX4I1, SDHB, COX6B1, or MAOB. The thera-peutic agents can be gene replacement therapy, saRNA, RNAa, CRISPR-Cas system, increasing RNA transcription or translation, and cell-based therapies.

Another embodiment provides a method of monitoring treatment of Fuchs' endothelial corneal dystrophy (FECD) comprising: (a) obtaining a first sample from a subject; (b) detecting gene expression levels of one or more of ADGRG7, FN1, KCNA1, VSIG2, CNN1, ABCB1, ABCB4, COCH, MAGED4, IGSF5, PCP4, MARVELD3, MIR5188, FRZB, ELMOD1, MSI1, HPGD, TPBG, F5, THBS2, ECEL1P1/2, CPVL, LINC02258, CD86, DLK1, FOXF2, GMNC, GPR34, IGKV3-20, IGKV6D-21, TMEM255A, CDKN2A, CLEC5A, MARCH1, GPC3, HLA-DQA1, HLA-DRA, CYBB, GRM5, NOX4, IGKC, IGKJ1, IGKJ2, C3AR1, DCX, MMP2-AS1, LYVE1, FAM198B, FCGR1B, FOLR2, FCGR3A, TNFRSF11B, PSG4, KRT7, COL4A2, CTGF, COL9A3, COL1A2, FGFR2, NOTCH2, TGFBR1, IFNGR1, TGFBR2, NOTCH1, HLA-DPB1, IL18, JAG1, CD4, SPI1, PIK3R5, ITGB2, NFATC2, HLA-DPA1, HLA-DOA, IKZF1, IL10RA, MAPK10, BCL2, COL5A2, ROR2, ACKR1, CADM3, VIPR2, ADAM33, CADM3-AS1, TSHR, DPP10, CLIC6, TMEM30B, LGR6, CST4, ICA1, ALPK2, RARRES2, MMP19, DCDC2C, CST1, ITPRIPL1, WNT3, SLC5A1, ARSJ, GREB1L, SLC16A9, EPHB6, MROH9, ENOX1, PLAC9, KIF21B, ADAMTS12, ITIH5, ANXA3, PROS1, PTPN3, DCLK1, SAA2/4, NPBWR1, GFAP, DNER, INPP5D, SYNDIG1, CSF3, SPATA18, CLEC4GP1, OVCH1, LINC01811, CLIC5, FAM107A, PNMT, CYTL1, SERPINA3/4/5, TMOD1, HMGN2P17, GPRC5B, DRD2, PSPHP1, CDH12, IL17REL, ARC, UBE2W, RNU5E-1, CXCL8, LINC00881, LINC02029, CXCL3, RNU2-63P, CXCL2, RASD1, RNU6-1208P, UTY, CD24P4, RNU6-255P, TTTY14, KDM5DP1, TTTY10, NLGN4Y, RNU1-59P, ZFY, STK40, RNU5B-1, LINC01783, RNU1-6P, RNU1-5P, EPS8L1, LUM, KDR, SOD3, IRF1, JUN, SOCS3, NFIL3, FGFR4, NFKB1, SOD2, MAOA, CYCS, SNCA, PDHA1, UQCRH, COX7B, COX5B, NDUFV1, UQCRC2, NDUFA1, CYC1, UQCRB, VDAC2, COX4I1, SDHB, COX6B1, or MAOB; or detect-ing one or more skipped exon events as shown in Table 8 in the first sample obtained from the subject; (c) administering a treatment to the subject; (d) obtaining a second sample from the subject at a later time and detecting gene expression levels or skipped exon events of (b) in the second sample; and (e) comparing the first sample gene expression levels or skipped exon events with the second sample gene expression levels or skipped exon events.

The first sample and second sample can be corneal tissue, aqueous humor, plasma, serum, blood, tear film, trabecular meshwork, or a combination thereof. The treatment can comprise therapeutic agents that increase gene expression, therapeutic agents that decrease gene expression, steroidal eye drops, sodium chloride eye drops, keratoprosthesis implantation, therapeutic contacts, corneal transplant, endothelial keratoplasty, penetrating keratoplasty, prosta-glandins, beta blockers, alpha-adrenergic agonists, carbonic anhydrase inhibitors, rho kinase inhibitors, miotic or cho-linergic agents, or combinations thereof. The method can further comprise repeating steps (a)-(e) one, two, three, or more times.

An additional embodiment provides a method of moni-toring progression of Fuchs' endothelial corneal dystrophy (FECD) comprising: (a) obtaining a first sample from a subject; (b) detecting gene expression levels of one or more of ADGRG7, FN1, KCNA1, VSIG2, CNN1, ABCB1, ABCB4, COCH, MAGED4, IGSF5, PCP4, MARVELD3, MIR5188, FRZB, ELMOD1, MSI1, HPGD, TPBG, F5, THBS2, ECEL1P1/2, CPVL, LINC02258, CD86, DLK1, FOXF2, GMNC, GPR34, IGKV3-20, IGKV6D-21, TMEM255A, CDKN2A, CLEC5A, MARCH1, GPC3,

5

HLA-DQA1, HLA-DRA, CYBB, GRM5, NOX4, IGKC, IGKJ1, IGKJ2, C3AR1, DCX, MMP2-AS1, LYVE1, FAM198B, FCGR1B, FOLR2, FCGR3A, TNFRSF11B, PSG4, KRT7, COL4A2, CTGF, COL9A3, COL1A2, FGFR2, NOTCH2, TGFBR1, IFNGR1, TGFBR2, NOTCH1, HLA-DPB1, IL18, JAG1, CD4, SPI1, PIK3R5, ITGB2, NFATC2, HLA-DPA1, HLA-DOA, IKZF1, IL10RA, MAPK10, BCL2, COL5A2, ROR2, ACKR1, CADM3, VIPR2, ADAM33, CADM3-AS1, TSHR, DPP10, CLIC6, TMEM30B, LGR6, CST4, ICA1, ALPK2, RARRES2, MMP19, DCDC2C, CST1, ITPRIPL1, WNT3, SLC5A1, ARSJ, GREB1L, SLC16A9, EPHB6, MROH9, ENOX1, PLAC9, KIF21B, ADAMTS12, ITIH5, ANXA3, PROS1, PTPN3, DCLK1, SAA2/4, NPBWR1, GFAP, DNER, INPP5D, SYNDIG1, CSF3, SPATA18, CLEC4GP1, OVCH1, LINC01811, CLIC5, FAM107A, PNMT, CYTL1, SERPINA3/4/5, TMOD1, HMGN2P17, GPRC5B, DRD2, PSPHP1, CDH12, IL17REL, ARC, UBE2W, RNU5E-1, CXCL8, LINC00881, LINC02029, CXCL3, RNU2-63P, CXCL2, RASD1, RNU6-1208P, UTY, CD24P4, RNU6-255P, TTTY14, KDM5DP1, TTTY10, NLGN4Y, RNU1-59P, ZFY, STK40, RNU5B-1, LINC01783, RNU1-6P, RNU1-5P, EPS8L1, LUM, KDR, SOD3, IRF1, JUN, SOCS3, NFIL3, FGFR4, NFKB1, SOD2, MAOA, CYCS, SNCA, PDHA1, UQCRH, COX7B, COX5B, NDUFV1, UQCRC2, NDUFA1, CYC1, UQCRB, VDAC2, COX4I1, SDHB, COX6B1, or MAOB; or detecting one or more skipped exon events as shown in Table 8 in the first sample obtained from the subject; (c) obtaining a second sample from the subject at a later time and detecting gene expression levels or skipped exon events of (b) in the second sample; and (d) comparing the first sample gene expression levels or skipped exon events with the second sample gene expression levels or skipped exon events.

The first sample and second sample can be corneal tissue, aqueous humor, plasma, serum, blood, tear film, trabecular meshwork, or a combination thereof. The method can further comprise repeating steps (a)-(d) one, two, three, or more times.

A further embodiment provides a method of detecting glaucoma in a subject comprising detecting an increase in expression of COCH in a sample obtained from the subject.

The sample can be corneal endothelial cells, corneal tissue, aqueous humor, plasma, serum, blood, tear film, trabecular meshwork, or a combination thereof. The method can further comprise treating the subject with one or more therapeutic agents that decrease COCH expression, prescription eyedrops, oral medications, prostaglandins, beta blockers, alpha-adrenergic agonists, carbonic anhydrase inhibitors, rho kinase inhibitors, miotic or cholinergic agents, laser trabeculoplasty, trabeculectomy, drainage tubes, minimally invasive glaucoma surgery (MIGS), peripheral iridotomy, aqueous shunts, or combinations thereof. The treatment can be delivered to the anterior segment of the eye, posterior segment of the eye, corneal endothelial cells, or other cells of the anterior segment of an eye. The therapeutic agents can be small molecule inhibitors, oligonucleotides, siRNAs, antibodies, RNAi, shRNA, miRNA, and CRISPR-Cas system, zinc finger nucleases, and TALENs.

Yet another embodiment provides a method of monitoring treatment of glaucoma comprising: (a) obtaining a first sample from a subject; (b) detecting gene expression levels of COCH in the first sample obtained from the subject; (c) administering a treatment to the subject; (d) obtaining a second sample from the subject at a later time and detecting gene expression levels of COCH in the second sample; and

6

(d) comparing the first sample gene expression levels with the second sample gene expression levels.

The sample can be corneal tissue, aqueous humor, plasma, serum, blood, tear film, trabecular meshwork, or a combination thereof. The treatment can be therapeutic agents that decrease COCH expression, prescription eyedrops, oral medications, prostaglandins, beta blockers, alpha-adrenergic agonists, carbonic anhydrase inhibitors, rho kinase inhibitors, miotic or cholinergic agents, laser trabeculoplasty, trabeculectomy, drainage tubes, minimally invasive glaucoma surgery (MIGS), peripheral iridotomy, aqueous shunts, or combinations thereof. The therapeutic agents can be small molecule inhibitors, oligonucleotides, siRNAs, antibodies, RNAi, shRNA, miRNA, viral vectors, non-viral delivery, CRISPR-Cas system, zinc finger nucleases, and TALENs. The method can further comprise repeating steps (a)-(e) one, two, three, or more times.

Still another embodiment provides a method of monitoring progression of glaucoma comprising: (a) obtaining a first sample from a subject; (b) detecting gene expression levels of COCH in the first sample obtained from the subject; (c) obtaining a second sample from the subject at a later time and detecting gene expression levels of COCH in the second sample; and (d) comparing the first sample gene expression levels with the second sample gene expression levels.

The sample can be corneal tissue, aqueous humor, plasma, serum, blood, tear film, trabecular meshwork, or a combination thereof. The method can further comprise repeating steps (a)-(d) one, two, three, or more times.

For purposes of summarizing, certain aspects, advantages, and novel features have been described herein. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein:

FIG. 1 show preparation of homogeneous tissue monolayers for analysis. (A) Human donor cornea in corneal viewing chamber with Optisol corneal storage media (Bausch & Lomb). (B) Corneal endothelium/Descemet's membrane monolayer being dissected from underlying stromal tissue. (C) Monolayer of corneal endothelial cells assumes a "scroll" shape. This single cell monolayer will be used for sequencing and other analyses. (D) Immunostaining of monolayer of cells with corneal endothelial specific marker, zonula occudens-1 (ZO-1) (nuclei-DAPI).

Figure 8:
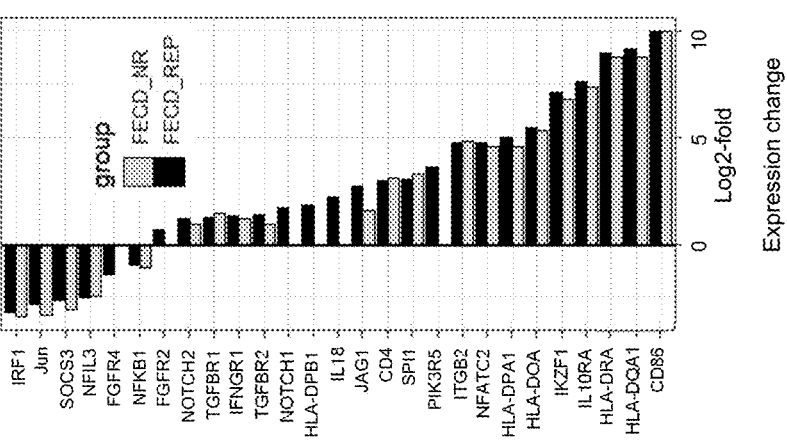
FIG. 8 shows pathway analysis. (A) Top 25 pathways based on FECD_REP. The p-values for three cohorts for each pathway are shown in the last three columns. (B) Shared differentially expressed genes in Fibrosis pathway between Pre-S and FECD_REP. (C) Changes in Th1/2 pathway genes for FECD_NR and FECD_REP. (D) Significant expression level changes in genes involved in mitochondrial dysfunction seen in FECD_REP but not in FECD_NR. FPKM>1.5, fold change>1.5, FDR<=0.05.
Figure 9:
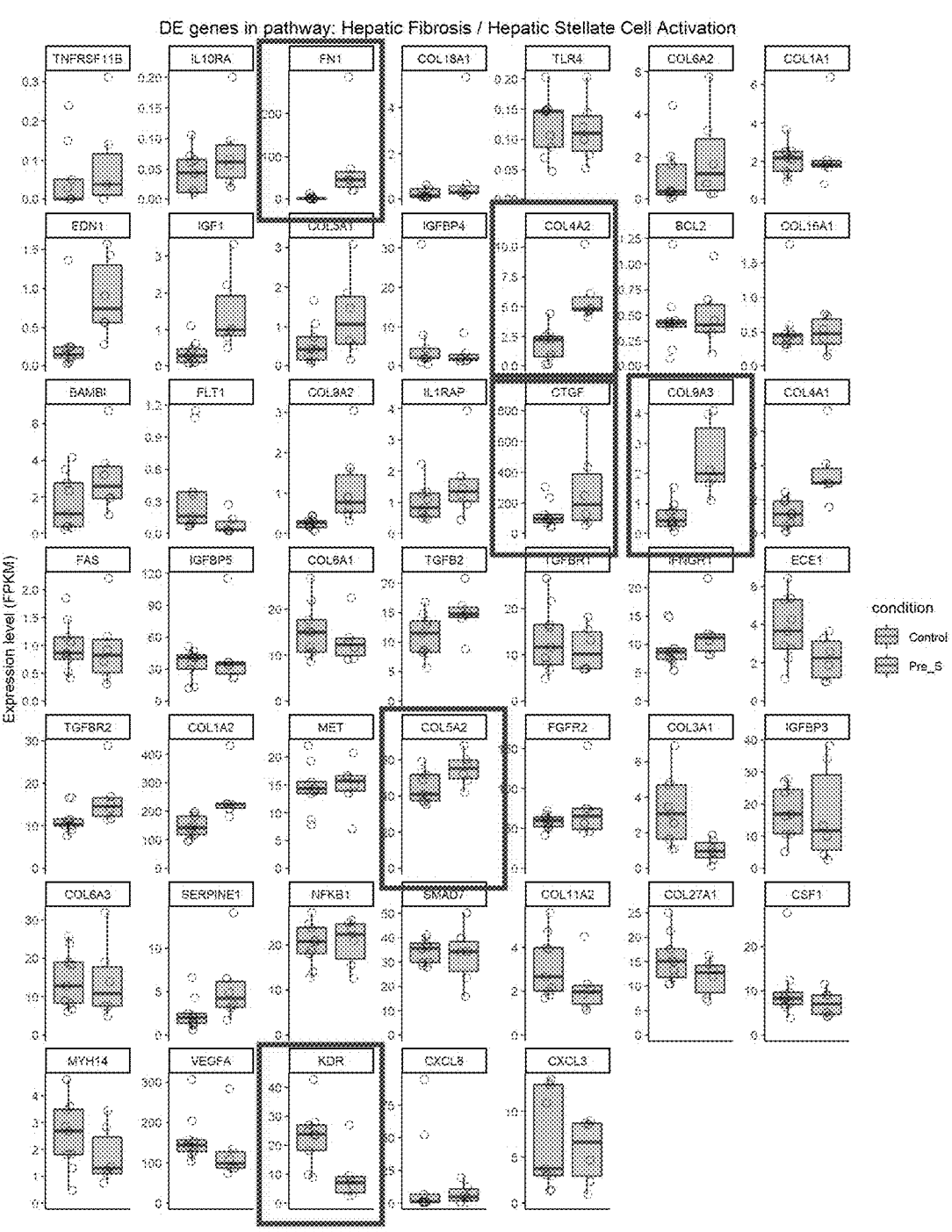

FIG. 9 shows expression profile of genes in Hepatic fibrosis pathway for Pre_S cohort. FPKM>1.5, fold change>1.5, FDR<=0.05. The six largest fold changes in gene expression (FIG. 8) are outlined in rectangles.

Figure 10:
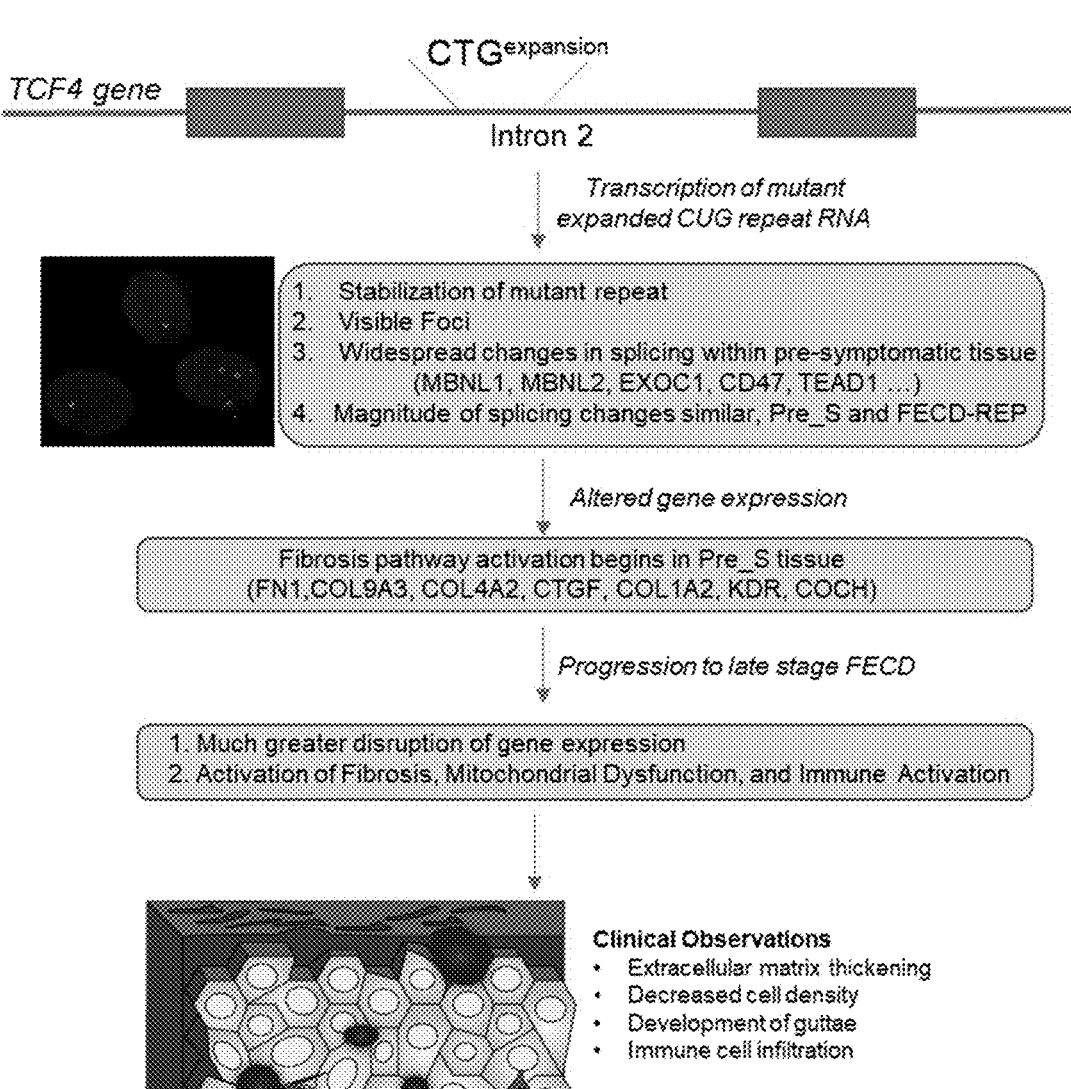

FIG. 10 shows schematic diagram of FECD molecular and disease progression from CTG expanded repeat mutation at the TCF4 locus to advanced FECD. Initially the GTC expansion expresses the CUG repeat RNA. Because the expanded repeat mutation that causes FECD-REP is a relatively common genetic mutation, Pre_S tissue is available for analysis. Pre_S tissue appears normal upon clinical observation. However, in Pre_S tissue foci can be detected, we observe changes in splicing and gene expression, the mutant intronic repeat is stabilized, and early signs of fibrosis pathway activation are apparent. In late stage disease, more pronounced changes in splicing and gene expression accompany clinically observable systems and loss of vision.

FIG. 11 shows sample characterization and clustering. (A) Principle Component Analysis (PCA) plot showing the group relationship based on gene expression for four groups of samples. (B) PCA plot for all the replicates.

FIG. 12 shows quality examination of all RNA samples used for RNA-seq. (A) Heatmap showing the gene body converge from 5-end to 3'-end for all the samples. (B) Gene body percentile plot from 5'- to 3'-end for all the samples.

Figure 13:
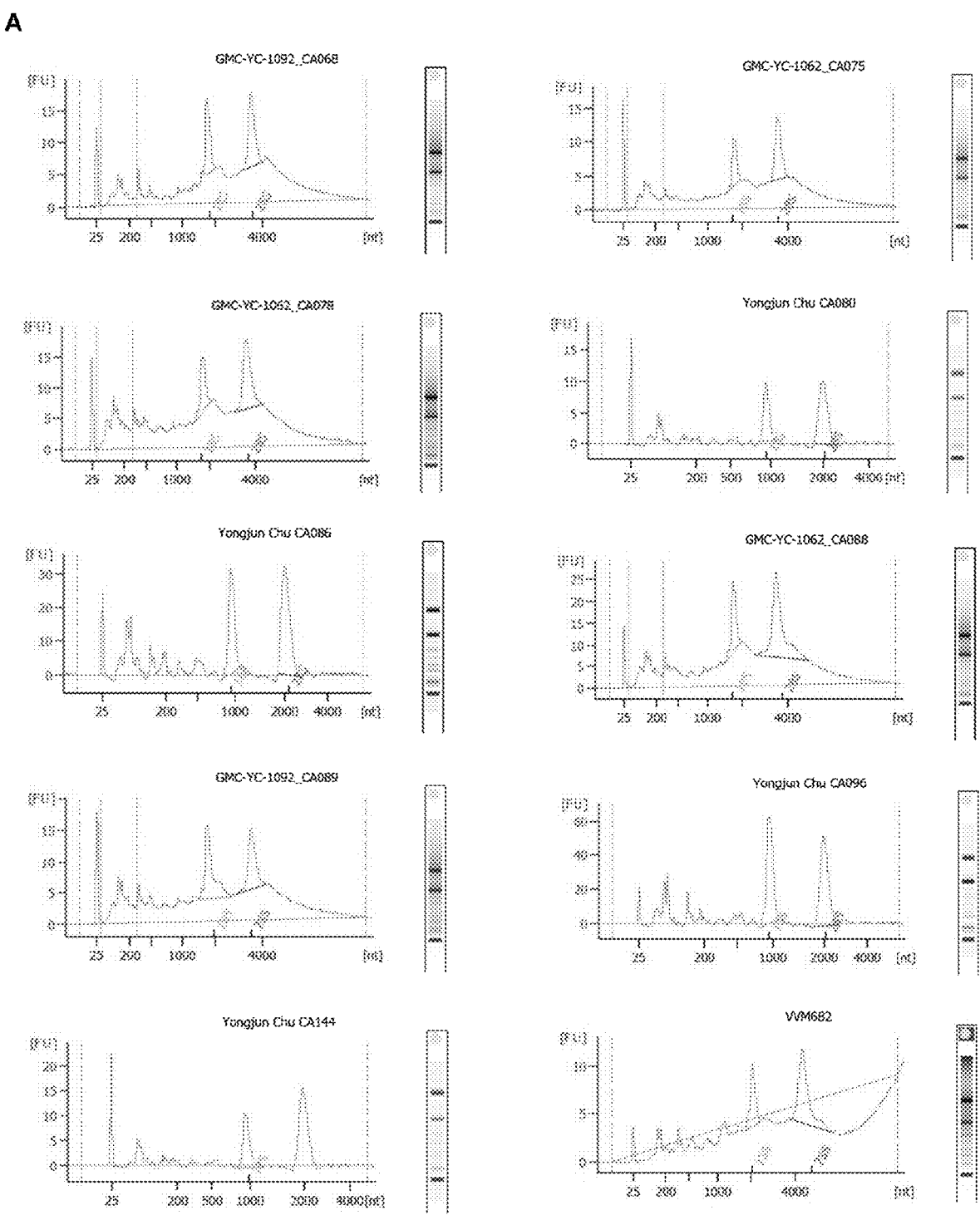
Figure 13:
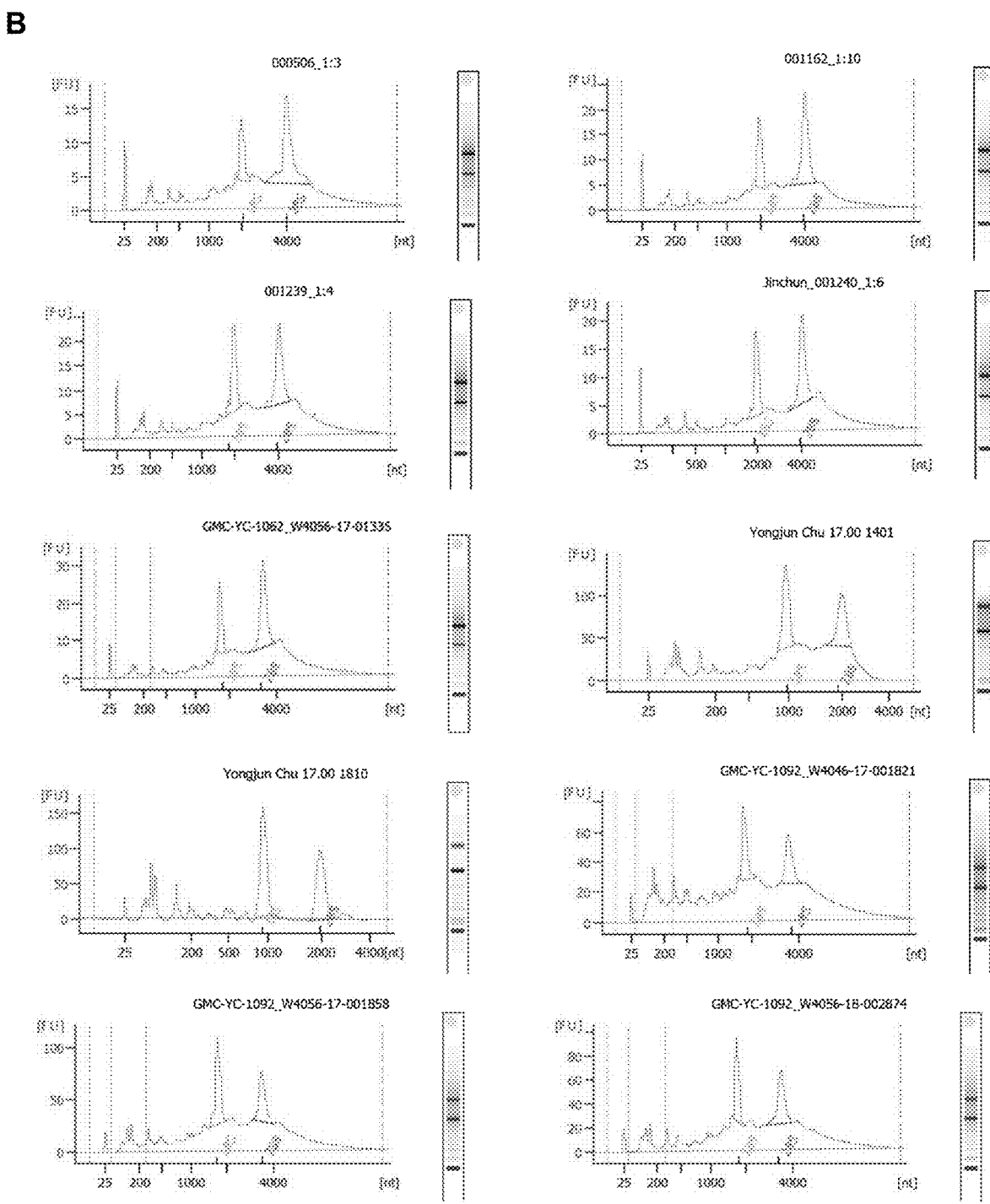

FIG. 13 shows RNA Electropherograms. (A) RNA Electropherogram for all the RNA-seq samples generated by Agilent Bioanalyzer 2100. (B) RNA Electropherogram for each of the RNA-seq samples generated by Agilent Bioanalyzer 2100. (C) RNA Electropherogram for all the RNA-seq samples generated by Agilent Bioanalyzer 2100.

Figure 14:
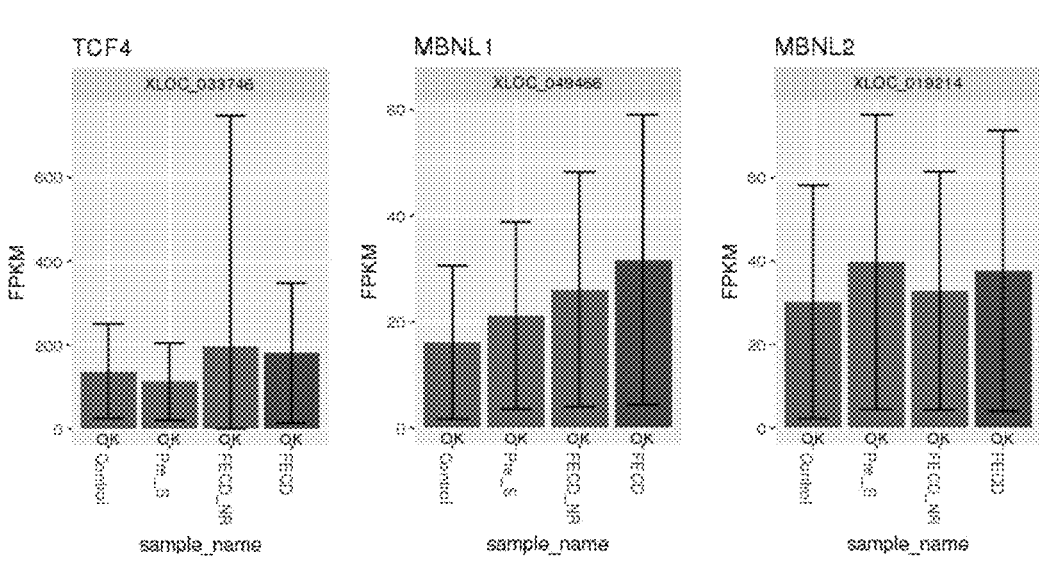

FIG. 14 shows expression levels of TCF4, MBNL1, and MBNL2 mRNA. Measurements were made using RNAseq and corneal endothelial tissue samples from the four sample cohorts. No statistically significant differences were observed. Error bar stands for 95% confidence interval.

Figure 15:
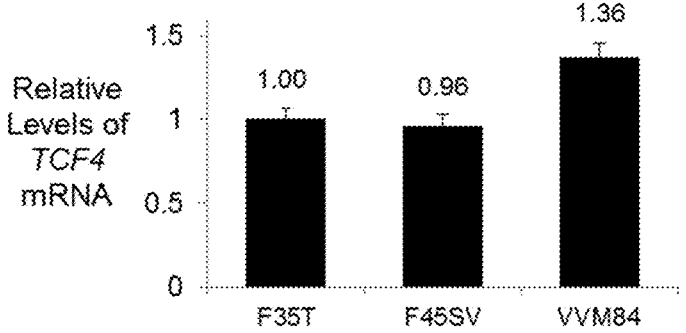

FIG. 15 shows comparison of TCF4 mRNA levels in FECD patient derived endothelial cell lines F35T, F45SV with VVM84 fibroblast cells by qPCR analysis. T-Test: F35T/VVM84, p=0.21; F45SV/VVM84, p=0.18; F35T/F45SV, p=0.82.

FIG. 16 shows the upstream region of intron 2 is not retained in mature mRNA. Primers were designed to target exon 2 and exon 3. Amplification yielded a product consistent with complete removal of intron 2.

Figure 17:
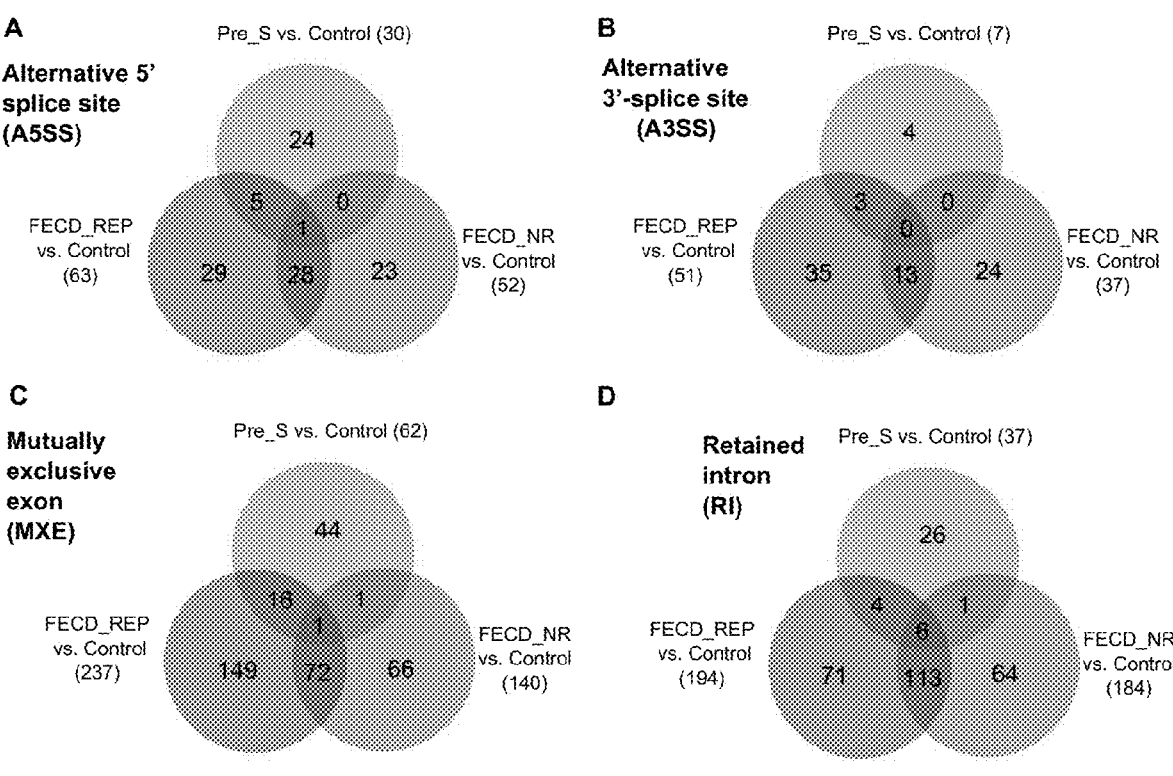
Figure 17:
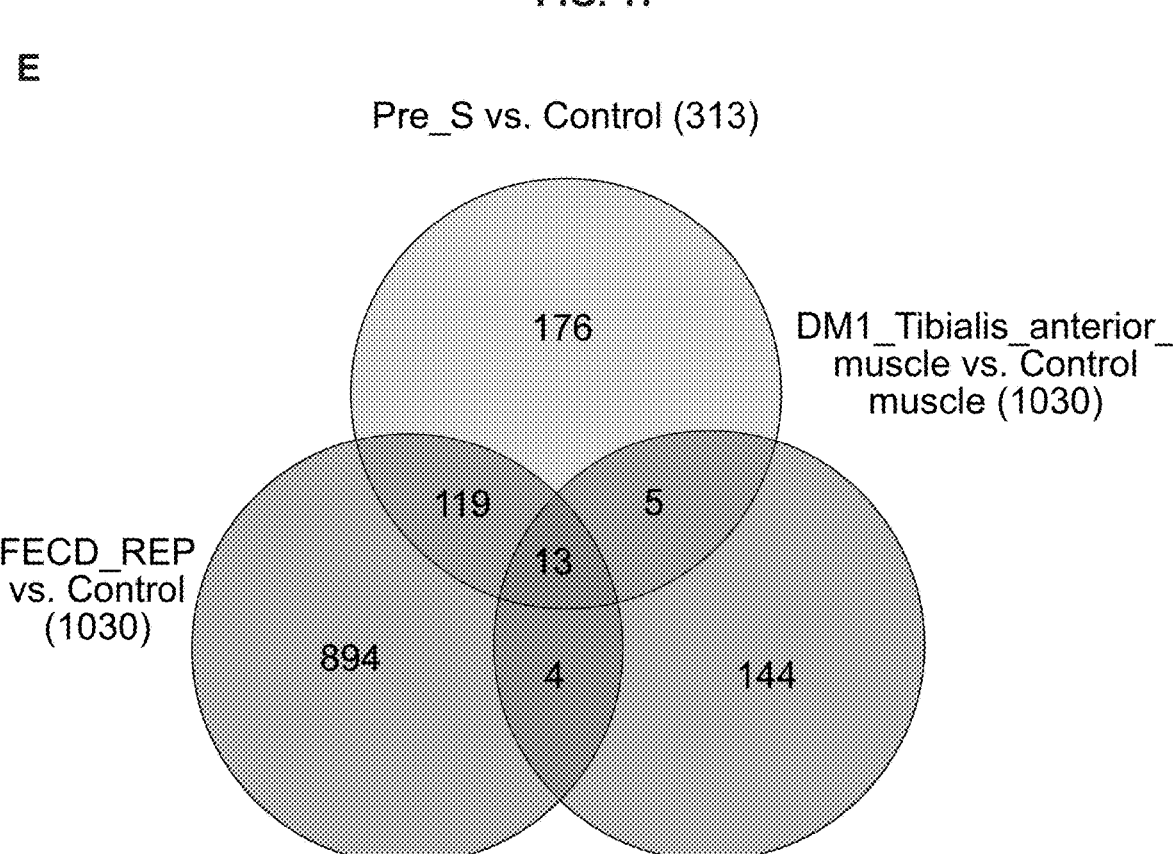

FIG. 17 shows RNAseq data demonstrates changes in splicing in pre-symptomatic, FECD_REP, and FECD_NR tissue. (A) Alternative 5' splice site (A5SS) in Pre_S, FECD_REP, and FECD_NR cohorts (relative to control). (B) Alternative 3'-splice site (A3SS) in Pre_S, FECD_REP, and FECD_NR cohorts (relative to control). (C) Mutually exclusive exon (MXE) in Pre_S, FECD_REP, and FECD_NR cohorts (relative to control). (D) Retained intron (RI) in Pre_S, FECD_REP, and FECD_NR cohorts (relative to control). The threshold used in identifying the significant events: FDR<0.001, |IncLevel Difference|>=0.15. (E) Skipped exon events are shared among Pre_S, FECD_REP and DM1. (F) Details of 13 shared SE events among three groups, FECD_REP, Pre_S, and DM1. DM1 raw data was obtained from Gene Expression Omnibus (GSE86356) and analyzed similarly as the FECD data (visit DMseq.org for more information). (G) Basic functions of commonly shared genes listed in (F).

Figure 18:
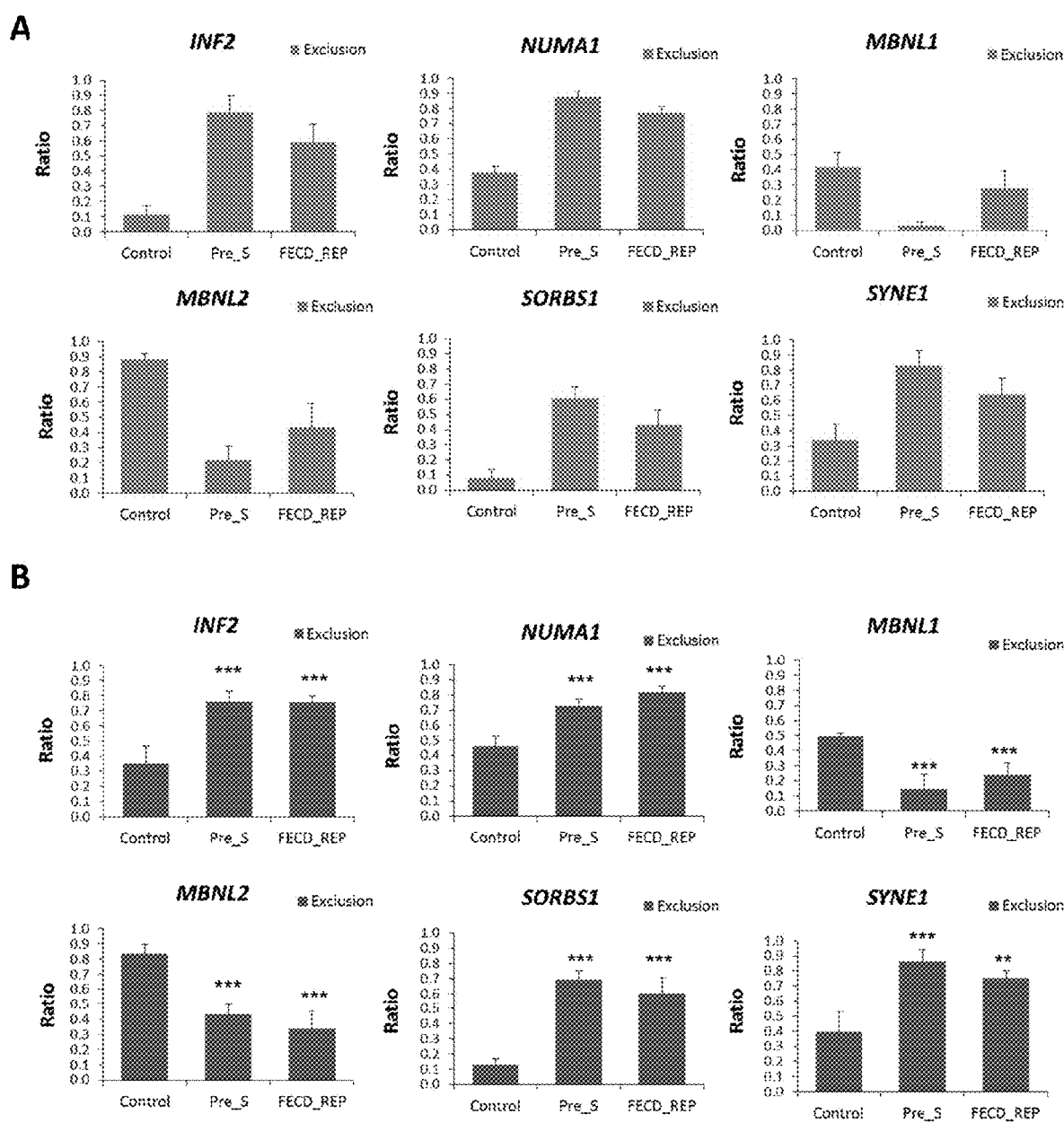

FIG. 18 shows quantification of mis-spliced genes in Pre_S, FECD_REP and healthy control endothelium tissues. (A) Ratio of selected exon exclusion verse inclusion found in samples by RNA_Seq analysis. (B) Ratio of the same exon exclusion verse inclusion verified in samples by RT-PCR showed in FIG. 5. T-Test: p<0.01, *p<0.001 relative to exon exclusion ratio with control group.

Figure 19:
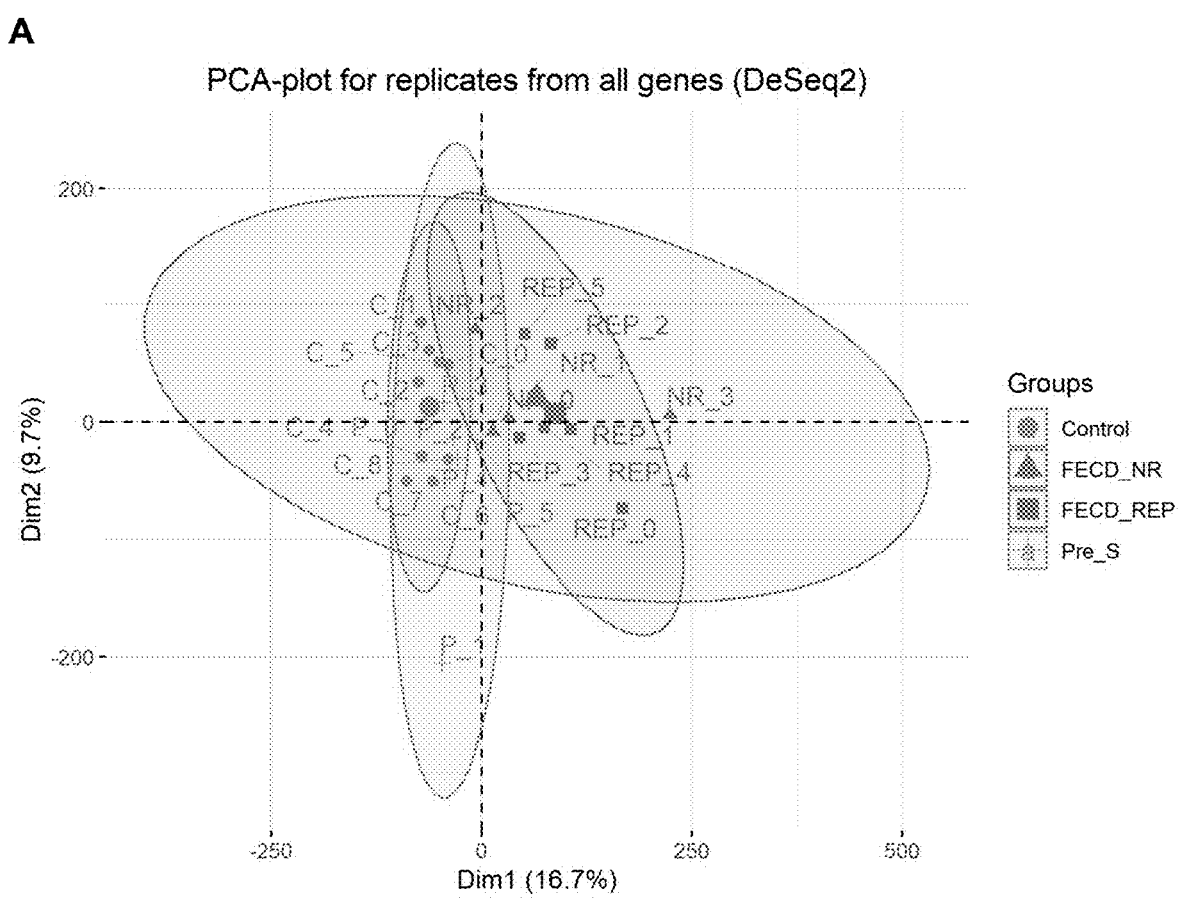
Figure 19:
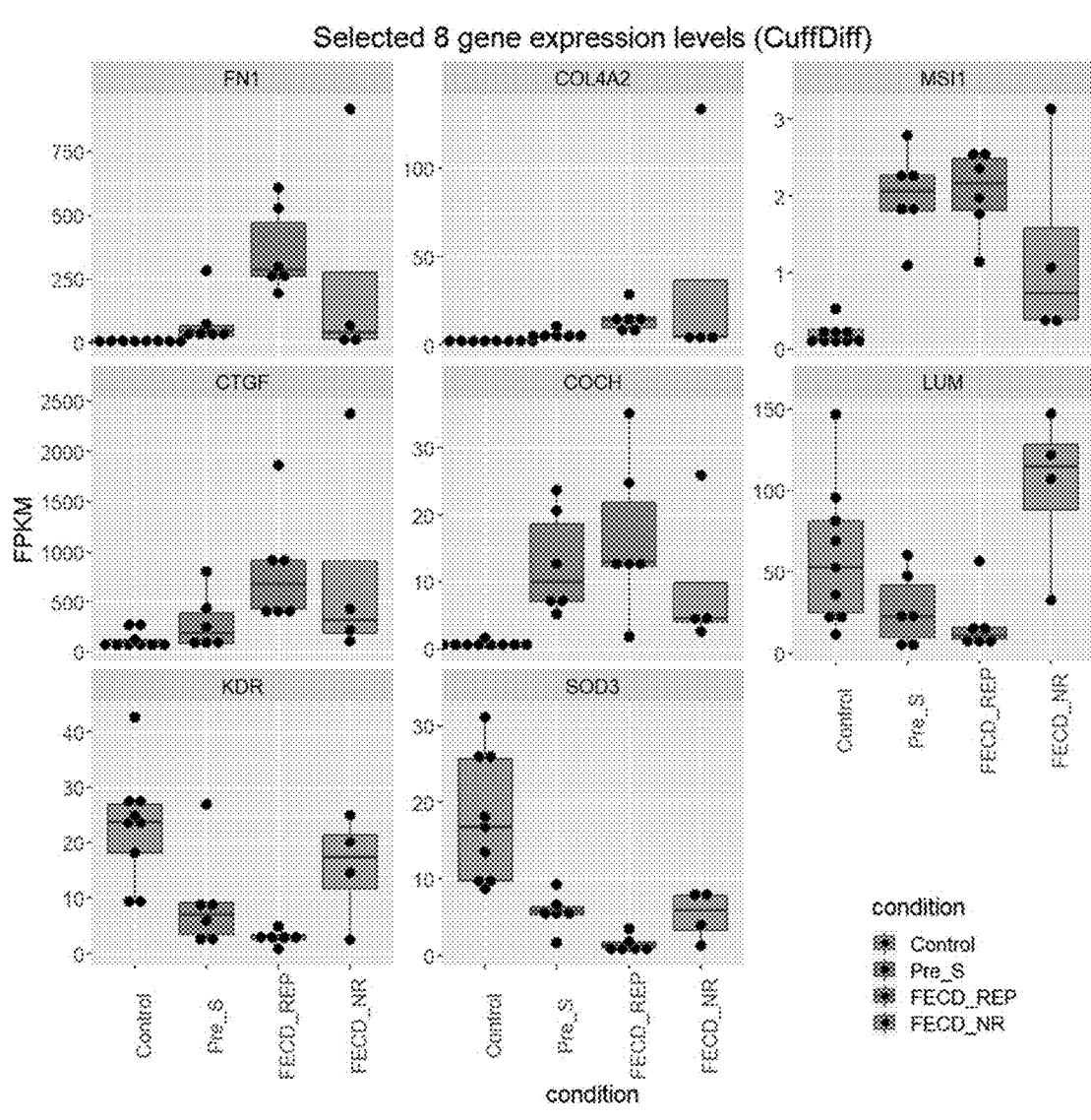
Figure 19:
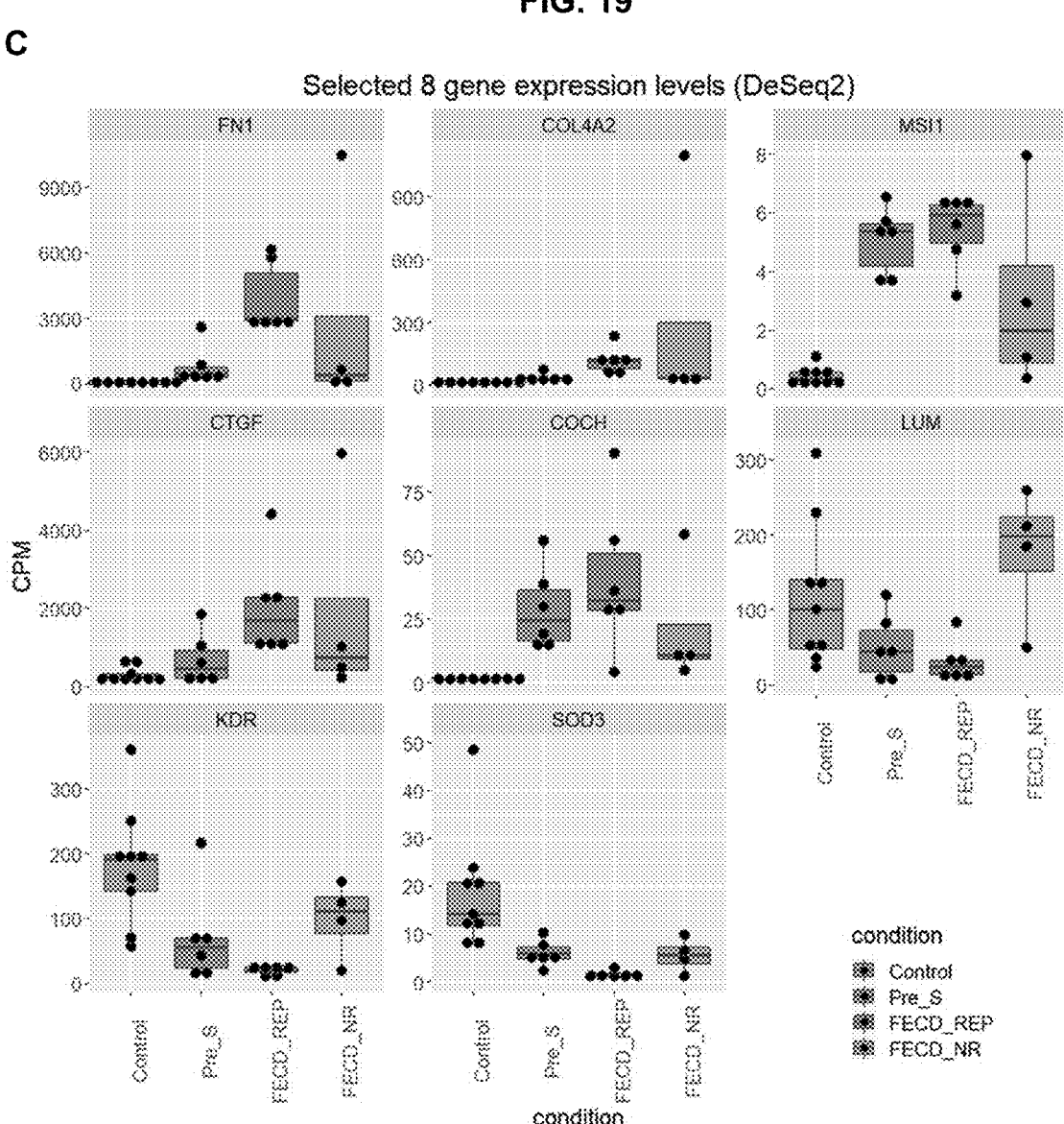

FIG. 19 shows differential gene expression analysis with DeSeq2. (A) PCA plot for all 25 replicates from all genes analyzed by DeSeq2. (B) Boxplot showing the expression levels of 8 selected genes in Control, Pre_S, FECD_REP and FECD_NR tissue replicates. The results were obtained with CuffDiff. (C) Boxplot showing the expression levels of 8 selected genes in Control, Pre_S, FECD_REP and FECD_NR tissue replicates. The results were obtained with DeSeq2.

Figure 20:
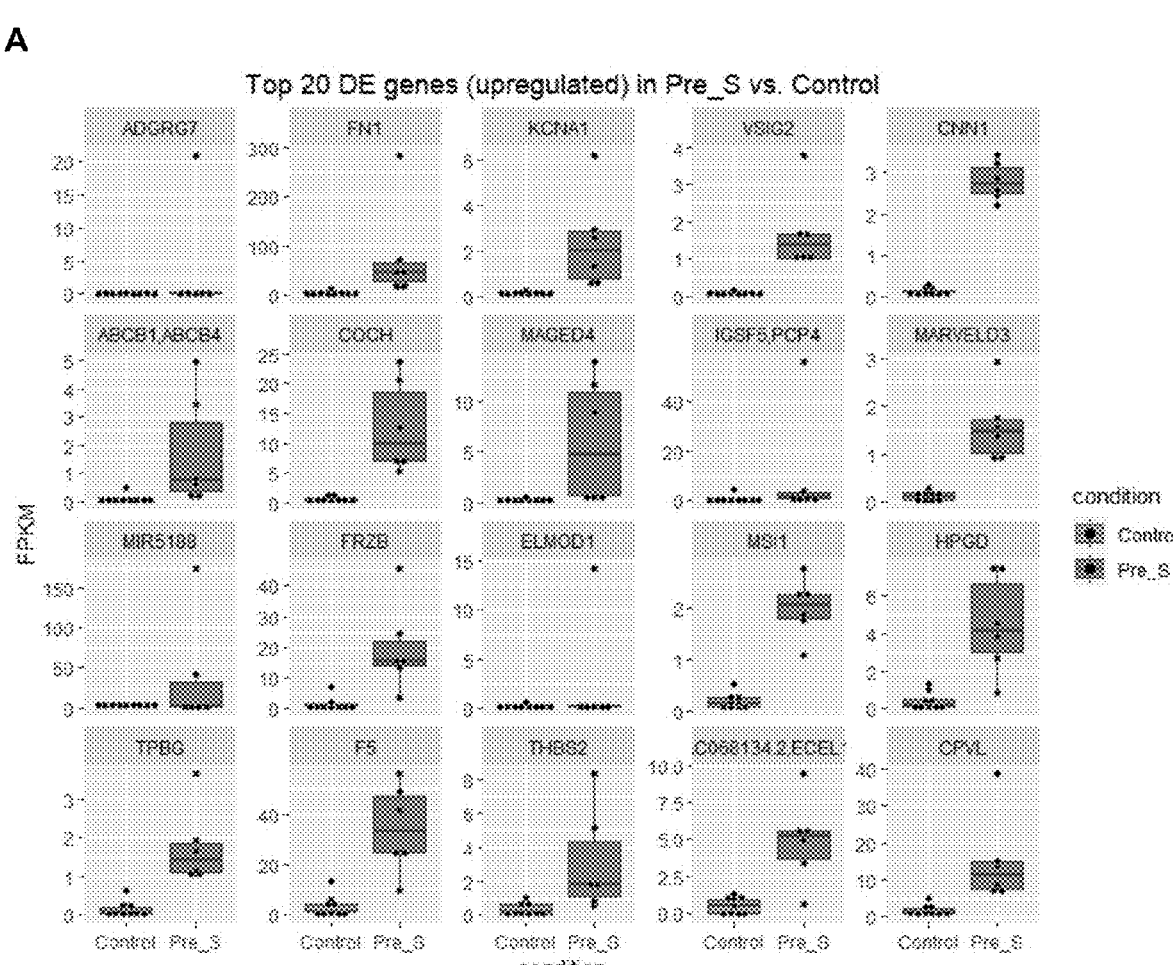
Figure 20:
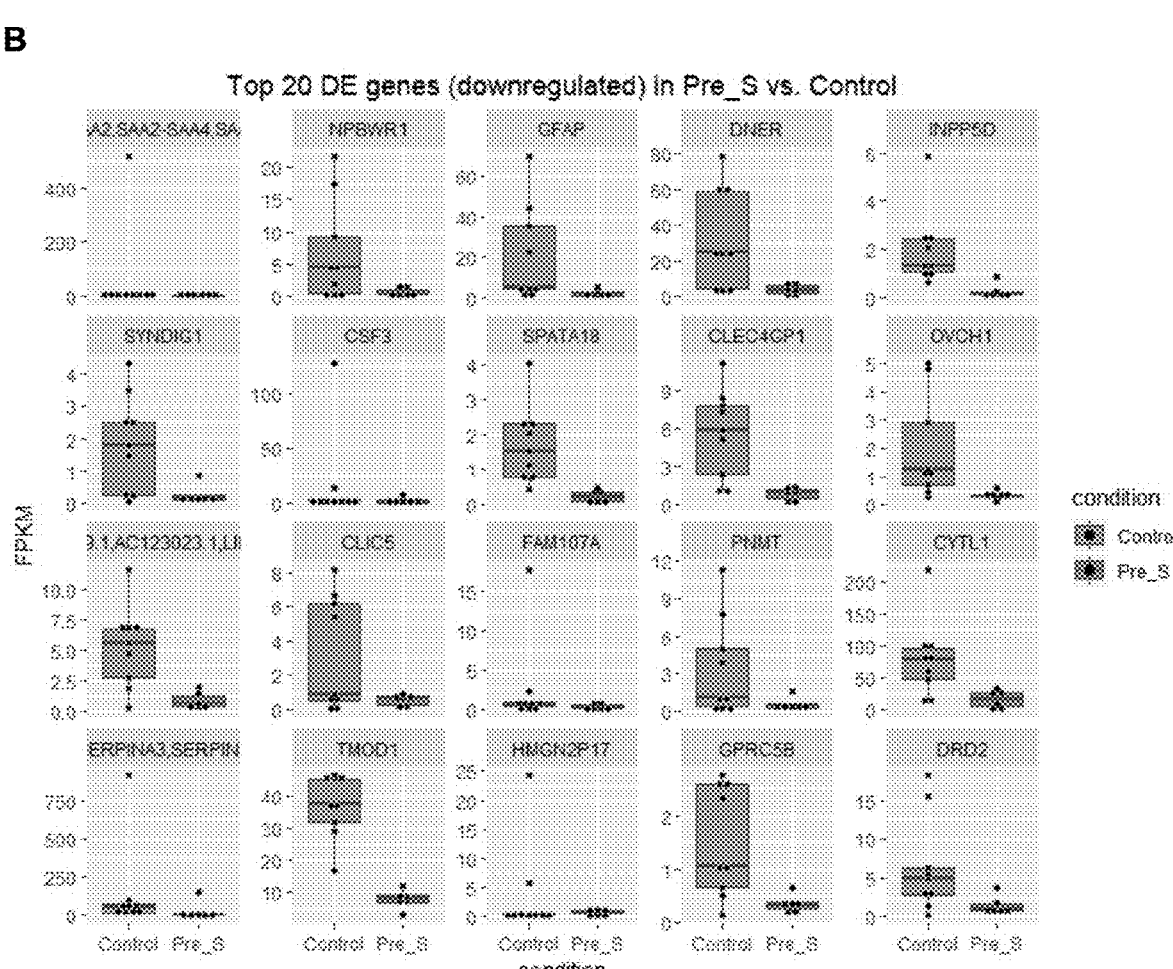

FIG. 20 shows top differentially expressed genes in Pre_S tissues. (A) Boxplot showing the level of top 20 upregulated differentially expressed genes in Pre_S tissue replicates. (B) Boxplot showing the level of top 20 downregulated differentially expressed genes in Pre_S tissue replicates. A total of 215 differentially expressed genes were identified in Pre_S vs. Control. FPKM>1.5, fold change>1.5, FDR<=0.05.

Figure 21:
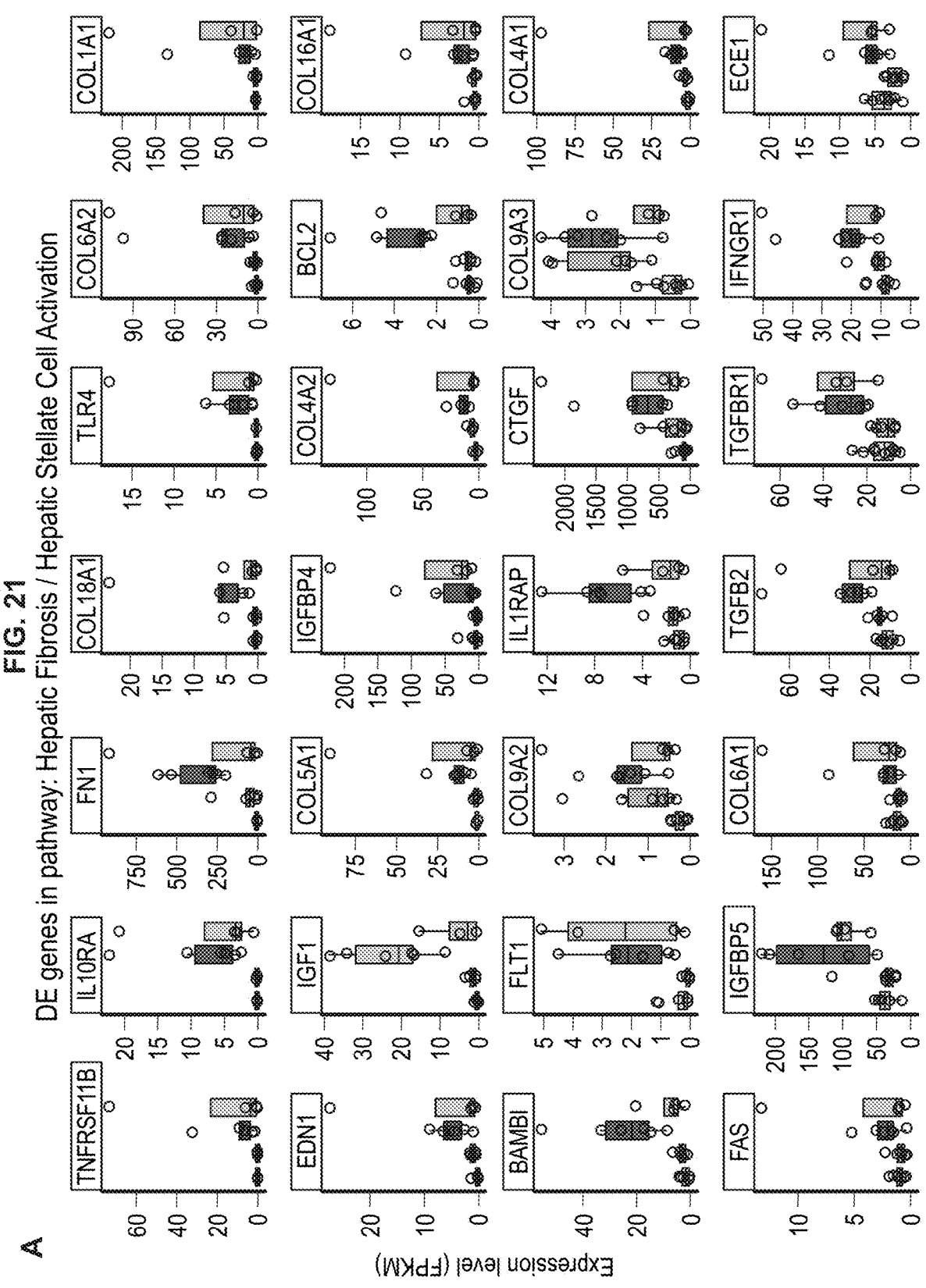
Figure 21:
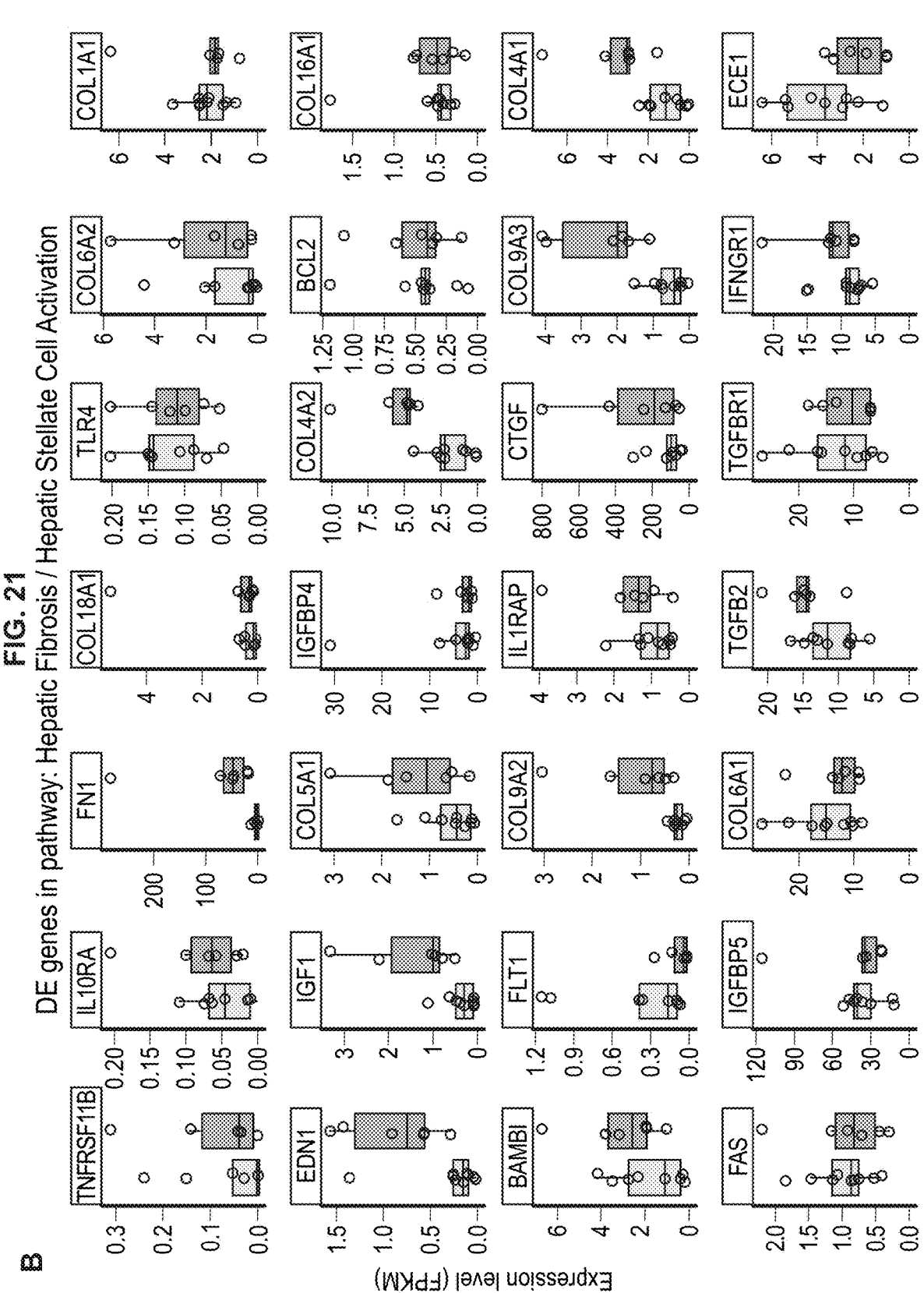
Figure 21:
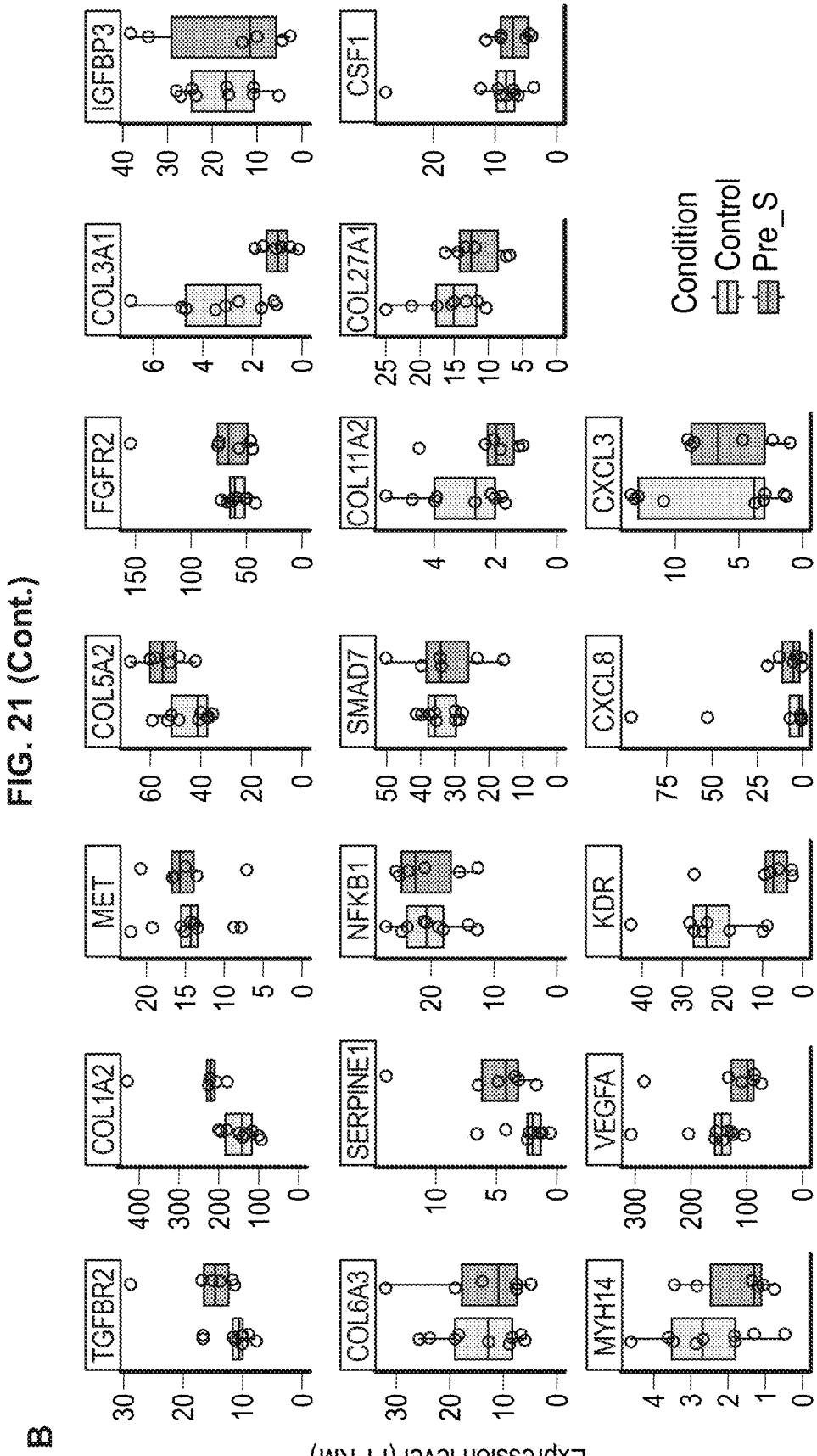
Figure 21:
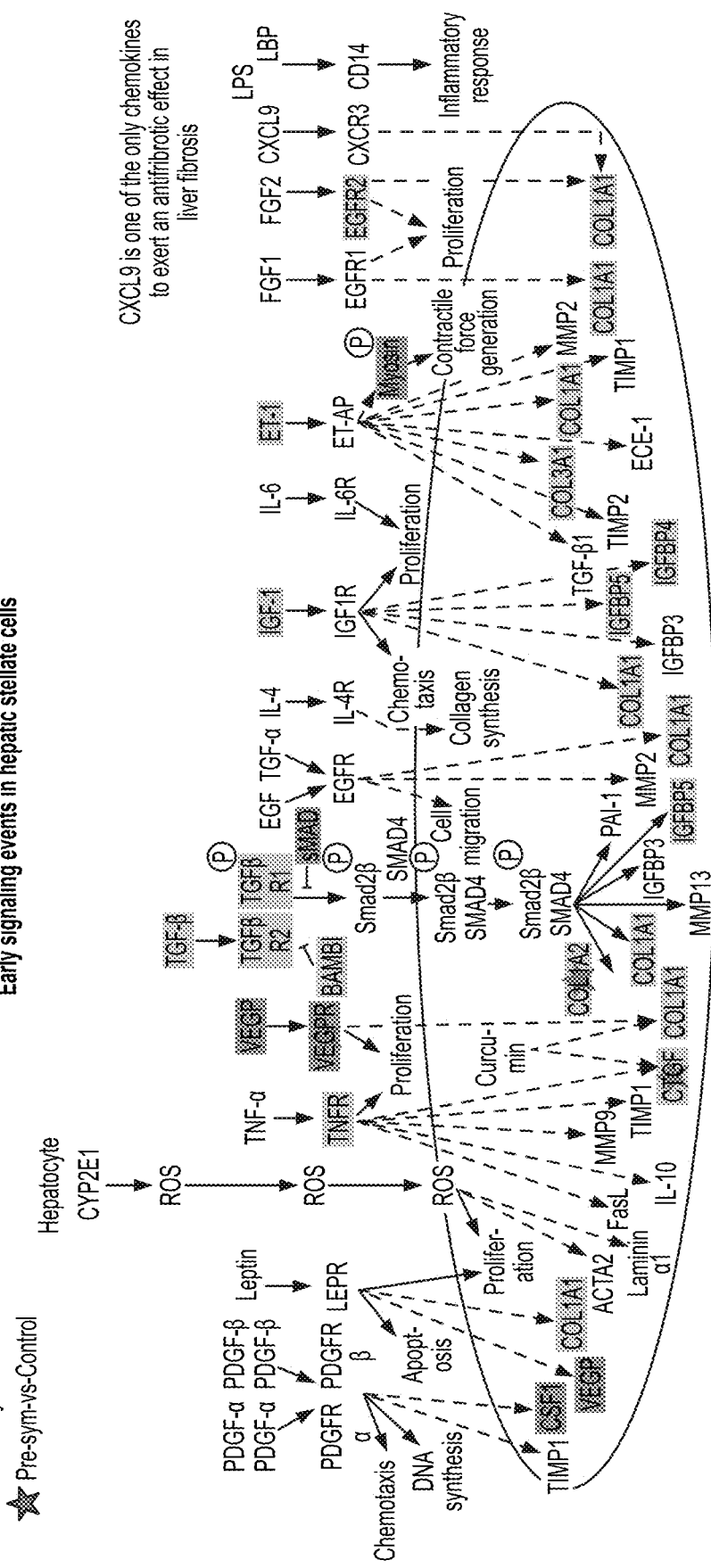
Figure 21:
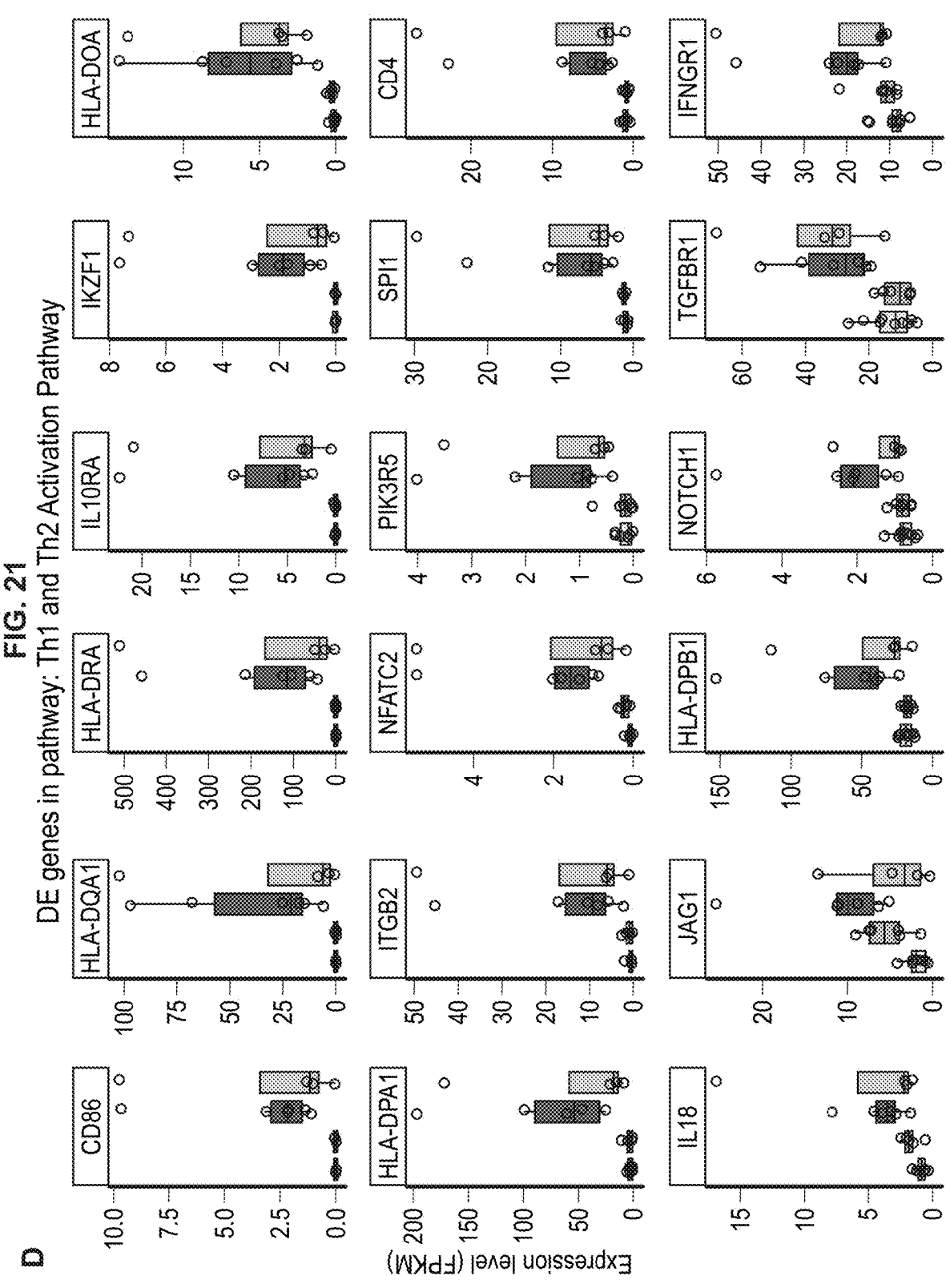
Figure 21:
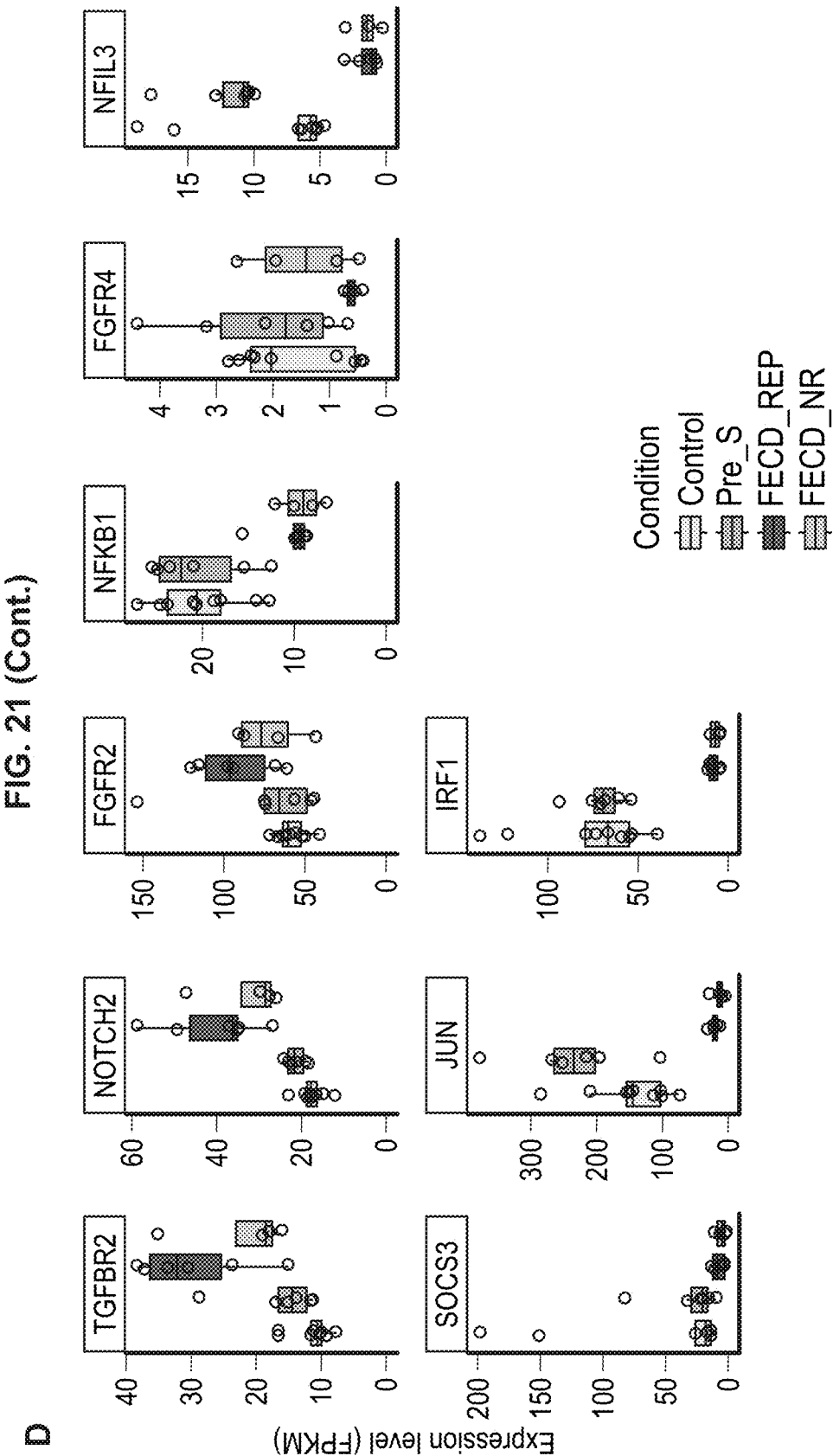
Figure 21:
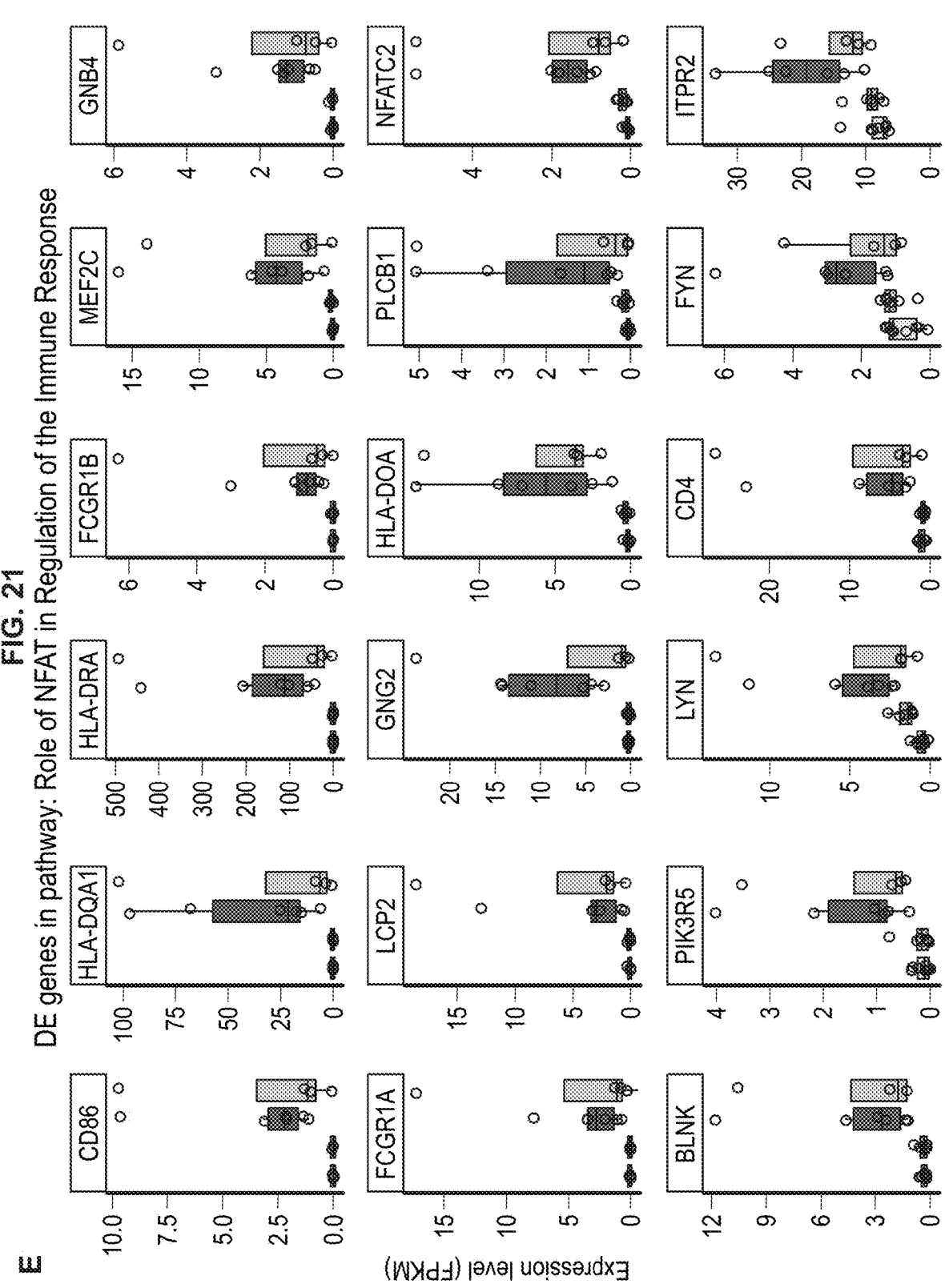
Figure 21:
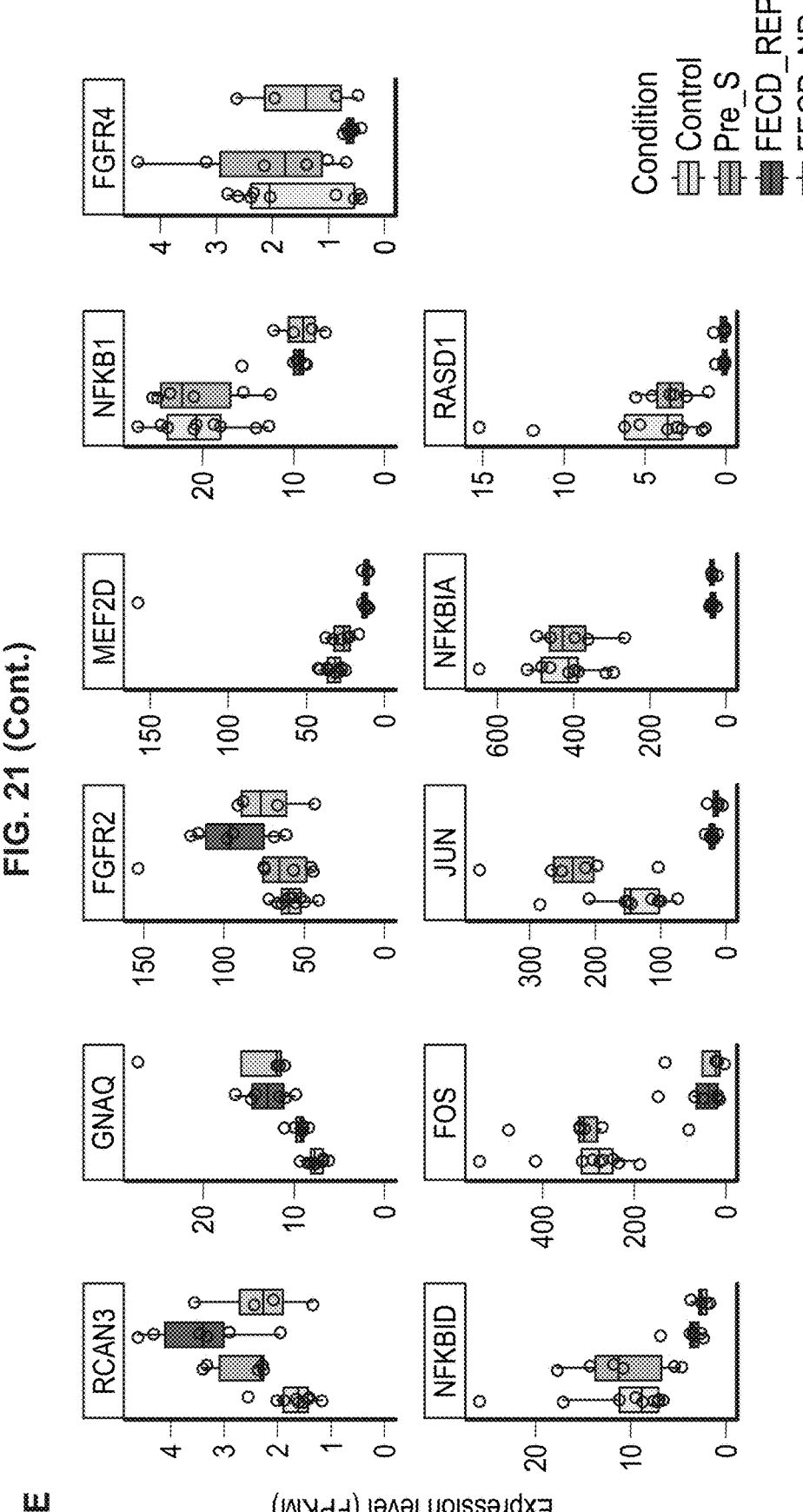
Figure 21:
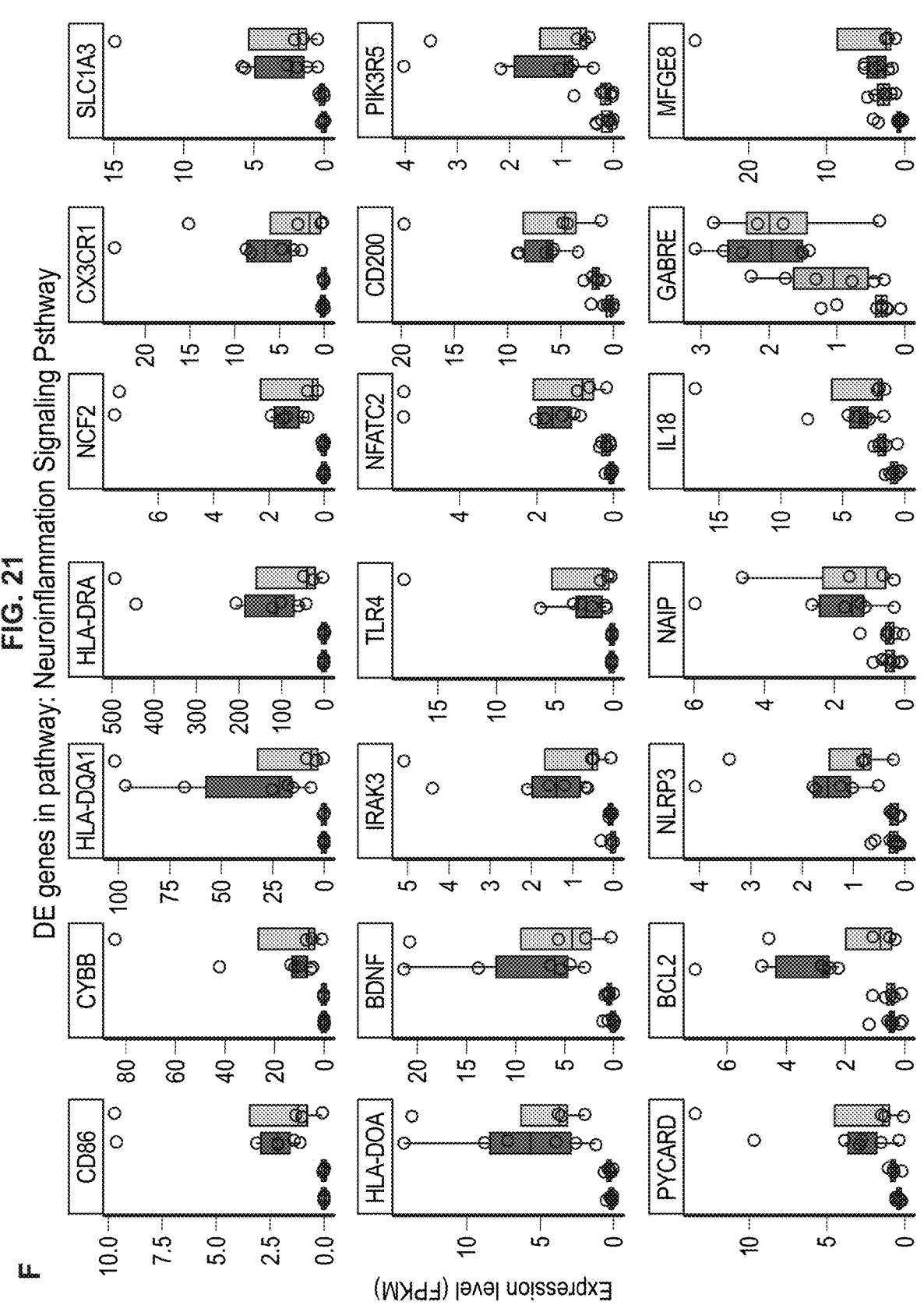
Figure 21:
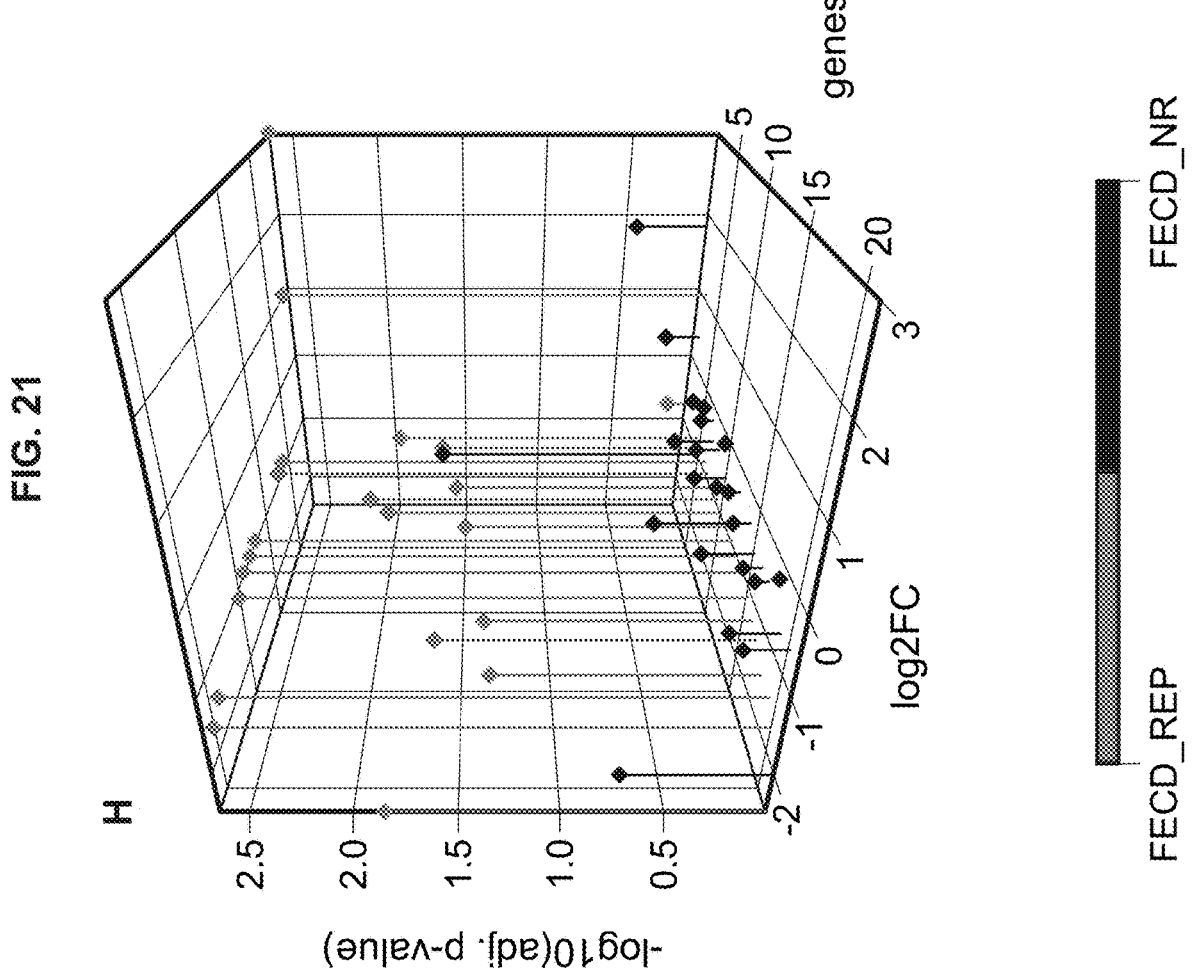

FIG. 21 shows detailed pathway analysis. (A). Expression profile of genes in hepatic fibrosis pathway, all cohorts. FPKM>1.5, fold change>1.5, FDR<=0.05. (B) Expression profile of genes in Hepatic fibrosis pathway for Pre_S cohort. FPKM>1.5, fold change>1.5, FDR<=0.05. First column in each gene panel is control, second column is Pre_S, third column is FEDC_REP, fourth column is FEDC_NR. (C) Diagram of hepatic fibrosis/hepatic stellate activation pathway based on the comparison of FECD_REP versus Control tissue. Differentially expressed genes that are upregulated are pink and downregulated genes are green. Stars mark genes that also change in Pre_S tissue compared to Control samples. (D) Th1/2 activation pathway. FPKM>1.5, fold change>1.5, FDR<=0.05. (E) Gene expression changes for NFAT pathway. FPKM>1.5, fold change>1.5, FDR<=0.05. (F) Neuroinflammation Signaling Pathway. FPKM>1.5, fold change>1.5, FDR<=0.05. (G) Volcano plot of DE genes involved in mitochondrial dysfunction in FECD_REP. (H) A scatter 3D plot showing a group of genes involved in mitochondrial dysfunction are differentially expressed in FECD_REP, but not in FECD_NR. X-axis: gene list, y-axis: log 2-fold change, z-axis: −log 10 (adjusted p-value).

FIG. 22 shows top 20 upregulated (left side) and top downregulated (right side) genes in (A) FECD_REP vs. Control; (B) FECD_NR vs. Control. Where Rna-seq analysis finds similar reads for two or more genes, those genes are listed together.

FIG. 23 shows the log 2FC values and adjusted p-values for 42 fibrosis-pathway associated genes in FECD_REP and Pre_S. These genes were found to be differentially expressed in FECD_REP. For a gene to be considered expressed, its expression level has to be higher than 1.5 FPKM. NA in the following table denotes that a gene is not expressed or its level<1.5 FPKM.

Figure 24:
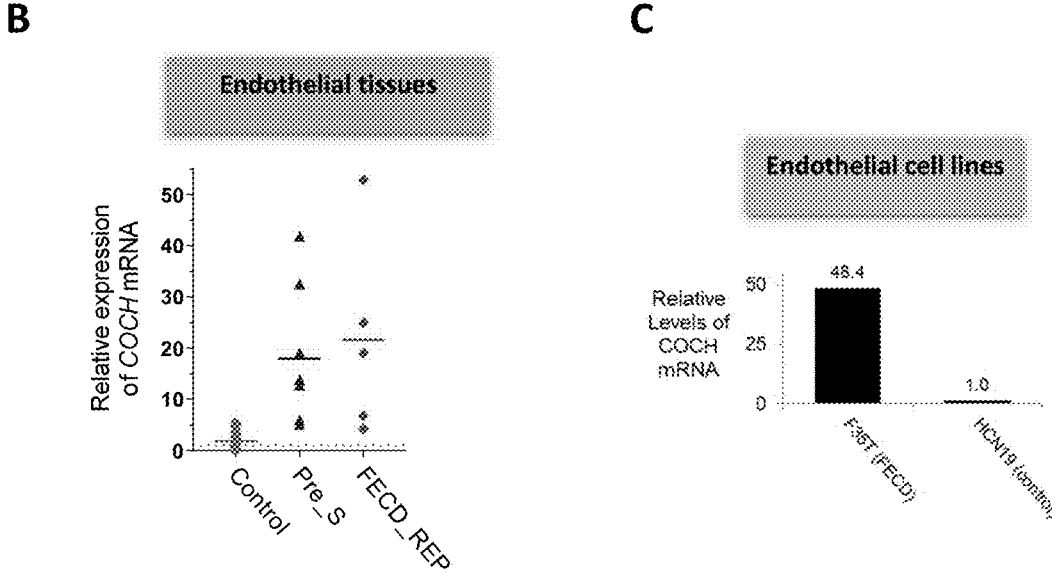

FIG. 24 shows COCH mRNA expression is up-regulated in FECD samples. (A) COCH expression is up-regulated in corneal endothelial cells from FECD/REP, FECD/NR or Pre_Sym corneal tissues analyzed by RNA-seq. (B) Higher COCH expressions are verified in endothelial cells from FECD/REP or Pre_Sym corneal tissues by qPCR analysis. (C) COCH expression is up-regulated in FECD endothelial cell line.

FIG. 25 shows TGFβ induces up-regulation of COCH. (A) COCH expression is up-regulated by adding increased concentration of TGFβ in HCN19 healthy control corneal endothelial cells. (B) TGFβ activated COCH in control corneal tissue.

FIG. 26 shows cochlin is a secreted protein. (A) Western blot image of cochlin detected in FECD (F35T) corneal endothelial cell culture media. HCN19, healthy control endothelial cell line. (B) The full length cochlin band is confirmed by siRNA knocking down in F35T culture media. si173, anti-cochlin siRNA; siCM, non-complementary control siRNA.

Figure 27:
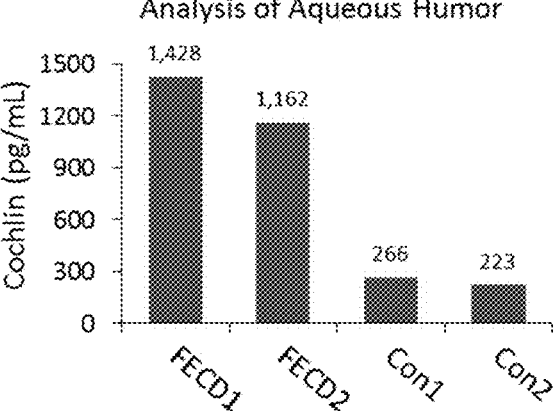

FIG. 27 shows secreted cochlin proteins were detected in FECD patient aqueous humor by ELISA assay.

FIG. 28 shows cochlin deposits in FECD patient corneal tissue by immunofluorescence. (A) Cochlin may deposit in Descemet's membrane of FECD patient cornea tissue. (B) Cochlin deposits in trabecular meshwork of FECD donor cornea samples. Cross sections 4056-19-4596, 4056-19-4540 are FECD samples without repeat expansion; 4056-19-4463 is considered pre-symptomatic, which has no guttae, but with expanded CTG repeat (CTG repeat number: 18,73).

The following detailed description is merely exemplary in nature and is not intended to limit the invention or the applications of its use.

Detection of an Increase of Expression of Marker Genes

Provided herein are methods of detecting pre-symptomatic, advanced, early-onset, or age-related (late-onset) Fuchs' endothelial corneal dystrophy (FECD), glaucoma, or other ocular diseases in a subject comprising detecting an increase of expression of one or more of ADGRG7, FN1, KCNA1, VSIG2, CNN1, ABCB1, ABCB4, COCH, MAGED4, IGSF5, PCP4, MARVELD3, MIR5188, FRZB, ELMOD1, MSI1, HPGD, TPBG, F5, THBS2, ECEL1P1/2, CPVL, LINC02258, CD86, DLK1, FOXF2, GMNC, GPR34, IGKV3-20, IGKV6D-21, TMEM255A, CDKN2A, CLEC5A, MARCH1, GPC3, HLA-DQA1, HLA-DRA, CYBB, GRM5, NOX4, IGKC, IGKJ1, IGKJ2, C3AR1, DCX, MMP2-AS1, LYVE1, FAM198B, FCGR1B, FOLR2, FCGR3A, TNFRSF11B, PSG4, KRT7, COL4A2, CTGF, COL9A3, COL1A2, FGFR2, NOTCH2, TGFBR1, IFNGR1, TGFBR2, NOTCH1, HLA-DPB1, IL18, JAG1, CD4, SPI1, PIK3R5, ITGB2, NFATC2, HLA-DPA1, HLA-DOA, IKZF1, IL10RA, MAPK10, BCL2, COL5A2, ROR2, ACKR1, CADM3, VIPR2, ADAM33, CADM3-AS1, TSHR, DPP10, CLIC6, TMEM30B, LGR6, CST4, ICA1, ALPK2, RARRES2, MMP19, DCDC2C, CST1, ITPRIPL1, WNT3, SLC5A1, ARSJ, GREB1L, SLC16A9, EPHB6, MROH9, ENOX1, PLAC9, KIF21B, ADAMTS12, ITIH5, ANXA3, PROS1, PTPN3, or DCLK1.

As used herein, the term "subject" refers to any individual or patient on which the methods disclosed herein are performed. The term "subject" can be used interchangeably with the term "individual" or "patient." The subject can be a mammal such as a human.

As used herein, the term "gene expression" or "expression" broadly refers to the level or presentation of a gene product in a cell, tissue, or subject. It should be appreciated that the gene product can be, for example, an RNA transcript or a protein. An RNA transcript can be one that encodes a protein. RNA transcripts can be non-protein-encoding, such as long non-coding RNA, long non-coding RNA between genes, non-coding RNA, miRNA, small nuclear RNA (snRNA), or other functional RNA.

As used herein, "detecting" or "measuring" means that a test or assay for detecting or measuring is performed. Such detection and/or measuring may result in a value of zero. Thus, if a test for detection or measuring results in a finding of no gene expression (expression of zero), the step of detecting or measuring the gene expression has nevertheless been performed.

RNA isolation and sequencing methods can be used to determine amounts of gene expression. Total RNA can be obtained using RNAseq, whole transcriptome sequencing using next generation DNA sequencing (NGS) technologies. The transcriptome is the complete set of transcripts in a cell, and their quantity, for a specific developmental stage or physiological condition. NGS can reveal very rare mRNA, splice variants, allelic variants, and SNPs.

In RNAseq, a population of RNA (total or fractionated, such as poly(A)+) is converted to a library of cDNA fragments with adaptors attached to one or both ends. Each molecule, with or without amplification, is then sequenced in a high-throughput manner to obtain short sequences from one end (single-end sequencing) or both ends (pair-end sequencing). The reads are typically 30-400 bp, depending on the DNA-sequencing technology used. In principle, any high-throughput sequencing technology can be used for RNA-Seq, including, but not limited to, the Illumina IG, Applied Biosystems SOLiD, and Roche 454 Life Science. Ribosomal RNA can be depleted from total RNA using kits such as Ribominus™ (Thermo Fischer Scientific). Following sequencing, the resulting reads are either aligned to a reference genome or reference transcripts, or assembled de novo without the genomic sequence to produce a genome-scale transcription map that consists of both the transcriptional structure and/or level of expression for each gene. Transcriptomic data obtained are can be confirmed with, for example, quantitative reverse transcription polymerase chain reaction (qRT-PCR) analysis.

Moreover, gene expression data can be obtained from, and comparisons can be made between, a number of different methods. Methods can include, for example, western blotting, northern blotting, real-time PCR, nucleic acid hybridization (e.g., microarrays), and nucleic acid amplification methods (e.g., RT-PCR).

The amount of gene expression can be determined in a test sample and compared to the expression of a previous test sample from the same subject or test sample or control level. "Control level" or "control" is an expression level of the same gene found in a subject not suffering from FECD, glaucoma, ocular disease, or another degenerative disease.

Upregulated gene expression in FECD, glaucoma, or other ocular diseases as described herein can be increased about 10%, 25%, 30%, 40%, 50%, 60%, 70%, 80%, 90% or more as compared to control level. Alternately, gene expression can be increased 1, 2, 3, 4, 5, 6, 7, 8, 9, 10, 20, 30, 40, 50, 60, 70, 80 or more fold compared to a control level.

Combinations of 2, 3, 4, 5, 6, 7, 8, 9, 10, 20, 30, 40, 50, 60, 70, 80, 90, 100 or more of the upregulated genes can be detected in methods of detecting expression marker genes. One or more of the genes described below can be upregulated in a patient having pre-symptomatic, advanced, early-onset, or age-related (late-onset) FECD, glaucoma, or other ocular diseases.

The ADGRG7 (GeneID: 84873) gene encodes for adhesion G Protein-Coupled Receptor G7, which is a member of the adhesion GPCR family.

The FN1 (GeneID: 2335) gene encodes for fibronectin 1, which is an extracellular matrix protein.

The KCNA1 (GeneID: 3736) gene encodes for potassium voltage-gated channel subfamily A member 1, which is a voltage-gated potassium channel that mediates transmembrane potassium transport in excitable membranes, present primarily in the brain and the central nervous system, but also present in the kidney and eye.

The VSIG2 (GeneID: 23584) gene encodes V-set and immunoglobulin domain-containing protein 2, which is a single-pass type I membrane protein that contains an Ig-like C2-type (immunoglobulin-like) domain and one Ig-like V-type (immunoglobulin-like) domain.

The CNN1 (GeneID: 1264) gene encodes Calponin-1, which is a thin filament-associated protein that is implicated in the regulation and modulation of smooth muscle contraction. It is capable of binding to actin, calmodulin and tropomyosin.

The ABCB1, ABCB4 (GeneID: 5243, GeneID: 5244) genes encode for ATP binding cassette subfamily B members 1 and 2, are members of the MDR/TAP subfamily of ATP-binding cassette transporters. These proteins transport molecules across extra- and intra-cellular membranes.

The COCH (GeneID: 1690) gene encodes cochlin, which is an extracellular matrix (ECM) protein highly abundant in the cochlea and vestibule of the inner ear, constituting the major non-collagen component of the ECM of the inner ear.

The MAGED4 (GeneID: 728239) gene encodes melanoma-associated antigen D4, which may enhance ubiquitin ligase activity of RING-type zinc finger-containing E3 ubiquitin-protein ligases.

The IGSF5, PCP4 (GeneID: 150084, GeneID: 5121) genes encode immunoglobulin superfamily member 5 and calmodulin regulator protein. IGSF5 is a protein that helps form an adhesion machinery at tight junctions and a PCP4 is protein that functions as a modulator of calcium-binding by calmodulin.

The MARVELD3 (GeneID: 91862) gene encodes MARVEL domain-containing protein 3, which functions as a component of tight junctions, plays a role in paracellular ion conductivity.

The MIR5188 (Gene ID: 100847004) gene is MicroRNA 5188.

The FRZB (GeneID: 2487) gene encodes secreted frizzled-related protein 3, which is a Wnt-binding protein.

The ELMOD1 (GeneID: 55531) gene encodes ELMO domain-containing protein 1, which acts as a GTPase-activating protein (GAP) toward guanine nucleotide exchange factors like ARL2, ARL3, ARF1 and ARF6, but not for GTPases outside the Arf family.

The MSI1 (GeneID: 4440) gene encodes RNA-binding protein Musashi homolog 1, which is an RNA binding protein that regulates the expression of target mRNAs at the translation level.

The HPGD (GeneID: 3248) gene encodes 15-hydroxy-prostaglandin dehydrogenase [NAD(+)], which is an enzyme.

The TPBG (GeneID: 7162) gene encodes trophoblast glycoprotein, which is an antagonist of Wnt/β-catenin signaling pathway.

The F5 (GeneID: 2153) gene encodes coagulation factor V, which is a regulator of hemostasis.

The THBS2 (GeneID: 7058) gene encodes thrombospondin-2, which is a disulfide-linked homotrimeric glycoprotein that mediates cell-to-cell and cell-to-matrix interactions.

ECEL1P1&2 (GeneID: 100131546, GeneID: 347694), endothelin converting enzyme like 1 pseudogene 1, endothelin converting enzyme like 1 pseudogene 2, which are pseudo genes.

The CPVL (GeneID: 54504) gene encodes a carboxypeptidase and bears strong sequence similarity to serine carboxypeptidases.

LINC02258 (Gene ID: 110806294) (Long Intergenic Non-Protein Coding RNA 2258) is an RNA Gene, and is affiliated with the lncRNA class.

The CD86 (GeneID: 942) gene encodes type I membrane protein that is a member of the immunoglobulin superfamily. Alternative splicing results in two transcript variants encoding different isoforms.

The DLK1 (GeneID: 8788) gene encodes a transmembrane protein that contains multiple epidermal growth factor repeats that functions as a regulator of cell growth.

The FOXF2 (GeneID: 2295) gene encodes forkhead box protein F2, which is a probable transcription activator for a number of lung-specific genes.

The GMNC (GeneID: 647309) gene encodes Geminin coiled-coil domain-containing protein 1, which regulates DNA replication.

The GPR34 (GeneID: 2857) gene encodes probably G-protein coupled receptor 34.

The IGKV3-20 (GeneID: 28912) gene encodes Immunoglobulin Kappa Variable 3-20, which is part of the V region of the variable domain of immunoglobulin light chains that participates in the antigen recognition.

The IGKV6D-21 (Gene ID: 28870) gene encodes Immunoglobulin Kappa Variable 6-21, which is part of the V region of the variable domain of immunoglobulin light chains that participates in the antigen recognition.

The TMEM255A (GeneID: 55026) gene encodes transmembrane protein 255A.

The CDKN2A (GeneID: 1029) (cyclin-dependent kinase inhibitor 2A) gene encodes two proteins, including the INK4 family member p16 (or p16INK4a) and p14arf, which both act as tumor suppressors by regulating the cell cycle.

The CLEC5A (GeneID: 23601) gene encodes a member of the C-type lectin/C-type lectin-like domain (CTL/CTLD) superfamily.

The MARCH1 (Gene ID: 55016) gene encodes E3 ubiquitin-protein ligase MARCHF1, which is an E3 ubiquitin-protein ligase that mediates ubiquitination of TFRC, CD86, FAS and MHC class II proteins, such as HLA-DR alpha and beta, and promotes their subsequent endocytosis and sorting to lysosomes via multivesicular bodies.

The GPC3 (GeneID: 2719) gene encodes Glypican-3, which is a cell surface proteoglycan that bears heparan sulfate.

The HLA-DQA1 (GeneID: 3117) gene encodes HLA class II histocompatibility antigen, DQ alpha 1 chain, which binds peptides derived from antigens that access the endocytic route of antigen presenting cells (APC) and presents them on the cell surface for recognition by the CD4 T-cells.

The HLA-DRA (GeneID: 3122) gene encodes HLA class II histocompatibility antigen, DR alpha chain, which binds peptides derived from antigens that access the endocytic route of antigen presenting cells (APC) and presents them on the cell surface for recognition by the CD4 T-cells.

The CYBB (GeneID: 1536) gene encodes Cytochrome b-245 heavy chain, which is a critical component of the membrane-bound oxidase of phagocytes that generates superoxide.

GRM5, NOX4, (GeneID: 2915, GeneID: 50507) glutamate metabotropic receptor 5, NADPH oxidase 4.

IGKC, IGKJ1, IGKJ2, (GeneID: 3514, GeneID: 28950, GeneID: 28949) (immunoglobulin kappa constant, immunoglobulin kappa joining 1, immunoglobulin kappa joining 2).

The C3AR1 (GeneID: 719) gene encodes C3a anaphylatoxin chemotactic receptor, which is a receptor for the chemotactic and inflammatory peptide anaphylatoxin C3a.

The DCX (GeneID: 1641) gene encodes Neuronal migration protein doublecortin, which is a microtubule-associated protein required for initial steps of neuronal dispersion and cortex lamination during cerebral cortex development.

MMP2-AS1, (Gene ID: 107984884) MMP2 antisense RNA 1, is non-coding RNA.

The LYVE1 (GeneID: 10894) gene encodes Lymphatic vessel endothelial hyaluronan receptor 1, which is a type I integral membrane glycoprotein. The encoded protein acts as a receptor and binds to both soluble and immobilized hyaluronan.

The FAM198B (Gene ID: 51313) gene encodes Golgi-associated kinase 1B.

The FCGR1B (Gene ID: 2210) is called the Fc Fragment of IgG Receptor Ib and it is a pseudogene.

The FOLR2 (Gene ID: 2350) gene encodes Folate receptor beta, which is a member of the folate receptor (FOLR) family.

The FCGR3A (Gene ID: 2214; called Fc Fragment of IgG Receptor 111a) gene encodes a receptor for the Fc portion of immunoglobulin G, and it is involved in the removal of antigen-antibody complexes from the circulation, as well as other responses, including antibody dependent cellular mediated cytotoxicity and antibody dependent enhancement of virus infections.

The TNFRSF11B (Gene ID: 4982) gene encodes Tumor necrosis factor receptor superfamily member 11B, which a cytokine receptor of the tumor necrosis factor (TNF) receptor superfamily.

The PSG4 (Gene ID: 5672) gene encodes a pregnancy-specific glycoprotein (PSG).

The KRT7 (Gene ID: 51350) gene encodes Keratin, type II cytoskeletal 7, which blocks interferon-dependent interphase and stimulates DNA synthesis in cells.

The COL4A2 (GeneID: 1284) gene is called collagen type IV alpha 2 chain, and it encodes a protein which is a structural component of basement membranes.

The CTGF (GeneID: 1490) gene encodes connective tissue growth factor, which is a growth factor related to the ECM.

The COL9A3 (GeneID: 1299) gene encodes collagen type IX alpha 3 chain, which is an ECM protein.

The COL1A2 (GeneID: 1278) gene encodes collagen type I alpha 2 chain, which is a fibrillar forming collagen.

The FGFR2, (GeneID: 2263) gene encodes fibroblast growth factor receptor 2, which is a member of the fibroblast growth factor receptor family, where amino acid sequence is highly conserved between members and throughout evolution.

The NOTCH2 (GeneID: 4853) gene encodes notch receptor 2, which a member of the Notch family. Members of this Type 1 transmembrane protein family share structural characteristics including an extracellular domain consisting of multiple epidermal growth factor-like (EGF) repeats, and an intracellular domain consisting of multiple, different domain types.

The TGFBR1 (Gene ID: 7046) gene encodes transforming growth factor beta receptor 1, which forms a heteromeric complex with type II TGF-beta receptors when bound to TGF-beta, transducing the TGF-beta signal from the cell surface to the cytoplasm. The encoded protein is a serine/threonine protein kinase.

The IFNGR1 (Gene ID: 3459) gene encodes interferon gamma receptor 1, which is the ligand-binding chain (alpha) of the gamma interferon receptor. Human interferon-gamma receptor is a heterodimer of IFNGR1 and IFNGR2.

The TGFBR2 (Gene ID: 7048) gene encodes transforming growth factor beta receptor 2, which is a transmembrane protein that has a protein kinase domain, forms a heterodimeric complex with TGF-beta receptor type-1, and binds TGF-beta. This receptor/ligand complex phosphorylates proteins, which then enter the nucleus and regulate the transcription of genes related to cell proliferation, cell cycle arrest, wound healing, immunosuppression, and tumorigenesis.

The NOTCH1 (Gene ID: 4851) gene encodes notch receptor 1, which is a member of the NOTCH family of proteins. Members of this Type I transmembrane protein family share structural characteristics including an extracellular domain consisting of multiple epidermal growth factor-like (EGF) repeats, and an intracellular domain consisting of multiple different domain types.

The HLA-DPB1 (Gene ID: 3115) gene encodes major histocompatibility complex, class II, DP beta 1, which belongs to the HLA class II beta chain paralogues. This class II molecule is a heterodimer consisting of an alpha (DPA) and a beta chain (DPB), both anchored in the membrane. It plays a central role in the immune system by presenting peptides derived from extracellular proteins.

The IL18 (Gene ID: 3606) gene encodes interleukin 18, which is a proinflammatory cytokine of the IL-1 family that is constitutively found as a precursor within the cytoplasm of a variety of cells including macrophages and keratinocytes.

The JAG1 (Gene ID: 182) gene encodes jagged canonical Notch ligand 1, which is the human homolog of the Drosophilia jagged protein. Human jagged 1 is the ligand for the receptor notch 1, the latter is involved in signaling processes.

The CD4 (Gene ID: 920) gene encodes CD4 molecule, which is the CD4 membrane glycoprotein of T lymphocytes. The CD4 antigen acts as a coreceptor with the T-cell receptor on the T lymphocyte to recognize antigens displayed by an antigen presenting cell in the context of class II MHC molecules.

The SPI1 (Gene ID: 6688) gene encodes Spi-1 proto-oncogene, which is an ETS-domain transcription factor that activates gene expression during myeloid and B-lymphoid cell development. The nuclear protein binds to a purine-rich sequence known as the PU-box found near the promoters of target genes, and regulates their expression in coordination with other transcription factors and cofactors.

The PIK3R5 (Gene ID: 23533) gene encodes phospho-inositide-3-kinase regulatory subunit 5. Phosphatidylinositol 3-kinases (PI3Ks) phosphorylate the inositol ring of phosphatidylinositol at the 3-prime position, and play important roles in cell growth, proliferation, differentiation, motility, survival and intracellular trafficking. The PI3Ks are divided into three classes: I, II and III, and only the class I PI3Ks are involved in oncogenesis. This gene encodes the 101 kD regulatory subunit of the class I PI3K gamma complex, which is a dimeric enzyme, consisting of a 110 kD catalytic subunit gamma and a regulatory subunit of either 55, 87 or 101 kD. This protein recruits the catalytic subunit from the cytosol to the plasma membrane through high-affinity interaction with G-beta-gamma proteins.

The ITGB2 (Gene ID: 3689) gene encodes integrin subunit beta 2, which is an integrin beta chain, which combines with multiple different alpha chains to form different integrin heterodimers.

The NFATC2 (Gene ID: 4773) gene encodes nuclear factor of activated T cells 2, which is a member of the nuclear factor of activated T cells (NFAT) family.

The HLA-DPA1 (Gene ID: 3113) gene encodes major histocompatibility complex, class II, DP alpha 1, which belongs to the HLA class II alpha chain paralogues. This class II molecule is a heterodimer consisting of an alpha (DPA) and a beta (DPB) chain, both anchored in the membrane.

The HLA-DOA (Gene ID: 3111) gene encodes major histocompatibility complex, class II, DO alpha, which belongs to the HLA class II alpha chain paralogues. HLA-DOA forms a heterodimer with HLA-DOB.

The IKZF1 (Gene ID: 10320) gene encodes IKAROS family zinc finger 1, which is a transcription factor that belongs to the family of zinc-finger DNA-binding proteins associated with chromatin remodeling.

The IL10RA (Gene ID: 3587) gene encodes interleukin 10 receptor subunit alpha, which is a receptor for interleukin 10. This protein is structurally related to interferon receptors.

The MAPK10 (Gene ID: 5602) gene encodes mitogen-activated protein kinase 10, which is a member of the MAP kinase family. This kinase is specifically expressed in a subset of neurons in the nervous system, and is activated by threonine and tyrosine phosphorylation.

The BCL2 (Gene ID: 596) gene encodes BCL2 apoptosis regulator, which an integral outer mitochondrial membrane protein that blocks the apoptotic death of some cells such as lymphocytes.

The COL5A2 (Gene ID: 1290) gene encodes collagen type V alpha 2 chain, which is an alpha chain for one of the low abundance fibrillar collagens.

The ROR2 (Gene ID: 4920) gene encodes receptor tyrosine kinase like orphan receptor 2. The protein encoded by this gene is a receptor protein tyrosine kinase and type I transmembrane protein that belongs to the ROR subfamily of cell surface receptors.

The ACKR1 (Gene ID: 2532) gene encodes atypical chemokine receptor 1 (Duffy blood group). The protein encoded by this gene is a glycosylated membrane protein and a non-specific receptor for several chemokines.

The CADM3 (Gene ID: 57863) gene encodes cell adhesion molecule 3. The protein encoded by this gene is a calcium-independent cell-cell adhesion protein that can form homodimers or heterodimers with other nectin proteins. The encoded protein has both homophilic and heterophilic cell-cell adhesion activity.

The VIPR2 (Gene ID: 7434) gene encodes vasoactive intestinal peptide receptor 2. This gene encodes a receptor for vasoactive intestinal peptide, a small neuropeptide. Vasoactive intestinal peptide is involved in smooth muscle relaxation, exocrine and endocrine secretion, and water and ion flux in lung and intestinal epithelia.

The ADAM33 (Gene ID: 80332) gene encodes DAM metallopeptidase domain 33. This gene encodes a member of the ADAM (a disintegrin and metalloprotease domain) family. Members of this family are membrane-anchored proteins structurally related to snake venom disintegrins, and have been implicated in a variety of biological processes involving cell-cell and cell-matrix interactions, including fertilization, muscle development, and neurogenesis. This protein is a type I transmembrane protein implicated in asthma and bronchial hyperresponsiveness.

The CADM3-AS1 (Gene ID: 100131825) gene encodes CADM3 antisense RNA 1.

The TSHR (Gene ID: 7253) gene encodes thyroid stimulating hormone receptor. The protein encoded by this gene is a membrane protein and a major controller of thyroid cell metabolism. The encoded protein is a receptor for thyrothropin and thyrostimulin, and its activity is mediated by adenylate cyclase.

The DPP10 (Gene ID: 57628) gene encodes dipeptidyl peptidase like 10. This gene encodes a single-pass type II membrane protein that is a member of the S9B family in clan SC of the serine proteases. This protein has no detectable protease activity, most likely due to the absence of the conserved serine residue normally present in the catalytic domain of serine proteases. However, it does bind specific voltage-gated potassium channels and alters their expression and biophysical properties.

The CLIC6 (Gene ID: 54102) gene encodes chloride intracellular channel 6. This gene encodes a member of the chloride intracellular channel family of proteins.

The TMEM30B (Gene ID: 161291) gene encodes transmembrane protein 30B.

The LGR6 (Gene ID: 59352) gene encodes leucine rich repeat containing G protein-coupled receptor 6. This gene encodes a member of the leucine-rich repeat-containing subgroup of the G protein-coupled 7-transmembrane protein superfamily. The encoded protein is a glycoprotein hormone receptor with a large N-terminal extracellular domain that contains leucine-rich repeats important for the formation of a horseshoe-shaped interaction motif for ligand binding.

The CST4 (Gene ID: 1472) gene encodes cystatin S. The cystatin superfamily encompasses proteins that contain multiple cystatin-like sequences. This gene is located in the cystatin locus and encodes a type 2 salivary cysteine peptidase inhibitor. The protein is an S-type cystatin, based on its high level of expression in saliva, tears and seminal plasma.

The ICA1 (Gene ID: 3382) gene encodes islet cell autoantigen 1. This gene encodes a protein with an arfaptin homology domain that is found both in the cytosol and as membrane-bound form on the Golgi complex and immature secretory granules.

The ALPK2 (Gene ID: 115701) gene encodes alpha kinase 2.

The RARRES2 (Gene ID: 5919) gene encodes retinoic acid receptor responder 2. This gene encodes a secreted chemotactic protein that initiates chemotaxis via the ChemR23 G protein-coupled seven-transmembrane domain ligand.

The MMP19 (Gene ID: 4327) gene encodes matrix metallopeptidase 19. This gene encodes a member of a family of proteins that are involved in the breakdown of extracellular matrix in normal physiological processes, such as embryonic development, reproduction, and tissue remodeling, as well as in disease processes, such as arthritis and metastasis. The encoded protein is secreted as an inactive proprotein, which is activated upon cleavage by extracellular proteases.

The DCDC2C (Gene ID: 728597) gene encodes doublecortin domain containing 2C.

The CST1 (Gene ID: 1469) gene encodes cystatin SN. The cystatin superfamily encompasses proteins that contain multiple cystatin-like sequences. This gene is located in the cystatin locus and encodes a cysteine proteinase inhibitor found in saliva, tears, urine, and seminal fluid.

The ITPRIPL1 (Gene ID: 150771) gene encodes ITPRIP like 1.

The WNT3 (Gene ID: 7473) gene encodes Wnt family member 3. The WNT gene family consists of structurally related genes which encode secreted signaling proteins. This gene is a member of the WNT gene family.

The SLC5A1 (Gene ID: 6523) gene encodes solute carrier family 5 member 1. This gene encodes a member of the sodium-dependent glucose transporter (SGLT) family. The encoded integral membrane protein is the primary mediator of dietary glucose and galactose uptake from the intestinal lumen.

The ARSJ (Gene ID: 79642) gene encodes arylsulfatase family member J.

The GREB1L (Gene ID: 80000) gene encodes GREB1 like retinoic acid receptor coactivator.

The SLC16A9 (Gene ID: 220963) gene encodes solute carrier family 16 member 9.

The EPHB6 (Gene ID: 2051) gene encodes EPH receptor B6. This gene encodes a member of a family of transmembrane proteins that function as receptors for ephrin-B family proteins. Unlike other members of this family, the encoded protein does not contain a functional kinase domain. Activity of this protein can influence cell adhesion and migration.

The MROH9 (Gene ID: 80133) gene encodes maestro heat like repeat family member 9.

The ENOX1 (Gene ID: 55068) gene encodes ecto-NOX disulfide-thiol exchanger 1. The protein encoded by this gene is involved in plasma membrane electron transport pathways. The encoded protein has both a hydroquinone (NADH) oxidase activity and a protein disulfide-thiol interchange activity. The two activities cycle with a periodicity of 24 minutes, with one activity being at its peak when the other is at its lowest.

The PLAC9 (Gene ID: 219348) gene encodes placenta associated 9.

The KIF21B (Gene ID: 23046) gene encodes kinesin family member 21B. This gene encodes a member of the kinesin superfamily. Kinesins are ATP-dependent microtubule-based motor proteins that are involved in the intracellular transport of membranous organelles.

The ADAMTS12 (Gene ID: 81792) gene encodes ADAM metallopeptidase with thrombospondin type 1 motif 12. This gene encodes a member of the ADAMTS (a disintegrin and metalloproteinase with thrombospondin motifs) protein family. Members of the family share several distinct protein modules, including a propeptide region, a metalloproteinase domain, a disintegrin-like domain, and a thrombospondin type 1 (TS-1) motif. Individual members of this family differ in the number of C-terminal TS-1 motifs, and some have unique C-terminal domains. The enzyme encoded by this gene contains eight TS-1 motifs.

The ITIH5 (Gene ID: 80760) gene encodes inter-alpha-trypsin inhibitor heavy chain 5. This gene encodes a heavy chain component of one of the inter-alpha-trypsin inhibitor (ITI) family members. ITI proteins are involved in extracellular matrix stabilization and in the prevention of tumor metastasis. They are also structurally related plasma serine protease inhibitors and are composed of a light chain and varying numbers of heavy chains.

The ANXA3 (Gene ID: 306) gene encodes annexin A3. This gene encodes a member of the annexin family. Members of this calcium-dependent phospholipid-binding protein family play a role in the regulation of cellular growth and in signal transduction pathways. This protein functions in the inhibition of phopholipase A2 and cleavage of inositol 1,2-cyclic phosphate to form inositol 1-phosphate.

The PROS1 (Gene ID: 5627) gene encodes protein S. This gene encodes a vitamin K-dependent plasma protein that functions as a cofactor for the anticoagulant protease, activated protein C (APC) to inhibit blood coagulation. It is found in plasma in both a free, functionally active form and also in an inactive form complexed with C4b-binding protein.

The PTPN3 (Gene ID: 5774) gene encodes protein tyrosine phosphatase non-receptor type 3. The protein encoded by this gene is a member of the protein tyrosine phosphatase (PTP) family. PTPs are known to be signaling molecules that regulate a variety of cellular processes including cell growth, differentiation, mitotic cycle, and oncogenic transformation. This protein contains a C-terminal PTP domain and an N-terminal domain homologous to the band 4.1 superfamily of cytoskeletal-associated proteins.

The DCLK1 (Gene ID: 9201) gene encodes doublecortin like kinase 1. This gene encodes a member of the protein kinase superfamily and the doublecortin family. The protein encoded by this gene contains two N-terminal doublecortin domains, which bind microtubules and regulate microtubule polymerization, a C-terminal serine/threonine protein kinase domain, which shows substantial homology to Ca2+/calmodulin-dependent protein kinase, and a serine/proline-rich domain in between the doublecortin and the protein kinase domains, which mediates multiple protein-protein interactions.

Detection of a Decrease of Expression of Marker Genes

Provided herein are methods of detecting pre-symptomatic, advanced, early-onset, or age-related (late-onset) Fuchs' endothelial corneal dystrophy (FECD), glaucoma, and other ocular diseases in a subject comprising detecting a decrease of expression of one or more of SAA2/4, NPBWR1, GFAP, DNER, INPP5D, SYNDIG1, CSF3, SPATA18, CLEC4GP1, OVCH1, LINC01811, CLIC5, FAM107A, PNMT, CYTL1, SERPINA3/4/5, TMOD1, HMGN2P17, GPRC5B, DRD2, PSPHP1, CDH12, IL17REL, ARC, UBE2W, RNU5E-1, CXCL8, LINC00881, LINC02029, CXCL3, RNU2-63P, CXCL2, RASD1, RNU6-1208P, UTY, CD24P4, RNU6-255P, TTTY14, KDM5DP1, TTTY10, NLGN4Y, RNU1-59P, ZFY, STK40, RNU5B-1, LINC01783, RNU1-6P, RNU1-5P, EPS8L1, LUM, KDR, SOD3, IRF1, JUN, SOCS3, NFIL3, FGFR4, NFKB1, SOD2, MAOA, CYCS, SNCA, PDHA1, UQCRH, COX7B, COX5B, NDUFV1, UQCRC2, NDUFA1, CYC1, UQCRB, VDAC2, COX4I1, SDHB, COX6B1, or MAOB.

The amount of gene expression can be determined in a test sample and compared to the amount of gene expression in a previous test sample from the same subject or test sample or control level.

Downregulated gene expression in FECD, glaucoma, or other ocular diseases as described herein can be decreased about 10%, 25%, 30,%, 40%, 50%, 60%, 70%, 80%, 90%, or more compared to a control level. Alternately, gene expression can be decreased 1, 2, 3, 4, 5, 6, 7, 8, 9, 10, 20, 30, 40, 50, 60, 70, 80 or more fold compared to a control level.

Combinations of 2, 3, 4, 5, 6, 7, 8, 9, 10, 20, 30, 40, 50, 60, 70, or more of the downregulated genes can be detected in methods of detecting expression marker genes. One or more of the genes described below can be downregulated in a patient having FECD, glaucoma, or other ocular diseases.

SAA2/4 (Gene ID: 6289, Gene ID: 6291) are serum amyloid A2 and serum amyloid A4. The SAA2 gene encodes a member of the serum amyloid A family of apolipoproteins.

NPBWR1 (GeneID: 2831) is neuropeptides B and W receptor 1.

GFAP (Gene ID: 2670) is glial fibrillary acidic protein. This gene encodes one of the major intermediate filament proteins of mature astrocytes. It is used as a marker to distinguish astrocytes from other glial cells during development.

DNER (Gene ID: 92737) is delta/notch like EGF repeat containing.

INPP5D (Gene ID: 3635) is inositol polyphosphate-5-phosphatase D. This gene is a member of the inositol polyphosphate-5-phosphatase (INPP5) family and encodes a protein with an N-terminal SH2 domain, an inositol phosphatase domain, and two C-terminal protein interaction domains.

SYNDIG1 (Gene ID: 79953) is synapse differentiation inducing 1. This gene encodes a protein that belongs to the interferon-induced transmembrane family of proteins.

CSF3 (Gene ID: 1440) is colony stimulating factor 3. This gene encodes a member of the IL-6 superfamily of cytokines.

SPATA18 (Gene ID: 132671) is spermatogenesis associated 18. This gene encodes a p53-inducible protein that is able to induce lysosome-like organelles within mitochondria that eliminate oxidized mitochondrial proteins, thereby contributing to mitochondrial quality control.

CLEC4GP1 (Gene ID: 440508) is C-type lectin domain family 4 member G pseudogene 1. CLEC4GP1 is a pseudo gene.

OVCH1 (Gene ID: 341350) is ovochymase 1.

LINC01811 (Gene ID: 101928114) is long intergenic non-protein coding RNA 1811.

CLIC5 (Gene ID: 53405) is chloride intracellular channel 5. This gene encodes a member of the chloride intracellular channel (CLIC) family of chloride ion channels.

FAM107A (Gene ID: 11170) has sequence similarity to 107 member A.

PNMT (Gene ID: 5409) is phenylethanolamine N-methyltransferase. The product of this gene catalyzes the last step of the catecholamine biosynthesis pathway, which methylates norepinephrine to form epinephrine (adrenaline).

CYTL1 (Gene ID: 54360) is cytokine like 1. C17 is a cytokine-like protein specifically expressed in bone marrow and cord blood mononuclear cells that bear the CD34 (MIM 142230) surface marker.

SERPINA3/4/5 (Gene ID: 12/Gene ID: 5267/Gene ID: 5104) is serpin family A member 3/serpin family A member 4/serpin family A member 5. The proteins encoded by these genes are members of the serpin family of proteins, a group of proteins that inhibit serine proteases.

TMOD1 (Gene ID: 7111) is tropomodulin 1. This gene encodes a member of the tropomodulin family. The encoded protein is an actin-capping protein that regulates tropomyosin by binding to its N-terminus, inhibiting depolymerization and elongation of the pointed end of actin filaments and thereby influencing the structure of the erythrocyte membrane skeleton.

HMGN2P17 (Gene ID: 100113373) is high mobility group nucleosomal binding domain 2 pseudogene 17. HMGN2P17 is a pseudogene.

GPRC5B (Gene ID: 51704) is G protein-coupled receptor class C group 5 member B. This gene encodes a member of the type 3 G protein-coupled receptor family. Members of this superfamily are characterized by a signature 7-transmembrane domain motif.

DRD2 (Gene ID: 1813) is dopamine receptor D2. This gene encodes the D2 subtype of the dopamine receptor. This G-protein coupled receptor inhibits adenylyl cyclase activity.

PSPHP1 (Gene ID: 8781) is phosphoserine phosphatase pseudogene 1. PSPHP1 is a pseudogene. This gene is significantly upregulated in Fanconi's anemia fibroblasts but downregulated or absent in fibroblasts from normal donors.

CDH12 (Gene ID: 1010) is cadherin 12. This gene encodes a type II classical cadherin of the cadherin superfamily. Alternative splicing of this gene results in multiple transcript variants.

IL17REL (Gene ID: 400935) is interleukin 17 receptor E like.

ARC (Gene ID: 23237) is activity regulated cytoskeleton associated protein.

UBE2W (Gene ID: 55284) is ubiquitin conjugating enzyme E2 W. This gene encodes a nuclear-localized ubiquitin-conjugating enzyme (E2) that, along with ubiquitin-activating (E1) and ligating (E3) enzymes, coordinates the addition of a ubiquitin moiety to existing proteins.

RNU5E-1 (Gene ID: 26829) is RNA, U5E small nuclear 1 and it is snRNA.

CXCL8 (Gene ID: 3576) is C-X-C motif chemokine ligand 8. The protein encoded by this gene is a member of the CXC chemokine family and is a major mediator of the inflammatory response. The encoded protein is commonly referred to as interleukin-8 (IL-8). IL-8 is secreted by mononuclear macrophages, neutrophils, eosinophils, T lymphocytes, epithelial cells, and fibroblasts.

LINC00881, LINC02029 (Gene ID: 100498859, Gene ID: 105374177) are long intergenic non-protein coding RNA 881 and long intergenic non-protein coding RNA 2029.

CXCL3 (Gene ID: 2921) is C-X-C motif chemokine ligand 3. This antimicrobial gene encodes a member of the CXC subfamily of chemokines. The encoded protein is a secreted growth factor that signals through the G-protein coupled receptor, CXC receptor 2.

RNU2-63P (Gene ID: 106480225) is RNA, U2 small nuclear 63, pseudogene.

CXCL2 (Gene ID: 2920) is C-X-C motif chemokine ligand 2. This antimicrobial gene is part of a chemokine superfamily that encodes secreted proteins involved in immunoregulatory and inflammatory processes.

RASD1 (Gene ID: 51655) is ras related dexamethasone induced 1. This gene encodes a member of the Ras superfamily of small GTPases and is induced by dexamethasone. The encoded protein is an activator of G-protein signaling and acts as a direct nucleotide exchange factor for Gi-Go proteins.

RNU6-1208P (Gene ID: 106480094) is RNA, U6 small nuclear 1208, pseudogene.

UTY (Gene ID: 7404) is ubiquitously transcribed tetratricopeptide repeat containing, Y-linked. This gene encodes a protein containing tetratricopeptide repeats which are thought to be involved in protein-protein interactions. The encoded protein is also a minor histocompatibility antigen which may induce graft rejection of male stem cell grafts.

CD24P4, RNU6-255P, TTTY14 (Gene ID: 938, Gene ID: 106481258, Gene ID: 83869) are CD24 molecule pseudogene 4, RNA, U6 small nuclear 255 pseudogene, and testis-specific transcript, Y-linked 14 (ncRNA).

KDM5DP1, TTTY10 (Gene ID: 359796, Gene ID: 246119) are lysine demethylase 5D pseudogene 1 and testis-specific transcript, Y-linked 10.

NLGN4Y (Gene ID: 22829) is neuroligin 4 Y-linked. This gene encodes a type I membrane protein that belongs to the family of neuroligins, which are cell adhesion molecules present at the postsynaptic side of the synapse, and may be essential for the formation of functional synapses.

RNU1-59P (Gene ID: 106480167) is RNA, variant U1 small nuclear 24, a pseudogene.

ZFY (Gene ID: 7544) is zinc finger protein Y-linked. This gene encodes a zinc finger-containing protein that may function as a transcription factor.

STK40 (Gene ID: 83931) is serine/threonine kinase 40.

RNU5B-1 (Gene ID: 26832) is RNA, U5B small nuclear 1, snRNA.

LINC01783, RNU1-6P (Gene ID: 100132147, Gene ID: 106480152) are long intergenic non-protein coding RNA 1783 and RNA U1 small nuclear 6 pseudogene.

RNU1-5P (Gene ID: 107105261) is RNA, U1 small nuclear 5, pseudogene.

EPS8L1 (Gene ID: 54869) is Epidermal growth factor receptor kinase substrate 8-like protein 1.

The LUM (GeneID: 4060) gene encodes lumican, which is an extracellular matrix protein related to collagen fibril organization.

KDR (Gene ID: 3791) is kinase insert domain receptor. Vascular endothelial growth factor (VEGF) is a major growth factor for endothelial cells. This gene encodes one of the two receptors of the VEGF. This receptor, known as kinase insert domain receptor, is a type III receptor tyrosine kinase.

SOD3 (Gene ID: 6649) is superoxide dismutase 3, which encodes a member of the superoxide dismutase (SOD) protein family.

IRF1 (Gene ID: 3659) is interferon regulatory factor 1, which is a transcriptional regulator and tumor suppressor, serving as an activator of genes involved in both innate and acquired immune responses.

JUN (Gene ID: 3725) is Jun proto-oncogene, AP-1 transcription factor subunit, is the putative transforming gene of avian sarcoma virus 17. It encodes a protein which is highly similar to the viral protein, and which interacts directly with specific target DNA sequences to regulate gene expression.

SOCS3 (Gene ID: 9021) is suppressor of cytokine signaling 3, which encodes a member of the STAT-induced STAT inhibitor (SSI), also known as suppressor of cytokine signaling (SOCS), family. SSI family members are cytokine-inducible negative regulators of cytokine signaling. The expression of this gene is induced by various cytokines, including IL6, IL10, and interferon (IFN)-gamma. The protein encoded by this gene can bind to JAK2 kinase, and inhibit the activity of JAK2 kinase.

NFIL3 (Gene ID: 4783) is nuclear factor, interleukin 3 regulated, which is a transcriptional regulator that binds as a homodimer to activating transcription factor (ATF) sites in many cellular and viral promoters. The encoded protein represses PER1 and PER2 expression and therefore plays a role in the regulation of circadian rhythm.

FGFR4 (Gene ID: 2264) is fibroblast growth factor receptor 4. The protein encoded by this gene is a tyrosine kinase and cell surface receptor for fibroblast growth factors.

NFKB1 (Gene ID: 4790) is nuclear factor kappa B subunit 1. This gene encodes a 105 kD protein which can undergo cotranslational processing by the 26S proteasome to produce a 50 kD protein. The 105 kD protein is a Rel protein-specific transcription inhibitor and the 50 kD protein is a DNA binding subunit of the NF-kappa-B (NFKB) protein complex.

SOD2 (Gene ID: 6648) is superoxide dismutase 2. This gene is a member of the iron/manganese superoxide dismutase family. It encodes a mitochondrial protein that forms a homotetramer and binds one manganese ion per subunit.

This protein binds to the superoxide byproducts of oxidative phosphorylation and converts them to hydrogen peroxide and diatomic oxygen.

MAOA (Gene ID: 4128) is monoamine oxidase A. This gene is one of two neighboring gene family members that encode mitochondrial enzymes which catalyze the oxidative deamination of amines, such as dopamine, norepinephrine, and serotonin.

CYCS (Gene ID: 54205) is cytochrome c, somatic. This gene encodes a small heme protein that functions as a central component of the electron transport chain in mitochondria. The encoded protein associates with the inner membrane of the mitochondrion where it accepts electrons from cytochrome b and transfers them to the cytochrome oxidase complex. This protein is also involved in initiation of apoptosis.

SNCA (Gene ID: 6622) is synuclein alpha. Alpha-synuclein is a member of the synuclein family, which also includes beta- and gamma-synuclein. Synucleins are abundantly expressed in the brain and alpha- and beta-synuclein inhibit phospholipase D2 selectively. SNCA may serve to integrate presynaptic signaling and membrane trafficking.

PDHA1 (Gene ID: 5160) is pyruvate dehydrogenase E1 subunit alpha 1. The pyruvate dehydrogenase (PDH) complex is a nuclear-encoded mitochondrial multienzyme complex that catalyzes the overall conversion of pyruvate to acetyl-CoA and CO(2), and provides the primary link between glycolysis and the tricarboxylic acid (TCA) cycle.

UQCRH (Gene ID: 7388) is ubiquinol-cytochrome c reductase hinge protein.

COX7B (Gene ID: 1349) is cytochrome c oxidase subunit 7B. Cytochrome c oxidase (COX), the terminal component of the mitochondrial respiratory chain, catalyzes the electron transfer from reduced cytochrome c to oxygen. This component is a heteromeric complex consisting of 3 catalytic subunits encoded by mitochondrial genes and multiple structural subunits encoded by nuclear genes.

COX5B (Gene ID: 1329) is cytochrome c oxidase subunit 5B. Cytochrome C oxidase (COX) is the terminal enzyme of the mitochondrial respiratory chain. It is a multi-subunit enzyme complex that couples the transfer of electrons from cytochrome c to molecular oxygen and contributes to a proton electrochemical gradient across the inner mitochondrial membrane. The complex consists of 13 mitochondrial- and nuclear-encoded subunits.

NDUFV1 (Gene ID: 4723) is NADH:ubiquinone oxidoreductase core subunit V1. The mitochondrial respiratory chain provides energy to cells via oxidative phosphorylation and consists of four membrane-bound electron-transporting protein complexes (I-IV) and an ATP synthase (complex V). This gene encodes a 51 kDa subunit of the NADH:ubiquinone oxidoreductase complex I; a large complex with at least 45 nuclear and mitochondrial encoded subunits that liberates electrons from NADH and channels them to ubiquinone.

UQCRC2 (Gene ID: 7385) is ubiquinol-cytochrome c reductase core protein 2. The protein encoded by this gene is located in the mitochondrion, where it is part of the ubiquinol-cytochrome c reductase complex (also known as complex III). This complex constitutes a part of the mitochondrial respiratory chain.

NDUFA1 (Gene ID: 4694) is NADH:ubiquinone oxidoreductase subunit A1. The human NDUFA1 gene codes for an essential component of complex I of the respiratory chain, which transfers electrons from NADH to ubiquinone.

CYC1 (Gene ID: 1537) is cytochrome c1. This gene encodes a subunit of the cytochrome bc1 complex, which plays an important role in the mitochondrial respiratory chain by transferring electrons from the Rieske iron-sulfur protein to cytochrome c.

UQCRB (Gene ID: 7381) is ubiquinol-cytochrome c reductase binding protein. This gene encodes a subunit of the ubiquinol-cytochrome c oxidoreductase complex, which consists of one mitochondrial-encoded and 10 nuclear-encoded subunits. The protein encoded by this gene binds ubiquinone and participates in the transfer of electrons when ubiquinone is bound. This protein plays an important role in hypoxia-induced angiogenesis through mitochondrial reactive oxygen species-mediated signaling.

VDAC2 (Gene ID: 7417) is voltage dependent anion channel 2. This gene encodes a member of the voltage-dependent anion channel pore-forming family of proteins that are considered the main pathway for metabolite diffusion across the mitochondrial outer membrane. The encoded protein is also thought to be involved in the mitochondrial apoptotic pathway via regulation of BCL2-antagonist/killer 1 protein activity.

COX4I1 (Gene ID: 1327) is cytochrome c oxidase subunit 4I1. Cytochrome c oxidase (COX) is the terminal enzyme of the mitochondrial respiratory chain. It is a multi-subunit enzyme complex that couples the transfer of electrons from cytochrome c to molecular oxygen and contributes to a proton electrochemical gradient across the inner mitochondrial membrane. This gene encodes the nuclear-encoded subunit IV isoform 1 of the human mitochondrial respiratory chain enzyme.

SDHB (Gene ID: 6390) is succinate dehydrogenase complex iron sulfur subunit B. Complex II of the respiratory chain, which is specifically involved in the oxidation of succinate, carries electrons from FADH to CoQ. The complex is composed of four nuclear-encoded subunits and is localized in the mitochondrial inner membrane.

COX6B1 (Gene ID: 1340) is cytochrome c oxidase subunit 6B1. Cytochrome c oxidase (COX), the terminal enzyme of the mitochondrial respiratory chain, catalyzes the electron transfer from reduced cytochrome c to oxygen. It is a heteromeric complex consisting of 3 catalytic subunits encoded by mitochondrial genes and multiple structural subunits encoded by nuclear genes. The mitochondrially-encoded subunits function in electron transfer, and the nuclear-encoded subunits may be involved in the regulation and assembly of the complex. This nuclear gene encodes subunit VIb.

MAOB (Gene ID: 4129) is monoamine oxidase B. The protein encoded by this gene belongs to the flavin monoamine oxidase family. It is a enzyme located in the mitochondrial outer membrane. It catalyzes the oxidative deamination of biogenic and xenobiotic amines and plays an important role in the metabolism of neuroactive and vasoactive amines in the central nervous system and peripheral tissues.

Detection of Skipped Exon Events

In an embodiment, a method of detecting pre-symptomatic, advanced, early-onset, or age-related (late-onset) Fuchs' endothelial corneal dystrophy, glaucoma, or other ocular diseases can comprise detecting one or more skipped exon events as shown in Table 8 in a sample obtained from a subject. In an embodiment a combination of 2, 3, 4, 5, 10, 15, 20, 20, 30, 40, 50, 60, 70, 80, 90, 100, or more of skipped exon events shown in Table 8 can be detected.

The complex and diverse process alternative splicing (AS) involves removing noncoding intronic sequences and remaining exons to generate mature mRNA. AS is generally divided into five basic types according to the process:

alternative 5' splice sites, alternative 3' splice sites, intron retention event, exon skipping (ES) events, and mutually exclusive exons. RNAseq can be used to evaluate splicing changes.

Strategies applied for differential splicing analysis can be divided into isoform-based or count-based. Isoform-based methods aim at reconstructing and quantifying full-length transcripts, prior to differential expression analysis. Statistical testing is then applied to identify significant differences in the relative transcript abundances between the different experimental conditions. Isoform-based methods can include, for example, Cufflinks/cuffdiff2 or DiffSplice.

Count-based methods include both exon-based and event-based approaches. In exon-based methods, read counts are assigned to different features, such as exons or junctions. Exon-based methods can include, for example, DEXSeq, edgeR, JunctionSeq, or limma. In event-based methods, splicing events themselves are quantified by calculating the percentage spliced in (PSI) values for each event, which measure the fraction of mRNAs expressed from a gene that contains a specific form of that event. Event-based methods can include, for example, dSpliceType, MAJIQ, rMATS, or SUPPA/SUPPA2.

In an embodiment, alternative splicing patterns can be validated by preparing cDNAs via reverse transcription, subsequent RT-PCR analysis, amplification products separated by gel electrophoresis, and qPCR.

Figure 4:
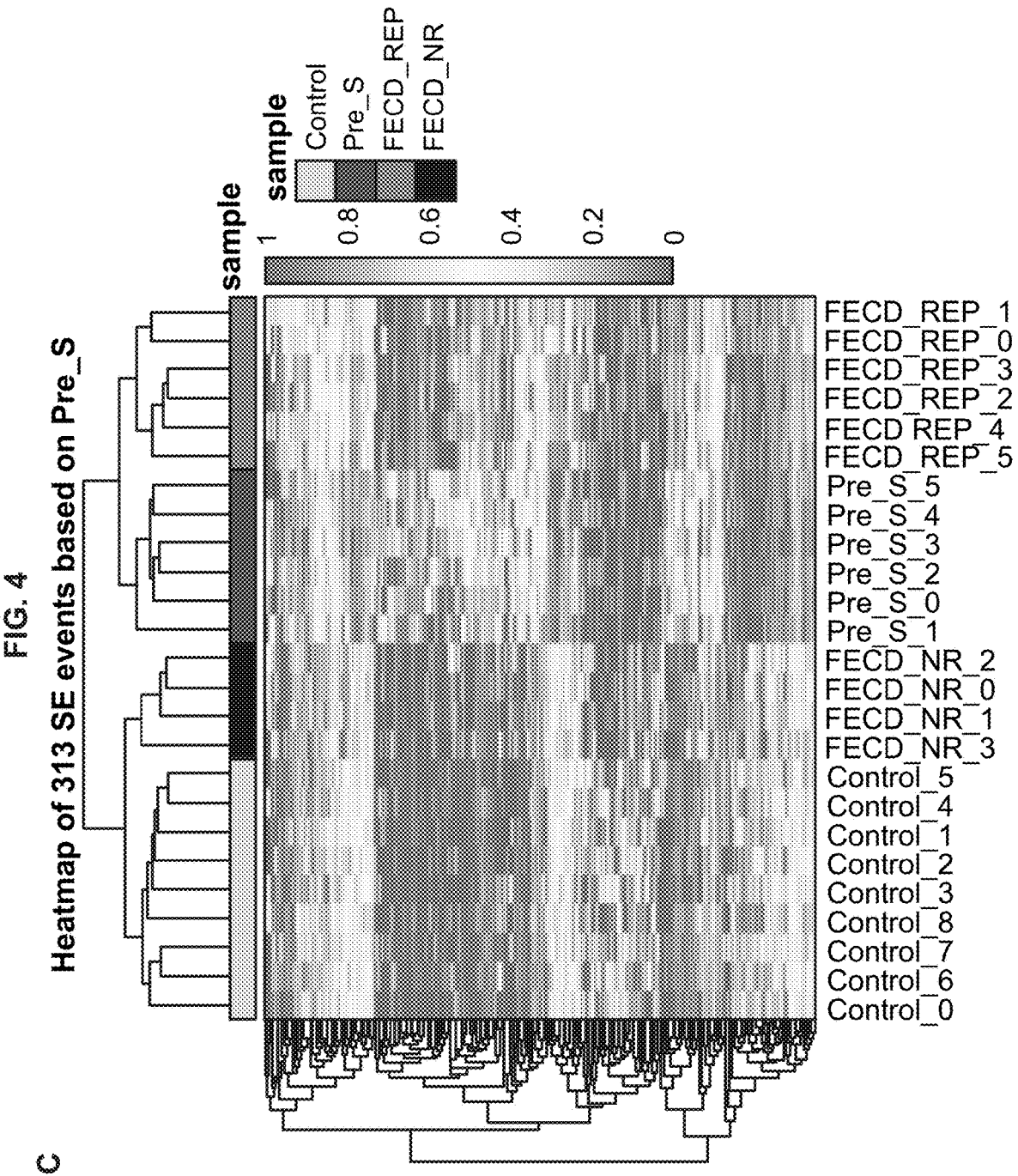
FIG. 4 shows RNAseq data demonstrates changes in splicing in pre-symptomatic, FECD_REP, and FECD_NR tissue. (A) Alternative splicing events in Pre_S, FECD_REP, and FECD_NR cohorts. (B) Overlap between sample cohorts for skipped exon (SE) events showing that late stage disease FECD_REP and Pre_S cohorts cluster differently from control or FECD_NR cohorts. (C) Heat map comparing inclusion levels of exons among 4 cohorts. The chosen SE events were based on the 313 significant skipped exon events identified in Pre_S tissues. The Pre_S cohort is more similar to FECD_REP than it is to the other two cohorts. (D) The similarity of Pre_S and FECD_REP is emphasized by a heat map comparing top 25 SE events in common between FECD_REP and Pre_S tissues and corresponding changes in FECD_NR and control tissues. (E) Identity of top 24 SE events in common between FECD_REP and Pre_S. Genes COPZ2, MBNL2, SORBS1, KIF13A, CLASP1, ARHGEF10L, NUMA1, and VPS39 are also observed in RNAseq data from DM1 tissue, demonstrating substantial overlap despite different tissue origins. The threshold used in identifying the significant events: FDR<0.001, |IncLevel Difference|>=0.15.
Figure 4:
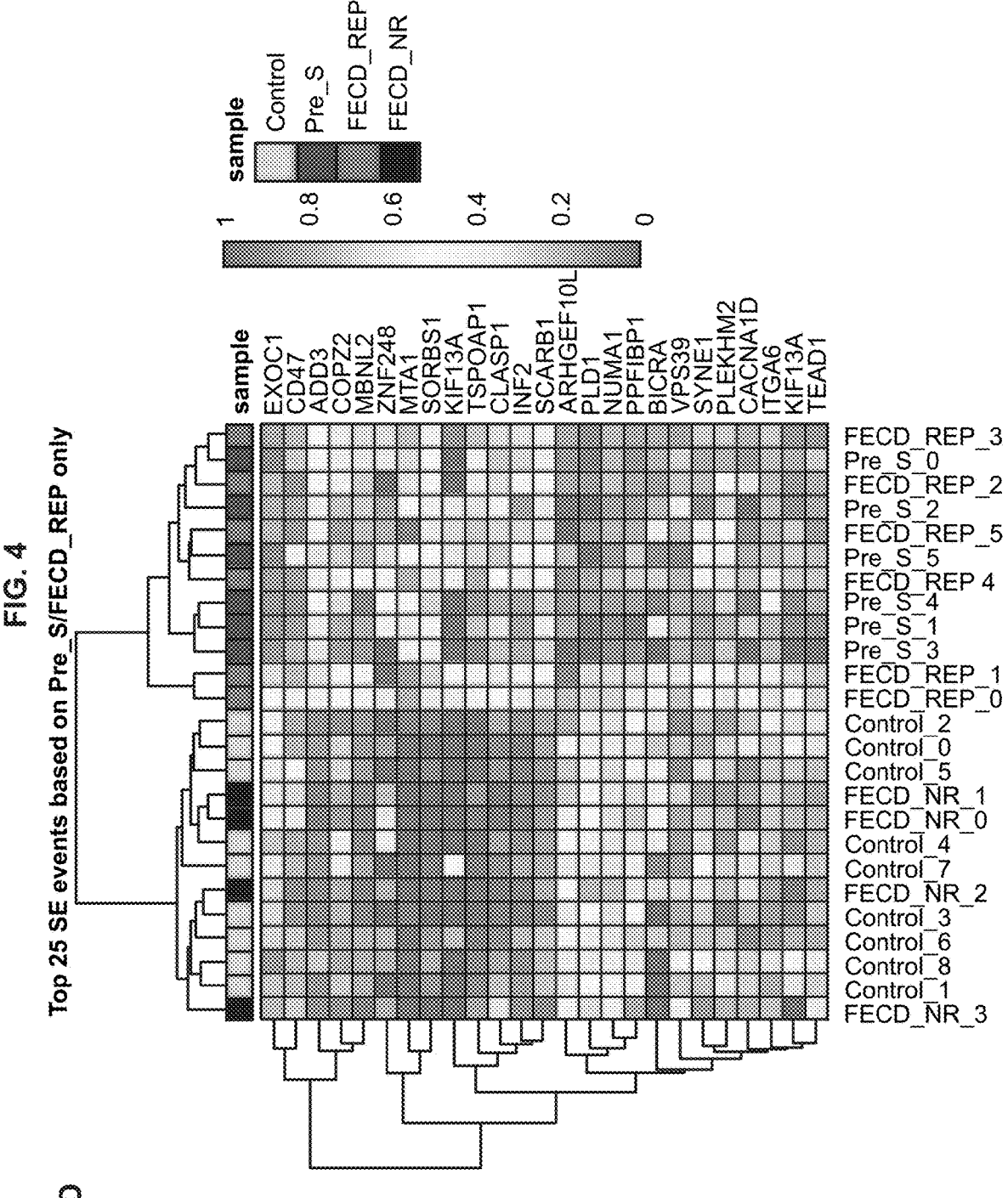

In an embodiment, RNAseq or other suitable methods can be used to evaluate splicing changes in subjects (FIG. 4).

In another embodiment, polymorphisms can be genotyped and RNA half-life can be measured.

TCF4 CTG18.1 polymorphism genotyping was conducted using short tandem repeat (STR) and triplet repeat primed polymerase chain reaction (TP-PCR). TCF4 RNA half-life was measured using qPCR.

Short tandem repeat analysis (STR) and triplet repeat primed polymerase chain reaction (TP-PCR) can be used in tandem. Short Tandem Repeat (STR) analysis is a common molecular biology method used to compare allele repeats at specific loci in DNA between two or more samples. A short tandem repeat is a microsatellite with repeat units that are 2 to 7 base pairs in length, polymerase chain reaction (PCR) is employed to discover the lengths of the short tandem repeats based on the length of the PCR product. TP-PCR can be performed on the samples in which the STR analysis revealed only one apparent allele or no alleles. Characteristic tracing patterns of the triplet repeat primed electropherograms can be used to distinguish samples. The TP-PCR assay is also used to screen for expanded alleles and it uses a locus-specific primer flanking the repeat together with paired primers amplifying from multiple priming sites within the repeat. Specificity is dictated by the fluorescently labeled, locus-specific primer. TP PCR gives a characteristic ladder on the fluorescence trace enabling the rapid identification of large pathogenic repeats that cannot be amplified using flanking primers. For example, TCF4 CTG18.1 polymorphism genotyping can be conducted using short tandem repeat (STR) and triplet repeat primed polymerase chain reaction (TP-PCR). Gel Electrophoresis, Southern blot, or other methods of separation and detection can be used to identify samples.

Furthermore, RNA half-life can be measured using qPCR.

In an embodiment, the methods of detection described herein (i.e., detection of upregulation of genes, down regulation of genes, or skipped exon events) can detect early stage or late stage Fuchs' endothelial corneal dystrophy earlier than detection by the Krachmer grading scale. In an embodiment, the methods of detection described herein (i.e., detection of upregulation of genes, down regulation of genes, or skipped exon events) can detect early stage or late stage FECD before a patient is at G0, at G1, at G2, at G3, at G4, or at G5 of the Krachmer grading scale.

The Hodapp, Parrish, and Anderson System (HPA) system, a commonly used classification system, is based upon the overall extent of visual field depression (calculated by the mean deviation value), the number of defective points in the Humphrey Statpac-2 pattern deviation probability map of the 24-2, SITA-STANDARD test, and proximity to damage to fixation point. In spite of its popularity, the HPA system has several limitations. There are only three stages of glaucoma classification: early, moderate, and severe. These broad categories make it difficult to monitor small, but meaningful, changes in functional loss over time. The system does not provide any information regarding the location and depth of defects in the visual field. Finally, the system is complicated and can be time-consuming, limiting its clinical use A more continuous staging system was proposed by the Advanced Glaucoma Intervention Study (AGIS). The AGIS system is based on the number and depth of neighboring depressed test locations on the total deviation plot in the nasal area, upper hemifield, and lower hemifield. Visual fields are scored between 0 and 20, with 0 indicating no measured defective points and 20 indicating severe visual field depression. AGIS visual fields are placed into five stages of severity based on the 20-point scale. However, as this system contains a high number of parameters, it is difficult to manually use in the clinic.

Other methods, such as Brusini's Glaucoma Staging System (GSS), are based on Standard Automated Perimetry (SAP) indices, which serve as the standard for assessing visual field damage indices, such as the Visual Field (VF) indices. VF indices are used to acquire information on both the severity of defects and the type of damage. However, this method does not supply information regarding the location, shape, and morphology of defects, leading to overlapping classifications in some instances. The Enhanced Glaucoma Staging System was derived from the GSS and is considered to be more easily implemented with more severe staging of abnormal fields.

The University of São Paulo Glaucoma Visual Field Staging System (USP-GVFSS), proposed in 2009, uses four main parameters. These parameters include the Visual Field Index (VFI-a Humphrey Visual Field Test value), location of the defect, involvement of the blind spot, and number of hemifields affected. The SCHEIE (Systematic Classification of Humphrey visual fields-Easy Interpretation and Evaluation) grading system improves on the quantitative aspects of the USP-GVFSS and combines them with qualitative measurements for grading glaucomatous visual field defects.

In an embodiment, the methods of detection described herein (i.e., detection of upregulation of genes, down regulation of genes, or skipped exon events) can detect glaucoma earlier than detection by the HPA scale, the AGIS system, Brusini's Glaucoma Staging System, or the USP-GVFSS. In an embodiment, the methods of detection described herein (i.e., detection of upregulation of genes, down regulation of genes, or skipped exon events) can detect glaucoma before a patient is at the early, at the moderate, or at the severe grades of the HPA scale. In an embodiment, the methods of detection described herein (i.e., detection of upregulation of genes, down regulation of genes, or skipped exon events) can detect glaucoma before a patient is at the 0, at the 1, at the 2, at the 3, at the 4, at the 5, at the 10, at the 15, or at the 20 score of the AGIS system.

In an embodiment, the methods of detection described herein can detect early stage or late stage FECD or glaucoma before a patient displays elevated intraocular pressure. In an embodiment, the methods of detection described herein can detect early stage or late stage FECD or glaucoma before a patient displays intraocular pressure above about 18, 19, 20, 21, 22, 23, 24, 25, 26, 27, 28 mm Hg intraocular pressure.

Methods of Treatment

In an embodiment, a method of detecting pre-symptomatic, advanced, early-onset, or age-related (late-onset) Fuchs' endothelial corneal dystrophy can comprise treating the subject with eyedrops, surgical interventions, or combinations thereof.

In some embodiments, medical or surgical treatment for FECD can be administered to a subject. Known methods of treatment include medical treatments of FECD to treat symptoms of early disease. Treatment can be steroidal eye drops, sodium chloride eyedrops, keratoprosthesis implantation, therapeutic contacts, corneal transplant, endothelial keratoplasty, and penetrating keratoplasty. FECD can also be treated with prostaglandins, beta blockers, alpha-adrenergic agonists, carbonic anhydrase inhibitors, rho kinase inhibitors, miotic or cholinergic agents (discussed in more detail below), or combinations thereof.

Medical management can include steroidal eyedrops, sodium chloride eyedrops, topical hypertonic saline, the use of a hairdryer to dehydrate the precorneal tear film, and therapeutic soft contact lenses. In using a hairdryer, the patient is instructed to hold a hairdryer at an arm's length or directed across the face, to dry out the epithelial blisters. This can be done two or three times a day. It has also been reported that botulinum toxin can produce improvement lasting several months. Definitive treatment, however, (especially with increased corneal edema) is surgical in the form of corneal transplantation.

Surgical procedures, called posterior lamellar keratoplasty or endothelial keratoplasty, were initially popularized as deep lamellar endothelial keratoplasty (DLEK) and Descemet's stripping with endothelial keratoplasty (DSEK) for treatment of FECD. DLEK and DSEK avoid some of the surgical complications of PKP such as wound dehiscence and high postoperative astigmatism. DSEK has become the dominant procedure for patients with corneal disease restricted to the endothelium. It can be technically easier for the surgeon compared to DLEK, and may provide superior visual results. With DSEK, patients must remain supine (face up positioning) for 24 or more hours following the procedure while the transplanted tissue adheres to the overlying cornea.

Improved surgical instrumentation for DSEK, such as DSEK graft injectors, and technical improvements in the surgical technique have facilitated reduced complications and the potential to perform DSEK through very small (3 mm) sutureless incision.

Endothelial keratoplasty has been further refined to Descemet Membrane Endothelial Keratoplasty (DMEK), in which only a donor Descemet membrane and its endothelium is transplanted. With DMEK, 90% of cases achieve a best spectacle corrected visual acuity 20/40 or better, and 60% of cases 20/25 or better within 1-3 months, although complications such as graft failure and detachment remain challenges for the patient and surgeon.

Keratoprosthesis implantation is a procedure that involves full-thickness removal of the cornea and replacement by an artificial cornea. The Boston Type I Keratoprosthesis is currently the most commonly used keratoprosthesis device in the US. It consists of a clear plastic polymethylmethacrylate (PMMA) optic and back plate sandwiched around a corneal graft and secured with a titanium locking ring. After the device is assembled, a partial-thickness trephination is performed on the host cornea. Full-thickness resection of the patient's cornea is then completed using curved corneal scissors. The keratoprosthesis is then secured to host tissue using interrupted or running sutures. Generally, patients who have a history of multiple failed penetrating keratoplasty procedures are candidates for a keratoprosthesis transplant.

Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

In an embodiment, a method of detecting glaucoma in a subject can comprise treating the subject with eyedrops, oral medications, surgical interventions, or combinations thereof.

Glaucoma can be treated with, for example prostaglandins, beta blockers, alpha-adrenergic agonists, carbonic anhydrase inhibitors, rho kinase inhibitors, miotic or cholinergic agents. These agents can be delivered via, for example, eye drops or orally. Oral medication and eye drops can be administered 1, 2, 3, 4, 5, 6, or more times a day.

Prostaglandins can increase the outflow of the fluid in the eye (aqueous humor), thereby reducing eye pressure. Medicines in this category include latanoprost (Xalatan), travoprost (Travatan Z), tafluprost (Zioptan), bimatoprost (Lumigan) and latanoprostene bunod (Vyzulta).

Beta blockers can reduce the production of fluid in the eye, thereby lowering the pressure in the eye (intraocular pressure). Examples include timolol (Betimol, Istalol, Timoptic) and betaxolol (Betoptic).

Alpha-adrenergic agonists can reduce the production of aqueous humor and increase outflow of the fluid in the eye. Examples include apraclonidine (Iopidine) and brimonidine (Alphagan P, Qoliana).

Carbonic anhydrase inhibitors can reduce the production of fluid in the eye. Examples include dorzolamide (Trusopt) and brinzolamide (Azopt).

Rho kinase inhibitors lower eye pressure by suppressing the rho kinase enzymes responsible for fluid increase. It is available as netarsudil (Rhopressa) and Y-27632.

Miotic or cholinergic agents can increase the outflow of fluid from the eye. An example is pilocarpine (Isopto Carpine).

Advanced, early-onset, or age-related (late-onset) Fuchs' endothelial corneal dystrophy involves fluid buildup and can sometimes accompany glaucoma. In some embodiments, a method of detecting pre-symptomatic, advanced, early-onset, or age-related (late-onset) Fuchs' endothelial corneal dystrophy can comprise treating the subject with prostaglandins, beta blockers, alpha-adrenergic agonists, carbonic anhydrase inhibitors, rho kinase inhibitors, miotic or cholinergic agents as described herein.

In an embodiment, a method of detecting glaucoma in a subject can comprise treatment with laser therapy, such as laser trabeculoplasty, filtering surgery, such as a trabeculectomy, drainage tubes to drain away excess fluid to lower eye pressure, minimally invasive glaucoma surgery (MIGS), and peripheral iridotomy. Furthermore, glaucoma can be treated with implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Methods for Decreasing Gene Expression of Upregulated Genes

In an embodiment a subject having early or late onset FECD, glaucoma, or other ocular disease can be treated by downregulating one or more of the genes described in the section entitled Detection of an Increase of Expression of Marker Genes herein.

In some embodiments, a method for decreasing gene expression of upregulated genes is provided. In some embodiments, the method of decreasing gene expression can include administration of antibodies, oligonucleotides, RNAi, siRNAs, shRNA, miRNA, small molecules; CRISPR systems, or combinations thereof to a subject in need thereof.

Antibodies

Therapeutic agents of the present disclosure can include various antibodies or specific binding fragment thereof. The term "antibody" as used herein is used broadly and can encompass polyclonal antibodies, monoclonal antibodies as well as specific binding fragments thereof. An antibody molecule can be monospecific, idiospecific, heterospecific, or polyspecific. Antibody molecules can have specific binding sites that bind to specific antigenic determinants, epitopes, on antigens. "Specific binding fragments" can comprise a portion of the full-length antibody. The portion can generally be the antigen binding or a variable region of the antibody. Examples of antibody fragments include Fab, Fab', F(ab')2 and Fv fragments; diabodies; linear antibodies; single-chain antibody molecules; and multispecific antibodies formed from antibody fragments.

In an embodiment, antibodies can be used to target intracellular molecules. In effect, this would achieve gene downregulation at the post-translational level. This approach was given impetus by the development of the single chain variable fragment (scFv) antibody format, which facilitates the engineering and expression of functional antibodies within the intracellular environment. The recombinant antibody expressed within the confines of the intracellular environment is commonly referred to as an intrabody.

Antibodies can be used, for example, to decrease or downregulate gene expression for one or more of the upregulated genes disclosed herein. Antibodies that can bind to COCH, an upregulated gene, to decrease expression include, for example, ABIN951612, orb30939, AP51001PU-N, PA5-48475, OAAB09196, BS6944, or LS-C166910, among others. Antibodies that can bind to FN1, an upregulated gene, to decrease expression include, for example, AMAb91223, HPA027066, and ab2413, among others. Antibodies that can bind to THBS2, an upregulated gene, to decrease expression include, for example, HPA044304, A16231, and ab112543, among others. Antibodies to downregulate expression of other genes encoding proteins as described in the section entitled "Detection of an Increase of Expression of Marker Genes" are readily available.

Gene Therapy

Gene therapy includes constructs designed to reduce the expression of a particular gene (DNA sequences coding for shRNA and miRNA, as well as siRNA that are delivered directly). All constructs can be delivered using the most common virus-based, as well as non-viral, methods. Therapeutic agents for decreasing gene expression of upregulated genes can include the use of oligonucleotides, RNAi, siRNA molecules, shRNA molecules, and miRNA molecules. Viral vectors or non-viral delivery can be used.

In another embodiment, viral vectors can be used for gene therapy. Adenoviruses, for example, are medium-sized, non-enveloped viruses with a nucleocapsid and a linear dsDNA genome. They are able to replicate in the nucleus of mammalian cells but do not efficiently integrate into the host's genome. AdVs are able to package approximately 8-30 kb of foreign DNA. Several AdV features are attractive for vector use. Adenoviral vectors are a common delivery method to introduce shRNA-expression cassettes (described below) into target cells in vitro. Another example is Adeno-associated viral vectors (AAV), one of the smallest viruses belonging to the genus Dependovirus and the family Parvoviridae. AAVs have a small, single-stranded DNA genome (4.8 kb) and are considered apathogenic in humans. The genome contains only two genes, which can be replaced with foreign ones, leaving only the terminal ITRs to allow high-level expression of the insert. However, the 5 kb packaging limit of AAV is still sufficient to accommodate at least eight individual shRNA expression cassettes.

In other embodiments, non-viral delivery can be used. Non-viral vectors are safer, of low cost, more reproducible and do not present DNA size limitations in comparison with viral vectors. For example, cationic liposomes associated with Tf form stable siRNA (described below) lipoplexes with reduced toxicity and enhanced specific gene knockdown activity compared to conventional lipoplexes. Thus, such formulations may constitute efficient delivery systems for therapeutic siRNA applications.

Oligonucleotides

Therapeutic agents of the present disclosure can include one or more antisense oligonucleotides targeting one or more of the genes, disclosed herein, with upregulated expression. The goal of the antisense approach is the downregulation of a molecular target, usually achieved by induction of RNase H endonuclease activity that cleaves the RNA-DNA heteroduplex with a significant reduction of the target gene translation. Antisense oligonucleotides are short, synthetic, single-stranded oligodeoxynucleotides that are complementary to the mRNA target. Antisense oligonucleotides can be about 20 nucleotides long and can be selected to target either the methionine (AUG) initiation codon, blocking translation, or the splice sites, to block splicing. Antisense oligonucleotides can be synthesized using chemically modified nucleotides, for example (without limitation), phosphorothioates, 2'-O-methyl RNA, or locked nucleic acids, which can confer nuclease resistance. Antisense oligonucleotides can hybridize to target RNA in a sequence-specific manner. Antisense oligonucleotides can inhibit gene expression, modulate splicing of a precursor mRNA, or inactivate microRNA. Antisense oligonucleotides can work by inducing RNase H endonuclease activity that cleaves the RNA-DNA heteroduplex and thereby can reduce target gene translation, for example, COCH, the gene encoding the protein cochlin. Antisense oligonucleotides can also inhibit 5' cap formation, alter the splicing process (splice-switching), and sterically hinder ribosomal activity).

Antisense oligonucleotides can be used, for example, to decrease or downregulate gene expression for one or more of the upregulated genes disclosed herein Antisense oligonucleotides that can bind the mRNA of an upregulated gene such as mRNA of COCH or FN1 to decrease expression. Examples include RNase H1-dependent antisense oligonucleotides, gapmer antisense oligonucleotides, and phosphorothioate antisense oligonucleotides, among others. For example, in FECD cases with an expanded intronic CUG tract in the TCF4 gene that forms nuclear foci, the foci sequester splicing factors and impair splicing. Synthetic oligonucleotides complementary to the CUG repeat in the TCG4 gene can reverse the splicing defect, inhibit foci, and reverse pathological changes in splicing.

RNAi

RNAi is a conserved biological response to double-stranded RNA that mediates resistance to both endogenous parasitic and exogenous pathogenic nucleic acids, and regulates the expression of protein-coding genes. RNAi interrogates gene function by blocking gene expression and analyzing its effect on phenotype. RNAi silences genes by generating knockdowns at the mRNA level.

siRNA

Therapeutic agents of the present disclosure can include one or more small interfering RNA (siRNA) targeting one or more of the upregulated genes disclosed herein. siRNA, also referred to as short interfering RNA or silencing RNA, is a class of double-stranded RNA non-coding molecules, which can be about 20-25 base pairs long. siRNA can operate within the RNA interference (RNAi) pathway. An endoribonuclease, Dicer, can cleave long dsRNA forming siRNA. Long dsRNA can come from hairpin, complementary RNAs, and/or RNA-dependent RNA polymerases. An siRNA can also be transfected into a host cell. Once siRNA enters the target cell, proteins can come together to form the RNA-Induced Silencing Complex (RISC). After RISC forms, the siRNA can unwind to form two single stranded siRNA segments, the passenger strand and the guide strand. The passenger strand is degraded while the less thermodynamically stable guide strand remains part of the RISC and scans to find complementary mRNA. When the siRNA (part of RISC) binds to target mRNA, it induces mRNA cleavage. The cut mRNA is identified as abnormal by the cell and is degraded, thereby preventing translation and silencing the gene that encodes that mRNA, for example, FN1.

siRNA can be used, for example, to decrease or down-regulate gene expression for one or more of the upregulated genes disclosed herein. For example, FNA siRNA can inhibit protein expression of FN1 (see EP2574930A1 and sequences disclosed within). siRNA that can inhibit expression of COCH can include, for example, NM_004086 (Rosetta Gene ID: HSG00288029; Entrez ID: 1690; probe ID 10023819878) from Sigma Aldrich. siRNA can inhibit expression of THBS2 can include, for example, NM_003247 (Rosetta Gene ID: HSG00242955; Entrez ID: 7058; probe ID 10023814096) from Sigma Aldrich. siRNAs are readily available for the other upregulated genes described in the section entitled "Detection of an Increase of Expression of Marker Genes".

shRNA

Therapeutic agents of the present disclosure can include one or more short hairpin RNA (shRNA) targeting one or more of the genes, disclosed herein, with upregulated expression. This shRNA, also referred to as small hairpin RNA or Hairpin Vector, is an artificial RNA molecule with a tight hairpin turn that can be used to silence target gene expression operating within the RNAi pathway. As discussed above, one method for gene knockdown can be transfection of exogenous siRNA, but transfected siRNA can degrade. An expression vector containing siRNA can be synthesized using shRNA. The expression vector can be viral or non-viral DNA vectors that encode shRNA. A common vehicle for shRNA delivery is viral transduction. Expression through AAV or adenovirus can prevent insertional mutagenesis since these vectors remain episomal, but this approach leads to more transient expression since the vectors are lost through multiple rounds of cell division. Expression through lentivirus provides a stable solution through chromosomal integration, but this also presents the risk of insertional mutagenesis. The siRNA sequence can be modified to contain a short loop between the two strands, creating the shRNA. Dicer can process shRNA, which can provide an advantage over transfected siRNA, which can degrade more rapidly than shRNA.

The one or more shRNAs targeting one or more of the genes, disclosed herein, with upregulated expression can be, for example, one or more of those in table 1. shRNAs are readily available for the other genes described in the section entitled Detection of an Increase of Expression of Marker Genes.

TABLE 1

| shRNA transcripts for upregulated genes. | | | | |
|---|---|---|---|---|
| Gene ID | Taxon | Gene Symbol | Gene Description | Current WT Transcripts |
| 5243 | human | ABCB1 | ATP binding cassette subfamily B member 1 | NM_001348946.2, NM_001348944.1, NM_001348945.1, NM_000927.4 |
| 5244 | human | ABCB4 | ATP binding cassette subfamily B member 4 | XR_001744809.2, NM_018849.3, XM_011516313.3, XM_011516312.3, XM_011516315.3, XM_011516311.3, XM_017012323.2, NM_000443.4, XM_011516308.3, XM_011516310.3, XM_011516309.3, XR_001744810.2, NM_018850.2 |
| 84873 | human | ADGRG7 | adhesion G protein-coupled receptor G7 | NM_032787.3, XM_011513245.2, NM_001308362.1 |
| 719 | human | C3AR1 | complement C3a receptor 1 | NM_001326475.2, NM_001326477.2, NM_004054.4 |
| 942 | human | CD86 | CD86 molecule | NM_001206925.1, NM_006889.4, NM_001206924.1, NM_176892.1, NM_175862.5 |

TABLE 1-continued shRNA transcripts for upregulated genes.

| Gene ID | Taxon | Gene Symbol | Gene Description | Current WT Transcripts |
|---|---|---|---|---|
| 1029 | human | CDKN2A | cyclin dependent kinase inhibitor 2A | XM_011517675.2, XR_929159.2, XM_011517676.2, XM_005251343.1, NM_000077.4, NM_001195132.1, NM_058195.3, NM_058197.4, NM_001363763.2 |
| 23601 | human | CLEC5A | C-type lectin domain containing 5A | NM_013252.3, NM_001301167.2, XM_017011916.2, XM_017011917.1, XM_017011915.1, XM_011515995.2 |
| 1264 | human | CNN1 | calponin 1 | XM_017026289.1, XM_005259741.2, XM_024451361.1, NM_001308341.2, NM_001299.6, NM_001308342.2, XM_024451362.1 |
| 1690 | human | COCH | cochlin | NM_001347720.1, XM_017021071.1, NM_001135058.1, XM_024449506.1, NM_004086.3 |
| 54504 | human | CPVL | carboxypeptidase vitellogenic like | NM_001371256.1, NM_001371267.1, NM_001371263.1, NM_031311.5, NM_001371264.1, NM_001371257.1, NM_001371261.1, NM_001371268.1, NM_001371265.1, NM_001371255.1, NM_001371258.1, NM_001371260.1, NM_001371266.1, NM_001371262.1, NM_001348054.1, NM_019029.3, NM_001348052.1, XM_017012366.1, XM_011515437.1 |
| 1536 | human | CYBB | cytochrome b-245 beta chain | NM_000397.4 |
| 1641 | human | DCX | doublecortin | NM_000555.3, NM_178151.2, NM_001369370.1, NM_178152.3, XM_011530879.3, NM_001369372.1, NM_001195553.2, NM_001369371.1, NM_001369373.1, NM_001369374.1, NM_178153.3 |
| 8788 | human | DLK1 | delta like non-canonical Notch ligand 1 | NM_003836.6, NM_001317172.2 |
| 347694 | human | ECEL1P2 | endothelin converting enzyme like 1 pseudogene 2 | NR_028501.1 |
| 55531 | human | ELMOD1 | ELMO domain containing 1 | NM_018712.4, XM_017017994.2, XM_017017995.2, NM_001308018.1, NM_001130037.1 |
| 2153 | human | F5 | coagulation factor V | NM_000130.5, XM_017000660.2 |
| 2210 | human | FCGR1B | Fc fragment of IgG receptor Ib | XR_002959729.1, XR_001737041.2, NR_045213.2, NM_001017986.4, NM_001004340.4, XM_017000661.1, XM_017000662.1, XR_001737040.1, NM_001244910.1 |
| 2335 | human | FN1 | fibronectin 1 | XM_017003692.1, XM_017003695.1, NM_001365524.1, XM_024452770.1, NM_001365521.1, NM_001365518.1, NM_001365522.1, XM_024452769.1, NM_212482.3, NM_001365517.1, NM_001365523.1, NM_001365519.1, NM_001365520.1, XM_005246402.1, XM_005246404.1, XM_005246410.1, XM_005246398.1, XM_005246397.1, XM_005246408.1, XM_005246411.1, XM_005246407.1, XM_005246399.1, XM_005246416.1, XM_005246403.1, XM_005246401.1, NM_054034.2, NM_002026.3, NM_212474.2, NM_212476.2, NM_212478.2, NM_001306131.1, NM_001306130.1, NM_001306129.1, NM_001306132.1 |
| 2350 | human | FOLR2 | folate receptor beta | XM_005273856.4, XM_024448412.1, NM_001113534.2, NM_001113536.2, NM_000803.5, NM_001113535.2 |
| 2295 | human | FOXF2 | forkhead box F2 | NM_001452.2 |
| 2487 | human | FRZB | frizzled related protein | NM_001463.4 |
| 51313 | human | GASK1B | golgi associated kinase 1B | NM_016613.7, XM_024454078.1, XM_024454079.1, NM_001031700.3, NM_001128424.2 |
| 647309 | human | GMNC | geminin coiled-coil domain containing | XR_924161.2, NM_001146686.3 |
| 2719 | human | GPC3 | glypican 3 | NM_004484.4, NM_001164619.2, XM_017029413.2, NM_001164618.2, NM_001164617.2 |
| 2857 | human | GPR34 | G protein-coupled receptor 34 | XM_005272597.4, NM_005300.4, NM_001097579.2 |
| 2915 | human | GRM5 | glutamate metabotropic receptor 5 | NM_000842.4, NM_001143831.2, XM_011542792.1, XM_017017627.2, XM_006718828.4 |
| 3117 | human | HLA-DQA1 | major histocompatibility complex, class II, DQ alpha 1 | XM_006715079.4, NM_002122.5 |
| 3122 | human | HLA-DRA | major histocompatibility complex, class II, DR alpha | NM_019111.5 |
| 3248 | human | HPGD | 15-hydroxyprostaglandin dehydrogenase | NM_001363574.2, XR_938728.2, NM_000860.6, NM_001145816.2, NM_001256301.1, NM_001256306.1, NM_001256307.1, NM_001256305.1 |
| 150084 | human | IGSF5 | immunoglobulin superfamily member 5 | NM_001080444.1, XM_011529472.2 |
| 3736 | human | KCNA1 | potassium voltage-gated channel subfamily A member 1 | NM_000217.3 |

TABLE 1-continued

| shRNA transcripts for upregulated genes. | | | | |
|---|---|---|---|---|
| Gene ID | Taxon | Gene Symbol | Gene Description | Current WT Transcripts |
| 10894 | human | LYVE1 | lymphatic vessel endothelial hyaluronan receptor 1 | NM_006691.4 |
| 728239 | human | MAGED4 | MAGE family member D4 | NM_001272061.1, NM_001272063.2, NM_001272062.2, NM_001098800.3 |
| 55016 | human | MARCHF1 | membrane associated ring-CH-type finger 1 | NM_017923.4, XM_011532055.3, NM_001166373.1, XM_017008334.1, XM_017008335.1, XM_017008336.1 |
| 91862 | human | MARVELD3 | MARVEL domain containing 3 | NM_001017967.4, NM_052858.6, XM_011523449.3, NM_001271329.2 |
| 100847004 | human | MIR5188 | microRNA 5188 | NR_049820.1 |
| 107984884 | human | MMP2-AS1 | MMP2 antisense RNA 1 | NR_147198.1 |
| 4440 | human | MSI1 | musashi RNA binding protein 1 | XM_011538363.2, XM_011538364.2, XM_006719404.3, XM_011538370.2, XM_011538362.2, XM_011538371.2, XM_011538365.2, XM_011538366.2, XM_006719403.3, XM_011538368.2, XM_011538361.3, NM_002442.4 |
| 50507 | human | NOX4 | NADPH oxidase 4 | XM_017017842.1, XM_017017844.1, XM_011542857.2, XM_017017845.1, NM_001300995.1, NM_001291927.1, NM_001143836.3, XM_017017843.2, NM_001291929.2, NR_120406.2, XM_006718849.4, XM_017017841.2, NM_016931.5, NM_001143837.2, NM_001291926.2 |
| 5121 | human | PCP4 | Purkinje cell protein 4 | NM_006198.3 |
| 7058 | human | THBS2 | thrombospondin 2 | NM_003247.3 |
| 55026 | human | TMEM255A | transmembrane protein 255A | NM_017938.3, NM_001104544.1, NM_001104545.1, XM_017029619.2, XR_001755706.2 |
| 7162 | human | TPBG | trophoblast glycoprotein | NM_006670.4, NM_001166392.1 |
| 23584 | human | VSIG2 | V-set and immunoglobulin domain containing 2 | NM_014312.5, NM_001329920.2 |
| 1490 | human | CCN2 | cellular communication network factor 2 | NM_001901.3 |
| 1278 | human | COL1A2 | collagen type I alpha 2 chain | NM_000089.4 |
| 1284 | human | COL4A2 | collagen type IV alpha 2 chain | NM_001846.4 |
| 1299 | human | COL9A3 | collagen type IX alpha 3 chain | XM_017027666.1, XM_011528545.1, NM_001853.4 |
| 2214 | human | FCGR3A | Fc fragment of IgG receptor IIIa | NM_000569.7, NM_001127592.2, NM_001329122.1, NM_001329120.1, NM_001127593.1, XM_024454064.1, NM_001127595.2, NM_001127596.2 |
| 51350 | human | KRT76 | keratin 76 | NM_015848.4 |
| 5672 | human | PSG4 | pregnancy specific beta-1-glycoprotein 4 | NM_002780.5, NM_213633.3, NM_001316339.2, XM_017027001.2, XM_017027002.2, XM_017026997.2, NM_001276495.1 |
| 4982 | human | TNFRSF11B | TNF receptor superfamily member 11b | NM_002546.4 |
| 596 | human | BCL2 | BCL2 apoptosis regulator | XM_017025917.2, XR_935248.3, XM_011526135.3, NM_000633.2, NM_000657.2 |
| 920 | human | CD4 | CD4 molecule | NM_001195016.3, NM_001195014.3, XM_017020228.2, NM_001195015.3, NM_000616.5, NM_001195017.3 |
| 1290 | human | COL5A2 | collagen type V alpha 2 chain | NM_000393.5, XM_011510573.3 |
| 2263 | human | FGFR2 | fibroblast growth factor receptor 2 | NM_001144915.1, NM_001144913.1, NM_001144916.1, NM_001320654.1, NM_001144914.1, NM_023029.2, NM_000141.4, NM_022970.3, XM_024447887.1, NM_001144917.2, NR_073009.2, XM_024447892.1, XM_017015924.2, XM_006717710.4, XM_017015920.2, XM_024447891.1, XM_006717708.3, NM_001144918.2, XM_017015921.2, XM_024447888.1, XM_024447890.1, XM_024447889.1, NM_001320658.2, NM_001144919.2, XM_017015925.2 |
| 3111 | human | HLA-DOA | major histocompatibility complex, class II, DO alpha | NM_002119.4 |
| 3113 | human | HLA-DPA1 | major histocompatibility complex, class II, DP alpha 1 | NM_033554.3, NM_001242524.2, NM_001242525.2 |
| 3115 | human | HLA-DPB1 | major histocompatibility complex, class II, DP beta 1 | NM_002121.6 |
| 3459 | human | IFNGR1 | interferon gamma receptor 1 | NM_000416.2, XM_011535794.1, XM_011535793.2, XM_006715470.3, NM_001363527.1, NM_001363526.1 |
| 10320 | human | IKZF1 | IKAROS family zinc finger 1 | XM_017011669.1, XM_011515060.2, XM_011515077.2, XM_011515076.2, XM_011515062.2, XM_017011670.1, XM_011515070.2, XM_011515073.2, XM_017011668.1, XM_011515066.2, |

TABLE 1-continued

| shRNA transcripts for upregulated genes. | | | | |
|---|---|---|---|---|
| Gene ID | Taxon | Gene Symbol | Gene Description | Current WT Transcripts |
| | | | | XM_011515074.2, XM_011515063.2, XM_011515072.2, XM_011515058.2, XM_017011667.1, XM_011515068.2, XM_011515069.2, XM_011515065.2, XM_011515071.2, XM_011515078.2, XM_011515075.2, NM_001291844.1, NM_001220770.2, NM_001291843.1, NM_001291841.1, NM_001220768.2, NM_001220767.2, NM_001291840.1, NM_001220771.2, NM_001291842.1, NM_006060.6, NM_001291837.2, NM_001291846.2, NM_001220765.3, NM_001291845.2, XM_011515064.3, XM_011515067.3, NM_001291839.2, NM_001291838.2, XM_011515059.3, NM_001291847.2, XM_011515061.3 |
| 3587 | human | IL10RA | interleukin 10 receptor subunit alpha | XM_024448493.1, NR_026691.2, NM_001558.3 |
| 3606 | human | IL18 | interleukin 18 | XM_011542805.1, XM_011542806.2, NM_001243211.2, NM_001562.4 |
| 3689 | human | ITGB2 | integrin subunit beta 2 | NM_000211.5, XM_006724001.2, NM_001303238.2, NM_001127491.3 |
| 182 | human | JAG1 | jagged canonical Notch ligand 1 | NM_000214.3 |
| 5602 | human | MAPK10 | mitogen-activated protein kinase 10 | XR_001741289.1, XM_017008441.2, XM_024454145.1, XM_006714268.3, XM_005263135.4, XM_017008428.2, NM_002753.5, XM_017008453.2, XM_005263130.3, XM_024454141.1, NM_001363657.2, XM_024454144.1, XM_017008435.2, XM_024454142.1, NM_001351624.2, XM_017008436.2, XM_017008450.2, XM_017008434.2, XM_017008454.2, XM_017008433.2, XM_017008429.2, XM_005263131.3, XM_005263129.3, XM_024454146.1, XM_017008448.2, XM_024454143.1, XM_017008447.2, XM_017008432.2, XM_017008420.2, XM_024454149.1, NM_138982.4, XM_017008422.2, XM_017008452.2, XM_024454148.1, XM_011532117.3, XM_024454139.1, NM_001318069.2, XM_017008445.2, XM_017008423.2, XM_017008449.2, XM_006714269.3, XM_024454147.1, XM_017008427.2, XM_017008430.2, XM_011532120.3, XM_011532121.3, NM_138980.4, XM_011532118.3, XM_017008451.2, NM_001351625.2, XM_017008437.2, XM_024454140.1, NM_001318068.1, NM_001318067.1 |
| 4773 | human | NFATC2 | nuclear factor of activated T cells 2 | XM_011528826.2, XM_011528824.2, XM_011528825.2, XM_017027851.1, XM_017027850.1, NM_001258296.2, NM_173091.4, NM_001258292.2, NM_001258294.2, NM_012340.5, NM_001258297.2, NM_001136021.3, NM_001258295.2 |
| 4851 | human | NOTCH1 | notch receptor 1 | XM_011518717.2, NM_017617.5 |
| 4853 | human | NOTCH2 | notch receptor 2 | NM_001200001.1, NM_024408.4 |
| 23533 | human | PIK3R5 | phosphoinositide-3-kinase regulatory subunit 5 | NM_001251851.2, NM_001251852.1, NM_001251855.1, NM_001251853.1, NM_001142633.2, XM_005256580.3, NM_014308.3 |
| 6688 | human | SPI1 | Spi-1 proto-oncogene | XM_017018173.1, XM_011520307.1, NM_001080547.2, NM_003120.3 |
| 7046 | human | TGFBR1 | transforming growth factor beta receptor 1 | NM_001130916.3, XM_024447658.1, NM_001306210.2, NM_004612.4, XM_011518950.2, XM_011518949.2, XM_011518948.2, XM_017015063.1 |
| 7048 | human | TGFBR2 | transforming growth factor beta receptor 2 | NM_001024847.2, XM_011534043.2, XM_017007106.1, NM_003242.6, XM_011534045.3 |
| 2532 | human | ACKR1 | atypical chemokine receptor 1 (Duffy blood group) | NM_001122951.3, NM_002036.4 |
| 80332 | human | ADAM33 | ADAM metallopeptidase domain 33 | XM_017028083.1, XM_017028082.1, XR_001754405.1, XM_006723640.1, XM_005260843.1, NM_001282447.2, NM_025220.4, NM_153202.3, XM_006723644.2, XM_011529366.1, XR_937151.1, XM_011529370.1, XR_937152.1, |

TABLE 1-continued

| shRNA transcripts for upregulated genes. | | | | |
|---|---|---|---|---|
| Gene ID | Taxon | Gene Symbol | Gene Description | Current WT Transcripts |
| | | | | XM_011529367.1, XM_017028081.2, XM_017028080.2, XM_011529371.2, XR_002958534.1, XM_011529373.2 |
| 81792 | human | ADAMTS12 | ADAM metallopeptidase with thrombospondin type 1 motif 12 | NM_030955.4, NM_001324512.2, NM_001324511.2, XM_017009909.1, XM_017009906.1, XM_017009907.1, XM_017009908.1, XM_017009905.1 |
| 115701 | human | ALPK2 | alpha kinase 2 | NM_052947.4 |
| 306 | human | ANXA3 | annexin A3 | NM_005139.3, XR_001741215.2 |
| 79642 | human | ARSJ | arylsulfatase family member J | XM_011532239.2, XM_017008600.1, XM_011532238.3, XM_017008598.2, XM_017008594.2, XM_017008595.2, XM_017008592.2, XM_024454216.1, NM_024590.4, NM_001354210.2, XM_017008599.2, NM_001354211.2, XM_024454214.1, XM_017008593.2, XM_024454215.1, XM_017008597.2 |
| 57863 | human | CADM3 | cell adhesion molecule 3 | XM_024448760.1, NM_021189.5, NM_001127173.3, NM_001346510.2 |
| 100131825 | human | CADM3-AS1 | CADM3 antisense RNA 1 | NR_037870.1 |
| 54102 | human | CLIC6 | chloride intracellular channel 6 | XM_017028406.1, NM_001317009.2, NM_053277.3 |
| 1469 | human | CST1 | cystatin SN | NM_001898.2 |
| 1472 | human | CST4 | cystatin S | NM_001899.2 |
| 728597 | human | DCDC2C | doublecortin domain containing 2C | XM_006711894.4, NM_001365580.1, XR_001738921.2, XM_017004837.2, XM_017004836.2, NM_001287444.2, XR_001738920.2 |
| 9201 | human | DCLK1 | doublecortin like kinase 1 | NM_001195415.1, XM_017020848.1, XM_017020847.1, NM_001195430.2, NM_001195416.2, NM_001330071.2, NM_004734.5, NM_001330072.2 |
| 57628 | human | DPP10 | dipeptidyl peptidase like 10 | NM_001178034.1, NM_001321906.1, NM_001321914.1, XM_017004566.1, NM_001321905.2, NM_001178036.2, NM_001178037.2, XM_024453023.1, NM_001321912.2, NM_001004360.4, NM_001321907.2, NM_001321910.2, NM_001321913.2, NM_001321909.2, NM_001321911.2, NM_020868.6, NM_001321908.2 |
| 55068 | human | ENOX1 | ecto-NOX disulfide-thiol exchanger 1 | NM_001127615.2, XR_001749594.1, XM_017020641.2, NM_001347965.2, NM_001347968.2, NM_017993.5, XM_011535127.3, NM_001347970.2, XR_001749593.2, NM_001242863.3, XM_024449374.1, NM_001347969.2, NM_001347963.2, XM_024449372.1, NR_145132.2, XM_011535126.3, XM_024449373.1, NM_001347967.2, XR_001749592.2, NM_001347964.2, NM_001347971.2, XM_024449371.1, NM_001347966.2, XM_017020642.2, XM_017020637.2 |
| 2051 | human | EPHB6 | EPH receptor B6 | XM_011515881.3, XM_024446674.1, XM_024446675.1, NM_004445.6, XM_011515880.1, XM_011515879.1, XM_011515882.2, NM_001280795.2, NM_001280794.2, NR_104001.2 |
| 80000 | human | GREB1L | GREB1 like retinoic acid receptor coactivator | XM_017025991.1, XM_017025988.1, XM_017025996.1, XM_017025989.1, XM_017025994.1, XM_017025990.1, XM_017025993.1, XM_017025995.1, XM_017025992.1, NM_001142966.2, XM_006722547.3, XM_011526179.3 |
| 3382 | human | ICA1 | islet cell autoantigen 1 | XM_011515351.1, XM_011515349.1, XM_011515348.1, XM_011515354.1, XM_011515353.2, XM_011515357.2, XM_017012125.1, XM_017012116.1, NM_004968.3, NR_146929.2, NM_001350829.2, NM_001350833.2, NM_001350838.2, NM_001350826.2, NR_146928.2, NM_001350837.2, XM_024446741.1, XR_002956426.1, NM_001350825.2, NM_001276478.2, NM_001350823.2, NM_001350834.2, NM_001350831.2, XM_024446740.1, NM_001350836.2, XM_011515347.3, NM_001350819.2, NM_001350830.2, NM_001350828.2, NM_001350827.2, NR_146926.2, XM_011515356.3, NM_001350835.2, NM_001136020.3, NM_001350821.2, NM_001350832.2, XM_011515355.3, NM_022307.3, XR_002956427.1, NM_001350824.2, NM_001350820.2, NR_146927.2 |

TABLE 1-continued shRNA transcripts for upregulated genes.

| Gene ID | Taxon | Gene Symbol | Gene Description | Current WT Transcripts |
|---|---|---|---|---|
| 80760 | human | ITIH5 | inter-alpha-trypsin inhibitor heavy chain 5 | NM_030569.7, XM_011519714.3, XM_011519713.3, NM_032817.6, NM_001001851.2 |
| 150771 | human | ITPRIPL1 | ITPRIP like 1 | NM_001163523.1, NM_001163524.1, NM_001008949.2, XM_017003427.1, NM_001324490.1, NM_178495.6 |
| 23046 | human | KIF21B | kinesin family member 21B | NM_001252102.2, NM_001252103.2, NM_017596.4, NM_001252100.2, XM_017000732.1, XM_017000731.1 |
| 59352 | human | LGR6 | leucine rich repeat containing G protein-coupled receptor 6 | NM_001017404.1, NM_001017403.1, XM_011509840.2, XM_011509841.2, XM_011509844.2, XM_011509838.2, XM_017001996.1, XM_011509842.2, XM_011509846.2, XM_011509843.2, XM_005245404.3, XM_011509839.2, XM_017001997.1, XM_017001998.1, NM_021636.3 |
| 4327 | human | MMP19 | matrix metallopeptidase 19 | XM_017019309.1, XM_006719401.3, XM_017019308.1, XR_429102.2, XM_011538359.1, XR_944553.1, NM_002429.6, NM_001272101.2, NR_073606.2 |
| 80133 | human | MROH9 | maestro heat like repeat family member 9 | NM_001163629.1, XM_011510006.2, XM_011510007.2, XM_011510005.2, NM_025063.4 |
| 219348 | human | PLAC9 | placenta associated 9 | NM_001012973.3, NM_001331125.2, NR_138551.2 |
| 5627 | human | PROS1 | protein S | NM_000313.4, NM_001314077.1 |
| 5774 | human | PTPN3 | protein tyrosine phosphatase non-receptor type 3 | XM_006717203.4, NM_001145371.2, NM_001145372.2, NM_001145368.2, NM_002829.4, NM_001145369.1, XM_017014956.1, XM_006717201.3, XM_017014955.1, XM_006717197.3, XM_011518889.2, XM_006717199.3, XM_006717204.3, XM_006717202.3, XM_011518888.2, XM_017014957.1, NM_001145370.1, NR_026918.1 |
| 5919 | human | RARRES2 | retinoic acid receptor responder 2 | XM_017012491.1, NM_002889.4 |
| 4920 | human | ROR2 | receptor tyrosine kinase like orphan receptor 2 | XM_005252008.4, XM_017014763.1, XM_017014762.1, XR_001746315.1, XM_006717121.3, XM_005252009.3, NM_001318204.2, NM_004560.4 |
| 220963 | human | SLC16A9 | solute carrier family 16 member 9 | XM_017015883.1, NM_001323979.1, NM_001323978.1, NM_001323981.1, NM_001323980.1, NM_001323977.1, NM_194298.2, XM_017015884.2, XM_024447878.1 |
| 6523 | human | SLC5A1 | solute carrier family 5 member 1 | NM_000343.4, XM_011530331.1, NM_001256314.1 |
| 161291 | human | TMEM30B | transmembrane protein 30B | NM_001017970.3 |
| 7253 | human | TSHR | thyroid stimulating hormone receptor | NM_000369.3, NM_001142626.3, NM_001018036.3, XM_006720245.1, XM_005268039.1, XM_005268037.4, XM_011537119.2 |
| 7434 | human | VIPR2 | vasoactive intestinal peptide receptor 2 | NM_001308259.1, NR_130758.1, NM_001304522.1, XM_005249561.3, XM_017012580.1, XM_006716107.2, XM_006716108.3, XM_011516550.2, XM_024446917.1, XM_024446916.1, XM_024446914.1, XM_024446915.1, XM_024446918.1, NM_003382.5 |
| 7473 | human | WNT3 | Wnt family member 3 | NM_030753.5 | miRNA.

MicroRNAs (miRNAs) are non-coding RNAs of 20-24 nucleotides in length that serve as central regulators of eukaryotic gene expression by targeting mRNAs for cleavage or translational repression and promoting mRNA degradation.

miRNAs that bind to mRNA of COCH, an upregulated gene, to decrease expression include, for example, hsa-mir-331-3p, hsa-mir-192-5p, hsa-mir-615-3p, hsa-mir-215-5p, and hsa-mir-1301-3p, among others. miRNAs that bind to mRNA of FN1, an upregulated gene, to decrease expression include, for example, hsa-mir-200b-3p, has-mir-1, has-mir-200c-3p, has-mir-26b-5p, and has-mir-615-3p, among others. miRNAs that bind to mRNA of THBS2, an upregulated gene, to decrease expression include, for example, miR-659-39, among others. miRNAs are readily available for the other genes described in the section entitled "Detection of an Increase of Expression of Marker Genes."

Small Molecule Therapeutics

Small-molecule gene-silencing strategies have rapidly evolved, driven largely by enhanced understanding of gene function in the pathogenesis of disease. Over this time, many genes have been targeted by specifically engineered agents from different classes of nucleic acid-based drugs in experimental models of disease to probe, dissect, and characterize further the complex processes that underpin molecular signaling. With the ongoing identification of new genes and an appreciation of their regulatory pathways and pathological roles, small-molecule antigen strategies have not only emerged as an important molecular approach to delineate the functions of these genes but also are now a clinical reality inching closer to mainstream therapeutics.

For example, pharmacologic targeting of NTRK3 with the small molecule inhibitor entrectinib can be effective in both in vitro and in vivo models of desmoplastic small round cell tumor, a sarcoma for which NTRK3 is a prominent neural marker (Ogura et al., *Clinical Cancer Research,* 27(4): 2021).

Genome Editing

Genome editing changes the actual DNA sequence in the genome. Therapeutic agents can use molecular tools for genome editing to decrease gene expression of upregulated genes, Methods can include the CRISPR-Cas system, zinc finger nucleases, and TALENs.

Therapeutic agents can include one or more gene-editing compositions directed to target at least one sequence of a polynucleotide of an unregulated gene described herein. The one or more gene editing compositions can comprise at least one polynucleotide encoding an RNA-guided DNA endonuclease protein, and at least one guide RNA (gRNA) having a spacer sequence complementary to a polynucleotide sequence of an upregulated gene described herein. These RNA-guided DNA endonucleases are directed by gRNA to cleave phosphodiester bonds within a polynucleotide chain. These gRNAs can be noncoding short RNA sequences that bind to complementary DNA sequences and can be used in DNA editing. One RNA-guided DNA endonuclease is CRISPR associated protein 9 (Cas9), which can cleave nearly any sequence complementary to the gRNA. However, any suitable RNA-guided DNA endonuclease can be used. The gRNA can confer target sequence specificity to the CRISPR-CAS9 system by first binding to the RNA-guided DNA endonuclease. Then, the gRNA sequence can guide the complex to a specific location on the DNA where RNA-guided DNA endonuclease performs its endonuclease activity cutting the target DNA strand.

CRISPR Systems

CRISPR interrogates gene function by blocking gene expression and analyzing its effect on phenotype. CRISPR generates knockouts at the DNA level. CRISPR-based genome editing requires two components: a guide RNA and a CRISPR-associated endonuclease protein (Cas). The guide RNA, analogous to a GPS system, directs the Cas nuclease to the specific target DNA sequence, which then cuts the DNA at that site. The most commonly used nuclease, SpCas9, is the one isolated from the bacterium *Streptococcus pyogenes.*

CRISPR systems can be used, for example, to decrease or downregulate gene expression for one or more of the upregulated genes disclosed herein. In an example, the following gRNA sequences uniquely target the COCH gene within the human genome. These gRNA sequences are for use with WT SpCas9, or as crRNA for use with WT SpCas9 protein, and introduce a DSB for genome editing. See, Sanjana et al., Improved vectors and genome-wide libraries for CRISPR screening. Nat Methods. 2014 August; 11(8): 783-4:

TABLE 2

| COCH CRISPR gRNA or crRNA | | |
|---|---|---|
| COCH CRISPR Guide RNA or crRNA 1 | (GCTTCTGTATCGAGCATATG) | (SEQ ID NO: 23) |
| COCH CRISPR Guide RNA or crRNA 2 | (ACCGGCTCCCTCGCTGCCCG) | (SEQ ID NO: 24) |
| COCH CRISPR Guide RNA or crRNA 3 | (CACCCACCGAGGCCGAGAGC) | (SEQ ID NO: 25) |
| COCH CRISPR Guide RNA or crRNA 4 | (TACACAGAGAATTCCTCAAG) | (SEQ ID NO: 26) |

TABLE 2-continued

| COCH CRISPR gRNA or crRNA | | |
|---|---|---|
| COCH CRISPR Guide RNA or crRNA 5 | (CAGTCACCATGTCCGCAGCC) | (SEQ ID NO: 27) |
| COCH CRISPR Guide RNA or crRNA 6 | (CCCGCGGGCAGCGAGGGAGC) | (SEQ ID NO: 28) |

In another example, the following gRNA sequences uniquely target the FN1 gene within the human genome. These gRNA sequences are for use with WT SpCas9, or as crRNA for use with WT SpCas9 protein, to introduce a DSB for genome editing. See Sanjana et al., Improved vectors and genome-wide libraries for CRISPR screening. Nat Methods. 2014 August; 11(8):783-4.

TABLE 3

| FN1 CRISPR gRNA or crRNA | | |
|---|---|---|
| FN1 CRISPR Guide RNA or crRNA 1 | (GACCTACCTAGGCAATGCGT) | (SEQ ID NO: 29) |
| FN1 CRISPR Guide RNA or crRNA 2 | (TACAAACCAACGCATTGCCT) | (SEQ ID NO: 30) |
| FN1 CRISPR Guide RNA or crRNA 3 | (GCTCATAAGTGTCACCCACT) | (SEQ ID NO: 31) |
| FN1 CRISPR Guide RNA or crRNA 4 | (GAATGGACCTGCAAGCCCAT) | (SEQ ID NO: 32) |
| FN1 CRISPR Guide RNA or crRNA 5 | (TCACACACCTATGGGCTTGC) | (SEQ ID NO: 33) |
| FN1 CRISPR Guide RNA or crRNA 6 | (GACTGTACCTGCATCGGGGC) | (SEQ ID NO: 34) |

In yet another example, the following gRNA sequences uniquely target the THBS2 gene within the human genome. These gRNA sequences are for use with WT SpCas9, or as crRNA for use with WT SpCas9 protein, to introduce a DSB for genome editing. See Sanjana et al., Improved vectors and genome-wide libraries for CRISPR screening. Nat Methods. 2014 August; 11(8):783-4.

TABLE 4

| THBS2 CRISPR gRNA or crRNA | | |
|---|---|---|
| THBS2 CRISPR Guide RNA or crRNA 1 | (CCTCACCTTGCAGGTACACG) | (SEQ ID NO: 35) |
| THBS2 CRISPR Guide RNA or crRNA 2 | (CTGCGCCAGTCCATCCTTTG) | (SEQ ID NO: 36) |
| THBS2 CRISPR Guide RNA or crRNA 3 | (GCAGCATTCGCCTTCCACAA) | (SEQ ID NO: 37) |
| THBS2 CRISPR Guide RNA or crRNA 4 | (CGAATGATAACCAGTTTCTC) | (SEQ ID NO: 38) |
| THBS2 CRISPR Guide RNA or crRNA 5 | (AGCAAGAAGGGTTGCCAGCA) | (SEQ ID NO: 39) |
| THBS2 CRISPR Guide RNA or crRNA 6 | (CCTAGTGTTTGAAAACTCTG) | (SEQ ID NO: 40) |

Zinc Finger Nucleases

Zinc finger nucleases (ZFNs) are comprised of a chain of zinc finger proteins fused to a bacterial nuclease to produce a system capable of making site-specific double stranded DNA breaks to enable gene edits. ZFNs allow site-specific manipulation of the genome. For example, a ZFN-based method suited for the silencing of protein-coding and non-coding genes relies on the ZFN-mediated integration of RNA destabilizing elements into the human genome, e.g., poly(A) signals functioning as termination elements and destabilizing downstream sequences. The biallelic integration of poly(A) signals into the gene locus of the long ncRNA MALAT1 resulted in a 1000-fold decrease of RNA expression. Thus, this approach is more specific and 300 times more efficient than RNA interference techniques. The opportunity to create a variety of loss-of-function tumor model cell lines in different cancer backgrounds will promote future functional analyses of important long noncoding RNA transcripts. ZFN's can be used to downregulate the upregulated genes described herein.

TALENs

Transcription Activator-Like Effector Nucleases (TAL-ENs) are artificial restriction enzymes that consist of a TAL effector DNA-binding domain fused to the DNA nuclease domain from the enzyme FokI. The TAL effector DNA-binding domain is composed of 33-35 amino acid repeats, which differ from each other by two amino acids (called the Repeat-Variable Di-residue (RVD)). The identity of those two amino acids determines which nucleotide each repeat will bind. A stretch of 12 to 31 repeats can be assembled in a row in order to target the TALEN to a specific DNA sequence in the genome.

In order for the nuclease domain to cut, the TALEN must dimerize. This means that two different TALENs must be supplied to the cell: one targeting each strand of DNA, separated by a small spacer sequence of 12-25 bp. After FokI cuts, it will cause a dsDNA break, which will be repaired by the cell's error-prone NHEJ pathway. As with CRISPR, this will sometimes result in InDel frameshift mutations which can knockout gene expression. Talens can be used to down-regulate the upregulated genes described herein.

Therapeutic agents of the present disclosure can include one or more agents that can lower or reduce the amount of one of more of the upregulated genes in a patient or subject. The one or more agents can lower or reduce the amount of one or more of the upregulated genes by about 30% to about 90% in the patient or subject, or by about 35%, about 40%, about 45%, about 50%, about 55%, about 60%, about 65%, about 70%, about 75%, about 80%, about 85%, about 90% or more. Alternatively, the one or more therapeutic agents can reduce the amount of one or more of the upregulated genes by about 1, 2, 3, 4, 5, 10, 20, 30 fold or more.

Methods of Increasing Expression of Downregulated Genes

In an embodiment a subject having pre-symptomatic, advanced, early-onset, or age-related (late-onset) FECD, glaucoma, or other ocular disease can be treated by down-regulating one or more of the genes described in the section entitled "Detection of a Decrease of Expression of Marker Genes" herein.

In some embodiments, a method for increasing gene expression of downregulated genes is provided. In some embodiments, the method of increasing gene expression can include gene replacement therapy, CRISPR-Cas system, saRNA, RNAa, increasing RNA transcription or translation, or cell-based therapies.

Gene Therapy

Gene therapy includes the delivery of wild-type (WT) and modified genes, as well as constructs designed to reduce the expression of a particular gene (DNA sequences coding for shRNA and miRNA, as well as siRNA that are delivered directly).

RNAa/saRNA

RNA activation (RNAa) allows specific gene upregulation mediated by a small activating RNA (saRNA). RNA activation (RNAa) is a process mediated by RNAs to enhance gene expression. This pathway is highly regulated and evolutionarily conserved; therefore, there is enormous potential to apply this gene activation mechanism to target undruggable diseases. In an example, small activating RNAs (saRNA), which were designed to have complementary sequences to the promoter regions of E-cadherin, p21WAF1/CIP1(p21) and VEGF, mediate sequence specific mRNA transcription activation of the respective targeted genes in mammalian cells.

Increasing RNA Transcription/Translation

The primary control point for gene expression is usually at the very beginning of the protein production process—the initiation of transcription. RNA transcription makes an efficient control point because many proteins can be made from a single mRNA molecule. The quantity of mRNA transcript for a single gene directly reflects how much transcription of that gene has occurred. Tracking and regulating that quantity will therefore indicate how vigorously a gene is transcribed or expressed. Furthermore, amino acids act through a number of signaling pathways and mechanisms to mediate control of gene expression at the level of translation. Although phosphorylation of eIF2α leads to a suppression of global protein synthesis, accumulating evidence demonstrates that it also results in the derepression of translation of a number of specific mRNA.

Increasing the expression of LUM mRNA, a downregulated gene, can be accomplished through interaction with, for example, tetrachlorodibenzodioxin, valproic acid, phenylmercuric acetate, 4-(5-benzo(1,3)dioxol-5-yl-4-pyridin-2-yl-1H-imidazol-2-yl)benzamide, (6-(4-(2-piperidin-1-ylethoxy)phenyl))-3-pyridin-4-ylpyrazolo(1,5-a) pyrimidine, or 8-Bromo Cyclic Adenosine Monophosphate, among other compounds. Increasing the expression of GFAP mRNA, a downregulated gene, can be accomplished through, for example, interaction with resveratrol, cadmium chloride, and kainic acid, among others.

Cell-Based Therapies

Although cell therapies have been used in medicine for several decades (e.g., blood transfusions), the use of cells manipulated ex vivo with therapeutic genes and then reintroduced into patients offers a new strategy by which to deliver gene-based medicines. The advantages of ex vivo genetic manipulation of cells include the ability to engineer highly purified cell populations and optimize the conditions for high-efficiency gene transfer outside the body. This obviates the issues of in vivo targeting of vectors and circulating host antibody responses. Furthermore, safety profiles of ex vivo modified cells can be stringently assessed prior to administration to the patient.

Cell therapies that can increase, for example, LUM expression include, for example, umbilical cord-derived mesenchymal stem cell therapy and corneal stromal stem cell therapy. Cell therapies that can increase GFAP expression include, for example, bone marrow stromal cell therapy. Cell therapies that can increase CXCL8 expression include, for example, mesenchymal stem cell therapy using exogenous CXCL8.

Nucleic Acid Delivery & Expression

In certain embodiments, expression cassettes are employed to express a gene product, either for subsequent purification and delivery to a cell/subject, or for use directly in a genetic-based delivery approach. Expression requires that appropriate signals be provided in the vectors, and include various regulatory elements such as enhancers/ promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Regulatory Elements

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Furthermore, selection of a promoter that is regulated in response to specific physiologic signals can permit inducible expression of the gene product.

Genome Editing

CRISPR activation (CRISPRa) is a type of CRISPR tool that uses modified versions of CRISPR effectors without endonuclease activity, with added transcriptional activators on dCas9 or the guide RNAs (gRNAs). Like for CRISPR interference, the CRISPR effector is guided to the target by a complementary guide RNA. However, CRISPR activation systems are fused to transcriptional activators to increase expression of genes of interest. Such systems are usable for many purposes including but not limited to, genetic screens and overexpression of proteins of interest. The most commonly-used effector is based on Cas9 (from Type II systems), but other effectors like Cas12a (Type V) have been used as well.

Furthermore, selection of a promoter that is regulated in response to specific physiologic signals can permit inducible expression of the gene product.

Methods of Monitoring Treatment

In an embodiment, a method of monitoring treatment of pre-symptomatic, advanced, early-onset, or age-related (late-onset) Fuchs' endothelial corneal dystrophy can comprise obtaining a first sample from a subject and then detecting in the first sample one or more of: gene expression levels of one or more upregulated genes as described herein, gene expression levels of one or more downregulated genes as described herein, or skipped exon events as shown in Table 8. The method can further comprise treating the subject and then, later, obtaining a second sample from a subject and then detecting in the second sample gene expression levels or skipped exon events. Furthermore, the method can comprise comparing the first sample gene expression levels or skipped exon events with the second sample gene expression levels or skipped exon events.

In another embodiment, a method of monitoring treatment of glaucoma can comprise obtaining a first sample from a subject, detecting gene expression levels of COCH in the first sample, administering a treatment to the subject; obtaining a second sample from the subject and, later, detecting gene expression levels in the second sample, and comparing the first sample gene expression levels to the second sample gene expression levels. The sample of the method can be corneal tissue, aqueous humor, plasma, serum, blood, tear film, trabecular meshwork, or a combination thereof. The method further includes treating the subject with any suitable means including, for example, therapeutic agents that decrease COCH expression, prescription eyedrops, oral medications, prostaglandins, beta blockers, alpha-adrenergic agonists, carbonic anhydrase inhibitors, rho kinase inhibitors, miotic or cholinergic agents, laser trabeculoplasty, trabeculectomy, drainage tubes, minimally invasive glaucoma surgery (MIGS), peripheral iridotomy, aqueous shunts, or combinations thereof. The method can be directed or performed in the anterior segment of the eye, posterior segment of the eye, corneal endothelial cells, or other cells of the anterior segment of the eye. The posterior segment of the eye comprises the back two-thirds of the eye, including the vitreous humor, the retina, the choroid, and the optic nerve. The anterior segment of the eye is the front-most region of the eye, and includes the cornea, iris, ciliary body, and lens. The anterior segment of the eye comprises the anterior chamber between the posterior surface of the cornea (i.e. the corneal endothelium) and the iris and the posterior chamber between the iris and the front face of the vitreous.

Detection Methods

Gene expression changes in a patient with FECD or glaucoma can be detected using a variety of different methodologies. mRNA of one or more of the up- or down-regulated genes described herein can detected and quantified. Alternatively, one or more proteins associated with the up- or down-regulated genes described herein can be detected and quantified. Some methods include fluorescence in situ hybridization (FISH), immunodetection, western Blot, northern blot, or microarray.

Fluorescence In Situ Hybridization

FISH (fluorescent in situ hybridization) is a cytogenetic technique developed to detect and localize the presence or absence of specific nucleic acid sequences. FISH uses fluorescent probes that bind to targets (e.g., parts of the chromosome with which they show a high degree of sequence complementarity). Fluorescence microscopy can be used to find out where the fluorescent probe is bound. FISH is often used for finding specific features in DNA for use in genetic counseling, medicine, and species identification, but can also be used to detect and localize specific RNA targets (mRNA, lncRNA and miRNA) in cells and tissue samples. In this context, it can help define the spatial-temporal patterns of gene expression within cells and tissues.

The differences between the various FISH techniques are usually due to variations in the sequence and labeling of the probes; and how they are used in combination. Probes are divided into two generic categories: cellular and acellular. "In situ" in fluorescent in situ hybridization refers to the placement of the probe placed cellularly. These few modifications make possible all FISH techniques. Probe size is important because longer probes hybridize less specifically than shorter probes. A short strand of DNA or RNA (often 10-25 nucleotides) which is complementary to a given target sequence, it can be used to identify or locate the target. The overlap defines the resolution of detectable features. A variety of other techniques use mixtures of differently colored probes. A range of colors in mixtures of fluorescent dyes can be detected, so that different targets can be identified by a characteristic color and a variety of ratios of colors.

Immunodetection

In further embodiments, there are immunodetection methods for identifying and/or quantifying gene expression. Some immunodetection methods include enzyme linked immunosorbent assay (ELISA), radioimmunoassay (RIA), immunoradiometric assay, fluoroimmunoassay, chemiluminescent assay, bioluminescent assay, and western blot to mention a few. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes. It is also possible to perform in vivo assays.

Contacting the chosen biological sample with an antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to proteins related to the up or downregulated genes disclosed herein. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

The detection of immunocomplex formation may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275, 149 and 4,366,241, incorporated by reference herein. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired. One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Western Blot or Northern Blot

The western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pi), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

The northern blot (RNA immunoblots for RNA isolation) is conceptually similar to western Blot. This type of blotting method is used to detect RNA. RNA is released once cells are broken open. Through northern blotting procedure, researchers can easily compare the cell type that contains the highest number of RNA. It also allows the researchers to find out if the cells from a certain disease contain less RNA or more RNA. It also helps in determining the progression of a certain disease based on RNA production. Northern blotting comprises the following steps: electrophoresis, transfer, and detection of specific sequences.

Microarray

DNA microarray technology is a high throughput technology for monitoring gene expression at the transcription level. Its use is akin to performing tens of thousands of northern blots simultaneously, and has the potential for parallel integration of the expression levels of an entire genome. A DNA microarray comprises DNA probes immobilized on a solid support such as a glass microscope slide. The DNA probes can be double stranded cDNA or short (25mers) or long (50-70mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 mers) sets are commercially available for human, mouse and other organisms (cgen.com, operon.com).

Another technique for fabricating oligonucleotide microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink-jet onto glass surfaces.

One method of utilizing gene expression data from microarrays is described by Tusher et al., PNAS 98(9) p. 5116-21, April, 2001. The method of Tusher is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

An embodiment provides methods of monitoring treatment of pre-symptomatic, advanced, early-onset, or age-related (late-onset) FECD, glaucoma, or other ocular disease. The methods can comprise obtaining a first sample from a subject having early stage FECD, late stage FECD, or FECD and detecting gene expression levels and or skipped exon events in the first sample. The first sample can be, for example, corneal tissue, aqueous humor, plasma, serum, blood, tear film, or a combination thereof. Gene expression levels and or skipped exon events can be detected as described herein. The genes of interest can comprise one or more of the upregulated genes and downregulated genes as described herein. Skipped exon events can comprise one or more of those listed in Table 8. The subject can be administered a treatment as described herein. At this point, the treatment can be administered 1, 2, 3, 4 or more times for 1, 2, 5, 7, 14, 21, 28 days, or 1, 2, 3, 4, 5, 6, or more months before the next step. When ready to proceed with the method, a second sample can be obtained from the subject. The second sample can be obtained from the subject and gene expression levels and or skipped exon events for the second sample can be determined at any time after both the first sample is obtained, and the treatment is administered. The second sample can be, for example, corneal tissue, aqueous humor, plasma, serum, blood, tear film, trabecular meshwork, or a combination thereof. Gene expression levels and skipped exon events can be detected as described herein. The method further includes comparing the first sample gene expression levels or skipped exon events with the second sample gene expression levels or skipped exon events.

Additionally, an embodiment provides methods of monitoring treatment of glaucoma. The methods can comprise obtaining a first sample from a subject having glaucoma and detecting gene expression levels of COCH in the first sample. The first sample can be, for example, corneal tissue, aqueous humor, plasma, serum, blood, tear film, trabecular meshwork, or a combination thereof. Gene expression levels can be detected as described herein. The subject can be administered a treatment as described herein. At this point, the treatment can be administered 1, 2, 3, 4 or more times for 1, 2, 5, 7, 14, 21, 28 days, or 1, 2, 3, 4, 5, 6, or more months before the next step. When ready to proceed with the method, a second sample can be obtained from the subject. The second sample can be obtained from the subject and gene expression levels for the second sample can be determined at any time after both the first sample is obtained, and the treatment is administered. The second sample can be, for example, corneal tissue, aqueous humor, plasma, serum, blood, tear film, trabecular meshwork, or a combination thereof. Gene expression levels can be detected as described herein. The method further includes comparing the first sample gene expression levels with the second sample gene expression levels. The method can be directed or performed in the anterior segment of the eye, posterior segment of the eye, corneal endothelial cells, or other cells of the anterior segment of the eye.

Treatments for FECD can be those described herein such as therapeutic agents that increase gene expression, therapeutic agents that decrease gene expression, conjunctival flaps, anterior stromal puncture, phototherapeutic keratectomy, amniotic membrane transplantation, collagen cross-linking, delivery of hyperosmotic solutions, steroidal eye drops, sodium chloride eye drops, keratoprosthesis implantation, therapeutic contacts such as bandage contact lenses, corneal transplant, lamellar transplant such as Descemet's stripping automated endothelial keratoplasty (DSAEK) and Descemet's membrane endothelial keratoplasty (DMEK), endothelial keratoplasty, penetrating keratoplasty, or combinations thereof. FECD can also be treated with, for example, Rho-associated kinase (ROCK) inhibitors such as Y-27632, optionally combined with transcorneal freezing. FECD can also be treated with transplantation of cultured corneal endothelial cells as a sheet or by injection of a cell suspension into the anterior chamber, optionally in combination with ROCK inhibitor. FECD can further be treated with prostaglandins, beta blockers, alpha-adrenergic agonists, carbonic anhydrase inhibitors, rho kinase inhibitors, miotic or cholinergic agents described herein.

In another embodiment, treatment for glaucoma can be those described herein such therapeutic agents that decrease the amount of expression of COCH, prescription eyedrops, oral medications, prostaglandins, beta blockers, alpha-adrenergic agonists, carbonic anhydrase inhibitors, rho kinase inhibitors, miotic or cholinergic agents, laser trabeculoplasty, trabeculectomy, drainage tubes, minimally invasive glaucoma surgery (MIGS), peripheral iridotomy, aqueous shunts, or combinations thereof.

Where the treatment is intended to treat symptoms, delay progression of disease, or decrease expression for upregulated genes, and the expression for upregulated genes measured in the second sample of a subject is the same or lower than the expression for upregulated genes measured in the first sample of the subject, the efficacy of the treatment is likely. Additionally, where the treatment is intended to treat symptoms, delay progression of disease, or decrease expression for upregulated genes, and the skipped exon events detected in the second sample of a subject are the same or fewer than the skipped exon events detected in the first sample of the subject, the efficacy of the treatment is likely.

Similarly, where the treatment is intended to treat symptoms, delay the progression of disease, or increase expression for downregulated genes, and the expression for downregulated genes measured in the second sample of a subject is the same or higher than the expression for downregulated genes measured in the first sample of the subject, the efficacy of the treatment is likely. Additionally, where the treatment is intended to treat symptoms, delay progression of disease, or increase expression for downregulated genes, and the skipped exon events detected in the second sample of a subject are the same or fewer than the skipped exon events detected in the first sample of the subject, the efficacy of the treatment is likely.

Where the treatment is intended to treat symptoms, delay progression of disease, or decrease expression of COCH, and the expression for COCH measured in the second sample of a subject is the same or lower than the expression for COCH measured in the first sample of the subject, the efficacy of the treatment is likely.

By "efficacious" is meant that the treatment leads to a reduction in expression of a pathologically upregulated gene, increase in expression of a pathologically downregulated gene or a decrease in size, prevalence, formation of guttae in a subject. When treatment is applied prophylactically, "efficacious" means that the treatment prevents onset of FECD symptoms.

Several treatments can be administered to a subject over the course of the treatment of FECD, glaucoma, or other ocular diseases. Each treatment can have individual effect progression of disease and symptomology. Accordingly, the determination of a change in gene expression and skipped exon events can be assessed after the administration of a therapy, whether or not it is the first to be administered to the subject, and as many times as required to follow the changes in gene expression over time. The treatment or treatments can be adjusted as needed based on the changes in gene expression levels and skipped exon events over time.

Therefore, the steps of obtaining a first sample from a subject; detecting gene expression levels and or detecting one or more skipped exon event in the first sample; administering a treatment to the subject; obtaining a second sample from the subject at a later time and detecting gene expression levels or skipped exon events of in the second sample; and comparing the first sample gene expression levels or skipped exon events with the second sample gene expression levels or skipped exon events can be repeated after each treatment regimen. Additionally, in cases of repeated measures, the latest amount gene expression or detection of skipped exon events in the sample of a subject can be compared to any one or to all of the previously measured samples to evaluate the changes over time and in response to the various treatments.

Furthermore, the steps of obtaining a first sample from a subject; detecting COCH gene expression levels in the first sample; administering a treatment to the subject; obtaining a second sample from the subject at a later time and detecting COCH gene expression levels in the second sample; and comparing the first sample COCH gene expression levels with the second sample COCH gene expression levels can be repeated after each treatment regimen. Additionally, in cases of repeated measures, the latest amount COCH gene expression in the sample of a subject can be compared to any one or to all of the previously measured samples to evaluate the changes over time and in response to the various treatments.

Methods of Monitoring Progression of Disease

An embodiment provides methods of detection of gene expression levels for monitoring the progression of a disease. The methods of detection can include Fluorescence In Situ Hybridization (FISH), immunodetection, western blot, northern blot, or microarray, as described above.

An embodiment provides methods of monitoring progression of pre-symptomatic, advanced, early-onset, or age-related (late-onset) FECD. The methods can comprise obtaining a first sample from a subject having early stage FECD, late stage FECD, or FECD and detecting gene expression levels and or skipped exon events in the first sample. The first sample can be, for example, corneal tissue, aqueous humor, plasma, serum, blood, tear film, trabecular meshwork, or a combination thereof. Gene expression levels and or skipped exon events can be detected as described herein. The genes of interest can comprise one or more of the upregulated genes and downregulated genes as described herein. Skipped exon events can comprise one or more of those listed in Table 8. A second sample can be obtained from the subject. The second sample can be obtained from the subject and gene expression levels and or skipped exon events for the second sample can be determined at any time after the first sample is obtained. The second sample can be, for example, corneal tissue, aqueous humor, plasma, serum, blood, tear film, trabecular meshwork, or a combination thereof. Gene expression levels and skipped exon events can be detected as described herein. The method further includes monitoring the progression of disease by comparing the first sample gene expression levels or skipped exon events with the second sample gene expression levels or skipped exon events.

Additionally, an embodiment provides methods of monitoring progression of glaucoma. The methods can comprise obtaining a first sample from a subject having glaucoma and detecting gene expression levels of COCH in the first sample. The first sample can be, for example, FECD cell line, aqueous humor, trabecular meshwork, or a combination thereof. Gene expression levels can be detected as described herein. A second sample can be obtained from the subject. The second sample can be obtained from the subject and gene expression levels for the second sample can be determined at any time after the first sample is obtained. The second sample can be, for example, corneal tissue, aqueous humor, plasma, serum, blood, tear film, trabecular meshwork, or a combination thereof. Gene expression levels can be detected as described herein. The method further includes comparing the first sample gene expression levels with the second sample gene expression levels to monitor progression of disease overtime. The method can be directed or performed in the anterior segment of the eye, posterior segment of the eye, corneal endothelial cells, or other cells of the anterior segment of the eye.

Where the expression for upregulated genes measured in the second sample of a subject is the same or lower than the expression for upregulated genes measured in the first sample of the subject, the disease is not likely to have progressed. Additionally, where the skipped exon events detected in the second sample of a subject are the same or fewer than the skipped exon events detected in the first sample of the subject, the disease is not likely to have progressed. Similarly, where the expression for downregulated genes measured in the second sample of a subject is the same or higher than the expression for downregulated genes measured in the first sample of the subject, the disease is not likely to have progressed.

Where the expression for upregulated genes measured in the second sample of a subject is higher than the expression for upregulated genes measured in the first sample of the subject, the disease is likely to have progressed. Additionally, where the skipped exon events detected in the second sample of a subject are greater than the skipped exon events detected in the first sample of the subject, the disease is likely to have progressed. Similarly, where the expression for downregulated genes measured in the second sample of a subject is the lower than the expression for downregulated genes measured in the first sample of the subject, the disease is likely to have progressed.

Where the treatment the expression for COCH measured in the second sample of a subject is the same or lower than the expression for COCH measured in the first sample of the subject, the disease is not likely to have progressed.

Where the treatment the expression for COCH measured in the second sample of a subject is the higher than the expression for COCH measured in the first sample of the subject, the disease is likely to have progressed.

Therefore, the steps of obtaining a first sample from a subject; detecting gene expression levels and or detecting one or more skipped exon event in the first sample; obtaining a second sample from the subject at a later time and detecting gene expression levels or skipped exon events of in the second sample; and comparing the first sample gene expression levels or skipped exon events with the second sample gene expression levels or skipped exon events can be repeated after each sample. Additionally, in cases of repeated measures, the latest amount gene expression or detection of skipped exon events in the sample of a subject can be compared to any one or to all of the previously measured samples to evaluate the changes over time.

The details of one or more variations of the subject matter described herein are set forth in the accompanying drawings and the description below. Other features and advantages of the subject matter described herein will be apparent from the description and drawings, and from the claims. The disclosed subject matter is not, however, limited to any particular embodiment disclosed.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and sub-ranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

These examples focus on isolating corneal tissue from FECD_REP, FECD_NR, Pre_S, and Control samples. TCF4 CTG18.1 polymorphism genotyping was conducted using short tandem repeat (STR) and triplet repeat primed polymerase chain reaction (TP-PCR). Total RNA was isolated using RNAseq. Whole transcriptomic sequencing data was analyzed to determine differentially expressed or spliced genes. TCF4 RNA half-life was measured using qPCR. Differential gene expression and alternative splicing patterns were validated by preparing cDNAs via reverse transcription, subsequent RT-PCR analysis, amplification products separated by gel electrophoresis, and qPCR. Additionally, an example assesses expression of COCH mRNA.

Materials and Methods for Examples 1-8

Isolation of Corneal Tissue

The study was conducted in compliance with the tenets of the Declaration of Helsinki and with the approval of the institutional review board of the University of Texas Southwestern Medical Center (UTSW). Subjects underwent a complete eye examination including slit lamp biomicroscopy by a cornea fellowship-trained ophthalmologist. Patients underwent endothelial keratoplasty for FECD severity Krachmer grade 5 (≥5 mm central confluent guttae without stromal edema) or 6 (≥5 mm central confluent guttae with stromal edema) assessed by slit lamp microscopy. After surgery, surgically explanted endothelium-Descemet's membrane monolayers were preserved in Optisol GS corneal storage media (Bausch & Lomb, Rochester, NY) prior to storage at −80 Celsius. Genomic DNA was extracted from peripheral blood leukocytes of each study subject using Autogen Flexigene (Qiagen, Valencia, CA).

Corneal endothelial samples from post-mortem donor corneas preserved in Optisol GS corneal storage media (Bausch & Lomb, Rochester, NY) were obtained from the eye bank of Transplant Services at UT Southwestern. Certified eye bank technicians screened the donor corneal endothelium with slit lamp biomicroscopy and Cellchek EB-10 specular microscopy (Konan Medical). Endothelium-Descemet's membrane monolayers from donor corneas were micro-dissected and stored as previously described (Mootha V V, et al., *Invest. Opthamol. Vis. Sci. (IOVS)*, 56(3):2015). DNA from the remaining corneal tissue of each sample was extracted with TRIzol reagent (ThermoScientific).

TCF4 CTG18.1 Polymorphism Genotyping

Genomic DNA from subjects' peripheral leukocytes or corneal tissue was used for genotyping. The CTG18.1 trinucleotide repeat polymorphism in the TCF4 gene was genotyped using a combination of short tandem repeat (STR) and triplet repeat primed polymerase chain reaction (TP-PCR) assays. On samples where STR assay detected only one allele or failed to detect any alleles, repeat primed PCR assay was performed to confirm the presence of an expanded allele(s). For the STR assay, a pair of primers, P1 and P2 (SEQ ID NO: 1 and SEQ ID NO: 2) flanking the CTG18.1 locus was utilized for PCR amplification with one primer labeled with FAM on 5' end. After PCR, 5 μL of DNA were mixed with 10 μL of Promega Internal Standard 600 (ILS600; Promega, Madison, WI). The TP-PCR assay was performed using the 5' FAM labeled primer specific for the repeat locus paired with repeat sequence targeted primers for PCR amplification. The P1 is a fluorescent primer designed to a region upstream from the CTG18.1 allele. The companion reverse primer P4 on the complementary strand is comprised of 5 units of the CTG repeat and a 5' tail to serve as an anchor for a second reverse primer P3, which prevents progressive shortening of the PCR products during subsequent cycles. The 5' tail of primer P4 and the "common" flag primer P3 share no homology with human sequence. For STR, 100 ng of genomic DNA was used, together with flanking primer pair 1 μM of primer P1 and 1 μM of primer P2, 200 μM dNTPs, 1.5 mM MgCl₂ and 1 U/10 μl reaction of AmpliTaq Gold™ DNA Polymerase (Applied Biosystems) in 1× Gold Buffer. Thermal cycling conditions were initial denaturation 5 minutes at 95° C., followed by 35 cycles 95° C. for 15 seconds, 60° C. for 15 seconds, and 72° C. for 1 minute and a final extension for 72° C. for 7 minutes. For TP-PCR, 200 ng of genomic DNA was used. 1 μM of primer P1 was added together with 1 μM of primer P3 and 0.03 μM of primer P4 to GoTaq® Master Mixes (Promega, Madison, WI, USA). Thermal cycling conditions were initial denaturation 9 minutes at 95° C., followed by 10 cycles of 95° C. for 30 seconds, 56° C. for 30 seconds, and 72° C. for 4 minutes, and then 30 cycles of 95° C. for 45 seconds, 56° C. for 45 seconds, and 72° C. for 4 minutes with a 15-second extension at each cycle. The final extension step was 72° C. for 10 minutes. PCR amplicons were loaded on an ABI 3730XL DNA analyzer (Applied Biosystems, Foster City, CA, USA) and the results analyzed with ABI GeneMapper 4.0 (Applied Biosystems). Large triplet repeat expansions were sized by Southern blot analysis using digoxigenin labeled probes.

TABLE 5

| Primers for STR Analysis and TR-PCR Assay | |
| --- | --- |
| Primer | Sequence, 5'-3' |
| P1 | AATCCAAACCGCCTTCCAAGT (SEQ ID NO: 1) |
| P2 | CAAAACTTCCGAAAGCCATTTCT (SEQ ID NO: 2) |
| P3 | TACGCATCCCAGTTTGAGACG (SEQ ID NO: 3) |
| P4 | TACGCATCCCAGTTTGAGACGCAGCAGCAGCAG (SEQ ID NO: 4) |

RNA Isolation and Sequencing

Total RNA was isolated from each of 25 tissue samples (6 FECD_REP, 4 FECD_NR, 6 Pre_S and 9 Controls) by homogenization in QIAzol lysis reagent, chloroform extraction and isolation with NucleoSpin RNA XS (Macherey-Nagel GmbH & Co., Germany). RNA quantity and quality were determined by Bioanalyzer 2100. RNA libraries were prepared for each tissue sample with high RIN (>5.0), using the TruSeq RNA sample Prep kit version 2 (Illumina, San Diego, CA, USA). For TruSeq stranded total RNAseq, ribosomal transcripts were depleted from total RNA, using Ribo-Zero Gold RNA removal kit followed by replacement of deoxythymidine triphosphate (dTTP) with deoxyuridine triphosphate (dUTP) during reverse transcription in the second strand synthesis, using TruSeq stranded total library preparation kit. The resulting libraries were minimally amplified to enrich for fragments using adapters on both ends and then quantified for sequencing at eight samples/flow cell by using a NextSeq 500/550 (Illumina) sequencer (PE 150).

Analysis of Differentially Expressed or Spliced Genes

Whole transcriptomic sequencing data from each tissue sample was analyzed using an analysis pipeline which includes STAR for initial mapping and Cufflinks (v2.21) for gene and isoform differential analysis, among other publicly available programs. For gene/isoform differential analysis, the minimum expression level of 1.5 FPKM and an FDR<0.05 were chosen as the threshold. The meta gene pathway analysis was carried out with IPA (Qiagene). The binary alignment map files from STAR were analyzed using rMATS (v.4.0) that quantitates the expression level of alternatively spliced genes between groups. To find the most significant events, we used stringent filtering criteria within rMATS to perform pairwise comparisons among 4 groups: percentage of spliced in (PSI) changes>0.15; FDR<0.001. For PSI, rMATS calculates a value for every differential splicing event, providing a range from 0 to 1, with 0 being completely excluded and 1 being uniformly included in the splicing products. Alternative splicing events were also compared to those obtained in tibialis anterior muscle of myotonic dystrophy type one patients (DM1). DM1 raw data was obtained from Gene Expression Omnibus (GSE86356, 6 Control and 6 DM1 tissue samples were used) and analyzed similarly as the FECD data (visit DMseq.org for more information).

Measurement of TCF4 RNA Half-Life

FECD corneal endothelial cell lines (F35T and F45SV) and a control corneal endothelial cells (W4056-17-001579) were cultured as described (Hu J et al., *Hum Mol Genet.* 27(6): 2018). The C9 and VVM84 skin fibroblasts were maintained at 37° C. and 5% CO2 in Minimal Essential Media Eagle (MEM) (Sigma, M4655) supplemented with 15% heat inactivated fetal bovine serum (Sigma) and 0.5% MEM nonessential amino acids (Sigma).

Endothelial or fibroblast cells were seeded in 6-well plate at 90% confluence. At the next day, actinomycin D was added into the wells at 5 µg/mL final concentration. Cells were harvest using Trizol agent (Sigma) at different time point. The TCF4 RNA levels were analyzed by qPCR.

Validation of Differential Gene Expression and Alternative Splicing Patterns

Total RNA was extracted from control, Pre_S or FECD corneal endothelial tissues (Table 6) by NucleoSpin RNA XS kit (Macherey-Nagel). cDNAs were prepared by reverse transcription. RT-PCR was performed using ChoiceTaq Blue Mastermix (Denville). PCR amplification was as follow: 94° C. for 3 minutes (1 cycle), 94° C. denaturation for 30 sec, 60° C. annealing for 30 sec, and 72° C. extension for 1 min (38 cycles), and a 7 minute 72° C. extension. The PCR primers were used as reported (Wieben et al., *Invest Ophthalmol Vis Sci. (IOVS)*, 58:2017) (Table 7). The amplification products were separated by 1.5% agarose gel electrophoresis. qPCR experiments were performed on a 7500 real-time PCR system (Applied Biosystems) using iTaq SYBR Green Supermix (Bio-Rad). Data was normalized relative to levels of RPL19 mRNA.

TABLE 6

Characteristics of cornea endothelial tissues used in the experimental validation.

| ID | Age | Phenotype | TCF4 CUG repeat |
|---|---|---|---|
| W4056-17-001398 | 54 | Healthy control | 12, 27 |
| W4056-17-001518 | 64 | Healthy control | 14, 26 |
| W4056-17-001449 | 64 | Healthy control | 13, 19 |
| 2015-1477 | 71 | Healthy control | 16, 16 |
| W4056-17-001831 | 59 | Healthy control | 13, 27 |
| W4056-18-002160 | 69 | Healthy control | 15, 15 |
| W4056-17-001754 | 73 | Healthy control | 12, 12 |
| W4056-17-001844 | 66 | Healthy control | 13, 16 |
| W4056-17-002127 | 65 | Healthy control | 12, 18 |
| W4056-17-001239 | 51 | Pre_S | 13, 84 |
| W4056-17-001810 | 57 | Pre_S | 15, 77 |
| W4056-18-002874 | 41 | Pre_S | 17, 86 |
| W4056-19-003507 | 38 | Pre_S | 12, 66 |
| 2015-1615 | 41 | Pre_S | 12, >100 |
| CA208 | 65 | FECD | 18, 60 |
| CA179 | 77 | FECD | 18, 73 |
| CA213 | 67 | FECD | 12, >100 |
| CA219 | 87 | FECD | 18, 76 |
| CA103 | 72 | FECD | 15, 87 |
| CA099 | 70 | FECD | 18, 78 |
| CA072 | 60 | FECD | 16, 84 |
| CA083 | 68 | FECD | 12, 84 |
| CA095 | 91 | FECD | 28, >100 |
| CA209 | 88 | FECD | 15, 53 |
| VVM669 | 66 | FECD | 17, 84 |

TABLE 7

Primer sequences for qPCR or RT-PCR

| Primer | Sequence (5'-3') |
|---|---|
| TCF4 mRNA | F: TGACGATGAGGACCTGACAC (SEQ ID NO: 5) |
| | R: GTCTGGGGCTTGTCACTCTT (SEQ ID NO: 6) |
| TCF4 intron-upstream | F: GTAGTCGTAGGATCAGCACAAAG (SEQ ID NO: 7) |
| | R: GGAAGCAAAGGGATGGAGAA (SEQ ID NO: 8) |
| TCF4 intron-downstream | F: GAGAGAGGGAGTGAAAGAGAGA (SEQ ID NO: 9) |
| | R: GGCAATGTCCATTTCCATCT (SEQ ID NO: 10) |
| CTGF | F: GCTGACCTGGAAGAGAACATTA (SEQ ID NO: 11) |
| | R: GTCGGTACATACTCCACAGAAT (SEQ ID NO: 12) |
| COCH | F: GATGGGCAGTCCTATGATGATG (SEQ ID NO: 13) |

TABLE 7-continued

Primer sequences for qPCR or RT-PCR

| Primer | Sequence (5'-3') |
| --- | --- |
| | R: GCATGAGACTCCTTCGGTTTAG (SEQ ID NO: 14) |
| MSI1 | F: GTTTCGGCTTCGTCACTTTC (SEQ ID NO: 15) |
| | R: CTTCGTTCGAGTCACCATCTT (SEQ ID NO: 16) |
| LUM | F: GGTCTCCCTGTCTCTCTTCTAA (SEQ ID NO: 17) |
| | R: AGCCAGTTCGTTGTGAGATAAA (SEQ ID NO: 18) |
| KDR | F: AGCAGGATGGCAAAGACTAC (SEQ ID NO: 19) |
| | R: TACTTCCTCCTCCTCCATACAG (SEQ ID NO: 20) |
| MBNL2 (RT-PCR) | F: ACACCGTAACCGTTTGTATGG (SEQ ID NO: 21) |
| | R: GCATCATGGGTACTGTTGGAATG (SEQ ID NO: 22) |

Example 1

This example describes the experimental design.

Figure 2:
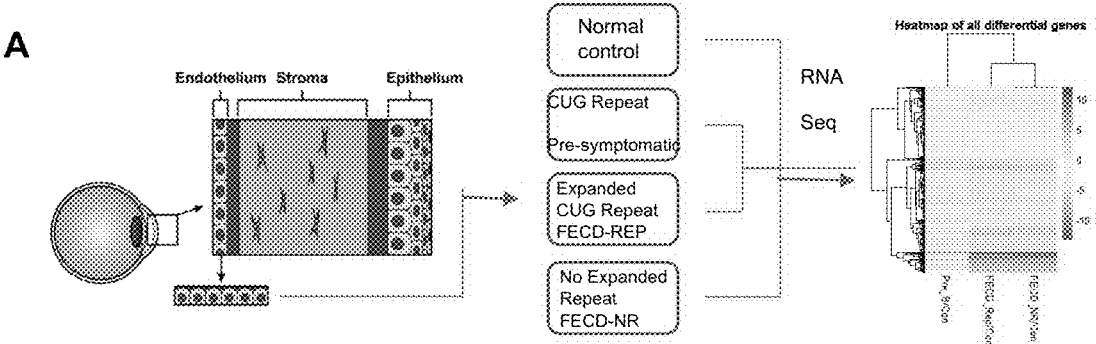
FIG. 2 shows experimental scheme and sample cohorts. (A) Homogenous samples of corneal endothelium are surgically removed from normal, presymptomatic and, affected (FECD or FECD_NR) tissue bank donors or patients and used for RNAseq followed by data analysis. (B) Detailed description of tissue samples. (C) Dendrogram for four groups of samples and (D) all replicates. RIN:RNA integrity number. CTG18.1: the number of repeats on each chromosome.
Figure 2:
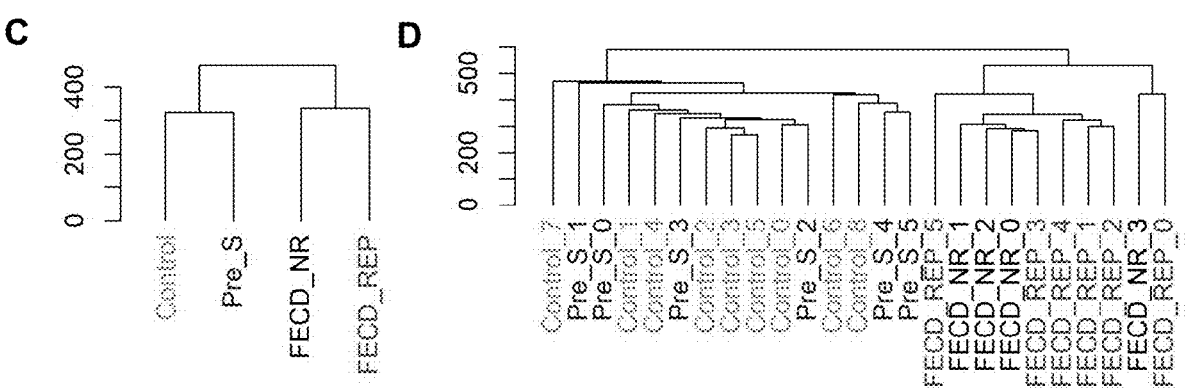

Analyzing the corneal endothelial monolayer presents several advantages as a model for gaining insight into the molecular mechanisms of delayed-onset degenerative disease: 1) corneal tissue is available for analysis because it is routinely removed during surgery (FIG. 1A-C); 2) tissue samples are a single near homogeneous layer of cells, facilitating RNAseq and other methods for analyzing gene expression (FIG. 1D); 3) donor corneal tissues that are not used for surgery are available from eye bank samples for comparison; 4) because the prevalence of the triplet repeat mutation within the TCF4 gene is relatively high, donor eyes provide a significant number of pre-symptomatic samples (Pre_S) that possess the CUG expanded repeat; 5) the availability of tissue from four different cohorts (FIG. 2), control, Pre_S, FECD_NR, FECD_REP allows multiple cross-comparisons into the different stages and types of FECD. Analysis of the Pre_S cohort has the potential to gain insights into early drivers of disease.

Here, the analysis of the corneal endothelial monolayer are used to evaluate transcriptomic data from four cohorts of corneal endothelial tissue: control, Pre_S, FECD_REP, and FECD_NR. Tissue samples were collected from 25 individuals [control (9), Pre_S (6), FECD_REP (6), and FECD_NR (4)] between the ages of 38 and 74 (FIG. 2B).

Figure 6:
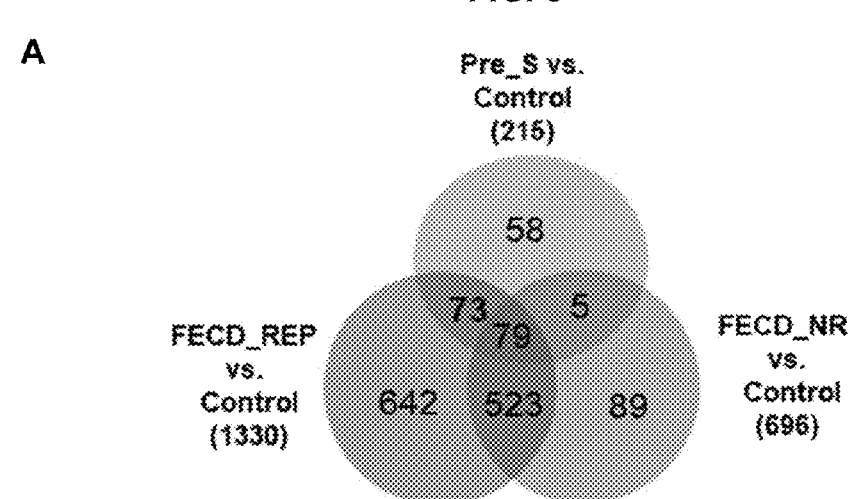
FIG. 6 shows RNAseq analysis of gene expression. (A) Overlap for gene expression of Pre-S, FECD_REP, and FECD_NR cohorts showing that Pre_S is more similar to FECD_REP than FECD_NR. Numbers indicate the number of differentially expressed genes identified in each individual region. (B) Volcano plots for Pre_S vs. Control, FECD_Rep vs. Control, FECD_NR vs. Control and FECD_REP vs. FECD_NR and top genes in each comparison. (C) Top 20 upregulated (left side) and downregulated (right side) genes in Pre_S vs. control comparison. Where Rna-seq analysis finds similar reads for two or more genes, those genes are listed together.
Figure 6:
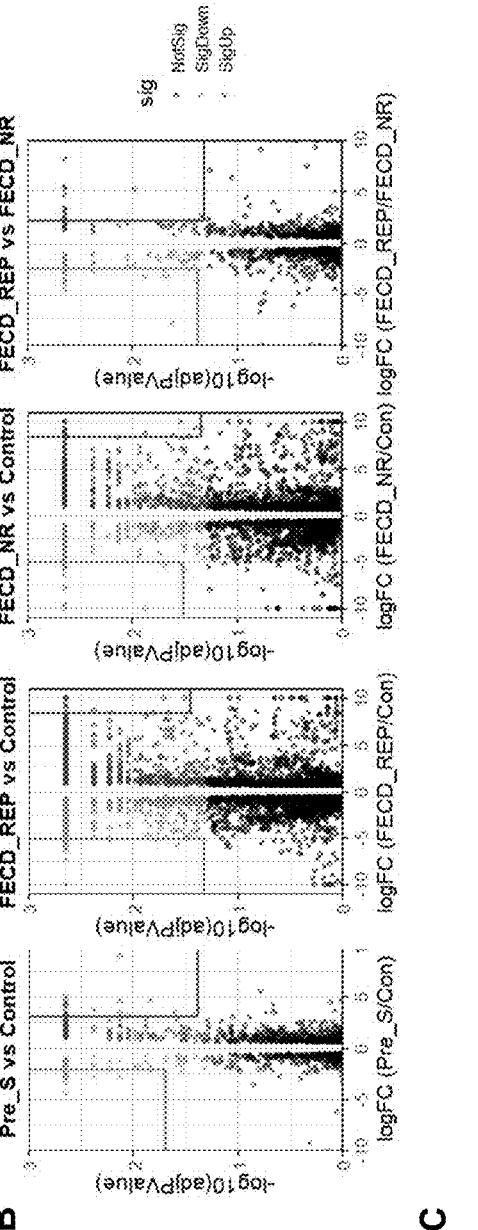

Additionally, among the top ten genes in pre-symptomatic tissue versus control tissue are cochlin (COCH) and fibronectin (FN1) with >16 and >32 fold change increases respectively (FIG. 6C).

Samples were homogeneous endothelial cell monolayers surgically removed from patients or dissected from donor tissue (FIG. 1, FIG. 2A). The homogenous nature of the tissue samples, in contrast to the more complex mixtures of cells often contained in tissues related to other disease, facilitates subsequent analysis and data interpretation.

Four groups of human tissue by RNA sequencing (RNAseq) were compared with attention to changes in alternative splicing, differential gene expression, and pathway analysis (FIG. 2A). Tissue that was mutant for the CUG expanded repeat within intron 2 of the TCF4 gene was obtained from pre-symptomatic eye bank donors (Pre_S) and from FECD patients after transplant surgery (FECD_REP). Tissue that was negative for the expanded CUG mutation within TCF4 was obtained from eye bank donors (Control) and from patients with non-CUG related FECD (FECD_NR). Genotype data indicated that all samples had normal numbers of CTG repeats within the DMPK gene (FIG. 2B).

Control tissues from the eye bank were chosen for analysis that possessed normal endothelial morphology by specular microscopy, were negative for the expanded CUG mutation, and were from donors with ages comparable to our FECD patient cohort (FIG. 2B). Obtaining tissue from Pre_S individuals was possible because of the relatively high prevalence, 3%, of the expanded triplet repeat mutation in TCF4 gene within the general Caucasian population. Pre_S tissue was identified by the presence of the CUG repeat expansion by genotyping. Normal corneal endothelial morphology (absence of central corneal guttae) in Pre_S tissues was confirmed by specular microscopy.

RNA sequencing (RNAseq) was performed on tissue samples from nine non-FECD/non-expanded repeat donors (Control), six pre-symptomatic donors with the expanded repeat (Pre_S), six patients with the expanded repeat and FECD (FECD_REP), and four patients with FECD who did not have the expanded CUG repeat mutation (FECD_NR) (FIG. 2B,11,12,13). Only samples with RNA integrity numbers greater than 5 were used (FIG. 13). Gene body coverage analysis suggests that all RNA samples were largely intact (FIG. 12). We carried out a paired-end 150 nt RNA-Seq on Illumina NextSeq sequencer. We regularly obtained an output of 50-60 million raw paired reads per sample.

Clustering analysis of overall gene expression patterns revealed that samples from control and Pre_S donors were closer to one another than to samples from patients with FECD_REP or FECD_NR late stage disease (FIG. 2C-D, 11A-B). This result is consistent with the clinical observation of large visible differences between diseased and non-diseased tissue and that the clinical manifestations of FECD_REP and FECD_NR are almost identical.

Example 2

This example describes the stability of TCF4 intron 2 in FECD mutant and non-mutant tissue.

Analysis of RNAseq data from intron 2 (the intron that contains the CUG repeat) within the TCF4 gene showed a striking difference between representative samples from individuals with the expanded CUG repeat mutation (FECD_REP and Pre_S) and individuals who lack the mutation (control and FECD_NR) (FIG. 3A). Samples from the cohort of control individuals showed similar low numbers of reads upstream or downstream relative to the trinucleotide repeat region. RNA obtained from FECD_NR patients' tissue also showed the same similarity between upstream and downstream reads.

By contrast, both Pre_S and FECD_REP tissue showed more reads for intronic RNA upstream of the trinucleotide repeat relative to downstream (FIG. 3A). The overall expression of mature TCF4 mRNA from the four cohorts was not significantly different making haploinsufficiency of gene product less likely as the mechanism of disease (FIG. 14).

These results suggest that an early molecular disease trigger—increased stability the mutant TCF4 intron 2 upstream of the expanded repeat—occurs at the presymptomatic stage and distinguishes FECD_REP from FECD_NR in late stage disease.

To investigate factors that might contribute to the prevalence of upstream intronic reads, we examined cultured cells derived from FECD_REP patient corneal endothelium (F35T), FECD_REP patient skin fibroblasts (VVM84), control (without CUG expanded repeat) corneal endothelium (W4056), or control skin fibroblasts (C9) (FIG. 3B-C). VVM84 FECD skin fibroblasts and F35T FECD corneal endothelial cells both have the expanded CUG repeat, but the F35T corneal cells have nuclear CUG foci that can be detected by RNA-FISH while VVM84 skin cells lack detectable foci indicating cell-specificity for expanded CUG repeat RNA accumulation. Expression of TCF4 is similar in F35T, F45SV and VVM84 cells (FIG. 15).

We treated cells with actinomycin D to arrest transcription and examine the half-life of mature TCF4 mRNA and sequences either upstream our downstream relative to the intronic TCF4 CUG repeat using quantitative PCR (qPCR) (FIG. 3B-C). Regardless of whether the expanded repeat mutation was present, the half-life of the mature TCF4 mRNA was similar, >8 hours (FIG. 3C top). Likewise, the half-life of the intron 2 downstream region was also similar in each cell line, varying from 10 to 30 minutes (FIG. 3C middle). These data suggest that the mutation does not affect stability of the parent mRNA and has only a modest effect on the downstream region of intron 2.

By contrast, we observe a striking ~20-fold increase in the half-life of the upstream region of intron 2 in FECD corneal cells (F35T and F45SV) that possess the expanded CTG mutation and have detectable foci (FIG. 3C bottom). For cell lines that lacked expanded CUG nuclear foci, this region had a half-life of only 10 min. For FECD corneal cells, the half-life was 3-4 h.

This increased half-life of upstream intronic RNA is consistent with the observation from RNAseq of many more reads covering the upstream region of intron 2 TCF4 from Pre_S or FECD_REP tissue relative to samples from individuals in the control or FECD_NR cohorts who lack the expanded CUG repeat (FIG. 3A). Stabilization of the upstream portion of TCF4 intron 2 in corneal endothelial tissue and cultured corneal endothelial cells makes more mutant repeat RNA available to perturb gene expression.

To address the possibility that the 5' half of intron 2 might be retained in the mature mRNA, we performed PCR using primers complementary to exon 2 and exon 3 in both FECD and control cells. We observed a single PCR product of the predicted length in both FECD and control cells (FIG. 16). This data supports the conclusion that the intron is not detectably retained.

Example 3

This example describes changes in alternative splicing triggered by the expanded repeat within TCF4.

CUG repeat RNA is known to bind the splicing factors muscle blind-like 1 and 2 (MBNL1 and MNBL2). We used RNAseq to evaluate splicing changes between control tissue and the Pre_S, FECD_REP, and FECD_NR tissue cohorts (FIG. 4). To classify changes, we used the FDR (false discovery rate) and delta PSI (the net change of inclusion percentage) as the determinant metrics. Any changes that are less than 0.001 on FDR and more than or equal to 0.15 on PSI were determined to be significant.

Regardless of which tissue was analyzed, the primary changes in alternative splicing relative to control tissue were increases in the number of skipped exons (SE) events (FIG. 4A). FECD_REP or FECD_NR tissues showed more splicing changes than Pre_S tissue (FIG. 4B). The greater number of splicing changes is consistent with the extensive cellular degeneration observed in late stage disease. However, while not as many as in tissue from advanced disease, ~450 changes in alternative splicing were observed in Pre_S tissue.

Three hundred thirteen of the alternative splicing events in Pre_S tissue involved exon skipping (Table 8). Heatmap evaluation of 313 skipped exons in Pre_S tissue revealed that the genes hosting the skipped exon events clustered most closely with FECD_REP tissue (FIG. 4B-C). 132 skipped exon events were shared between Pre_S and FECD_REP tissue, compared to only 28 were shared between Pre_S and FECD_NR tissue (FIG. 4B), consistent with the hypothesis that the changes in Pre_S tissue foreshadow the alterations observed in FECD-REP.

Table 8. Significant skipped exon events (313) identified in Pre_S. The delta exon inclusion levels for Pre_S, FECD_REP and FECD_NR vs. Control are shown in the last three columns.

| Gene_name | SE_locus | Pre_S | FECD_REP | FECD_NR |
|---|---|---|---|---|
| KIF13A | −: chr6: 17787775-17787875: 17789871-17789910: 17794571-17794704 | 0.761 | 0.617 | −0.084 |
| TSPOAP1 | −: chr17: 58307841-58307941: 58308540-58309380: 58309966-58310158 | 0.741 | 0.674 | 0.051 |
| INF2 | +: chr14: 104714202-104714856: 104715283-104715340: 104718794-104719603 | 0.674 | 0.48 | −0.034 |
| EXOC2 | −: chr6: 637700-637861: 657162-657250: 689138-689212 | 0.672 | 0.438 | 0.845 |
| NEBL | −: chr10: 20852544-20852649: 20858239-20858344: 20859712-20859826 | 0.67 | 0.199 | −0.207 |
| BICRA | +: chr19: 47679320-47681276: 47681975-47682152: 47694114-47694726 | 0.636 | 0.52 | 0.208 |
| CACNA1D | +: chr3: 53718300-53718388: 53718681-53718741: 53719754-53719781 | 0.626 | 0.42 | −0.062 |
| CLASP1 | −: chr2: 121430072-121430177: 121445448-121445496: 121447336-121447507 | 0.602 | 0.457 | −0.018 |
| VPS39 | −: chr15: 42191495-42191560: 42192065-42192098: 42199895-42199961 | 0.581 | 0.568 | 0.137 |
| KIF13A | −: chr6: 17787775-17787875: 17789871-17789910: 17794248-17794395 | 0.58 | 0.455 | −0.185 |
| TEAD1 | +: chr11: 12864837-12864900: 12878888-12878900: 12879707-12879842 | 0.567 | 0.524 | −0.047 |
| INCENP | +: chr11: 62140912-62141044: 62141499-62141511: 62144981-62145091 | 0.555 | 0.493 | 0.318 |
| MDM1 | −: chr12: 68316077-68316253: 68316580-68316610: 68321346-68321446 | 0.553 | 0.592 | 0.033 |
| SORBS1 | −: chr10: 95346405-95346452: 95351215-95351376: 95354881-95354967 | 0.529 | 0.349 | −0.074 |
| CENPBD1P1 | +: chr19: 58575444-58575588: 58591497-58591624: 58598966-58599801 | 0.522 | 0.487 | 0.462 |
| SP110 | −: chr2: 230170620-230170761: 230171695-230171767: 230172065-230172174 | 0.522 | 0.234 | 0.051 |
| MTA1 | +: chr14: 105465333-105466578: 105466706-105466742: 105469466-105469498 | 0.503 | 0.19 | −0.019 |
| NUMA1 | −: chr11: 72010785-72010854: 72012400-72012442: 72012894-72016260 | 0.5 | 0.395 | −0.041 |
| PLEKHM2 | +: chr1: 15719733-15719920: 15721328-15721388: 15725316-15725545 | 0.497 | 0.381 | −0.036 |
| ITGA6 | +: chr2: 172497974-172498100: 172501771-172501901: 172504090-172504534 | 0.496 | 0.401 | −0.023 |
| SYNE1 | −: chr6: 152143622-152143765: 152145486-152145555: 152148044-152148378 | 0.496 | 0.305 | −0.1 |

-continued

| Gene_name | SE_locus | Pre_S | FECD_REP | FECD_NR |
|---|---|---|---|---|
| ARHGEF10L | +: chr1: 17632320-17632466: 17634547-17634562: 17634834-17635016 | 0.489 | 0.481 | 0.055 |
| SCARB1 | −: chr12: 124777632-124778586: 124782682-124782811: 124786356-124786503 | 0.482 | 0.334 | −0.053 |
| TMEM177 | +: chr2: 119679202-119679276: 119680831-119681123: 119685657-119686507 | 0.481 | 0.24 | 0.14 |
| PPFIBP1 | +: chr12: 27676427-27676599: 27677063-27677096: 27679488-27679639 | 0.468 | 0.365 | −0.127 |
| PLD1 | −: chr3: 171677565-171677694: 171686684-171686798: 171687370-171687584 | 0.462 | 0.331 | −0.095 |
| ZNF248 | −: chr10: 37856295-37856337: 37856434-37856532: 37858004-37858084 | 0.454 | 0.224 | 0.143 |
| DESI1 | −: chr22: 41604043-41604153: 41607839-41607861: 41620751-41621096 | 0.45 | 0.267 | 0.148 |
| ABH | −: chr10: 26770244-26770345: 26771074-26771089: 26777064-26777241 | 0.447 | 0.218 | −0.094 |
| MAP2K7 | +: chr19: 7903884-7904068: 7905807-7905855: 7909754-7909896 | 0.438 | 0.341 | −0.079 |
| ZNF528-AS1 | −: chr19: 52389018-52389303: 52394790-52394847: 52395597-52395750 | 0.436 | 0.157 | 0.147 |
| ACOT9 | −: chrX: 23733171-23733217: 23734340-23734367: 23735918-23736016 | 0.43 | 0.249 | −0.005 |
| ZNF75D | −: chrX: 135291008-135291135: 135292280-135292473: 135295767-135296039 | 0.428 | 0.021 | 0.325 |
| ZNF75D | −: chrX: 135291008-135291135: 135293729-135294258: 135295767-135296033 | 0.426 | 0.051 | 0.091 |
| FAM135A | +: chr6: 70413424-70413702: 70426438-70426532: 70452491-70452565 | 0.424 | −0.006 | −0.012 |
| NDUFA3 | +: chr19: 54105933-54106011: 54106352-54106446: 54106763-54106961 | 0.42 | 0.163 | −0.03 |
| PHKA2 | −: chrX: 18897162-18897333: 18900669-18900699: 18901484-18901603 | 0.414 | 0.503 | 0.145 |
| WASF3 | +: chr13: 26671871-26671989: 26680034-26680201: 26681053-26681320 | 0.412 | 0.235 | −0.04 |
| SMPD4 | −: chr2: 130157250-130157396: 130161185-130161272: 130164373-130164445 | 0.404 | 0.196 | 0.005 |
| CATSPERE | +: chr1: 244479716-244479784: 244490446-244490471: 244499001-244499079 | 0.402 | 0.461 | 0.49 |
| NSUN5P2 | −: chr7: 72950057-72950196: 72952151-72952295: 72954624-72954717 | 0.402 | 0.184 | 0.222 |
| RBX1 | +: chr22: 40951358-40951476: 40964046-40964117: 40972475-40973309 | 0.402 | −0.025 | −0.025 |
| PLPP1 | −: chr5: 55467868-55468149: 55475298-55475450: 55534571-55535050 | 0.401 | 0.402 | 0.068 |
| SORBS1 | −: chr10: 95346405-95346452: 95351208-95351376: 95354881-95354967 | 0.398 | 0.258 | −0.042 |
| GOLGA2 | −: chr9: 128268419-128268524: 128272784-128272865: 128273849-128273972 | 0.398 | 0.37 | 0.027 |
| AC010203.1 | −: chr12: 100180552-100180716: 100198843-100198972: 100199519-100199783 | 0.391 | 0.495 | 0.32 |
| ZBED3-AS1 | +: chr5: 77098654-77098747: 77100235-77100391: 77118319-77118521 | 0.388 | 0.121 | 0.361 |
| BAZ2B | −: chr2: 159395768-159395834: 159397073-159397100: 159397344-159397389 | 0.387 | −0.002 | −0.377 |
| SOS1 | −: chr2: 38987472-38987591: 38989269-38989314: 38995122-38995387 | 0.371 | 0.438 | −0.03 |
| TMEM63B | +: chr6: 44135016-44135096: 44135327-44135366: 44136348-44136439 | 0.37 | 0.226 | −0.006 |
| RUBCN | −: chr3: 197684156-197684217: 197691073-197691148: 197693714-197693816 | 0.368 | 0.365 | −0.07 |
| ZNF202 | −: chr11: 123730509-123730985: 123740116-123740232: 123740416-123740536 | 0.363 | −0.048 | 0.037 |
| ZNF202 | −: chr11: 123730751-123730985: 123740189: 123740416-123740536 | 0.355 | −0.027 | 0.031 |
| LRRFIP2 | −: chr3: 37083635-37083806: 37091466-37091538: 37094791-37094908 | 0.353 | 0.228 | −0.068 |
| MICAL3 | −: chr22: 17822946-17823060: 17826453-17826516: 17831853-17831927 | 0.351 | 0.17 | −0.234 |
| CAPN3 | +: chr15: 42403740-42403777: 42408210-42408324: 42409302-42409380 | 0.342 | 0.148 | −0.084 |
| CACNA1F | −: chrX: 49210589-49210686: 49210964-49211092: 49211321-49211481 | 0.336 | 0.508 | 0.458 |
| CYTH1 | −: chr17: 78692416-78692493: 78696006-78696009: 78698268-78698380 | 0.333 | 0.098 | −0.015 |
| OSBPL3 | −: chr7: 24842278-24842413: 24849068-24849176: 24852503-24852634 | 0.332 | 0.174 | −0.11 |
| PICALM | −: chr11: 85976622-85976682: 85978069-85978093: 85981128-85981228 | 0.331 | 0.059 | −0.219 |
| ARHGEF40 | +: chr14: 21087000-21087105: 21087319-21087363: 21087967-21088098 | 0.331 | 0.188 | −0.009 |
| GATS | −: chr7: 100200652-100202603: 100211393-100211994: 100213046-100213133 | 0.331 | 0.131 | 0.049 |
| ADAMTS13 | +: chr9: 133440343-133440525: 133442613-133442743: 133443375-133443561 | 0.329 | −0.078 | −0.078 |
| SEC16A | −: chr9: 136443822-136443900: 136445051-136445111: 136445644-136445719 | 0.326 | 0.229 | 0.073 |
| MACF1 | +: chr1: 39463611-39463686: 39465094-39465112: 39468614-39468732 | 0.324 | 0.236 | −0.041 |
| NFYA | +: chr6: 41079028-41079164: 41080810-41080897: 41084045-41084093 | 0.324 | 0.182 | −0.152 |
| CSNK1G3 | +: chr5: 123604723-123604830: 123605338-123605362: 123614341-123614455 | 0.322 | 0.231 | −0.081 |
| DCAF6 | +: chr1: 168004532-168004793: 168015780-168015951: 168022987-168023047 | 0.318 | 0.316 | −0.014 |
| TM7SF3 | −: chr12: 26975495-26975658: 26976259-26976357: 26980565-26980608 | 0.316 | 0.254 | 0.032 |
| OBSCN | +: chr1: 228288624-228288888: 228294151-228294415: 228305122-228305386 | 0.312 | 0.381 | 0.178 |
| GIT2 | −: chr12: 109939164-109939247: 109945259-109945349: 109947255-109947504 | 0.309 | 0.175 | −0.015 |
| TMEM161B-AS1 | +: chr5: 88270525-88270585: 88410072-88410194: 88436272-88436602 | 0.306 | 0.266 | 0.243 |
| CCDC57 | −: chr17: 82178473-82178605: 82179026-82179189: 82183773-82183932 | 0.306 | 0.3 | 0.05 |
| MAP2 | +: chr2: 209709913-209710254: 209723594-209723687: 209725708-209725790 | 0.301 | 0.229 | −0.167 |
| PSAP | −: chr10: 71821875-71822007: 71823887-71823896: 71825836-71825893 | 0.3 | 0.339 | 0.1 |
| DEF8 | +: chr16: 89948774-89948814: 89949564-89949638: 89954242-89954376 | 0.299 | 0.088 | 0.12 |
| PIGP | −: chr21: 37067261-37067380: 37072144-37072310: 37072433-37072537 | 0.296 | NA | NA |
| CENPBD1P1 | +: chr19: 58575444-58575588: 58586154-58586356: 58598966-58599575 | 0.292 | 0.308 | 0.243 |
| ZBED3 | −: chr5: 77072071-77077895: 77078593-77078728: 77087110-77087323 | 0.29 | 0.221 | 0.04 |
| AC109583.3 | −: chr3: 46756041-46756629: 46811105-46811873: 46812221-46812558 | 0.29 | 0.011 | 0.079 |
| CD46 | +: chr1: 207785618-207785682: 207790252-207790345: 207793518-207793873 | 0.289 | 0.303 | 0.086 |
| NEB | −: chr2: 151531791-151531896: 151534214-151534319: 151535690-151535795 | 0.289 | 0.033 | −0.126 |
| ZNF202 | −: chr11: 123730486-123730985: 123740116-123740192: 123740416-123740536 | 0.289 | −0.027 | 0.017 |
| FAM47E-STBD1 | +: chr4: 76263703-76263843: 76268659-76268768: 76309143-76311120 | 0.288 | NA | NA |
| NUMA1 | −: chr11: 72009267-72009387: 72012400-72012442: 72012894-72016260 | 0.284 | −0.002 | −0.005 |
| MYO6 | +: chr6: 75908495-75908627: 75911671-75911698: 75914062-75914281 | 0.281 | 0.306 | 0.045 |
| TCF3 | −: chr19: 1609289-1611849: 1612206-1612433: 1615284-1615485 | 0.278 | 0.174 | 0.083 |
| EPB41L2 | −: chr6: 130869562-130870126: 130878103-130878250: 130885095-130885268 | 0.276 | 0.095 | −0.088 |
| ARFIP1 | +: chr4: 152863605-152863714: 152870752-152870848: 152872451-152872564 | 0.275 | 0.175 | −0.091 |
| ZNF75D | −: chrX: 135291008-135291135: 135291471-135291563: 135295767-135296039 | 0.274 | NA | NA |
| FAM228B | +: chr2: 24146929-24147086: 24161505-24161613: 24164197-24164335 | 0.269 | 0.072 | 0.021 |
| HP1BP3 | −: chr1: 20779811-20779911: 20780344-20780540: 20787194-20787272 | 0.268 | 0.167 | −0.045 |
| IQSEC2 | −: chrX: 53266641-53267064: 53279563-53279776: 53281495-53281581 | 0.263 | −0.022 | −0.031 |
| C1orf43 | −: chr1: 154214456-154214574: 154219835-154219937: 154220341-154220533 | 0.261 | 0.145 | 0.029 |
| EPB41L2 | −: chr6: 130869562-130870126: 130880143-130880206: 130885095-130885268 | 0.26 | 0.117 | −0.074 |
| AFDN | +: chr6: 167911283-167911489: 167913402-167913423: 167914167-167914313 | 0.257 | 0.174 | −0.314 |
| BPTF | +: chr17: 67874816-67875020: 67875555-67875744: 67891843-67892034 | 0.256 | 0.167 | −0.02 |
| SUN1 | +: chr7: 843340-843520: 849922-850033: 851383-851481 | 0.254 | 0.251 | −0.025 |

| Gene_name | SE_locus | Pre_S | FECD_REP | FECD_NR |
|---|---|---|---|---|
| C20orf194 | −: chr20: 3340503-3340639: 3343675-3343731: 3359515-3359593 | 0.253 | 0.013 | −0.061 |
| TNRC6A | +: chr16: 24789231-24791817: 24793472-24793649: 24794543-24794719 | 0.25 | 0.207 | 0.076 |
| SLMAP | +: chr3: 57922888-57923023: 57925844-57925934: 57927295-57927486 | 0.249 | −0.023 | −0.096 |
| KIFC3 | −: chr16: 57758216-57758909: 57759124-57759153: 57759727-57759836 | 0.248 | 0.189 | −0.01 |
| AKAP13 | +: chr15: 85658536-85658590: 85662387-85662453: 85664562-85664755 | 0.247 | 0.231 | 0.07 |
| SH3YL1 | −: chr2: 253004-253115: 262630-262786: 263210-263368 | 0.247 | 0.023 | 0.479 |
| IZUMO4 | +: chr19: 2098435-2098450: 2098786-2098804: 2099254-2099580 | 0.244 | 0.162 | −0.166 |
| MFF | +: chr2: 227340291-227340380: 227347225-227347384: 227355676-227355761 | 0.241 | 0.257 | 0.077 |
| FAM47E-STBD1 | +: chr4: 76263703-76263843: 76268659-76268813: 76309143-76310044 | 0.239 | −0.002 | 0.095 |
| AKAP13 | +: chr15: 85655416-85655787: 85658536-85658590: 85664562-85664755 | 0.237 | 0.048 | −0.125 |
| APBB2 | −: chr4: 40934613-40934699: 40935076-40935139: 40944864-40945070 | 0.237 | −0.051 | −0.287 |
| FNBP1 | −: chr9: 129908889-129908999: 129915965-129915980: 129923843-129923939 | 0.237 | 0.194 | 0.092 |
| CLEC2D | +: chr12: 9693033-9693115: 9693415-9693948: 9694759-9695138 | 0.236 | −0.116 | −0.092 |
| ZNF2 | +: chr2: 95165437-95165860: 95176187-95176259: 95177482-95177609 | 0.234 | 0.14 | 0.016 |
| OBSCN | +: chr1: 228288060-228288324: 228305122-228305386: 228306371-228306638 | 0.233 | 0.164 | 0.011 |

| Gene_name | SE_locus | Pre_S | FECD_REP | FECD_NR |
|---|---|---|---|---|
| CLASP2 | −: chr3: 33560807-33560971: 33563963-33563966: 33570726-33570790 | 0.233 | 0.045 | −0.012 |
| CDH23 | +: chr10: 71617204-71617393: 71643860-71643866: 71645830-71645980 | 0.231 | 0.245 | −0.072 |
| FAM208B | +: chr10: 5684837-5685175: 5712822-5712918: 5720543-5720611 | 0.231 | 0.238 | 0.156 |
| BNIP2 | −: chr15: 59663378-59664120: 59668102-59668138: 59668891-59668949 | 0.231 | 0.182 | −0.048 |
| DIP2C | −: chr10: 310030-310092: 311536-311566: 327005-327176 | 0.229 | 0.191 | −0.074 |
| MRPS6 | +: chr21: 34102834-34102908: 34103496-34103519: 34125340-34125480 | 0.226 | −0.007 | 0.051 |
| GOLGA4 | +: chr3: 37251394-37251484: 37266841-37266940: 37273535-37273601 | 0.226 | 0.205 | −0.022 |
| TTC8 | +: chr14: 88841036-88841196: 88841424-88841557: 88852970-88853056 | 0.225 | −0.074 | 0.029 |
| ZNF613 | +: chr19: 51927219-51927540: 51929731-51929896: 51936027-51936235 | 0.224 | 0.1 | 0.038 |
| COL6A3 | −: chr2: 237387581-237388184: 237394586-237395204: 237396726-237396847 | 0.223 | 0.228 | 0.056 |
| CAD | +: chr2: 27240264-27240361: 27240566-27240617: 27240910-27240955 | 0.222 | 0.247 | 0.218 |
| NF2 | +: chr22: 29681438-29681601: 29683019-29683079: 29694751-29694811 | 0.221 | 0.227 | −0.024 |
| FBXL12 | −: chr19: 9810266-9811717: 9813230-9813274: 9818727-9819079 | 0.221 | 0.165 | −0.049 |
| PPHLN1 | +: chr12: 42374862-42375074: 42384939-42384996: 42387455-42387535 | 0.221 | 0.148 | −0.015 |
| NDUFAF7 | +: chr2: 37241577-37241791: 37242634-37242693: 37243862-37243973 | 0.218 | 0.05 | 0.087 |
| SPTAN1 | +: chr9: 128609121-128609284: 128609650-128609665: 128611713-128611845 | 0.217 | 0.221 | 0.097 |
| MACF1 | +: chr1: 39463611-39463686: 39465094-39465112: 39468614-39468732 | 0.324 | 0.236 | −0.041 |
| NFYA | +: chr6: 41079028-41079164: 41080810-41080897: 41084045-41084192 | 0.324 | 0.182 | −0.152 |
| CSNK1G3 | +: chr5: 123604723-123604830: 123605338-123605362: 123614341-123614455 | 0.322 | 0.231 | −0.081 |
| DCAF6 | +: chr1: 168004532-168004793: 168015780-168015951: 168022987-168023047 | 0.318 | 0.316 | −0.014 |
| TM7SF3 | −: chr12: 26975495-26975658: 26976239-26976357: 26980565-26980608 | 0.316 | 0.254 | 0.032 |
| OBSCN | +: chr1: 228288624-228288888: 228294151-228294415: 228305122-228305386 | 0.312 | 0.381 | 0.178 |
| GIT2 | −: chr12: 109939164-109939247: 109945259-109945349: 109947255-109947504 | 0.309 | 0.175 | −0.015 |
| TMEM161B-AS1 | +: chr5: 88270525-88270585: 88410072-88410194: 88436272-88436602 | 0.306 | 0.266 | 0.243 |
| CCDC57 | −: chr17: 82178473-82178605: 82179026-82179189: 82183773-82183932 | 0.306 | 0.3 | 0.05 |
| MAP2 | +: chr2: 209709913-209710254: 209723594-209723687: 209725050-209725790 | 0.301 | 0.229 | −0.167 |
| PSAP | −: chr10: 71821875-71822007: 71823887-71823896: 71825836-71825893 | 0.3 | 0.339 | 0.1 |
| DEF8 | +: chr16: 89948774-89948814: 89949564-89949638: 89954242-89954376 | 0.299 | 0.088 | 0.12 |
| PIGP | −: chr21: 37067261-37067380: 37072144-37072310: 37072433-37072537 | 0.296 | NA | NA |
| CENPBD1P1 | +: chr19: 58575444-58575588: 58586154-58586356: 58598966-58599575 | 0.292 | 0.308 | 0.243 |
| ZBED3 | −: chr5: 77072071-77077895: 77078593-77078728: 77087110-77087323 | 0.29 | 0.221 | 0.04 |
| AC109583.3 | −: chr3: 46756041-46756629: 46811105-46811873: 46812221-46812558 | 0.29 | 0.011 | 0.079 |
| CD46 | +: chr1: 207785618-207785682: 207790252-207790345: 207793518-207793873 | 0.289 | 0.303 | 0.086 |
| NEB | −: chr2: 151531791-151531896: 151534214-151534319: 151535690-151535795 | 0.289 | 0.033 | −0.126 |
| ZNF202 | −: chr11: 123730486-123730985: 123740116-123740192: 123740416-123740536 | 0.289 | −0.027 | 0.017 |
| FAM47E-STBD1 | +: chr4: 76263703-76263843: 76268659-76268768: 76309143-76311120 | 0.288 | NA | NA |
| NUMA1 | −: chr11: 72009267-72009387: 72012400-72012442: 72012894-72016260 | 0.284 | −0.002 | −0.005 |
| MYO6 | +: chr6: 75908495-75908627: 75911671-75911698: 75914082-75914281 | 0.281 | 0.306 | 0.045 |
| TCF3 | −: chr19: 1609289-1611849: 1612206-1612433: 1615284-1615485 | 0.278 | 0.174 | 0.083 |
| EPB41L2 | −: chr6: 130869562-130870126: 130878103-130878250: 130885095-130885268 | 0.276 | 0.095 | −0.088 |
| ARFIP1 | +: chr4: 152863605-152863714: 152870752-152870848: 152872451-152872564 | 0.275 | 0.175 | −0.091 |
| ZNF75D | −: chrX: 135291008-135291135: 135291471-135291563: 135295767-135296039 | 0.274 | NA | NA |
| FAM228B | +: chr2: 24146929-24147086: 24161505-24161613: 24164197-24164335 | 0.269 | 0.072 | 0.021 |
| HP1BP3 | −: chr1: 20779811-20779911: 20780344-20780540: 20787194-20787272 | 0.268 | 0.167 | −0.045 |

| Gene_name | SE_locus | Pre_S | FECD_REP | FECD_NR |
|---|---|---|---|---|
| IQSEC2 | −: chrX: 53266641-53267064: 53279563-53279776: 53281495-53281581 | 0.263 | −0.022 | −0.031 |
| C1orf43 | −: chr1: 154214456-154214574: 154219835-154219937: 154220341-154220533 | 0.261 | 0.145 | 0.029 |
| EPB41L2 | −: chr6: 130869562-130870126: 130880143-130880206: 130885095-130885268 | 0.26 | 0.117 | −0.074 |
| AFDN | +: chr6: 167911283-167911489: 167913402-167913423: 167914167-167914313 | 0.257 | 0.174 | −0.314 |
| BPTF | +: chr17: 67874816-67875020: 67875555-67875744: 67891843-67892034 | 0.256 | 0.167 | −0.02 |
| SUN1 | +: chr7: 843340-843520: 849922-850033: 851383-851481 | 0.254 | 0.251 | −0.025 |
| C20orf194 | −: chr20: 3340503-3340639: 3343675-3343731: 3359515-3359593 | 0.253 | 0.013 | −0.061 |
| TNRC6A | +: chr16: 24789231-24791817: 24793472-24793649: 24794543-24794719 | 0.25 | 0.207 | 0.076 |

-continued

| | | | | |
|---|---|---|---|---|
| SLMAP | +: chr3: 57922888-57923023: 57925844-57925934: 57927295-57927486 | 0.249 | −0.023 | −0.096 |
| KIFC3 | −: chr16: 57758216-57758909: 57759124-57759153: 57759727-57759836 | 0.248 | 0.189 | −0.01 |
| AKAP13 | +: chr15: 85658536-85658590: 85662387-85662453: 85664562-85664755 | 0.247 | 0.231 | 0.07 |
| SH3YL1 | −: chr2: 253004-253115: 262630-262786: 263210-263368 | 0.247 | 0.023 | 0.479 |
| IZUMO4 | +: chr19: 2098435-2098450: 2098786-2098804: 2099254-2099580 | 0.244 | 0.162 | −0.166 |
| MFF | +: chr-2: 227340291-227340380: 227347225-227347384: 227355676-227355761 | 0.241 | 0.257 | 0.077 |
| FAM47E-STBD1 | +: chr4: 76263703-76263843: 76268659-76268813: 76309143-76310044 | 0.239 | −0.002 | 0.095 |
| AKAP13 | +: chr15: 85655416-85655787: 85658536-85658590: 85664562-85664755 | 0.237 | 0.048 | −0.125 |
| APBB2 | −: chr4: 40934613-40934699: 40935076-40935139: 40944864-40945070 | 0.237 | −0.051 | −0.287 |
| FNBP1 | −: chr9: 129908889-129908999: 129915965-129915980: 129923843-129923939 | 0.237 | 0.194 | 0.092 |
| CLEC2D | +: chr12: 9693033-9693115: 9693415-9693948: 9694759-9695138 | 0.236 | −0.116 | −0.092 |
| ZNF2 | +: chr2: 95165437-95165860: 95176187-95176259: 95177482-95177609 | 0.234 | 0.14 | 0.016 |
| OBSCN | +: chr1: 228288060-228288324: 228305122-228305386: 228306371-228306638 | 0.233 | 0.164 | 0.011 |
| CLASP2 | −: chr3: 33560807-33560971: 33563963-33563966: 33570726-33570790 | 0.233 | 0.045 | −0.012 |
| CDH23 | +: chr10: 71617204-71617393: 71643860-71643866: 71645830-71645980 | 0.231 | 0.245 | −0.072 |
| FAM208B | +: chr10: 5684837-5685175: 5712822-5712918: 5720543-5720611 | 0.231 | 0.238 | 0.156 |
| BNIP2 | −: chr15: 59663378-59664120: 59668102-59668138: 59668891-59668949 | 0.231 | 0.182 | −0.048 |
| DIP2C | −: chr10: 310030-310092: 311536-311566: 327005-327176 | 0.229 | 0.191 | −0.074 |
| MRPS6 | +: chr21: 34102834-34102908: 34103496-34103519: 34125340-34125480 | 0.226 | −0.007 | 0.051 |
| GOLGA4 | +: chr3: 37251394-37251484: 37266841-37266940: 37273535-37273601 | 0.226 | 0.205 | −0.022 |
| TTC8 | +: chr14: 88841036-88841196: 88841424-88841557: 88852970-88853056 | 0.225 | −0.074 | 0.029 |
| ZNF613 | +: chr19: 51927219-51927540: 51929731-51929896: 51936027-51936235 | 0.224 | 0.1 | 0.038 |
| COL6A3 | −: chr2: 237387581-237388184: 237394586-237395204: 237396726-237396847 | 0.223 | 0.228 | 0.056 |
| CAD | +: chr2: 27240264-27240361: 27240566-27240617: 27240910-27240955 | 0.222 | 0.247 | 0.218 |
| NF2 | +: chr22: 29681438-29681601: 29683019-29683079: 29694751-29694811 | 0.221 | 0.227 | −0.024 |
| FBXL12 | −: chr19: 9810266-9811717: 9813230-9813240: 9818727-9819079 | 0.221 | 0.165 | −0.049 |
| PPHLN1 | +: chr12: 42374862-42375074: 42384939-42384996: 42387455-42387535 | 0.221 | 0.148 | −0.015 |
| NDUFAF7 | +: chr2: 37241577-37241791: 37242634-37242693: 37243862-37243973 | 0.218 | 0.05 | 0.087 |
| SPTAN1 | +: chr9: 128609121-128609284: 128609650-128609665: 128611713-128611845 | 0.217 | 0.221 | 0.097 |
| PPIL3 | −: chr2: 200876941-200877037: 200877496-200877604: 200881420-200881488 | 0.156 | 0.12 | 0.136 |
| SULF1 | +: chr8: 69466623-69466950: 69495764-69495926: 69501873-69501968 | 0.156 | 0.142 | 0.075 |
| ITGB1BP1 | −: chr2: 9418625-9418732: 9419989-9420100: 9423372-9423480 | 0.155 | 0.096 | 0.089 |
| SORCS3 | +: chr10: 105255701-105255801: 105256818-105256924: 105262330-105262491 | 0.155 | 0.059 | 0.018 |
| SCARB1 | −: chr12: 124777632-124778586: 124782682-124782811: 124786440-124786503 | 0.154 | 0.024 | −0.015 |
| DESI1 | −: chr22: 41604043-41604153: 41607261-41607331: 41620751-41621096 | 0.153 | 0.111 | 0.045 |
| BPTF | +: chr17: 67874816-67875020: 67875555-67875744: 67886127-67886316 | 0.153 | 0.167 | 0.029 |
| PC | −: chr11: 66952295-66952468: 66954248-66954436: 66958321-66958370 | 0.152 | 0.063 | 0.12 |
| SUGP2 | −: chr19: 18990887-18991149: 18993637-18993740: 18994365-18994486 | 0.152 | −0.003 | −0.129 |
| TEAD3 | −: chr6: 35479304-35479316: 35480311-35480374: 35484559-35484624 | 0.152 | −0.02 | −0.019 |
| MYH10 | −: chr17: 8569719-8569812: 8576642-8576672: 8577235-8577338 | 0.152 | 0.204 | 0.056 |
| TFAP2B | +: chr6: 50818722-50818972: 50822133-50822160: 50823406-50823865 | 0.151 | 0.126 | −0.048 |
| DNM3 | +: chr1: 172092823-172092875: 172093695-172093725: 172131174-172131288 | 0.151 | 0.074 | 0.09 |
| ERC1 | +: chr12: 1110191-1110347: 1112214-1112307: 1115865-1116033 | 0.151 | 0.017 | −0.055 |
| SPAG9 | −: chr17: 50974770-50974947: 50975862-50975901: 50977107-50977221 | 0.151 | −0.003 | −0.31 |
| NSF | +: chr17: 46626612-46626712: 46630410-46630450: 46637375-46637542 | 0.15 | 0.146 | 0.039 |
| ARHGEF12 | +: chr11: 120407737-120407823: 120409393-120409450: 120420752-120420851 | 0.15 | 0.269 | 0.098 |
| TUFT1 | +: chr1: 151540304-151540426: 151562090-151562165: 151562584-151562686 | 0.15 | 0.064 | −0.097 |
| USP28 | −: chr11: 113841662-113841768: 113854257-113854335: 113875444-113875528 | −0.15 | 0.049 | −0.229 |
| FAM126A | −: chr7: 22941268-22946163: 22946951-22947247: 22960255-22960415 | −0.15 | −0.318 | −0.207 |
| PAK1 | −: chr11: 77392442-77392541 77397026-77397093: 77411773-77411944 | −0.15 | 0.006 | −0.031 |
| CD47 | −: chr3: 108047078-108047292: 108050577-108050602: 108051938-108051970 | −0.16 | −0.044 | 0.015 |
| DVL1 | −: chr1: 1336411-1336515: 1337017-1337055: 1337976-1338183 | −0.16 | −0.056 | −0.002 |
| ENAH | −: chr1: 225514595-225514900: 225517195-225517990: 225519197-225519565 | −0.16 | −0.083 | 0.099 |
| HPS5 | −: chr11: 18297558-18297717: 18300827-18300916: 18306134-18306347 | −0.17 | −0.156 | −0.258 |
| TJAP1 | +: chr6: 43477568-43477628: 43478136-43478232: 43497880-43497977 | −0.17 | −0.124 | −0.203 |
| LIAS | +: chr4: 39465284-39465342: 39467517-39467646: 39470018-39470611 | −0.17 | −0.114 | −0.18 |
| PLD3 | +: chr19: 40365552-40365585: 40365717-40365930: 40366418-40366464 | −0.17 | −0.171 | −0.088 |
| DNM1L | +: chr12: 32737104-32737161: 32737864-32737942: 32740063-32740240 | −0.17 | −0.291 | −0.055 |
| GPRC5D-AS1 | +: chr12: 12927725-12927803: 12978940-12979021: 12979523-12979622 | −0.17 | 0.037 | −0.028 |
| CDKL3 | −: chr5: 134304404-134304567: 134306608-134306702: 134308137-134308466 | −0.17 | −0.075 | 0.083 |
| AL772307.1 | −: chr9: 39983792-39984410: 39988443-39988564: 40106357-40106611 | −0.18 | −0.066 | 0.115 |
| AC091901.1 | −: chr5: 162561784-162561944: 162591609-162591685: 162623334-162623461 | −0.18 | 0.031 | 0.003 |
| AGBL3 | +: chr7: 134987874-134987996: 134989249-134989310: 134993492-134993678 | −0.18 | −0.106 | 0.047 |
| NCOR2 | −: chr12: 124326190-124326370: 124327408-124327633: 124330844-124330898 | −0.18 | −0.125 | 0.093 |
| MARK2 | +: chr11: 63903060-63903158: 63903985-63904147: 63904785-63905043 | −0.18 | −0.056 | 0.195 |
| PLCD4 | +: chr2: 218615706-218615761: 218615903-218615959: 218618570-218618807 | −0.18 | −0.138 | −0.126 |
| TSNARE1 | −: chr8: 142270474-142271691: 142274780-142274863: 142279859-142279997 | −0.18 | −0.203 | −0.249 |
| HERPUD1 | +: chr16: 56939248-56939359: 56940176-56940245: 56943125-56943297 | −0.18 | 0.066 | −0.23 |
| REPS1 | −: chr6: 138921036-138921124: 138926400-138926481: 138929976-138930098 | −0.19 | 0.013 | 0.08 |
| PLK5 | +: chr19: 1531737-1531883: 1533930-1534041: 1535064-1535365 | −0.19 | −0.068 | −0.056 |
| LIAS | +: chr4: 39465284-39465342: 39467319-39468427: 39470018-39470164 | −0.19 | −0.115 | −0.222 |
| AHSA2 | +: chr2: 61185501-61185618: 61185979-61186081: 61186445-61186497 | −0.2 | −0.142 | −0.128 |
| TTC28 | −: chr22: 27989877-27990007: 27990788-27990812: 27992586-27992663 | −0.2 | −0.197 | 0.141 |
| NRXN3 | +: chr14: 78243036-78243802: 78278644-78278662: 78297830-78297860 | −0.2 | −0.136 | 0.142 |
| ZNF527 | +: chr19: 37379119-37379246: 37380047-37380372: 37388305-37393066 | −0.2 | −0.211 | −0.236 |
| SPIN1 | +: chr9: 88415606-88415699: 88416643-88416766: 88418777-88418951 | −0.2 | −0.037 | 0.208 |
| ERBIN | +: chr5: 66068876-66069020: 66072168-66072291: 66075023-66075230 | −0.2 | 0.199 | 0.12 |

-continued

| | | | | |
|---|---|---|---|---|
| ABI3BP | −: chr3: 100789453-100789516: 100792690-100792768: 100794922-100795003 | −0.2 | −0.243 | −0.104 |
| CDC42BPA | −: chr1: 227213135-227213219: 227219262-227219420: 227254063-227254155 | −0.2 | −0.17 | −0.012 |
| EIF5 | +: chr14: 103334001-103334260: 103334388-103334597: 103335652-103335844 | −0.2 | −0.351 | −0.349 |

| | | | | |
|---|---|---|---|---|
| WNK1 | +: chr12: 878211-878361: 879572-880031: 881691-881789 | −0.21 | 0.039 | 0.079 |
| SORBS1 | −: chr10: 95410632-95410777: 95414493-95414655: 95421960-95422073 | −0.21 | −0.271 | −0.033 |
| CADM1 | −: chr11: 115178643-115178775: 115198405-115198438: 115209573-115209657 | −0.21 | −0.121 | 0.036 |
| BCS1L | +: chr2: 218659759-218659800: 218660306-218660421: 218660938-218661217 | −0.21 | −0.125 | −0.142 |
| SRCAP | +: chr16: 30722121-30722286: 30722562-30722748: 30722962-30723229 | −0.22 | −0.093 | 0.055 |
| CLCN3 | +: chr4: 169713078-169713295: 169717791-169717867: 169719906-169720545 | −0.22 | −0.117 | −0.049 |
| CD46 | +: chr1: 207767012-207767195: 207767778-207767823: 207783291-207783330 | −0.22 | −0.189 | −0.123 |
| NCOR2 | −: chr12: 124326179-124326370: 124327546-124327633: 124330844-124330898 | −0.22 | −0.098 | 0.087 |
| PRKD1 | −: chr14: 29638693-29638904: 29656475-29656499: 29663698-29663859 | −0.22 | −0.227 | 0.006 |
| NFIX | +: chr19: 13075534-13075671: 13078612-13078735: 13081679-13081835 | −0.22 | −0.195 | 0.049 |
| IGSF3 | −: chr1: 116603623-116604025: 116606491-116606551: 116607941-116608331 | −0.23 | −0.343 | −0.052 |
| AC004980.1 | +: chr7: 76551463-76551522: 76615493-76615663: 76621115-76621388 | −0.23 | −0.148 | −0.162 |
| DONSON | −: chr21: 33581950-33582055: 33582164-33582246: 33584589-33584768 | −0.23 | −0.12 | 0.089 |
| FGFR2 | −: chr10: 121503789-121503941: 121515116-121515319: 121519978-121520169 | −0.23 | −0.268 | −0.335 |
| MED15 | +: chr22: 20508056-20508444: 20518877-20518995: 20537116-20537183 | −0.23 | −0.072 | 0.227 |
| RAB11FIP5 | −: chr2: 73075992-73076182: 73079650-73081663: 73088049-73088749 | −0.24 | −0.061 | 0.083 |
| AL392172.1 | +: chr1: 222815058-222815078: 222823855-222823945: 222835118-222835215 | −0.25 | 0.05 | −0.079 |
| LIAS | +: chr4: 39465284-39465342: 39468118-39468427: 39470018-39470164 | −0.25 | −0.149 | −0.296 |
| FAM114A1 | +: chr4: 38867815-38867834: 38868397-38868546: 38891742-38891830 | −0.25 | 0.145 | 0.037 |
| PLK5 | +: chr19: 1531737-1531883: 1533718-1533848: 1535064-1535365 | −0.26 | −0.219 | −0.139 |
| KIF13A | −: chr6: 17763692-17764946: 17771113-17771208: 17771907-17772059 | −0.26 | −0.233 | −0.015 |
| CD46 | +: chr1: 207767012-207767195: 207767778-207767823: 207770320-207770362 | −0.27 | −0.343 | −0.3 |
| TCF7L2 | +: chr10: 113158020-113158069: 113158666-113158717: 113160618-113160691 | −0.27 | −0.282 | −0.201 |
| AKAP11 | +: chr13: 42308453-42308609: 42313046-42313130: 42313893-42313940 | −0.27 | −0.409 | −0.106 |
| TCF7L2 | +: chr10: 113158020-113158069: 113159919-113159992: 113160618-113160691 | −0.28 | −0.427 | −0.248 |
| SORBS2 | −: chr4: 185678795-185678822: 185684753-185684846: 185775226-185775366 | −0.28 | −0.081 | 0.159 |
| CCDC18-AS1 | −: chr1: 93309714-93309790: 93318167-93318228: 93324634-93324691 | −0.29 | −0.047 | −0.574 |
| ZFYVE21 | +: chr14: 103729090-103729182: 103729792-103729846: 103732619-103732762 | −0.29 | −0.203 | −0.004 |
| ENAH | −: chr1: 225500991-225501070: 225504990-225505053: 225507950-225508017 | −0.3 | −0.08 | 0.025 |
| ZEB1 | +: chr10: 31319215-31319292: 31373017-31373173: 31387123-31387266 | −0.3 | 0.122 | −0.18 |
| DEPDC5 | +: chr22: 31857444-31857553: 31861367-31861433: 31870589-31870744 | −0.31 | −0.04 | 0.097 |
| TCF4 | −: chr18: 55585279-55585352: 55586920-55587136: 55589296-55589778 | −0.31 | −0.259 | 0.026 |
| TMEM50B | −: chr21: 33455726-33455784: 33456003-33456097: 33465341-33465409 | −0.31 | NA | NA |
| ZCCHC11 | −: chr1: 52526019-52526373: 52529767-52529885: 52534986-52535122 | −0.32 | −0.315 | −0.315 |
| ANKRD36 | +: chr2: 97207810-97207839: 97209680-97209709: 97209799-97209872 | −0.32 | −0.211 | −0.3 |
| SORBS2 | −: chr4: 185678795-185678822: 185684753-185684846: 185690561-185690599 | −0.32 | −0.157 | 0.132 |
| CCDC18-AS1 | −: chr1: 93305387-93305470: 93318167-93318228: 93324634-93324691 | −0.32 | −0.002 | −0.309 |
| STX2 | −: chr12: 130790833-130791977: 130795994-130796120: 130798524-130798635 | −0.32 | −0.298 | −0.054 |
| SORBS1 | −: chr10: 95410632-95410777: 95414493-95414862: 95421960-95422073 | −0.32 | −0.332 | −0.057 |
| RAPGEF6 | −: chr5: 131446482-131446703: 131450022-131450046: 131453053-131453177 | −0.33 | −0.213 | −0.025 |
| CAMKK2 | −: chr12: 121245139-121245240: 121248605-121248734: 121249786-121249874 | −0.33 | −0.271 | −0.016 |
| HIVEP3 | −: chr1: 41518401-41518488: 41524734-41524910: 41575543-41575689 | −0.33 | −0.034 | −0.251 |
| MSH5 | +: chr6: 31758164-31758293: 31758532-31758620: 31758765-31758875 | −0.34 | −0.295 | −0.335 |

| | | | | |
|---|---|---|---|---|
| HOOK3 | +: chr8: 42997589-42997637: 43000270-43000276: 43002106-43002141 | −0.34 | −0.167 | 0.041 |
| MROH7-TTC4 | +: chr1: 54678741-54678854: 54679262-54679439: 54682655-54682794 | −0.34 | −0.314 | −0.211 |
| SOCS7 | +: chr17: 38361710-38361775: 38364751-38364856: 38366286-38366417 | −0.35 | −0.403 | −0.074 |
| SSBP3 | −: chr1: 54257126-54257186: 54258068-54258149: 54281437-54281527 | −0.35 | −0.282 | 0.001 |
| FGFR1 | −: chr8: 38428345-38428435: 38429681-38429948: 38457355-38457446 | −0.36 | −0.264 | 0.157 |
| SORBS2 | −: chr4: 185678795-185678822: 185684753-185684842: 185690561-185690611 | −0.36 | −0.145 | 0.123 |
| NHSL1 | −: chr6: 138430392-138433680: 138441982-138442114: 138447000-138447193 | −0.38 | −0.345 | −0.039 |
| ARVCF | −: chr22: 19969895-19970743: 19971215-19971335: 19971885-19971971 | −0.38 | −0.237 | 0.077 |
| MBD1 | −: chr18: 50275128-50275245: 50275369-50275444: 50275599-50275728 | −0.39 | −0.125 | 0.014 |
| ZMAT1 | −: chrX: 101886631-101886731: 101887917-101887304: 101894453-101894904 | −0.39 | −0.133 | −0.141 |
| WNK1 | +: chr12: 878211-878361: 880720-880999: 881691-881789 | −0.39 | −0.231 | 0.071 |
| MBNL1 | +: chr3: 152445281-152445539: 152446703-152446757: 152447619-152447773 | −0.39 | −0.143 | 0.142 |
| TTN | −: chr2: 178640540-178640630: 178641240-178641315: 178644547-178644616 | −0.43 | −0.507 | −0.086 |
| TTN | −: chr2: 178640540-178640630: 178642236-178642317: 178644547-178644616 | −0.43 | −0.524 | −0.181 |
| AC139713.2 | +: chr4: 143738974-143739117: 143808313-143808370: 143859015-143859115 | −0.43 | −0.225 | 0.095 |
| ADD3 | +: chr10: 110130362-110130486: 110132304-110132400: 110133325-110134211 | −0.46 | −0.305 | 0.053 |
| CLINT1 | −: chr5: 157787601-157787992: 157790599-157790651: 157791702-157791841 | −0.46 | −0.168 | −0.406 |
| MICAL2 | +: chr11: 12249940-12250273: 12255642-12255750: 12256784-12256909 | −0.47 | −0.474 | −0.461 |
| AC138409.2 | −: chr5: 34218294-34218450: 34239374-34239448: 34244615-34244796 | −0.48 | −0.234 | −0.004 |
| IZUMO4 | +: chr19: 2098786-2098804: 2098975-2099029: 2099254-2099590 | −0.5 | −0.32 | −0.106 |
| COPZ2 | −: chr17: 48026166-48026475: 48027675-48027789: 48028471-48028510 | −0.5 | −0.353 | 0.094 |

-continued

| | | | | |
|---|---|---|---|---|
| EXOC1 | +: chr4: 55882726-55883928: 55888887-55888932: 55890222-55890386 | −0.54 | −0.405 | 0.037 |
| CD47 | −: chr3: 108047078-108047292: 108049618-108049651: 108050577-108050602 | −0.55 | −0.57 | −0.019 |
| TMEM184A | −: chr7: 1548648-1548688: 1549546-1549604: 1549853-1549945 | −0.58 | −0.103 | −0.008 |
| MBNL2 | +: chr13: 97347040-97347067: 97356795-97356849: 97357481-97357635 | −0.66 | −0.448 | 0.061 |

While not nearly as frequent, other forms of alternative splicing events, alternative 5' splice site (A5SS), alternative 3'-splice site (A3SS), mutually exclusive exon (MXE) and retained intron (RI), also showed that the Pre_S cohort was more similar to the FECD_REP group than the FECD_NR cohort (FIGS. 17A-D). Taken together, these data demonstrate that splicing changes in Pre_S tissue are precursors to the changes in FECD_REP—but not FECD_NR—late stage disease.

We then separated the top 24 skipped exon events in Pre_S tissue, which are shared with FECD_REP for evaluation. As with the overall group of 313 events, the splicing of these genes was much more like FECD_REP tissue than to control or FECD_NR tissue (FIG. 4D). Of the top 24 skipped exon events shared by FECD_REP and Pre_S tissue, approximately half are also seen in tibialis anterior muscle of myotonic dystrophy type 1 (DM1) subjects (FIGS. 4D-E, 17E-G). This similarity, in spite of the comparison being made between samples from different tissues, suggests that the expanded CUG repeats in DM1 and FECD_REP have a common mechanism for producing splicing changes and that this mechanism is activated in Pre_S tissue.

Notable genes that show changes in splicing include the splicing factors MBNL1 and MBNL2. Changes in MBNL1 and MBNL2 splicing in Pre_S (Table 8) cells may trigger other splicing changes and eventually lead to the larger scale change that characterizes late stage disease (Table 8).

Example 4

This example describes changes in alternative splicing are quantitatively similar in Pre_S and FECD_REP tissue.

Figure 5:
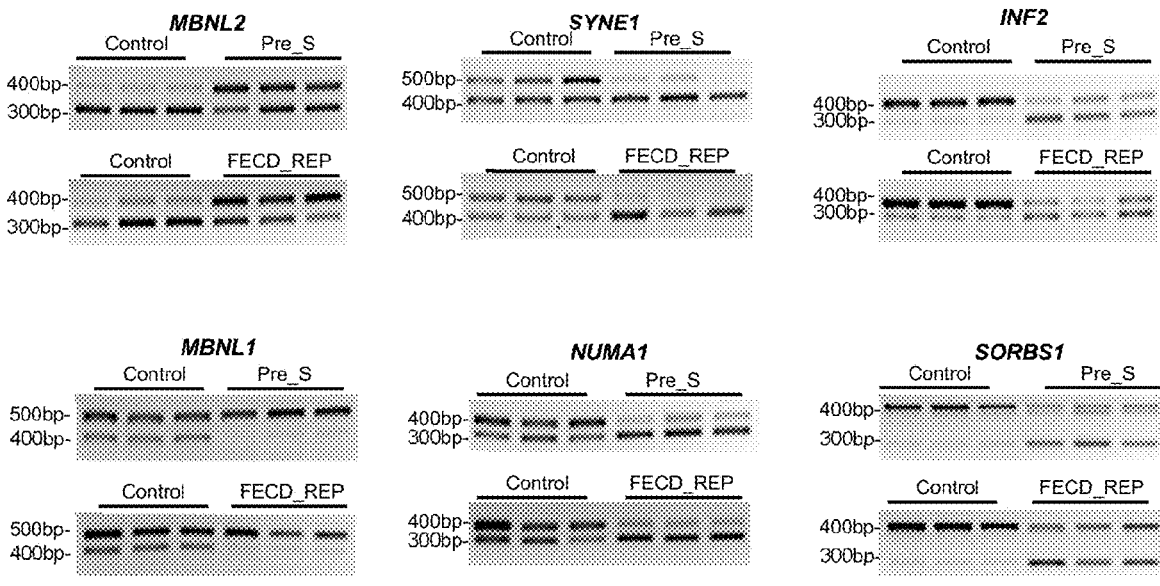
FIG. 5 show differential gene splicing is similar in Pre_S and FECD_REP tissue. (A) Representative Sashimi plots showing changes in alternative splicing for MBNL2 and SYNE1 transcripts in Control versus Pre_S and FECD_REP tissues. (B) Reverse-transcriptase PCR evaluation of RNA splicing changes in Control, Pre_S and FECD_REP tissue. All measurements used surgically prepared corneal endothelium from disease patients or donors detailed in Table 6.

We experimentally validated changes in splicing and levels of gene expression for Pre_S relative to control tissues (FIG. 5; FIG. 18). Genes were chosen for validation based on the significance of altered expression and the potential biological role of the gene expression suggested by pathway analysis (FIG. 8).

We used reverse-transcription PCR to evaluate changes of splicing for six genes, INF2, NUMA1, SORBS1, SYNE1, MBNL1, and MBNL2 (FIG. 5). INF2 protein associates with microtubules, and may affect cell shape. NUMA1 protein is component of the nuclear matrix and may affect mitotic spindle organization and proper cell division. SORBS1 was chosen for its protein product's involvement in cell adhesion and extracellular matrix. SYNE1 encodes nesprin-1 which links the nuclear membrane to the actin cytoskeleton and may also affect cell morphology. MBNL1 and MBNL2 were chosen because potential alterations in their expression might feed back into even greater changes in splicing.

The changes in splicing predicted by global RNAseq analysis were confirmed by visual inspection of genes using Sashimi plots (FIG. 5A) and validated by semi-quantitative analysis using reverse-transcriptase PCR (RT-PCR) (FIG. 5B) using monolayer human corneal endothelial tissue. Pre_S tissue showed the changes in splicing predicted by our RNAseq data (FIG. 5). Both Sashimi plots and semi-quantitative reverse transcriptase PCR (RT-PCR) analysis reveal that the absolute magnitude of splicing changes are similar in FECD_REP late stage disease tissues. The amount of change in splicing in Pre_S tissue is substantial, similar to that observed in late stage tissue.

We also carried out a differential alternative splicing analysis between Pre_S and FECD_REP tissues directly, rather than using the Control as the reference as described above. Although there are hundreds of significant skipped exon events identified between Pre_S and FECD_REP, out of 132 skipped exon events shared between Pre_S/Control and FECD_REP/Control comparison, only five of them are significantly different between Pre_S and FECD_REP (Table 9). This means that majority of shared skipped exon events identified between Pre_S/Control and FECD_REP/Control have similar magnitude in inclusion of exon level changes, This observation suggests that missplicing of key genes does not gradually increase as disease symptoms progress, rather substantial missplicing is a leading indicator of disease.

Table 9. Overlapped significant differential skipped exon events between Pre_S/FECD_REP and 132 shared SE events between Pre_S/Control and FECD_REP/Control. (FDR<0.001, |IncLevel Difference|>=0.15)

| Gene Symbol | locus | FDR | IncLevel1 | IncLevel2 | IncLevel Difference |
|---|---|---|---|---|---|
| MTA1 | +: chr14: 105465333-105466578: 105466706-105466742: 105469466-105469498 | 8.6149E−07 | 0.674, 0.322, 0.487, 0.388, 0.523, 0.474 | 0.797, 0.841, 0.652, 0.752, 0.783, 0.924 | −0.313 |
| ABI1 | −: chr10: 26770244-26770345: 26771074-26771089: 26777064-26777241 | 0.000412057 | 0.348, 0.391, 0.197, 0.531, 0.256, 0.114 | 0.543, 0.513, 0.425, 0.521, 0.598, 0.612 | −0.229 |
| INF2 | +: chr14: 104714202-104714856: 104715283-104715340: 104718794-104719603 | 0.000481285 | 0.274, 0.138, 0.133, 0.16, 0.137, 0.434 | 0.571, 0.546, 0.4, 0.303, 0.348, 0.272 | −0.194 |

-continued

| Gene Symbol | locus | FDR | IncLevel1 | IncLevel2 | IncLevel Difference |
|---|---|---|---|---|---|
| EIF5 | +: chr14: 103334001-103334260: 103334388-103334597: 103335652-103335844 | 6.60555E−13 | 0.568, 0.899, 0.887, 0.786, 0.959, 0.921 | 0.984, 0.976, 1.0, 0.988, 0.971, 1.0 | −0.15 |
| SYNE1 | −: chr6: 152143622-152143765: 152145486-152145555: 152148044-152148378 | 0.000142873 | 0.147, 0.125, 0.082, 0.134, 0.15, 0.388 | 0.486, 0.471, 0.199, 0.25, 0.408, 0.359 | −0.191 |

Example 5

This example describes differential gene expression.

We compared gene expression level changes in Pre_S, FECD_REP, and FECD_NR tissue cohorts relative to control tissue. To classify changes as significant, we used the adjusted p-value generated by Cuffdiff, one of the programs within Cufflinks suite, as the determining metric. Changes with a p-value less than 0.05 were deemed significant and included in our analysis. Analysis by DeSeq2, an alternate program for evaluating RNAseq data, produced similar results when compared with the output of CuffDiff (FIG. 19 and Table 10).

TABLE 10

Differential expression level analysis results for 8 selected genes by CuffDiff and DeSeq2.

CuffDiff

| gene_name | log2FoldChange_Pre_S/Con | q_value_Pre_S/Con | log2FoldChange_FECD_REP/Con | q_value_FECD_REP/Con |
|---|---|---|---|---|
| FN1 | 5.08031 | 0.00226223 | 7.2246 | 0.00226223 |
| COL4A2 | 1.68119 | 0.00226223 | 3.04457 | 0.00226223 |
| MSI1 | 3.41382 | 0.00226223 | 3.44233 | 0.00226223 |
| CTGF | 1.22263 | 0.00226223 | 2.72282 | 0.00226223 |
| COCH | 4.34706 | 0.00226223 | 4.73065 | 0.00226223 |
| LUM | −1.13075 | 0.045657 | −1.69472 | 0.00226223 |
| KDR | −1.30521 | 0.00226223 | −2.927 | 0.00226223 |
| SOD3 | −1.63529 | 0.0103752 | −3.48636 | 0.00226223 |

CuffDiff

| gene_name | log2FoldChange_Pre_S/Con | log2FoldChange_FECD_NR/Con | q_value_FECD_NR/Con |
|---|---|---|---|
| FN1 | 5.08031 | 6.69992 | 0.00226223 |
| COL4A2 | 1.68119 | 4.33504 | 0.00226223 |
| MSI1 | 3.41382 | 2.70827 | 0.00226223 |
| CTGF | 1.22263 | 2.65112 | 0.00226223 |
| COCH | 4.34706 | 3.90575 | 0.00738683 |
| LUM | −1.13075 | 0.773072 | 0.347028 |
| KDR | −1.30521 | −0.56167 | 0.378425 |
| SOD3 | −1.63529 | −1.75043 | 0.00738683 |

| DeSeq2 gene_name | log2FoldChange_Pre_S/Con | padj_Pre_S/Con | log2FoldChange_FECD_REP/Con |
|---|---|---|---|
| FN1 | 5.055555154 | 0.000769717 | 7.282987556 |
| COL4A2 | 1.795732091 | 0.16084414 | 3.341905792 |
| MSI1 | 3.737811696 | 1.24E−10 | 3.823524012 |
| CTGF | 1.09560732 | 0.342783282 | 2.701641399 |
| COCH | 4.189351978 | 5.77E−09 | 4.675618865 |
| LUM | −1.22262908 | 0.258691241 | −1.911846973 |
| KDR | −1.356276847 | 0.105249236 | −3.06676426 |
| SOD3 | −1.646170275 | 0.004935301 | −3.550948801 |

| DeSeq2 gene_name | padj_FECD_REP/Con | log2FoldChange_FECD_NR/Con | padj_FECD_NR/Con |
|---|---|---|---|
| FN1 | 1.17E−09 | 6.760739221 | 2.11E−06 |
| COL4A2 | 4.15E−05 | 4.634801232 | 7.80E−07 |
| MSI1 | 9.62E−13 | 3.382481453 | 9.23E−08 |
| CTGF | 3.08E−05 | 2.636468101 | 0.00083336 |
| COCH | 6.27E−13 | 3.881906815 | 5.48E−07 |
| LUM | 0.004338117 | 0.722945995 | 0.484968174 |
| KDR | 1.95E−08 | −0.667292478 | 0.4512983 |
| SOD3 | 4.45E−15 | −1.638591521 | 0.004506258 |

All sample cohorts showed expression changes relative to control tissue (Pre_S: 215, FECD_REP: 1330; FECD_NR: 696) (FIG. 6A-B). The greater number of gene expression changes in the FECD_REP and FECD_NR tissues is consistent with the severe cellular phenotype observed in late stage disease. 602 out of the 696 genes differentially expressed in the FECD_NR tissues were also found in the FECD_REP group suggesting significant overlap of the common final molecular genetic mechanisms in the two forms of late-stage disease.

Pre_S tissue had 215 genes with significantly altered expression levels relative to control tissue. Only five changes in gene expression were uniquely shared between Pre_S and FECD_NR tissue, compared to 73 shared changes with FECD_REP. (FIG. 6A). The closer relationship between Pre-S and FECD_REP is consistent with our splicing data (FIGS. 4-5) and supports the conclusion that patterns of gene expression in mutant expanded repeat cells are established long before symptoms or disease findings are observable.

Volcano plots allow a global overview of individual gene expression changes. They are useful for visualizing patterns of changes and identifying "outlier" genes that combine highly significant changes in gene expression with higher fold changes. The fold change among top genes are less in Pre_S than in FECD_REP or FECD_NR and the identity of top genes differ (FIGS. 6B-C, 20, 22). This finding is consistent with the severity of late stage disease and the disruption of many gene expression programs.

Evaluation of Pre_S tissue may provide a window to identify early gene drivers before symptom-driven secondary changes in gene expression overwhelm analysis. The top twenty differentially over-expressed genes identified in Pre_S tissue (FIG. 6C) include genes involved in the extracellular matrix and its assembly, cochlin (COCH), fibronectin (FN1), and thrombospondin (THBS2).

We found 279 statistically significant up regulated genes that are common to Pre-S and FECD_REP of which the top 50 are shown in Table 11.

TABLE 11

| Top 50 up regulated genes common to Pre-S and FECD_REP. | | | | |
|---|---|---|---|---|
| FEATURE_NAME | Control-VS-Pre_S.logFC | Control-VS-Pre_S.LR | Control-VS-Pre_S.PValue | Control-VS-FECD_REP.logFC | Control-VS-FECD_REP.Pvalue |
| ROR2 | 6.524075 | 43.41713 | 4.42E−11 | 7.198885 | 8.82E−13 |
| ACKR1 | 5.839108 | 34.54291 | 4.17E−09 | 7.615229 | 8.47E−13 |
| CADM3 | 5.578438 | 20.98525 | 4.63E−06 | 7.107443 | 4.32E−08 |
| ABCB1 | 5.459433 | 48.71004 | 2.97E−12 | 8.276607 | 8.4E−22 |
| CNN1 | 5.117924 | 45.30649 | 1.68E−11 | 4.418321 | 2.89E−09 |
| VIPR2 | 5.082804 | 19.28708 | 1.12E−05 | 6.334537 | 1.42E−07 |
| FN1 | 5.080174 | 29.43764 | 5.77E−08 | 7.26223 | 1.4E−12 |
| ADAM33 | 5.048453 | 24.75297 | 6.52E−07 | 5.918941 | 1.57E−08 |
| CADM3-AS1 | 5.030838 | 23.8002 | 1.07E−06 | 6.795826 | 2.6E−10 |
| TSHR | 4.901685 | 31.98023 | 1.56E−08 | 10.49244 | 3.3E−27 |
| COCH | 4.403612 | 61.33316 | 4.82E−15 | 4.90102 | 1.17E−17 |
| PCP4 | 4.357451 | 16.39757 | 5.14E−05 | 5.995339 | 1.82E−07 |
| KCNA1 | 4.352557 | 51.10559 | 8.75E−13 | 4.478258 | 2.41E−13 |
| DPP10 | 4.304371 | 23.64629 | 1.16E−06 | 7.820025 | 1.4E−16 |
| VSIG2 | 4.073351 | 67.82251 | 1.79E−16 | 4.976104 | 1.82E−23 |
| CLIC6 | 4.072688 | 37.32171 | 1E−09 | 6.315357 | 6.76E−19 |
| TMEM30B | 3.818031 | 42.12119 | 8.58E−11 | 3.883178 | 4.15E−11 |
| MARVELD3 | 3.81801 | 49.05871 | 2.48E−12 | 2.798854 | 2.01E−07 |
| LGR6 | 3.660003 | 23.71591 | 1.12E−06 | 3.351386 | 7.12E−06 |
| CST4 | 3.652591 | 13.24441 | 0.000273 | 5.927597 | 6.12E−08 |
| THBS2 | 3.644255 | 31.45097 | 2.05E−08 | 4.491004 | 2E−11 |
| ICA1 | 3.64345 | 27.63457 | 1.47E−07 | 5.191539 | 6.53E−13 |
| ALPK2 | 3.614404 | 11.37385 | 0.000745 | 10.3664 | 7.87E−16 |
| RARRES2 | 3.590468 | 23.52695 | 1.23E−06 | 1.910993 | 0.007297 |
| MMP19 | 3.583226 | 26.33872 | 2.86E−07 | 5.252943 | 4.61E−13 |
| FRZB | 3.567747 | 31.43543 | 2.06E−08 | 3.340459 | 1.23E−07 |
| DCDC2C | 3.552476 | 28.69988 | 8.45E−08 | 5.752764 | 1.25E−18 |
| CST1 | 3.518193 | 11.74597 | 0.00061 | 7.105067 | 1.89E−09 |
| MSI1 | 3.512031 | 62.99815 | 2.07E−15 | 3.424204 | 8.93E−15 |
| ITPRIPL1 | 3.507736 | 41.89734 | 9.62E−11 | 3.000683 | 2.92E−08 |
| WNT3 | 3.451001 | 32.10989 | 1.46E−08 | 3.821713 | 4.39E−10 |
| HPGD | 3.43778 | 32.01004 | 1.53E−08 | 3.370523 | 2.74E−08 |
| SLC5A1 | 3.40064 | 49.65363 | 1.83E−12 | 3.170105 | 4.5E−11 |
| ARSJ | 3.368825 | 16.85727 | 4.03E−05 | 4.257335 | 4.15E−07 |
| TPBG | 3.350721 | 29.45705 | 5.72E−08 | 4.952642 | 2.23E−14 |
| GREB1L | 3.297108 | 15.28293 | 9.25E−05 | 5.382995 | 1.55E−09 |
| SLC16A9 | 3.278027 | 25.65742 | 4.08E−07 | 4.385272 | 5.22E−11 |
| EPHB6 | 3.272468 | 12.02168 | 0.000526 | 6.79661 | 6.39E−11 |
| MROH9 | 3.264793 | 37.8166 | 7.77E−10 | 4.571302 | 1.48E−18 |
| ENOX1 | 3.263818 | 75.75422 | 3.21E−18 | 2.699152 | 4.02E−13 |
| ECEL1P2 | 3.225493 | 24.59929 | 7.06E−07 | 3.032914 | 2.82E−06 |
| PLAC9 | 3.220549 | 12.43297 | 0.000422 | 6.410981 | 9.79E−11 |
| KIF21B | 3.2063 | 18.13876 | 2.05E−05 | 6.318319 | 1.62E−16 |
| F5 | 3.174819 | 23.69059 | 1.13E−06 | 4.601282 | 2.05E−11 |
| ADAMTS12 | 3.164387 | 26.30854 | 2.91E−07 | 4.291849 | 1.72E−11 |
| ITIH5 | 3.155392 | 16.01146 | 6.3E−05 | 7.171555 | 5.44E−15 |

TABLE 11-continued

| | Top 50 up regulated genes common to Pre-S and FECD_REP. | | | | |
| --- | --- | --- | --- | --- | --- |
| FEATURE_NAME | Control-VS-Pre_S.logFC | Control-VS-Pre_S.LR | Control-VS-Pre_S.PValue | Control-VS-FECD_REP.logFC | Control-VS-FECD_REP.Pvalue |
| ANXA3 | 3.119277 | 11.12734 | 0.000851 | 6.788408 | 1.06E−10 |
| PROS1 | 3.107313 | 27.84953 | 1.31E−07 | 4.800437 | 1.42E−14 |
| PTPN3 | 3.090466 | 28.54363 | 9.16E−08 | 3.693209 | 3.56E−10 |
| DCLK1 | 3.073859 | 22.09089 | 2.6E−06 | 5.060074 | 5.74E−13 |

Example 6

This example describes quantitative analysis of gene expression changes

We used quantitative PCR (qPCR) to confirm the changes in the level of gene expression detected by RNAseq in both Pre_S and FECD tissue (FIG. 7). qPCR measurements of corneal endothelial tissues were challenging because of the limited amount of material available, but we could compare expression of eight genes identified in our RNAseq data, FN1, COL4A2, COCH, CTGF, MSI1, LUM, KDR, and SOD3. Four of these genes, FN1, COL4A2, CTGF, KDR, were within the fibrosis pathway. COCH and LUM encode extracellular matrix proteins, MSI1 encodes an RNA binding protein/splicing factor, and SOD3 protein is related to oxidative stress. The observed changes in gene expression confirm our RNAseq results (FIGS. 6B, 23).

Example 7

This example describes pathway analysis.

To elucidate the potential impact of changes in the expression of individual genes on physiologic processes, we applied Ingenuity Pathway Analysis (IPA) to our RNAseq data. Overwhelmingly, the top common canonical pathway was hepatic fibrosis/hepatic stellate cell activation (FIGS. 8A, 23). Involvement of the hepatic fibrosis pathway genes in FECD_REP and FECD_NR is consistent with the observed accumulation of extracellular matrix (ECM) in advanced FECD with thickening of Descemet's membrane with focal excrescences (guttae) and with RNA measurements using tissue from late stage disease. Our FECD transcriptome data indicates robust ECM production in late-stage disease possibly regulated by transforming growth factor-β (TGF-β), the most potent fibrogenic cytokine released by a number of cell populations in the body including the liver (FIG. 21A-B).

Figure 7:
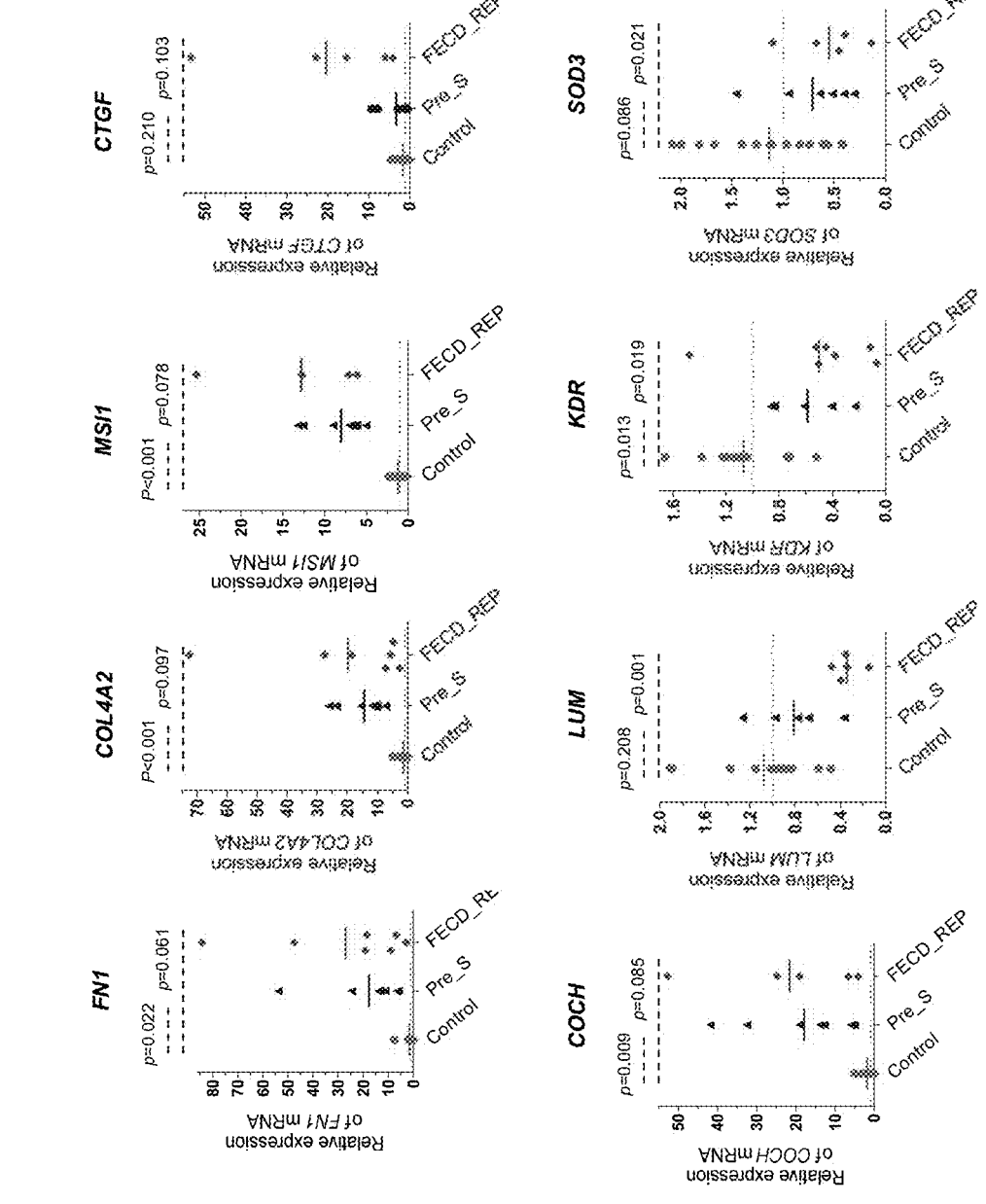
FIG. 7 shows changes in gene expression in Pre_S and FECD_REP tissue. qPCR evaluation of gene expression levels in Control, Pre_S, and FECD_REP tissue. All measurements used surgically prepared single cell monolayer corneal endothelium from disease patients or donors detailed in Table 6.

Activation of the fibrosis pathway was also observed in Pre_S tissue (FIGS. 8A-B, 9). Genes that showed statistically significant increases in expression include fibronectin FN1, one of the highest differentially expressed genes in Pre_S tissue (FIG. 7). Other genes include connective tissue growth factor (CTGF) and four members of the collagen alpha chain family including COL1A2 which is also abundant in liver fibrosis (FIG. 20). Kinase insert domain receptor (KDR, also known as vascular endothelial growth factor receptor-2) showed decreased expression. Relevant in the fibrosis pathway, KDR protein interacts with VEGF to mediate vascular endothelial cell proliferation. These genes are also disturbed in advanced disease—another indication that gene expression programs associated with fibrosis are activated in presymptomatic carriers prior to observable symptoms of disease.

The pathways underlying FECD_REP and FECD_NR advanced stage disease had significant overlap. There were numerous shared pathways implicating the immune system related to helper T cell activation, signaling, and neuroinflammation. (FIGS. 8A,C). Marked overexpression of genes encoding proteins on the surface of antigen-presenting cells including the B7 protein, CD86 (>2,000 fold increase), and class II major histocompatibility proteins (>250 fold) both required for these cells to activate helper T cells implicate the immune system in both FECD groups in late-stage disease (FIGS. 8C, 21C-E).

A few molecular pathways were changed in FECD_REP but not FECD_NR (FIG. 8D). The canonical pathway related to mitochondrial dysfunction showed the large difference with p values of $10^{-5}$ and zero respectively for FECD_REP and FECD_NR (FIGS. 8A, 21F-H). Decreased expression of oxidative phosphorylation genes was more pronounced in FECD_REP compared to the FECD_NR (FIG. 8D).

Example 8

This example provides a discussion of examples 1-7.

Identifying the early drivers of late-onset disease is important for understanding disease progression and developing therapeutics. Studying early drivers, however, is often not practical because pre-symptomatic tissue is difficult to obtain. Because the expanded CUG repeat mutation within TCF4 intron 2 that causes FECD_REP is so prevalent (3% of the Caucasian population), significant numbers of pre-symptomatic samples can be obtained from individual donors positive for the CUG expansion. These tissues, together with FECD_REP, FECD_NR, and control tissues (FIGS. 1-2) provide an advantageous model for better investigating the early links between expanded trinucleotide repeat mutations and disease.

The goal of this study was to understand whether the expanded CUG repeat was changing gene expression in Pre_S tissue and how such changes might relate to the gene expression and phenotypic changes known to occur in late-stage FECD.

FECD is a Disease of Mutant RNA

FECD_REP is caused by an expanded CUG trinucleotide repeat within mutant TCF4 intronic RNA (FIG. 10). Remarkably, FECD is also caused by the mutant CUG expanded repeat within the 3'-untranslated region of the DMPK gene is also associated with myotonic dystrophy. Unlike other trinucleotide repeat diseases where the contribution of mutant RNA is debated, data demonstrating that CUG RNAs expressed from two different genes are both responsible for FECD offers strong support for RNA playing a central role in the molecular origins of the disease.

The expanded CUG RNA can be detected by fluorescent in situ hybridization (FISH) as RNA foci. These RNA foci are a hallmark of both Pre_S and FECD_REP corneal endothelium (FIG. 10). While Pre_S and FECD_REP tissue both possess the RNA trigger for FECD, Pre_S tissue is visually indistinguishable from control tissue upon specular imaging. By contrast, FECD_REP tissue is dramatically different from control tissue, with reduced cell density and the formation of focal collagen accumulations known as guttae.

Figure 3:
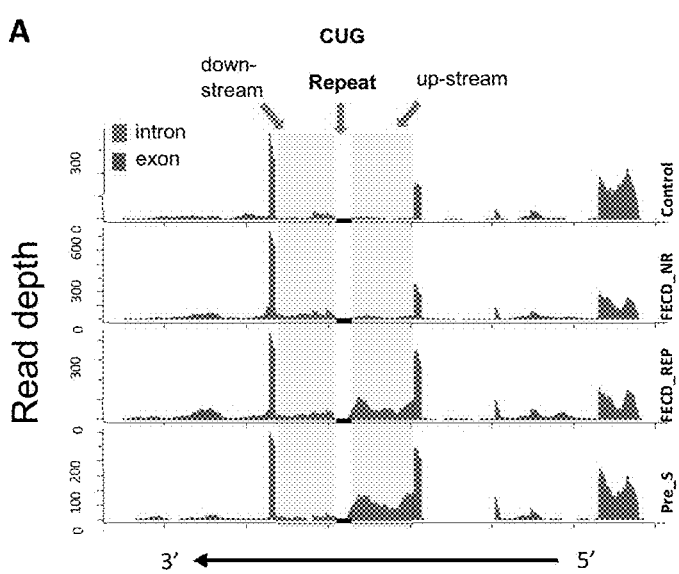
FIG. 3 shows intronic RNA stabilized in Pre_S and FECD_REP tissue and FECD_REP patient-derived F35T and F45SV corneal endothelial cells. (A) Representative RNAseq data showing relative read number for TCF4 intron 2 RNA from each sample cohort. (B) Summary of RNA half-life of different cell lines after treatment with actinomycin D. The much longer half life of intron 2 up-stream RNA in F35T and F45SV cells is listed in the second row, sixth column and third row, sixth column. (C) Graphs of time-dependent RNA decay following treatment with actinomycin D.

The FECD CUG repeat RNA is present at only a few (<10) copies per cell in disease tissue. It is likely that each "foci" detected by FISH is a single RNA molecule. A low copy number for a disease-causing RNA has also been observed for myotonic dystrophy type 1(DM1) and C9orf72 ALS/FTD. We find that the CUG repeat expansion stabilizes TCF4 intronic RNA in a corneal cell-specific manner (FIG. 3). This enhanced stability may contribute to an ability of a small number of RNA molecules to bind protein sufficiently to affect overall function in cells and eventually produce observable symptoms that characterize a delayed onset disease like FECD.

The CUG repeat within intronic TCF4 and other microsatellite expansions may be associated with intron retention. Our detection of nuclear CUG RNA foci by FISH and upstream intronic RNA due to its increased half-life may be compatible with a disease model where the TCF4 intron with the expanded repeat is spliced out, forms a linear stable intronic sequence RNA, and undergoes preferential 3' to 5' exonuclease degradation in the nucleus.

There is no definitive mechanistic insight into how the relatively rare expanded CUG repeat RNA can cause FECD. How one or a few copies of RNA triggers widespread changes in gene expression and late onset disease remains a major unanswered question. However, the mutant RNA may act by binding to MBNL and affecting splicing (FIG. 10).

There is relatively little MBNL protein is in the nuclei of FECD_REP cells and human tissue. Using quantitative protein titrations against a known standard, we calculated that there were 65,000 copies of MBNL1 and MBNL2 per cell and less than 2000 copies were present in cell nuclei. Low copy numbers for MNBL in the nuclei of affected tissue are consistent with the hypothesis that even a small amount of mutant expanded CUG repeat RNA may be sufficient to affect the available pool of MNBL protein. A reduction in available MBNL protein would produce the alterations of splicing that are a hallmark of FECD_REP disease (FIGS. 4-5). It is also possible that the MNBL:mutant RNA interaction may nucleate additional protein or RNA interactions to amplify disruptive effects on gene expression and changes in alternative splicing.

Expanded CUG Mutant RNA Causes Splicing Changes in Presymptomatic Tissue

Many of the alterations in splicing observed in FECD_REP tissue also define gene expression in presymptomatic tissue, Pre_S (FIGS. 4-5). The splicing factors MBNL1 and MBNL2 are among the genes showing altered splicing in Pre_S samples and these changes may amplify other splicing changes to push corneal endothelial cells towards full blown FECD.

The similarity of alternative splicing changes between symptomatic FECD_REP and presymptomatic Pre_S tissue is much greater than that between Pre_S and FECD_NR samples. The data suggest that there are fundamental differences in the origins of the two forms of FECD. While their origins differ, late-stage FECD_REP and FECD_NR converge at a common set of clinical findings.

The data also suggest that splicing changes and perturbation of extracellular matrix (ECM) genes seen in FECD_REP late stage disease tissue begin to be observed long before symptoms are observed during standard clinical evaluation. The molecular trigger, mutant RNA, and early molecular changes, altered splicing and observable RNA foci, co-exist in cells that appear to have a normal phenotype. The changes in the magnitude of RNA splicing between control tissue and either Pre_S or late stage FECD_REP samples are similar. This observation suggests that the mutant RNA triggers the splicing changes in key genes independent of the progression of disease.

The finding that splicing is an early trigger has important implications for the development of agents to treat FECD. It is reasonable to expect that such agents would be most effective when administered early in disease progression prior to exuberant production of ECM with degeneration of the corneal endothelium and activation of the immune system. During drug development it should be possible to monitor the changes in alternative splicing and expression of ECM biomarkers caused by expression of the mutant trinucleotide repeat and rank drug candidates by their ability to return splicing to a more normal state—agents that reverse the splicing defect would be promising development candidates. Monitoring splicing of key genes would offer a rapid and definitive assay for screening compounds.

Some individuals without previously noted guttae who possessed the expanded repeat but developed "non-FECD corneal edema" do not show changes in alternative splicing. These results might appear to be in conflict with our observation that all CUG expanded repeat individuals exhibited substantial changes in alternative splicing, including many shared between Pre_S and FECD_REP individuals (FIG. 4). We note that the expanded repeat positive individuals with corneal decompensation without findings of FECD were between 67 and 83 years old, much older than any individual in our Pre_S cohort. It is possible that these individuals possessed protective mutations that might prevent splicing changes and block the molecular events leading to symptomatic FECD.

The Fibrosis Pathway is Activated in Pre_S Tissue

In the clinic, late stage FECD is a disease of cellular degeneration and aberrant extracellular matrix deposition (FIG. 10). Previous studies of FECD_REP tissue have supported activation of the fibrosis pathway as a primary cause for late stage disease pathology. We confirmed fibrosis as the highest ranked canonical pathway in both late stage FECD_REP and FECD_NR (FIG. 8A). The fibrosis pathway is also activated in Pre_S tissue (FIGS. 8A-B). These results demonstrate that changes in splicing, changes in gene expression, and changes in a key disease pathway begin years before symptoms are observed.

Among the top ten genes in pre-symptomatic tissue versus control tissue are cochlin (COCH) and fibronectin (FN1) with >16 and >32 fold change increases respectively (FIG. 6C). Cochlin is a secretory extracellular matrix protein originally identified in the cochlear cells of the inner ear. COCH is also expressed by the endothelial cells the trabecular meshwork of subjects with primary open-angle glaucoma (POAG), another common age-related degenerative disorder. There appears to be a convergence of two age-related disorders of the anterior segment of the eye mediated by COCH. Primary open-angle glaucoma may be more prevalent in patients with advanced FECD. Primary open angle glaucoma is also a disease mediated by transforming growth factor-which increases aqueous humor outflow resistance by dysregulation of ECM genes in the endothelial cells lining the trabecular meshwork.

Late Stage FECD Tissue is Characterized by Changes in Immune Cell-Related and Mitochondrial Dysfunction Pathways Both FECD_REP and FECD_NR tissues show activation of genes related to immune system required for helper T cell activation, signaling, and neuroinflammation (FIGS. 8A-C, 15C-E, 10). In both groups, we detected a 2000-fold increase in CD86 and marked upregulation of major histocompatibility genes (MHC) required by antigen presenting cells to activate helper T cells. This gene expression data along with the observation of cells with a dendritic morphology and positive for the hematopoietic marker CD45 in the endothelial tissue keratoplasty specimens of patients suggest an important role for antigen presenting cells in late-stage disease in both forms of FECD.

The mitochondrial dysfunction pathway is activated in FECD_REP tissue with the expression of over twenty genes changed, little change was seen in FECD_NR tissue (FIG. 8D).

Conclusion

FECD has many advantages as a model for understanding the origins of trinucleotide repeat disease because presymptomatic tissue is relatively accessible. Examination of Pre_S tissue reveals changes in gene expression that preview the more extensive changes in late stage disease. In particular, there is early activation of key genes associated with the fibrosis pathway, the pathway that defines the primary phenotype observe during advanced disease. Splicing patterns and levels of expression for key genes change decades prior to observation of the clinical manifestations of FECD_REP. Surprisingly, many changes in alternative splicing are similar in magnitude in Pre_S and advanced stage FECD_REP tissue. Many altered alternative splicing changes are shared with myotonic dystrophy, another disease caused by expanded CUG trinucleotide repeats, and it is possible that our findings will also be applicable to the genesis and temporal progression of other trinucleotide repeat diseases.

Example 9

This example describes methods for example 10.
Cell Culture, qPCR and Western Blot FECD(F35T) or control(HCN19) corneal endothelial cell lines were cultured Cells were grown in modified Eagle's minimal essential media (OptiMEM) (ThermoFisher) supplemented with 8% fetal bovine serum, 5 ng/mL human epidermal growth factor (ThermoFisher), 20 ng/mL nerve growth factor (Fisher Scientific), 100 µg/mL bovine pituitary extract (ThermoFisher), 20 µg/mL ascorbic acid (Sigma-Aldrich), 200 mg/L calcium chloride (Sigma-Aldrich), 0.08% chondroitin sulfate (Sigma-Aldrich), 50 µg/mL gentamicin (ThermoFisher), and antibiotic/antimycotic solution (diluted 1/100) (Sigma-Aldrich). Cultures were incubated at 37° C. in 5% CO2 and passed when confluent.

Endothelial cells were seeded in 6-well plate at 50% confluence. At the next day, TGFβ was added into the wells at indicated concentrations. Cells were harvest after 24 hr using TRIzol agent (Sigma). The COCH mRNA levels were analyzed by qPCR. Primers for COCH are: F: GATGGGCAGTCCTATGATGATG (SEQ ID NO:13); R: GCATGAGACTCCTTCGGTTTAG (SEQ ID NO:14).

F35T or HCN19 cells were seeded in 6-well plate at 90% confluence. At the next day, culture media was replaced with OptiMEM. After one or two days, the media was collected for western blot. Equal amount of total proteins was loaded and separated using 4-20% acrylamide pre-cast gels (Bio-Rad). Monoclonal rat cochlin antibody (Millipore, MABF267) was used for detection of cochlin protein.
ELISA Assay ELISA assay was performed using DuoSet ELISA kit (R&D Systems) according to the manufacture's protocol. In brief, 96-well plate was coated with anti-cochlin capture antibody overnight. Then blotted with Reagent Diluent. 7 Cochlin standard solutions, which was prepared by 2-fold serial dilution in PBS, were added into the wells. 10-15 uL of AH samples were also added into wells, then filled with PBS to 200 uL total volumes. After incubation for 2 hrs, anti-cochlin detection antibody was added. Next, the wells were treated with Streptavidin-HRP B, Substrate Solution, and Stop Solution. The plate was read using a microplate reader set to 450 nm. All the standards and samples were tested in duplicate. A cochlin standard curve was generated by a four-parameter logistic (4-PL) curve-fit.
Immunofluorescence for Cochlin The paraffin-embedded cornea cross sections were deparaffinated with xylene and rehydrated with 100%, 70%, 50% ethanol, and then water. The slides were blotted with 10% serum in PBS, then incubate with anti-cochlin antibody (Millipore, MABF267; 1:50 dilution) overnight. After PBS wash, the slides were incubated with secondary antibody: Alexa Fluor 488 Goat Anti-rat IgG (H+L) Antibody (Invitrogen A11008), diluted 1:200 in 1% NGS in PBS for 1 hr at room temperature. After PBS wash and DAPI staining, the slides were imaged at 20× or 60× magnification using a Widefield Deltavision microscope. Images were processed using ImageJ.

Example 10

Cochlin

Cochlin is a secretory extracellular matrix protein originally identified in the cochlear cells of the inner ear. The cochlin protein has also been detected in the trabecular meshwork (TM) of subjects with primary open-angle glaucoma (POAG), another common age-related degenerative disorder. Here, we analyzed cochlin as a diagnostic marker and therapeutic target for FECD and glaucoma.

The cochlin protein has two van Willebrand factor A (vWFA) domains on the C-terminal end, which enables its multimerization and adhesion with other ECM components, especially those containing vWFA domains such as collagen proteins. Importantly, the LCCL domain on the N-terminal end can be cleaved off to recruit innate immune cells in the inner ear in response to infection. Mutations in COCH result in deafness, resulting from distinct aggregative extracellular histopathology in the inner ear similar to protein aggregates seen in neurodegenerative disorders such as Huntington's disease, which we note are also reminiscent of FECD guttae histopathology.

The cellular origin of cochlin protein is unclear as evidenced by conflicting published results on the levels of cochlin mRNA levels in trabecular meshwork cells. In POAG, the cochlin deposition is thought to retard the outflow of aqueous humor through the trabecular meshwork resulting in increased intraocular pressure.

We investigated COCH mRNA expression in FECD samples. We found that COCH expression is up-regulated in corneal endothelial cells from FECD/REP, FECD/NR or Pre_Sym corneal tissues analyzed by RNA-seq (FIG. 24A). Higher COCH expressions are verified in endothelial cells from FECD/REP or Pre_Sym corneal tissues by qPCR analysis (FIG. 24B). COCH expression is up-regulated in FECD endothelial cell line (FIG. 24C).

FIGS. 25A-B show TGFβ induces up-regulation of COCH. (A) COCH expression is up-regulated by adding increased concentration of TGFβ in HCN19 healthy control corneal endothelial cells. (B) TGFβ activated COCH in control corneal tissue.

FIGS. 26A-B show cochlin is a secreted protein. (A) Western blot image of cochlin detected in FECD (F35T) corneal endothelial cell culture media. HCN19, healthy control endothelial cell line. (B) The full length cochlin band is confirmed by siRNA knocking down in F35T culture media. si173, anti-cochlin siRNA; siCM, non-complementary control siRNA.

FIG. 27 shows secreted cochlin proteins were detected in FECD patient aqueous humor by ELISA assay.

FIGS. 28A-B show cochlin deposits in FECD patient corneal tissue by immunofluorescence. (A) Cochlin may deposit in Descemet's membrane of FECD patient cornea tissue. (B) Cochlin deposits in trabecular meshwork of FECD donor cornea samples. Cross sections 4056-19-4596, 4056-19-4540 are FECD samples without repeat expansion; 4056-19-4463 is considered pre-symptomatic, which has no guttae, but with expanded CTG repeat (CTG repeat number: 18,73).

Therefore, an embodiment provides methods of detecting glaucoma in a subject comprising detecting an increase in expression of COCH in a corneal endothelial sample obtained from the subject. The subject can be treated with one or more therapeutic agents that decrease the amount of expression of COCH, prescription eyedrops, oral medications, laser trabeculoplasty, trabeculectomy, drainage tubes, or combinations thereof. Therapeutic agents can be, for example, small molecule inhibitors, oligonucleotides, siRNAs, antibodies, RNAi, shRNA, miRNA, and CRISPR-Cas system, zinc finger nucleases, and TALENs. The therapeutic agents can be delivered to the anterior segment of the eye, posterior segment of the eye, corneal endothelial cells, or other cells of the anterior segment of a glaucoma patient.

---

The invention claimed is:

1. A method of monitoring treatment of Fuchs' endothelial corneal dystrophy (FECD) comprising:
   (a) detecting from a first sample obtained from a presymptomatic subject:
      (i) gene expression levels of COCH and one or more of FN1, CD86, CDKN2A, HLA-DRA, CTGF, COL9A3, COL4A2, BCL2, ACKR1, CADM3, KDR, SOD3, and ANXA3; and
      (ii) one or more skipped exon events selected from the group consisting of MBNL1, SORBS1, INF2, NUMA1, SYNE1, and MBNL2;
   (b) administering a first treatment to the presymptomatic subject based on the gene expression levels and/or skipped exon events of (a);
   (c) detecting from a second sample obtained from the presymptomatic subject after the first treatment is administered:
      (i) gene expression levels of COCH, and one or more of FN1, CD86, CDKN2A, HLA-DRA, CTGF, COL9A3, COL4A2, BCL2, ACKR1, CADM3, KDR, SOD3, and ANXA3; and
      (ii) one or more skipped exon events selected from the group consisting of MBNL1, SORBS1, INF2, NUMA1, SYNE1, and MBNL2;
   (d) comparing the first sample gene expression levels and skipped exon events with the second sample gene expression levels and skipped exon events; and
   (e) administering a second treatment to the presymptomatic subject based on the gene expression levels and skipped exon events of (d);
   thereby monitoring treatment of FECD.

2. The method of claim 1, wherein the first sample and second sample comprise corneal tissue, aqueous humor, plasma, serum, blood, tear film, trabecular meshwork, or a combination thereof.

3. The method of claim 1, wherein the treatment comprises a therapeutic agent that increases gene expression, a therapeutic agent that decreases gene expression, a therapeutic agent that modulates exon skipping, a steroidal eye drop, a sodium chloride eye drop, a keratoprosthesis implantation, a therapeutic contact, a corneal transplant, endothelial keratoplasty, penetrating keratoplasty, a prostaglandin, a beta blocker, an alpha-adrenergic agonist, a carbonic anhydrase inhibitor, a rho kinase inhibitor, a miotic or cholinergic agent, or a combination thereof.

4. The method of claim 1, further comprising repeating (a)-(e) one, two, three, or more times.

5. A method of monitoring progression of Fuchs' endothelial corneal dystrophy (FECD) comprising:
   (a) detecting from a first sample obtained from a presymptomatic subject:
      (i) gene expression levels of COCH and one or more of FN1, CD86, CDKN2A, HLA-DRA, CTGF, COL9A3, COL4A2, BCL2, ACKR1, CADM3, KDR, SOD3, and ANXA3; and
      (ii) one or more skipped exon events selected from the group consisting of MBNL1, SORBS1, INF2, NUMA1, SYNE1, and MBNL2;
   (b) detecting from a second sample obtained from the presymptomatic subject after a first treatment is administered:
      (i) gene expression levels of COCH, and one or more of FN1, CD86, CDKN2A, HLA-DRA, CTGF, COL9A3, COL4A2, BCL2, ACKRI, CADM3, KDR, SOD3, and ANXA3; and (ii) one or more skipped exon events selected from the group consisting of MBNL1, SORBS1, INF2, NUMA1, SYNE1, and MBNL2;

(c) comparing the first sample gene expression levels and skipped exon events with the second sample gene expression levels and skipped exon events; and thereby monitoring the progression of FECD.

6. The method of claim 5, wherein the first sample and second sample comprise corneal tissue, aqueous humor, plasma, serum, blood, tear film, trabecular meshwork, or a combination thereof.

7. The method of claim 5, further comprising repeating steps (a)-(c) one, two, three, or more times.

* * * * *